(12) United States Patent
Schaffer et al.

(10) Patent No.: US 9,157,108 B2
(45) Date of Patent: *Oct. 13, 2015

(54) CELLS, NUCLEIC ACIDS, ENZYMES AND USE THEREOF, AND METHODS FOR THE PRODUCTION OF SOPHOROLIPIDS

(71) Applicant: Evonik Degussa GmbH, Essen (DE)

(72) Inventors: Steffen Schaffer, Herten (DE); Mirja Wessel, Bochum (DE); Anja Thiessenhusen, Muenster (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/487,718

(22) Filed: Sep. 16, 2014

(65) Prior Publication Data

US 2015/0056658 A1 Feb. 26, 2015

Related U.S. Application Data

(62) Division of application No. 13/509,716, filed as application No. PCT/EP2010/065713 on Oct. 19, 2010, now Pat. No. 8,911,982.

(30) Foreign Application Priority Data

Nov. 18, 2009 (DE) .......................... 10 2009 046 799
Apr. 12, 2010 (DE) .......................... 10 2010 014 680

(51) Int. Cl.
*C12N 1/21* (2006.01)
*C12P 7/64* (2006.01)
*C12P 19/44* (2006.01)
*C12N 9/02* (2006.01)
*C12N 9/10* (2006.01)
*A61K 31/704* (2006.01)

(52) U.S. Cl.
CPC ............... *C12P 19/44* (2013.01); *A61K 31/704* (2013.01); *C12N 9/0071* (2013.01); *C12N 9/1029* (2013.01); *C12N 9/1051* (2013.01)

(58) Field of Classification Search
CPC .. A61K 31/704; C12N 9/0071; C12N 9/1029; C12N 9/1051; C12P 19/44
See application file for complete search history.

(56) References Cited

U.S. PATENT DOCUMENTS

| 8,604,227 B2 | 12/2013 | Petrat et al. |
| 2010/0068773 A1 | 3/2010 | Marx et al. |
| 2010/0190224 A1 | 7/2010 | Poetter et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0118433 A1 | 5/2011 | Poetter et al. |
| 2011/0171702 A1 | 7/2011 | Reinecke et al. |
| 2011/0189742 A1 | 8/2011 | Haas et al. |
| 2011/0257429 A1 | 10/2011 | Schraven et al. |
| 2012/0264182 A1 | 10/2012 | Reinecke et al. |
| 2013/0052700 A1 | 2/2013 | Poetter et al. |
| 2013/0130319 A1 | 5/2013 | Schaffer et al. |
| 2013/0165685 A1 | 6/2013 | Hannen et al. |
| 2013/0183725 A1 | 7/2013 | Poetter et al. |

OTHER PUBLICATIONS

Branden et al., Introduction to Protein Structure, Garland Publishing Inc., New York, p. 247, 1991.
Witkowski et al., Biochemistry 38:11643-11650, 1999.
Seffernick et al., J. Bacteriol. 183(8):2405-2410, 2001.
Saerens et al., FEMS Yeast Res 11:123-132, published online Nov. 12, 2010.
Van Bogaert, I.N.A., et al., "Importance of the cytochrome P450 monooxygenase CYP52 family for the sophorolipid-producing yeast Candida bombicola," FEMS Yeast Research, vol. 9, No. 1, pp. 87-94, (Feb. 2009).
Lottermoser, K., et al., "Cytochromes P450 of the Sophorose Lipid-producing Yeast Candida apicola: Heterogeneity and Polymerase Chain Reaction-mediated Cloning of Two Genes," Yeast, vol. 12, No. 6, pp. 565-575, (1996).
Van Bogaert, I.N.A., et al., "Knocking out the MFE-2 gene of Candida bombicola leads to improved medium-chain sophorolipid production," FEMS Yeast Research, vol. 9, No. 4, pp. 610-617, (Jun. 1, 2009).
Van Bogaert, I.N.A., et al., "Microbial production and application of sophorolipids," Applied Microbiology and Biotechnology, vol. 76, No. 1, pp. 23-34, (May 3, 2007).
Van Bogaert, I.N.A., et al., "Development of a transformation and selection system for the glycolipid-producing yeast Candida bombicola," Yeast, vol. 25, No. 4, pp. 273-278, (Apr. 1, 2008).
International Search Report Issued Jul. 20, 2011 in PCT/EP10/65713 Filed Oct. 19, 2010.

*Primary Examiner* — Delia Ramirez
(74) *Attorney, Agent, or Firm* — Oblon, McClelland, Maier & Neustadt, L.L.P.

(57) ABSTRACT

The invention relates to cells, nucleic acids, and enzymes, the use thereof for producing sophorolipids, and methods for producing sophorolipids.

27 Claims, 2 Drawing Sheets

US 9,157,108 B2

Figure 1:
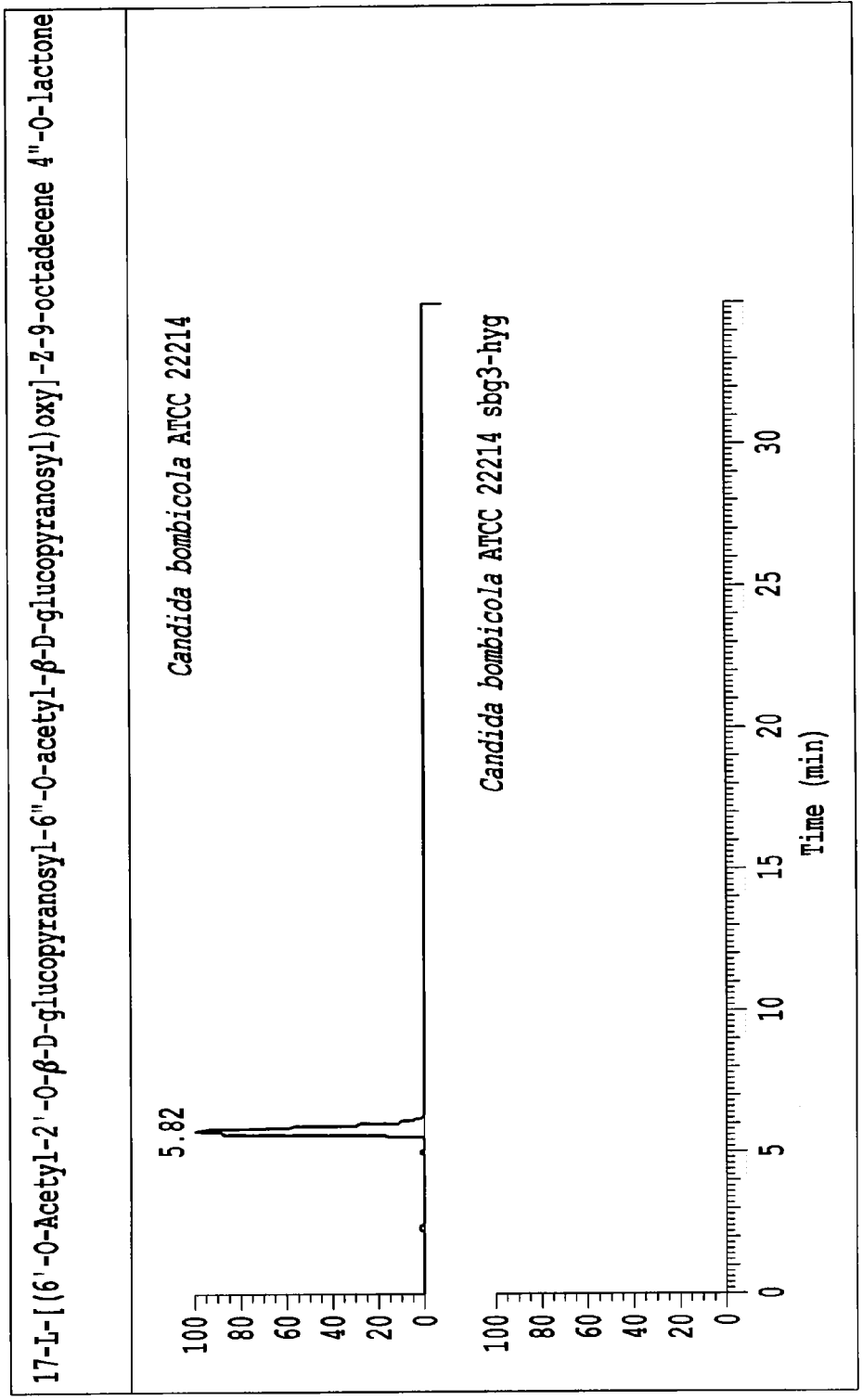

CELLS, NUCLEIC ACIDS, ENZYMES AND USE THEREOF, AND METHODS FOR THE PRODUCTION OF SOPHOROLIPIDS

This application is a Divisional and claims benefit under 35 U.S.C. §120 and §365 of U.S. application Ser. No. 13/509, 716, filed May 14, 2012 (now U.S. Pat. No. 8,911,982), which is the U.S. national-stage of PCT/EP10/065713, filed Oct. 19, 2010. Priority is also claimed to Germany 10 2009 046 799.8, filed Nov. 18, 2009, and Germany 10 2010 014 680.3, filed Apr. 12, 2010.

FIELD OF THE INVENTION

The invention relates to nucleic acids, enzymes and cells and to their use for producing sophorolipids, and also to processes for producing sophorolipids.

PRIOR ART

Currently the production of surfactants is essentially based on the basis of petrochemical raw materials. The utilization of surfactants based on renewable raw materials is a suitable alternative due to the foreseeable shortage of petrochemical raw materials and the increasing demand for products which are based on renewable raw materials and/or which are biodegradable.

Sophorolipids have the surface-active properties required for use as a surfactant.

These lipids are currently produced using wild-type isolates of a variety of yeasts, in particular *Candida bombicola*.

Performance parameters of product formation, such as carbon yield, space-time yield, product concentration, product homogeneity (degree of acetylation, fatty acid species, lactone form vs. open-chain form) have to date been improved exclusively via the optimization of the process control (pH, oxygen supply, media composition, feeding strategies, nitrogen supply, temperature, choice of substrate and the like).

The only exception is the genetic modification of *Candida bombicola* in as far as β-oxidation has been eliminated so that triglycerides, fatty acids, fatty alcohols and the like which are fed by way of substrate can no longer be utilized as a carbon source, in other words degraded (Van Bogaert et al. FEMS Yeast Res. 2009 June; 9(4):610-7). In this manner, it should be possible, by choosing the substrate, specifically to control the fatty acid moiety of the sophorolipids in order to influence the product properties.

Since the improvement of performance parameters in the biotechnological production of sophorolipids via optimizing the process control is possible to a limited extent only, the cells also have to be subjected to genetic modification.

This comprises, firstly, the enhancement of the enzymes involved in sophorolipid synthesis: cytochrome P450 monooxygenase, glycosyltransferase I, glycosyltransferase II, acetyltransferase, sophorolipid exporter with the aim of improving the performance parameters of product formation such as carbon yield, space-time yield, product concentration, product homogeneity (degree of acetylation, fatty acid species) and the like.

This secondly comprises attenuating some of the enzymes involved in sophorolipid synthesis: glycosyltransferase II, acetyltransferase with the aim of modifying the structure and the properties of the sophorolipids produced: glycosyltransferase II: production of monoglycosyl-sophorolipids; acetyltransferase: production of nonacetylated sophorolipids.

If sophorolipids are to be employed on a large scale as surfactants in cleaning applications, cosmetic applications and other applications, they will have to compete with the currently employed surfactants. The latter are bulk chemicals which can be produced at very low cost. Therefore, sophorolipids must be produced at the lowest possible costs. This is not possible by merely optimizing the performance parameters via process optimization.

There is therefore an increasing demand for efficient productions of sophorolipids with high product yields.

The present invention was therefore based on the problem of providing tools and/or processes with the aid of which specific sophorolipids can be synthesized in a simple manner and in large amounts.

DESCRIPTION OF THE INVENTION

Surprisingly, it has been found that the cells, nucleic acids, polypeptides and processes described hereinbelow are capable of solving the above problem.

The subject matter of the present invention are, therefore, genetically modified cells with a modified enzymatic equipment for the synthesis of sophorolipids.

A further subject matter of the invention are novel nucleic acids and vectors as described in claim 11 and 12.

Yet another subject matter of the present invention are novel enzymes which are useful in sophorolipid biosynthesis.

The advantage of the present invention is that not only are the performance parameters of sophorolipid formation, such as carbon yield and space-time yield, improved, but also that the product homogeneity as regards for example the degree of acetylation and the fatty acid species can be improved.

A subject matter of the invention is a cell which is capable of forming sophorolipids, which cell has been genetically modified in such a way that it has an activity, as specified in each case hereinbelow, of at least one of the enzymes selected from the group hereafter, which activity is modified in comparison with its wild type:

at least one enzyme $E_1$ with the polypeptide sequence SEQ ID NO:7, SEQ ID NO:53, SEQ ID NO:55, SEQ ID NO:57, SEQ ID NO:59, SEQ ID NO:61 or SEQ ID NO:63, in particular SEQ ID NO:7, or with a polypeptide sequence where up to 25%, preferably up to 20%, especially preferably up to 15%, in particular up to 10, 9, 8, 7, 6, 5, 4, 3, 2, 1% of the amino acid residues are modified over the respective reference sequence SEQ ID NO:7, SEQ ID NO:53, SEQ ID NO:55, SEQ ID NO:57, SEQ ID NO:59, SEQ ID NO:61 or SEQ ID NO:63, in particular SEQ ID NO:7, by deletion, insertion, substitution or a combination of these and which retains at least 50%, preferably 65%, especially preferably 80%, in particular more than 90% of the enzymatic activity of the enzyme with the respective reference sequence SEQ ID NO:7, SEQ ID NO:53, SEQ ID NO:55, SEQ ID NO:57, SEQ ID NO:59, SEQ ID NO:61 or SEQ ID NO:63, where enzymatic activity for an enzyme $E_1$ is understood as meaning the ability to convert Z-9-octadecenoic acid into 17-hydroxy-Z-9-octadecenoic acid, at least one enzyme $E_2$ with the polypeptide sequence SEQ ID NO:8 or SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:8 or SEQ ID NO:11 by deletion, insertion, substitution or a combination of these and which retains at least 50%, preferably 65%, especially preferably 80%, in particular more than 90% of the enzymatic activity of the enzyme with the respective reference sequence SEQ ID NO:8 or SEQ ID NO:11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid, at least one enzyme $E_3$ with the polypeptide sequence SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:11 by deletion, insertion, substitution or a combination of these and which retains at least 50%, preferably 65%, especially preferably 80%, in particular more than 90% of the enzymatic activity of the enzyme with the reference sequence SEQ ID NO:11, where enzymatic activity for an enzyme $E_3$ is understood as meaning the ability to convert 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, at least one enzyme $E_4$ with the polypeptide sequence SEQ ID NO:9 or with a polypeptide sequence where up to 50%, preferably up to 25%, especially preferably up to 15%, in particular up to 10, 9, 8, 7, 6, 5, 4, 3, 2, 1% of the amino acid residues are modified over SEQ ID NO:9 by deletion, insertion, substitution or a combination of these and which retains at least 50%, preferably 65%, especially preferably 80%, in particular more than 90% of the enzymatic activity of the enzyme with SEQ ID NO:9, where enzymatic activity for an enzyme $E_4$ is understood as meaning the ability to convert 17-L-[(2'-O-β-D-glucopyranosyl-β-D-glucopyranosyl) oxy]-Z-9-octadecenoic acid 1',4"-lactone and acetyl-coenzyme A into 17-L-[(2'-β-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, at least one enzyme $E_5$ with the polypeptide sequence SEQ ID NO:10 or with a polypeptide sequence where up to 45%, preferably up to 25%, especially preferably up to 15% and in particular up to 10, 9, 8, 7, 6, 5, 4, 3, 2, 1% of the amino acid residues are modified over SEQ ID NO:10 by deletion, insertion, substitution or a combination of these and which retains at least 50%, preferably 65%, especially preferably 80%, in particular more than 90% of the enzymatic activity of the enzyme with SEQ ID NO:10, where enzymatic activity for an enzyme $E_5$ is understood as meaning the ability to transfer a sophorolipid out of a cell into the surrounding medium.

In the context of the present invention, the expression "sophorolipids" is understood as meaning compounds of the general formulae (Ia) and (Ib)

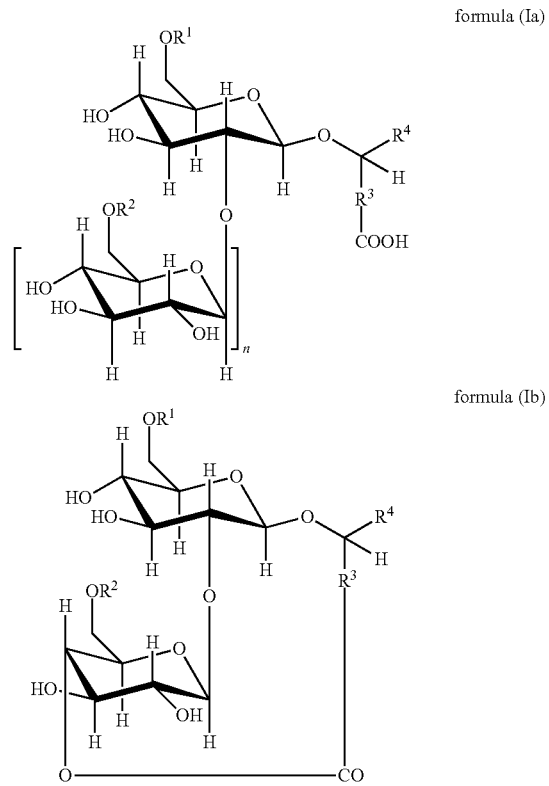

in which
$R^1$=H or CO—CH$_3$,
$R^2$=H or CO—CH$_3$,
$R^3$=a divalent organic moiety which comprises 6 to 32 carbon atoms and which is unsubstituted or substituted by hydroxyl functions, is unbranched and optionally comprises one to three double or triple bonds,
$R^4$=H, CH$_3$ or a monovalent organic radical which comprises 2 to 10 carbon atoms and which is unsubstituted or substituted by hydroxyl functions, which is unbranched and which optionally comprises one to three double or triple bonds, and
n=1 or 0.

In connection with the present invention, a "wild type" of a cell is preferably understood as meaning the original strain from which the cell according to the invention has been developed as the result of recombinant manipulation of the genetic elements which are responsible for the activities of the enzymes of the abovementioned Seq ID Nos.

The expression "modified activity of an enzyme" is preferably understood as meaning modified intracellular activity.

Modifications of amino acid residues of a given polypeptide sequence which do not lead to any substantial modifications of the properties and function of the given polypeptide are known to a person skilled in the art. Thus, for example, it is possible to exchange what are known as conserved amino acids for each other; examples of such suitable amino acid substitutions are: Ala for Ser; Arg for Lys; Asn for Gln or His; Asp for Glu; Cys for Ser; Gln for Asn; Glu for Asp; Gly for Pro; His for Asn or Gln; Ile for Leu or Val; Leu for Met or Val; Lys for Arg or Gln or Glu; Met for Leu or Ile; Phe for Met or Leu or Tyr; Ser for Thr; Thr for Ser; Trp for Tyr; Tyr for Trp or Phe; Val for Ile or Leu. Likewise, it is known that modifications in particular at the N- or C-terminal end of a polypeptide in the form of, for example, amino acid insertions or deletions frequently have no substantial effect on the function of the polypeptide.

The activity of an enzyme $E_1$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can be carried out in a total volume of 200 µl of 200 mM sodium phosphate buffer (pH 7.4), 0.5 mM NADPH, 0.5 mM dithiothreitol, 3 mM glucose 6-phosphate and 0.5 U glucose-6-phosphate dehydrogenase and 50 µl of crude protein extract (approx. 1 mg of total protein) or purified protein in solution (10 µg of purified protein). The reaction is started by the addition of a) 5 µl of a 10 mM solution of the substrate (Z-9-octadecenoic acid) in ethanol or of b) 5 µl of a 10 mM solution of the substrate (Z-9-octadecenoic acid) in 0.1% Triton X-100 which had previously been pretreated by two sonication treatments for in each case 30 seconds, and incubated for 30 minutes at 30° C. Thereafter, the reaction is extracted with 200 µl of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra.

The activity of an enzyme $E_2$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can consist of 185 µl of 10 mM Tris-HCl (pH 7.5), 10 µl of 125 mM UDP-glucose and 50 µl of crude protein extract (approx. 1 mg of total protein) or purified protein in solution (10 µg of purified protein). The reaction is started by the addition of a) 5 µl of a 10 mM solution of the substrate (such as, for example, 18-hydroxy-Z-9-octadecenoic acid) in ethanol or of b) 5 µl of a 10 mM solution of the substrate (such as, for example, 18-hydroxy-Z-9-octadecenoic acid) in 0.1% Triton X-100 which had previously been pretreated by two sonication treatments for in each case 30 seconds and incubated for 30 minutes at 30° C. Thereafter, the reaction is extracted with 200 µl of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra. In this assay it is preferred to employ, as the substrate, 18-hydroxy-Z-9-octadecenoic acid because it is commercially available and because it has already been demonstrated variously that the enzymes of the sophorolipid biosynthesis accept, as substrate, not only 18-hydroxy-Z-9-octadecenoic acid, 17-hydroxy-Z-9-octadecenoic acid and also hydroxy fatty acids of different chain lengths (saturated or unsaturated) and hydroxylated on the ω- or ω-1-carbon, but also the mono- and diglucosides generated therefrom during sophorolipid biosynthesis (Asmer, H. J., Lang, S., Wagner, F., Wray, V. (1988). Microbial production, structure elucidation and bioconversion of sophorose lipids. J. Am. Oil Chem. Soc. 65:1460-1466; Nunez, A., Ashby, R., Foglia, T. A. et al. (2001). Analysis and characterization of sophorolipids by liquid chromatography with atmospheric pressure chemical ionization. Chromatographia 53:673-677; Ashby, R. D., Solaiman, D. K., Foglia, T. A. (2008). Property control of sophorolipids: influence of fatty acid substrate and blending. Biotechnology Letters 30:1093-1100).

The activity of an enzyme $E_3$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can consist of 185 µl of 10 mM Tris-HCl (pH 7.5), 10 µl of 125 mM UDP-glucose and 50 µl of crude protein extract (approx. 1 mg of total protein) or purified protein in solution (10 µg of purified protein). The reaction is started by the addition of a) 5 µl of a 10 mM solution of the substrate (such as, for example, 18-(β-D-glucopyranosyloxy)-Z-9-octadecenoic acid) in ethanol or of b) 5 µl of a 10 mM solution of the substrate (18-(β-D-glucopyranosyloxy)-Z-9-octadecenoic acid) in 0.1% Triton X-100 which had previously been pretreated by two sonication treatments for in each case 30 seconds or c) by addition of the reaction mixture described for the activity determination of the enzyme $E_2$, and incubated for 30 minutes at 30° C. Thereafter, the reaction is extracted with 200 µl (substrate added, as described in a) and b)) or 400 µl (substrate added, as described in c)) of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra. In this assay it is preferred to employ, as the substrate, because its precursor molecule 18-hydroxy-Z-9-octadecenoic acid is commercially available and because it has already been demonstrated variously that the enzymes of the sophorolipid biosynthesis accept, as substrate, not only 18-hydroxy-Z-9-octadecenoic acid, 17-hydroxy-Z-9-octadecenoic acid and also hydroxy fatty acids of different chain lengths (saturated or unsaturated) and hydroxylated on the ω- or ω-1-carbon, but also the mono- and diglucosides generated therefrom during sophorolipid biosynthesis.

The activity of an enzyme $E_4$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can consist of 185 µl of 10 mM Tris-HCl (pH 7.5), 2.5 µl of 100 mM acetyl-coenzyme A and 50 µl of crude protein extract (approx. 1 mg of total protein) or purified protein in solution (10 µg of purified protein). The reaction is started by the addition of a) 5 µl of a 10 mM solution of the substrate (chemically deacetylated sophorolipids) in ethanol or of b) 5 µl of a 10 mM solution of the substrate (chemically deacetylated sophorolipids) in 0.1% Triton X-100 which had previously been pretreated by two sonication treatments for in each case 30 seconds, or c) by addition of the reaction mixture described for the activity determination of the enzyme $E_3$ (in the manner of the substrate addition described therein under c) followed by incubation for 30 minutes at 30° C.), and incubated for 30 minutes at 30° C. Thereafter, the reaction is extracted with 200 µl (substrate added as described in a) and b)) or 600 µl (substrate added as described in c)) of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra. It is preferred in accordance with the invention that the enzyme $E_4$ not only accepts as substrates the lactone forms of the sophorolipids as chosen here for the reference activities, but is also capable of at least monoacetylating the acid form of the sophorolipids at suitable sites, as shown in general in formula (Ia) where $R^1$ and $R^2$=H.

The modified activity of an enzyme $E_5$ in comparison with its wild type can be determined in the simplest manner indirectly via the absolute amount of enzyme $E_5$ per cell, since it can be assumed that an increased presence causes an increased activity and a reduced presence a reduced activity based on the cell and that these relationships are directly dependent on each other. The modified presence of the enzyme $E_5$ in comparison with the wild type can be determined by conventional methods. Thus, the protein concentration can be analyzed by Western Blot hybridization with an antibody which is specific for the protein to be detected (Sambrook et al., *Molecular Cloning: a laboratory manual*, 2nd Ed. Cold Spring Harbor Laboratory Press, Cold Spring Harbor, N.Y. USA, 1989), followed by visual evaluation with suitable software for the concentration determination (Lohaus and Meyer (1989) *Biospektrum*, 5: 32-39; Lottspeich (1999), *Angewandte Chemie* 111: 2630-2647).

Cells which are preferred in accordance with the invention are microorganisms, preferably bacterial cells, yeast cells or fungal cells, with *Ascomycetes* of the genera *Candida* and *Wickerhamiella*, in particular *Candida bombicola, Candida bogoriensis, Candida batistae, Candida apicola* and *Wickerhamiella domericqiae* being especially preferred.

The strains *Candida bombicola* ATCC 22214, *Candida bogoriensis* NRRL Y-5980, *Candida batistae* CBS 8550, *Candida apicola* IMET 42747 and *Wickerhamiella domericqiae*, in particular, are especially suitable cells.

Since the sophorolipids are formed by the cell according to the invention starting from glucose and fatty acids, it is advantageous when cells according to the invention are at least partially blocked in their β-oxidation since this prevents the outflow of substrate and therefore makes possible higher product concentrations and carbon yields. *Candida* cells which are blocked in their β-oxidation are described for example in WO 03/100013, *Candida bombicola* cells which are blocked in the β-oxidation in Van Bogaert et al. FEMS Yeast Res. 2009 June; 9(4):610-7.

In cells which are preferred in accordance with the invention, the modified enzyme activity is preferably an increased enzyme activity.

In accordance with the invention, preferred cells are those which show increased activities of the following enzyme combinations:
$E_1E_2, E_1E_3, E_1E_4, E_1E_5, E_2E_3, E_2E_4, E_2E_5, E_3E_4, E_3E_5, E_4E_5,$
$E_1E_2E_3, E_1E_2E_4, E_1E_2E_5, E_1E_3E_4, E_1E_3E_5, E_1E_4E_5, E_2E_3E_4,$
$E_2E_4E_5, \quad E_3E_4E_5, \quad E_1E_2E_3E_4, \quad E_2E_3E_4E_5, \quad E_1E_3E_4E_5,$
$E_1E_2E_4E_5, E_1E_2E_3E_5, E_1E_2E_3E_4$ and $E_1E_2E_3E_4E_5,$
with the combinations
$E_1E_2, E_1E_3, E_1E_4, E_1E_5, E_2E_3, E_2E_4, E_2E_5, E_3E_4, E_3E_5, E_4E_5,$
$E_1E_2E_3, E_1E_2E_4, E_1E_2E_5, E_1E_3E_4, E_1E_3E_5, E_1E_4E_5, E_2E_3E_4,$
$E_2E_4E_5, E_3E_4E_5$ and $E_1E_2E_3E_4E_5,$
in particular
$E_1E_2, E_1E_3, E_1E_4, E_1E_5, E_2E_3, E_2E_4, E_2E_5, E_3E_4, E_3E_5, E_4E_5$
and $E_1E_2E_3E_4E_5$
being preferred.

To prepare sophorolipids of the general formula (Ia) where n=0, as little as possible enzymatic activity of an enzyme $E_3$ should be present in the cell. Thus, in a specific embodiment of the cell according to the invention, the modified activity of an enzyme $E_3$ is a reduced activity.

Cells which are preferred in accordance with the invention in this context are those which show a reduced activity of an enzyme $E_3$ and optionally simultaneously an increased activity of at least one of the enzymes $E_1, E_2, E_4$ and $E_5$ and which show in particular besides the reduced activity of an enzyme $E_3$ an increased activity of the following enzyme combinations:
$E_1E_2, \quad E_1E_4, \quad E_1E_5, \quad E_2E_4, \quad E_2E_5, \quad E_4E_5, \quad E_1E_2E_4, \quad E_1E_2E_5,$
$E_1E_4E_5$ and $E_1E_2E_4E_5,$
especially preferably
$E_1E_2, E_1E_4, E_1E_5, E_2E_4, E_2E_5, E_4E_5$ and $E_1E_2E_4E_5.$ In this context, the cell according to the invention is preferably a *Candida bombicola, Candida bogoriensis, Candida batistae, Candida apicola* or *Wickerhamiella domericqiae* cell.

Furthermore preferred in this context are cells according to the invention in which the reduction of the enzymatic activity is achieved by the modification of a gene comprising a nucleic acid sequence selected from the group consisting of SEQ ID NO:6 and a sequence which is to at least 80%, especially preferably to at least 90%, more preferably to at least 95% and most preferably to at least 99% identical to the reference sequence SEQ ID NO:6,
where the modification is selected from the group comprising, preferably consisting of,
insertion of foreign DNA into the gene, deletion of at least portions of the gene, point mutations in the gene sequence, RNA interference (siRNA), antisense RNA or modification (insertion, deletion or point mutations) of regulatory sequences which flank the gene.

A nucleic acid which is suitable for the preparation of such cells is, for example, one with the SEQ ID NO:16, which is also subject matter of the invention.

To prepare sophorolipids of the general formula (Ia) or (Ib) where $R^1$ and $R^2$ equal H, as little as possible enzymatic activity of an enzyme $E_4$ should be present in the cell. Thus, in a specific embodiment of the cell according to the invention, the modified activity of an enzyme $E_4$ is a reduced activity.

In this context, cells which are preferred in accordance with the invention are those which show a reduced activity of at least one enzyme $E_4$ and which optionally simultaneously show an increased activity of at least one of the enzymes $E_1$, $E_2$, $E_3$ and $E_5$ and which show in particular besides the reduced activity of an enzyme $E_4$ an increased activity of the following enzyme combinations:

$E_1E_2$, $E_1E_3$, $E_1E_5$, $E_2E_3$, $E_2E_5$, $E_3E_5$, $E_1E_2E_3$, $E_1E_2E_5$, $E_1E_3E_5$ and $E_1E_2E_3E_5$,
especially preferably
$E_1E_2$, $E_1E_3$, $E_1E_5$, $E_2E_3$, $E_2E_5$, $E_3E_5$ and $E_1E_2E_3E_5$.

In this context, the cell according to the invention is preferably a *Candida bombicola, Candida bogoriensis, Candida batistae, Candida apicola* or *Wickerhamiella domericqiae* cell.

Furthermore preferred in this context are cells according to the invention in which the reduction of the enzymatic activity is achieved by the modification of a gene comprising a nucleic acid sequence selected from the group consisting of SEQ ID NO:4 and a sequence which is to at least 80%, especially preferably to at least 90%, more preferably to at least 95% and most preferably to at least 99% identical to SEQ ID NO:4, where the modification is selected from the group comprising, preferably consisting of,
insertion of foreign DNA into the gene, deletion of at least portions of the gene, point mutations in the gene sequence, RNA interference (siRNA), antisense RNA or modification (insertion, deletion or point mutations) of regulatory sequences which flank the gene.

A nucleic acid which is suitable for the preparation of such cells is, for example, one with the SEQ ID NO:14, which is also subject matter of the invention.

To prepare sophorolipids of the general formula (Ia) where n=0 and $R^1$ equals H, as little as possible enzymatic activity of the enzymes $E_3$ and $E_4$ should be present in the cell. Thus, in a specific embodiment of the cell according to the invention, the modified activity of the enzymes $E_3$ and $E_4$ is a reduced activity.

In this context, cells which are preferred in accordance with the invention are those which show a reduced activity of in each case at least one enzyme $E_3$ and $E_4$ and which simultaneously show an increased activity of at least one of the enzymes $E_1$, $E_2$ and $E_5$ and which show in particular besides the reduced activity of the in each case at least one enzyme $E_3$ and $E_4$ an increased activity of the following enzyme combinations:
$E_1E_2$, $E_1E_5$, $E_2E_5$, $E_1E_2E_5$
especially preferably
$E_1E_2$, $E_1E_5$ and $E_2E_5$.

In this context, the cell according to the invention is preferably a *Candida bombicola, Candida bogoriensis, Candida batistae, Candida apicola* or *Wickerhamiella domericqiae* cell.

Furthermore preferred in this context are cells according to the invention in which the reduction of the enzymatic activity is achieved by the modification of a gene comprising a nucleic acid sequence selected from the group consisting of SEQ ID NO:4 and a sequence which is to at least 80%, especially preferably to at least 90%, more preferably to at least 95% and most preferably to at least 99% identical to SEQ ID NO:4 and of a gene comprising a nucleic acid sequence selected from the group consisting of SEQ ID NO:6 and a sequence which is to at least 80%, especially preferably to at least 90%, more preferably to at least 95% and most preferably to at least 99% identical to the reference sequence SEQ ID NO:6, where the modification is selected from the group comprising, preferably consisting of,
insertion of foreign DNA into the gene, deletion of at least portions of the gene, point mutations in the gene sequence, RNA interference (siRNA), antisense RNA or modification (insertion, deletion or point mutations) of regulatory sequences which flank the genes.

Nucleic acids which are suitable for preparing such cells are, for example, those of SEQ ID NO:14 and 16.

What will be said hereinbelow regarding the increasing of the enzyme activity in cells applies both to increasing the activity of the enzymes $E_1$ to $E_5$ and to all enzymes mentioned hereinbelow whose activity may optionally be increased.

In principle, an increase of the enzymatic activity can be achieved by increasing the copy number of the gene sequence(s) which encode(s) the enzyme, by using a strong promoter, by modifying the codon usage of the gene, by increasing in various ways the half-life of the mRNA or of the enzyme, by modifying the regulation of gene expression or by using a gene or allele which encodes a suitable enzyme with an increased activity, and optionally by combining these measures. Cells which are genetically modified in accordance with the invention are generated for example by transformation, transduction, conjugation or a combination of these methods with a vector which comprises the desired gene, an allele of this gene or parts thereof and a promoter which makes possible the expression of the gene. Heterologous expression in particular is achieved by integrating the gene or the alleles into the chromosome of the cell or into an extrachromosomally replicating vector.

An overview over the possibilities of increasing the enzyme activity in cells with reference to the enzyme isocitrate lyase can be found in EP0839211, which is herewith incorporated by reference and whose disclosure content in respect of the possibilities of increasing the enzyme activity in cells forms part of the disclosure of the present invention.

The expression of the enzymes or genes mentioned hereinabove, and the expression of all enzymes or genes mentioned hereinbelow, can be detected with the aid of 1- and 2-dimensional protein gel separation followed by visual identification of the protein concentration in the gel using suitable evaluation software. If the increase of an enzyme activity is based exclusively on an increase of the expression of the gene in question, the quantitative determination of the increase of the enzyme activity can be determined in a simple manner by comparing the 1- or 2-dimensional protein separations between the wild type and the genetically modified cell. A customary method of preparing the protein gels in coryneform bacteria and of identifying the proteins is the procedure described by Hermann et al. (Electrophoresis, 22: 1712.23 (2001)). The protein concentration can also be analyzed by Western Blot hybridization with an antibody which is specific for the protein to be detected (Sambrook et al., Molecular Cloning: a laboratory manual, 2nd ed. Cold Spring Harbor Laboratory Press, Cold Spring Harbor, N.Y. USA, 1989) followed by visual evaluation using suitable concentration determination software (Lohaus and Meyer (1989) Biospektrum, 5: 32-39; Lottspeich (1999), Angewandte Chemie 111: 2630-2647). The activity of DNA-binding proteins can be measured by means of DNA band shift assays (also referred to as gel retardation) (Wilson et al. (2001) Journal of Bacteriology, 183: 2151-2155). The effect of DNA-binding proteins on the expression of other genes can be detected by various well-described reporter gene assay methods (Sambrook et al., Molecular Cloning: a laboratory manual, 2nd ed. Cold Spring Harbor Laboratory Press, Cold Spring Harbor, N.Y. USA, 1989). The intracellular (specific) enzymatic activities can be determined by various described methods (Donahue et al. (2000) Journal of Bacteriology 182 (19):

5624-5627; Ray et al. (2000) Journal of Bacteriology 182 (8): 2277-2284; Freedberg et al. (1973) Journal of Bacteriology 115 (3): 816-823). Unless specific methods for determining the activity of a specific enzyme are stated in what follows, the increase of the enzyme activity, but also the reduction of an enzyme activity, are preferably determined by the methods described in Hermann et al., Electrophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the enzyme activity is increased by mutating the endogenous gene, such mutations can either be generated in an undirected manner using traditional methods, such as, for example, by UV irradiation or by mutagenic chemicals, or in a specific fashion by means of recombinant methods such as deletion(s), insertion(s) and/or nucleotide substitution(s). These mutations give rise to modified cells. Especially preferred mutants of enzymes are, in particular, also those enzymes which are no longer feedback-inhibitable, or at least show a degree of reduced feedback inhibition in comparison with the wild-type enzyme.

If the enzyme activity is increased by increasing the synthesis of an enzyme, then for example the copy number of the genes in question is increased or the promoter region and the regulation region or the ribosomal binding site which is located upstream of the structural gene are mutated. Expression cassettes which are introduced upstream of the structural gene are active in the same manner. In addition, inducible promoters allow the expression to be increased at any desired point in time. Furthermore, the enzyme gene may also have assigned to it regulatory sequences also referred to as "enhancers", which likewise bring about an increased gene expression via improving the interaction between RNA polymerase and DNA. Measures for extending the life of the mRNA likewise improve expression. Furthermore, the enzyme activity will also be increased by preventing enzyme degradation. Here, the genes or gene constructs are either present in plasmids with different copy numbers or else are integrated into and amplified in the chromosome. As an alternative, overexpression of the genes in question may furthermore be achieved by modifying the media composition and the culture conditions. A person skilled in the art may find information in this context in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993)), in JP-A-10-229891, in Jensen and Hammer (Biotechnology and Bioengineering 58, 191-195 (1998)) and in known textbooks of genetics and molecular biology, inter alia. The above-described measures result in genetically modified cells, as do the mutations.

Expression of the genes in question is increased for example by using episomal plasmids. Suitable plasmids and vectors are, in principle, all embodiments available to a person skilled in the art for this purpose. Such plasmids and vectors may be found for example in brochures from Novagen, Promega, New England Biolabs, Clontech or Gibco BRL. Other preferred plasmids and vectors may be found in: Glover, D. M. (1985), DNA cloning: a practical approach, Vol. I-III, IRL Press Ltd., Oxford; Rodriguez, R. L. and Denhardt, D. T (ed.) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The vectors, such as expression vectors, gene deletion cassettes, gene insertion cassettes or gene overexpression cassettes, which comprise the gene to be amplified or portions of the gene to be inactivated are subsequently transferred into the desired strain by means of transformation. Transformation methods, in particular electroporation, lithium-acetate-mediated transformation, freeze-thaw transformation, are described for example in Gietz, R. D., Schiestl, R. H. (2007). Frozen competent yeast cells that can be transformed with high efficiency using the LiAc/SS carrier DNA/PEG method. Nat. Protoc. 2:1-4; Suga, M., Hatakeyama, T. (2003). High-efficiency electroporation by freezing intact yeast cells with addition of calcium. Curr Genet. 43:206-211; Hubberstey, A. V., Wildeman, A. G. (1991). Transformation of *Saccharomyces cerevisiae* by use of frozen spheroplasts. Trends Genet. 7:41; Bröker, M. (1993). Rapid transformation of cryopreserved competent *Schizosaccharomyces pombe* cells. Biotechniques. 15:598-600; Gietz, R. D., Schiestl, R. H. (1989). High efficiency transformation of intact yeast cells using single stranded nucleic acids as a carrier. Curr Genet. 16:339-346 and in "Nonconventional yeast in biotechnology" (ed. Klaus Wolf, Springer-Verlag Berlin, 1996). After the transformation, the vectors, in particular gene deletion cassettes, gene insertion cassettes or gene overexpression cassettes, integrate by means of a crossover event into the chromosome of the desired strain as a result of homologous or heterologous, preferably homologous, recombination. As an alternative, the vectors, in particular expression vectors, may also replicate episomally, in other words as an independent replication unit, in cells of the desired strain. This ensures in all cases that the vectors, such as expression vectors, gene deletion cassettes, gene insertion cassettes or gene overexpression cassettes, will also be passed on to the daughter cells upon cell division.

The wording "an activity of an enzyme $E_x$ which is increased in comparison with its wild type" used hereinabove and in what follows preferably always means an activity of the respective enzyme $E_x$ which is increased by a factor of at least 1.5, especially preferably of at least 10, more preferably of at least 100, even more preferably of at least 1000 and most preferably of at least 10 000. Furthermore, the cell according to the invention which shows "an activity of an enzyme $E_x$ which is increased in comparison with its wild type" comprises in particular also a cell whose wild type shows no, or at least no detectable, activity of this enzyme $E_x$ and which only shows a detectable activity of this enzyme $E_x$ after increasing the enzyme activity, for example by overexpression. In this context, the term "overexpression" or the wording "increase of the expression" used in what follows also comprises the case in which a starting cell, for example a wild-type cell, shows no or at least no detectable expression and a detectable synthesis of the enzyme $E_x$ is induced only by recombinant methods.

Accordingly, the wording "reduced activity of an enzyme $E_x$" used is understood as meaning an activity which is reduced preferably by a factor of at least 0.5, especially preferably of at least 0.1, more preferably of at least 0.01, even more preferably of at least 0.001 and most preferably of at least 0.0001. The wording "reduced activity" also includes no detectable activity ("zero activity"). The activity of a specific enzyme may be reduced for example by targeted mutation or by other measures of reducing the activity of a specific enzyme which are known to a person skilled in the art.

Methods of reducing enzymatic activities in microorganisms are known to a person skilled in the art.

Techniques of molecular biology, in particular, are the method of choice here. Information on modifying and reducing protein expression and the associated reduction of enzymatic activities specifically for *Candida*, in particular for disrupting specific genes, can be found by a person skilled in the art in WO91/006660 and WO03/100013. Cells which are preferred in accordance with the invention are characterized in that the reduction of the enzymatic activity is achieved by modifying a gene comprising one of the abovementioned nucleic acid sequences, with the modification being selected from the group comprising, preferably from the group consisting of, insertion of foreign DNA into the gene, deletion of at least parts of the gene, point mutations in the gene sequence, RNA interference (siRNA), antisense RNA or modification (insertion, deletion or point mutations) of regulatory sequences which flank the gene.

In this context, foreign DNA is understood as meaning any DNA sequence which is "foreign" to the gene (and not to the organism), in other words *Candida-bombicola*-endogenous DNA sequences may in this context also act as "foreign DNA". In this context, it is especially preferred for the gene to be interrupted by the insertion of a selection marker gene, the foreign DNA thus being a selection marker gene, where the insertion has preferably been performed by homologous recombination into the gene locus.

Cells which are preferred in accordance with the invention are characterized in that they have been transformed with at least one nucleic acid according to the invention described hereinbelow and/or a vector according to the invention described hereinbelow.

Cells according to the invention may be used advantageously for the production of sophorolipids.

Thus, a further object of the invention is the use of cells according to the invention for the production of compounds of the general formulae (Ia) and (Ib)
in which
$R^1$=H or CO—CH$_3$,
$R^2$=H or CO—CH$_3$,
$R^3$=a divalent organic moiety which comprises 6 to 32, preferably 7 to 19 carbon atoms and which is unsubstituted or substituted by hydroxyl functions, is unbranched and optionally comprises one to three double or triple bonds,
$R^4$=H, CH$_3$ or a monovalent organic radical which comprises 2 to 10 carbon atoms and which is unsubstituted or substituted by hydroxyl functions, which is unbranched and which optionally comprises one to three double or triple bonds, and
n=0 or 1,
in particular of those compounds of the general formulae (Ia) and (Ib)
in which
$R^1$=H or CO—CH$_3$,
$R^2$=H or CO—CH$_3$,
$R^3$=a divalent organic moiety which comprises 6 to 32, preferably 7 to 19 carbon atoms and which is unsubstituted or substituted by hydroxyl functions, is unbranched and optionally comprises one to three double or triple bonds,
$R^4$=H, CH$_3$ or C$_9$H$_{19}$, and
n=0 or 1,
and very especially preferably compounds of the general formulae (Ia) and (Ib)
in which
$R^1$=H or CO—CH$_3$,
$R^2$=H or CO—CH$_3$,
$R^3$=a divalent organic moiety which comprises 6 to 32, preferably 7 to 19 carbon atoms and which is unsubstituted or substituted by hydroxyl functions, is unbranched and optionally comprises one to three double or triple bonds, in particular C$_8$H$_{15}$=C$_7$H$_{14}$,
$R^4$=H, CH$_3$ or C$_9$H$_{19}$, in particular H or CH$_3$, and
n=1.

A further subject matter of the present invention is a process for the production of sophorolipids, preferably of compounds of the general formulae (Ia) and (Ib)
in which
$R^1$=H or CO—CH$_3$,
$R^2$=H or CO—CH$_3$,
$R^3$=a divalent organic moiety which comprises 6 to 32, preferably 7 to 19 carbon atoms and which is unsubstituted or substituted by hydroxyl functions, is unbranched and optionally comprises one to three double or triple bonds,
$R^4$=H, CH$_3$ or a monovalent organic radical which comprises 2 to 10 carbon atoms and which is unsubstituted or substituted by hydroxyl functions, which is unbranched and which optionally comprises one to three double or triple bonds, and
n=0 or 1,
in particular of those compounds of the general formulae (Ia) and (Ib)
in which
$R^1$=H or CO—CH$_3$,
$R^2$=H or CO—CH$_3$,
$R^3$=a divalent organic moiety which comprises 6 to 32, preferably 7 to 19 carbon atoms and which is unsubstituted or substituted by hydroxyl functions, is unbranched and optionally comprises one to three double or triple bonds,
$R^4$=H, CH$_3$ or C$_9$H$_{19}$, and
n=0 or 1,
and very especially preferably of compounds of the general formulae (Ia) and (Ib)
in which
$R^1$=H or CO—CH$_3$,
$R^2$=H or CO—CH$_3$,
$R^3$=a divalent organic moiety which comprises 6 to 32, preferably 7 to 19 carbon atoms and which is unsubstituted or substituted by hydroxyl functions, is unbranched and optionally comprises one to three double or triple bonds, in particular C$_8$H$_{15}$=C$_7$H$_{14}$,
$R^4$=H, CH$_3$ or C$_9$H$_{19}$, in particular H or CH$_3$, and
n=1
comprising the process steps:
I) bringing a cell according to the invention into contact with a medium comprising a carbon source
II) culturing the cell under conditions which allow the cell to form a sophorolipid from the carbon source, and
III) optionally isolating the formed sophorolipids.

The genetically modified cells according to the invention may be brought into contact with the nutrient medium continuously or batchwise by the batch method or the fed-batch method or the repeated-fed-batch method for the purposes of producing the abovementioned products and thereby cultured. Also feasible is a semicontinuous process as described in GB-A-1009370. An overview of known cultivation methods can be found in the textbook by Chmiel ("Bioprozesstechnik 1. Einführung in die Bioverfahrenstechnik" (Gustav Fischer Verlag, Stuttgart, 1991)) or in the textbook by Storhas ("Bioreaktoren and periphere Einrichtungen", Vieweg Verlag, Brunswick/Wiesbaden, 1994).

The culture medium to be used in each case must satisfy the demands of the strains in question in a suitable manner. The textbook "Nonconventional yeast in biotechnology" (ed. Klaus Wolf, Springer-Verlag Berlin, 1996) contains descriptions of culture media for various yeast strains. Carbon sources which can be employed are carbohydrates such as, for example, glucose, sucrose, arabinose, xylose, lactose, fructose, maltose, molasses, starch, cellulose and hemicelluloses, vegetable and animal oils and fats such as, for example, soya oil, safflower oil, groundnut oil, hemp oil, jatropha oil, coconut fat, pumpkinseed oil, linseed oil, corn oil, poppyseed oil, evening primrose oil, olive oil, palm kernel oil, palm oil, rapeseed oil, sesameseed oil, sunflower oil, grapeseed oil, walnut oil, wheatgerm oil and coconut fat, fatty acids such as, for example, caprylic acid, capric acid, lauric acid, myristic acid, palmitic acid, palmitolenic acid, stearic acid, arachidonic acid, behenic acid, oleic acid, linoleic acid, linolenic acid, gamma-linolenic acid and their methyl or ethyl esters, and fatty acid mixtures, mono-, di- and triglycerides with the fatty acids which have just been mentioned, alcohols such as, for example, glycerol, ethanol and methanol, hydrocarbons such as methane, carbon-containing gases and gas mixtures, such as CO, $CO_2$, synthesis gas, flue gas, amino acids such as L-glutamate or L-valine or organic acids such as, for example, acetic acid. These substances may be employed singularly or as a mixture. It is especially preferred to employ carbohydrates, in particular monosaccharides, oligosaccharides or polysaccharides, as the carbon source, as is described in U.S. Pat. No. 6,01,494 and U.S. Pat. No. 6,136,576, and hydrocarbons, in particular alkanes, alkenes and alkynes and the monocarboxylic acids derived from these and the mono-, di- and triglycerides derived from these monocarboxylic acids, and glycerol and acetate. Very especially preferred are mono-, di- and triglycerides comprising the esterification products of glycerol with caprylic acid, capric acid, lauric acid, myristic acid, palmitic acid, palmitolenic acid, stearic acid, arachidonic acid, behenic acid, oleic acid, linoleic acid, linolenic acid and/or gamma-linoleic acid.

Nitrogen sources which may be used are organic compounds comprising nitrogen, such as peptones, yeast extract, meat extract, malt extract, corn steep liquor, soybean meal and urea or inorganic compounds such as ammonium sulfate, ammonium chloride, ammonium phosphate, ammonium carbonate and ammonium nitrate, ammonia, ammonium hydroxide or ammonia water. The nitrogen sources may be employed singularly or as a mixture.

Phosphorus sources which may be used are phosphoric acid, potassium dihydrogen phosphate or dipotassium hydrogen phosphate or the corresponding sodium-containing salts. The culture medium must furthermore comprise salts of metals, such as, for example, magnesium sulfate or iron sulfate, which are required for growth. Finally, essential growth factors such as amino acids and vitamins may be employed in addition to the abovementioned substances. Furthermore, suitable precursors may be added to the culture medium. The feedstock mentioned may be added to the culture as a single batch or fed in a suitable manner during culturing.

The pH of the culture is controlled by employing basic compounds such as sodium hydroxide, potassium hydroxide, ammonia or ammonia water, or acidic compounds such as phosphoric acid and sulfuric acid. Foaming may be controlled by using antifoams such as, for example, fatty acid polyglycol esters. To maintain the stability of plasmids, suitable selective substances such as, for example, antibiotics may be added to the medium. Oxygen or oxygen-containing gas mixtures such as, for example, air are introduced into the culture in order to maintain aerobic conditions.

The temperature of the culture is normally more than 20° C., preferably more than 25° C., it may also be more than 40° C., with a culture temperature of 95° C., especially preferably 90° C. and most preferably 80° C. not being exceeded. In step III) of the process according to the invention, the sophorolipids formed by the cells may optionally be isolated from the cells and/or the nutrient medium, where all methods of isolating low-molecular-weight substances from complex compositions which are known to a person skilled in the art may be used for the isolation, such as, for example, filtration, extraction, adsorption (chromatography) or crystallization. As a rule, work-up of the sophorolipids is performed as a function of the product form. In the case of a sophorolipid which is present in the water-insoluble lactone form, the following procedure may be the procedure of choice: the product in lactone form is removed from the aqueous phase by centrifugation.

In addition, the product phase comprises biomass residues and various contaminants such as oils, fatty acids and other nutrient media components. Oil residues can be removed for example by extraction by means of suitable solvents, advantageously by means of organic solvents. An alkane such as, for example, n-hexane, is preferred by way of solvent. The product may be removed from the aqueous phase for example by means of a suitable ester, for example by means of ethyl acetate. The abovementioned extraction steps may be carried out in any order.

Alternatively, sophorolipids may be isolated from the nutrient medium by converting the lactone form into the water-soluble open acid form. For example, the conversion into the open acid form is performed by means of hydrolysis, advantageously by alkaline hydrolysis. Thereafter, the open-chain sophorolipids are dissolved in an aqueous acid, for example aqueous sulfuric acid, in order to remove any salts which may have formed in the solution. The further purification of the product is carried out by means of extraction. Here, it is preferred to employ solvents, in particular organic solvents. n-Pentanol is preferred by way of solvent. To remove the solvent, for example a distillation is performed. Thereafter, the lyophilized product may be purified further, for example by means of chromatographic methods. Examples which may be mentioned at this point are the precipitation by means of suitable solvents, the extraction by means of suitable solvents, complexing, for example by means of cyclodextrins or cyclodextrin derivatives, crystallization, purification or isolation by means of chromatographic methods, or the conversion of the sophorolipids into derivatives which can be removed readily.

The sophorolipids produced by the process according to the invention may be employed advantageously in cleaning compositions, in cosmetic or pharmaceutical formulations and in crop protection formulations.

Thus, a further subject of the present invention is the use of the sophorolipids obtained by the process according to the invention for the preparation of cosmetic, dermatological or pharmaceutical formulations, crop protection formulations and care and cleaning compositions and surfactant concentrates.

The term "care composition" is understood here as meaning a formulation which satisfies the purpose of retaining an object in its original form, of reducing or avoiding the effects of external influences (for example time, light, temperature, pressure, soiling, chemical reaction with other reactive compounds that come into contact with the object) such as, for example, ageing, soiling, material fatigue, bleaching, or even of improving desired positive properties of the object. For the last point, mention may be made for example of improved hair shine or greater elasticity of the object under consideration.

"Crop protection formulations" are to be understood as meaning those formulations which are obviously used for the protection of plants depending on the nature of their preparation; this is the case especially if at least one compound from the classes of the herbicides, fungicides, insecticides, acaricides, nematicides, bird repellents, plant nutrients and soil conditioners is present in the formulation.

It is preferred in accordance with the invention to use sophorolipids prepared by the process according to the invention in care and cleaning compositions for domestic purposes, for industry, in particular for hard surfaces, leather or textiles.

A contribution to solve the problem is provided by an isolated DNA which is selected from among the following sequences:

A1a) a sequence according to SEQ ID NO:2, SEQ ID NO:52 or SEQ ID NO:54, in particular SEQ ID NO:2, where this sequence encodes a protein which is capable of converting Z-9-octadecenoic acid into 17-hydroxy-Z-9-octadecenoic acid, B1a) an intron-free sequence which is derived from a sequence according to A1a) and which encodes for the same protein or peptide as the sequence according to SEQ ID NO:2, SEQ ID NO:52 or SEQ ID NO:54, in particular according to SEQ ID NO:2, C1a) a sequence which encodes a protein or peptide which comprises the amino acid sequence according to SEQ ID NO:7, SEQ ID NO:53 or SEQ ID NO:55, in particular SEQ ID NO:7, and which is preferably capable of converting Z-9-octadecenoic acid into 17-hydroxy-Z-9-octadecenoic acid, D1a) a sequence which is identical to at least 80%, especially preferably to at least 90%, more preferably to at least 95% and most preferably to at least 99% to a sequence according to any of groups A1a) to C1a), especially preferably according to group A1a), where this sequence preferably encodes a protein or peptide which is capable of converting Z-9-octadecenoic acid into 17-hydroxy-Z-9-octadecenoic acid, E1a) a sequence which hybridizes, or which, taking into consideration the degeneracy of the genetic code, would hybridize with the counterstrand of a sequence according to any of groups A1a) to D1a), especially preferably according to group A1a), where this sequence preferably encodes a protein or peptide which is capable of converting Z-9-octadecenoic acid into 17-hydroxy-Z-9-octadecenoic acid, F1a) a derivative of a sequence according to any of groups A1a) to E1a), especially preferably according to group A1a), which is obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting Z-9-octadecenoic acid into 17-hydroxy-Z-9-octadecenoic acid, and G1a) a sequence which is complementary to a sequence according to any of groups A1a) to F1a), especially preferably according to group A1a).

A further contribution to the solution of the problem is provided by an isolated DNA which is selected from among the following sequences:

A1b) a sequence according to SEQ ID NO:56, SEQ ID NO:58 or SEQ ID NO:60, where this sequence encodes a protein which is capable of converting Z-9-octadecenoic acid into 17-hydroxy-Z-9-octadecenoic acid, B1b) an intron-free sequence which is derived from a sequence according to A1b) and which encodes for the same protein or peptide as the sequence according to SEQ ID NO:56, SEQ ID NO:58 or SEQ ID NO:60, C1b) a sequence which encodes a protein or peptide which comprises the amino acid sequence according to SEQ ID NO:57, SEQ ID NO:59 or SEQ ID NO:61, and which is preferably capable of converting Z-9-octadecenoic acid into 17-hydroxy-Z-9-octadecenoic acid, D1b) a sequence which is identical to at least 800, especially preferably to at least 86%, more preferably to at least 95% and most preferably to at least 99% to a sequence according to any of groups A1b) to C1b), especially preferably according to group A1b), where this sequence preferably encodes a protein or peptide which is capable of converting Z-9-octadecenoic acid into 17-hydroxy-Z-9-octadecenoic acid, E1b) a sequence which hybridizes, or which, taking into consideration the degeneracy of the genetic code, would hybridize with the counterstrand of a sequence according to any of groups A1b) to D1b), especially preferably according to group A1b), where this sequence preferably encodes a protein or peptide which is capable of converting Z-9-octadecenoic acid into 17-hydroxy-Z-9-octadecenoic acid, F1b) a derivative of a sequence according to any of groups A1b) to E1b), especially preferably according to group A1b), which is obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting Z-9-octadecenoic acid into 17-hydroxy-Z-9-octadecenoic acid, and G1b) a sequence which is complementary to a sequence according to any of groups A1b) to F1b), especially preferably according to group A1b).

A further contribution to the solution of the problem is provided by an isolated DNA which is selected from among the following sequences:

A1c) a sequence according to SEQ ID NO:62, where this sequence encodes a protein which is capable of converting Z-9-octadecenoic acid into 17-hydroxy-Z-9-octadecenoic acid, B1c) an intron-free sequence which is derived from a sequence according to A1c) and which encodes for the same protein or peptide as the sequence according to SEQ ID NO:62, C1c) a sequence which encodes a protein or peptide which comprises the amino acid sequence according to SEQ ID NO:63, and which is preferably capable of converting Z-9-octadecenoic acid into 17-hydroxy-Z-9-octadecenoic acid, D1c) a sequence which is identical to at least 60%, especially preferably to at least 85%, more preferably to at least 90% and most preferably to at least 99% to a sequence according to any of groups A1c) to C1c), especially preferably according to group A1c), where this sequence preferably encodes a protein or peptide which is capable of converting Z-9-octadecenoic acid into 17-hydroxy-Z-9-octadecenoic acid, E1c) a sequence which hybridizes, or which, taking into consideration the degeneracy of the genetic code, would hybridize with the counterstrand of a sequence according to any of groups A1c) to D1c), especially preferably according to group A1c), where this sequence preferably encodes a protein or peptide which is capable of converting Z-9-octadecenoic acid into 17-hydroxy-Z-9-octadecenoic acid, F1c) a derivative of a sequence according to any of groups A1c) to E1c), especially preferably according to group A1c), which is obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting Z-9-octadecenoic acid into 17-hydroxy-Z-9-octadecenoic acid, and G1c) a sequence which is complementary to a sequence according to any of groups A1c) to F1c), especially preferably according to group A1c).

A further subject of the invention is an isolated DNA which is selected from among the following sequences:

A2) a sequence according to SEQ ID NO:3, where this sequence encodes a protein which is capable of converting UDP-glucose and 17-hydroxy-Z-9-octadecenoic acid into 17-(β-D-glucopyranosyloxy)-Z-9-octadecenoic acid, B2) an intron-free sequence which is derived from a sequence according to A2) and which encodes for the same protein or peptide as the sequence according to SEQ ID NO:3, C2) a sequence which encodes a protein or peptide which comprises the amino acid sequence according to SEQ ID NO:8 and which is preferably capable of converting UDP-glucose and 17-hydroxy-Z-9-octadecenoic acid into 17-(β-D-glucopyranosyloxy)-Z-9-octadecenoic acid, D2) a sequence which is to at least 80%, especially preferably to at least 90%, more preferably to at least 95% and most preferably to at least 99% identical to a sequence according to any of groups A2) to C2), especially preferably according to group A2), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid, E2) a sequence which hybridizes or which, taking into consideration the degeneracy of the genetic code, would hybridize to the counterstrand of a sequence according to any of groups A2) to D2), especially preferably according to group A2), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid, F2) a derivative of a sequence according to any of groups A2) to E2), especially preferably according to group A2), which is obtainable by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting UDP-glucose and 17-hydroxy-Z-9-octadecenoic acid into 17-(β-D-glucopyranosyloxy)-Z-9-octadecenoic acid, and G2) a sequence which is complementary to a sequence according to any of groups A2) to F2), especially preferably according to group A2).

A further subject matter of the invention is an isolated DNA which is selected from among the following sequences: A3) a sequence according to SEQ ID NO:4, where this sequence encodes a protein which is capable of converting 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl)oxy]-Z-9-octadecenoic acid 1',4''-lactone monoacetate or 17-L-[(2'-O-β-D-glucopyranosyl-β-D-glucopyranosyl)oxy]-Z-9-octadecenoic acid 1',4''-lactone monoacetate and acetyl-coenzyme A into 17-L-[(2'-O-β-D-glucopyranosyl-β-D-glucopyranosyl)oxy]-Z-9-octadecenoic acid 1',4''-lactone diacetate or 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl)oxy]-Z-9-octadecenoic acid 1',4''-lactone diacetate, with the first option being preferred, B3) an intron-free sequence which is derived from a sequence according to A3) and which encodes for the same protein or peptide as the sequence according to SEQ ID NO:4, C3) a sequence which encodes a protein or peptide which comprises the amino acid sequence according to SEQ ID NO:9 and which is preferably capable of converting 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl) oxy]-Z-9-octadecenoic acid 1',4''-lactone monoacetate or 17-L-[(2'-O-β-D-glucopyranosyl-β-D-glucopyranosyl) oxy]-Z-9-octadecenoic acid 1',4''-lactone monoacetate and acetyl-coenzyme A into 17-L-[(2'-O-β-D-glucopyranosyl-β-D-glucopyranosyl)oxy]-Z-9-octadecenoic acid 1',4''-lactone diacetate or 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl)oxy]-Z-9-octadecenoic acid 1',4''-lactone diacetate, with the first option being preferred, D3) a sequence which is identical to at least 80%, especially preferably to at least 90%, more preferably to at least 95% and most preferably to at least 99% to a sequence according to any of groups A3) to C3), especially preferably according to group A3), where this sequence preferably encodes a protein or peptide which is capable of converting 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl)oxy]-Z-9-octadecenoic acid 1',4''-lactone monoacetate or 17-L-[(2'-O-β-D-glucopyranosyl-β-D-glucopyranosyl)oxy]-Z-9-octadecenoic acid 1',4''-lactone monoacetate and acetyl-coenzyme A into 17-L-[(2'-O-β-D-glucopyranosyl-β-D-glucopyranosyl)oxy]-Z-9-octadecenoic acid 1',4''-lactone diacetate or 17-L-[(2'-β-β-D-glucopyranosyl-β-D-glucopyranosyl)oxy]-Z-9-octadecenoic acid 1',4''-lactone diacetate, with the first option being preferred, E3) a sequence which hybridizes or, taking into consideration the degeneracy of the genetic code, would hybridize with the counterstrand of a sequence according to any of groups A3) to D3), especially preferably according to group A3), where this sequence preferably encodes a protein or peptide which is capable of converting 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl)oxy]-Z-9-octadecenoic acid 1',4''-lactone monoacetate or 17-L-[(2'-O-β-D-glucopyranosyl-β-D-glucopyranosyl)oxy]-Z-9-octadecenoic acid 1',4''-lactone monoacetate and acetyl-coenzyme A into 17-L-[(2'-O-β-D-glucopyranosyl-β-D-glucopyranosyl)oxy]-Z-9-octadecenoic acid 1',4''-lactone diacetate or 17-L-[(2'-O-β-D-glucopyranosyl-β-D-glucopyranosyl)oxy]-Z-9-octadecenoic acid 1',4''-lactone and acetyl-coenzyme A into 17-L-[(2'-O-β-D-glucopyranosyl-β-D-glucopyranosyl)oxy]-Z-9-octadecenoic acid 1',4''-lactone diacetate, with the first option being preferred, F3) a derivative of a sequence according to any of groups A3) to E3), especially preferably according to group A3), which has been obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-β-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-β-β-D-glucopyranosyl-β-D-glucopyranosyl)oxy]-Z-9-octadecenoic acid 1',4"-lactone diacetate, with the first option being preferred, and G3) a sequence which is complementary to a sequence according to any of groups A3) to F3), especially preferably according to group A3).

A further subject matter of the invention is an isolated DNA which is selected from among the following sequences:

A4) a sequence according to SEQ ID NO:5, where this sequence encodes a protein which is capable of transferring a sophorolipid out of a cell into the surrounding medium, B4) an intron-free sequence which is derived from a sequence according to A4) and which encodes for the same protein or peptide as the sequence according to SEQ ID NO:5, C4) a sequence which encodes a protein or peptide which comprises the amino acid sequence according to SEQ ID NO:10 and which is preferably capable of transferring a sophorolipid out of a cell into the surrounding medium, D4) a sequence which is to at least 80%, especially preferably to at least 90%, more preferably to at least 95% and most preferably to at least 99% identical to a sequence according to any of groups A4) to C4), especially preferably according to group A4), where this sequence preferably encodes a protein or peptide which is capable of transferring a sophorolipid out of a cell into the surrounding medium, E4) a sequence which hybridizes, or which, taking into consideration the degeneracy of the genetic code, would hybridize with the counterstrand of a sequence according to any of groups A4) to D4), especially preferably according to group A4), where the sequence preferably encodes a protein or peptide which is capable of transferring a sophorolipid out of a cell into the surrounding medium, F4) a derivative of a sequence according to any of groups A4) to E4), especially preferably according to group A4), which has been obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of transferring a sophorolipid out of a cell into the surrounding medium, and G4) a sequence which is complementary to a sequence according to any of groups A4) to F4), especially preferably according to group A4).

A further subject matter of the invention is an isolated DNA which is selected from among the following sequences:

A5) a sequence according to SEQ ID NO:6, where this sequence encodes a protein which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, B5) an intron-free sequence which is derived from a sequence according to A5) and which encodes for the same protein or peptide as the sequence according to SEQ ID NO:6, C5) a sequence which encodes a protein or peptide which comprises the amino acid sequence according to SEQ ID NO:11 and which is preferably capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, D5) a sequence which is to at least 80%, especially preferably to at least 90%, more preferably to at least 95% and most preferably to at least 99% identical to a sequence according to any of groups A5) to C5), especially preferably according to group A5), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, E5) a sequence which hybridizes or which, taking into consideration the degeneracy of the genetic code, would hybridize to the counterstrand of a sequence according to any of groups A5) to D5), especially preferably according to group A5), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, F5) a derivative of a sequence according to any of groups A5) to E5), especially preferably according to group A5), which has been obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, and G5) a sequence which is complementary to a sequence according to any of groups A5) to F5), especially preferably according to group A5).

The "nucleotide identity" or "amino acid identity" here is determined with the aid of known methods. In general, one uses special computer programs with algorithms, taking into consideration specific requirements.

Preferred methods of determining the identity first generate the largest match between the sequences to be compared. Computer programs for determining the identity comprise, but are not limited to, the GCG software package, including GAP (Deveroy, J. et al., Nucleic Acid Research 12 (1984), page 387, Genetics Computer Group University of Wisconsin, Medicine (Wi), and BLASTP, BLASTN and FASTA (Altschul, S. et al., Journal of Molecular Biology 215 (1990), pages 403-410. The BLAST program can be obtained from the National Center For Biotechnology Information (NCBI) and from other sources (BLAST Handbuch, Altschul S. et al., NCBI NLM NIH Bethesda N. Dak. 22894; Altschul S. et al., hereinabove).

Likewise, the known Smith-Waterman algorithm may be used for determining the nucleotide identity.

Preferred parameters for determining the "nucleotide identity" when using the BLASTN program (Altschul, S. et al., Journal of Molecular Biology 215 (1990), pages 403-410) are:
Expect Threshold: 10
Word size: 28
Match Score: 1
Mismatch Score: −2
Gap costs: Linear The above parameters are the default parameters for comparing nucleotide sequences.

The GAP program is likewise suitable for use with the above parameters.

Preferred parameters for determining the "amino acid identity" when using the BLASTP program (Altschul, S. et al., Journal of Molecular Biology 215 (1990), pages 403-410) are:
Expect Threshold: 10
Word size: 3
Matrix: BLOSUM62
Gap costs: Existence: 11; Extension: 1
Compositional adjustments: Conditional compositional score matrix adjustment The above parameters are the default parameters when comparing amino acid sequences.

The GAP program is likewise suitable for use with the above parameters.

An identity of 80% according to the above algorithm means 80% identity in connection with the present invention. The same applies to higher identities.

The feature "sequence which hybridizes or which, taking into consideration the degeneracy of the genetic code, would hybridize to the counterstrand of a sequence" indicates a sequence which hybridizes or which, taking into consideration the degeneracy of the genetic code, would hybridize with the counterstrand of a reference sequence under preferably stringent conditions. For example, the hybridizations may be carried out at 68° C. in 2×SSC or according to the protocol of the digoxigenin labeling kit from Boehringer (Mannheim). Preferred hybridization conditions are, for example, incubation at 65° C. overnight in 7% SDS, 1% BSA, 1 mM EDTA, 250 mM sodium phosphate buffer (pH 7.2), followed by washing at 65° C. with 2×SSC; 0.1% SDS.

The derivatives of the isolated DNA according to the invention which, according to alternative F1a), F1b), F1b), F1c), F2), F3), F4) or F5), can be obtained by substitution, addition, inversion and/or deletion of one or more bases of a sequence according to any of groups A1a) to E1a), A1b) to E1b), A1c) to E1c), A2) to E2), A3) to E3), A4) to E4) and A5) to E5), include in particular the sequences which, in the protein which they encode, result in conservative amino acid substitutions such as, for example, the substitution of glycine for alanine or of aspartic acid for glutamic acid. Such function-neutral mutations are referred to as sense mutations and do not lead to any major modification of the activity of the polypeptide. Furthermore, it is known that modifications of the N- and/or C-terminal end of a polypeptide do not have a profound adverse effect on its function and indeed are even capable of stabilizing it, so that, accordingly, DNA sequences in which bases are added at the 3'-end or at the 5'-end of the sequence with the nucleic acids according to the invention are comprised by the present invention, too. Information in this context can be found by a person skilled in the art in, inter alia, Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology.

A contribution to solving the problems specified at the outset is furthermore provided by a vector, preferably an expression vector, a gene deletion cassette, gene insertion cassette or gene overexpression cassette, comprising a DNA with a sequence according to any of groups A1a) to G1a), A1b) to G1b), A1c) to G1c), A2) to G2), A3) to G3), A4) to G4) and A5) to G5), as defined hereinabove. Suitable vectors are all the vectors which are known to a person skilled in the art and which are conventionally employed for introducing DNA into a host cell. These vectors are not only capable of autonomous replication since they have origins of replication such as for example those of the 2μ plasmid or of the ARS (autonomously replicating sequences) but are also capable of integration into the chromosomes (nonreplicating plasmids). Vectors are also understood as meaning linear DNA fragments which have no origins of replication whatsoever, such as, for example, gene deletion cassettes, gene insertion cassettes or gene overexpression cassettes. Gene deletion cassettes are usually composed of a selection marker and DNA fragments which flank the region to be deleted. Gene insertion cassettes are usually composed of a marker and fragments of the gene to be inactivated. Gene overexpression cassettes are usually composed of a marker, the gene to be overexpressed and regulatory regions which are relevant for the expression of the gene, such as, for example, promoter and terminator. Preferred vectors are selected from the group comprising plasmids and cassettes, such as, for example *E. coli* yeast shuttle plasmids; especially preferred are expression vectors, gene deletion cassettes, gene insertion cassettes or gene overexpression cassettes, in particular the gene deletion cassettes described hereinbelow with SEQ ID NO:12, SEQ ID NO:13, SEQ ID NO:14, SEQ ID NO:15 and SEQ ID NO:16 and the expression cassettes with SEQ ID NO:70, SEQ ID NO:71, SEQ ID NO:72, SEQ ID NO:73 and SEQ ID NO:74. According to a preferred embodiment of the vector according to the invention, the DNA with a sequence according to any of groups A1) to F5) is under the control of a constitutive promoter or a promoter capable of being regulated, which promoter is suitable for expressing the polypeptide encoded by these DNA sequences in the cell of a microorganism, preferably a bacterial cell, a yeast cell or a fungal cell, especially preferably a yeast cell, most preferably a *Candida bombicola, Candida bogoriensis, Candida batistae, Candida apicola* or *Wickerhamiella domericqiae* cell. Examples of such constitutive promoters are for example the TSC3 promoter, the ENO1 promoter, the FBA1 promoter, the GPD promoter, the GPM promoter, the FBA1 promoter, the ICL1 promoter or the ACT1 promoter. Examples of such promoters which are capable of being regulated are for example the GAL1 promoter, the GAL2 promoter, the GALT promoter, the MEL1 promoter, the GAL10 promoter, the SBG1 promoter, the SBG2 promoter, the SBG3 promoter, the SBG4 promoter, the SBG5 promoter or the MAL2 promoter. Besides a promoter, the vector according to the invention should preferably comprise a ribosome binding site and a terminator. In this context, it is especially preferred that the DNA according to the invention is incorporated into an expression cassette of the vector comprising the promoter, the ribosome binding site and the terminator. Besides the above-mentioned structural elements, the vector may furthermore comprise selection marker genes which are known to a person skilled in the art.

The nucleic acids SEQ ID NO:12, SEQ ID NO:13, SEQ ID NO:14, SEQ ID NO:15, SEQ ID NO:16, IntEx-CbSBG1 (SEQ ID NO:70), IntEx-CbSBG2 (SEQ ID NO:71), IntEx-CbSBG3 (SEQ ID NO:72), IntEx-CbSBG4 (SEQ ID NO:73) and IntEx-CbSBG5 (SEQ ID NO:74) described in the examples are vectors which are preferred in accordance with the invention.

A further contribution to the solution of the problem is provided by the novel enzymes $E_1$ to $E_5$.

Thus, a further subject matter of the invention is an isolated polypeptide selected from the group consisting of an enzyme $E_1$ with the polypeptide sequence SEQ ID NO:7, SEQ ID NO:53, SEQ ID NO:55, SEQ ID NO:57, SEQ ID NO:59, SEQ ID NO:61 or SEQ ID NO:63, especially SEQ ID NO:7, or with a polypeptide sequence where up to 25%, preferably up to 20%, especially preferably up to 15%, in particular up to 10, 9, 8, 7, 6, 5, 4, 3, 2, 1% of the amino acid residues are modified over the respective reference sequence SEQ ID NO:7, SEQ ID NO:53, SEQ ID NO:55, SEQ ID NO:57, SEQ ID NO:59, SEQ ID NO:61 or SEQ ID NO:63, especially SEQ ID NO:7, by deletion, insertion, substitution or a combination of these and which retains at least 50%, preferably 65%, especially preferably 80%, in particular more than 90% of the enzymatic activity of the enzyme with the respective reference sequence, where enzymatic activity for an enzyme $E_1$ is understood as meaning the ability to convert Z-9-octadecenoic acid into 17-hydroxy-Z-9-octadecenoic acid, an enzyme $E_2$ with the polypeptide sequence SEQ ID NO:8 or SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:8 or SEQ ID NO:11 by deletion, insertion, substitution or a combination of these and which retains at least 50%, preferably 65%, especially preferably 80%, in particular more than 90% of the enzymatic activity of the enzyme with the respective reference sequence No. 8 or 11, where enzymatic activity for an enzyme $E_2$ is understood as meaning the ability to convert UDP-glucose and 17-hydroxy-Z-9-octadecenoic acid into 17-β-D-glucopyranosyloxy)-Z-9-octadecenoic acid, an enzyme $E_3$ with the polypeptide sequence SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:11 by deletion, insertion, substitution or a combination of these and which retains at least 50%, preferably 65%, especially preferably 80%, in particular more than 90% of the enzymatic activity of the enzyme with the respective reference sequence No. 11, where enzymatic activity for an enzyme $E_3$ is understood as meaning the ability to convert 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, an enzyme $E_4$ with the polypeptide sequence SEQ ID NO:9 or with a polypeptide sequence where up to 50%, preferably up to 25%, especially preferably up to 15%, in particular up to 10, 9, 8, 7, 6, 5, 4, 3, 2, 1% of the amino acid residues are modified over SEQ ID NO:9 by deletion, insertion, substitution or a combination of these and which retains at least 50%, preferably 65%, especially preferably 80%, in particular more than 90% of the enzymatic activity of the enzyme with SEQ ID NO:9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-β-β-D-glucopyranosyl-β-D-glucopyranosyl)oxy]-Z-9-octadecenoic acid 1',4"-lactone diacetate, with the first option being preferred, and an enzyme $E_5$ with the polypeptide sequence SEQ ID NO:10 or with a polypeptide sequence where up to 45%, preferably up to 25%, especially preferably up to 15% and in particular up to 10, 9, 8, 7, 6, 5, 4, 3, 2, 1% of the amino acid residues are modified over SEQ ID NO:10 by deletion, insertion, substitution or a combination of these and which retains at least 50%, preferably 65%, especially preferably 80%, in particular more than 90% of the enzymatic activity of the enzyme with SEQ ID NO:10, where enzymatic activity for an enzyme $E_5$ is understood as meaning the ability to transfer a sophorolipid out of a cell into the surrounding medium.

In the examples given hereinbelow, the present invention is described by way of example without it being intended to limit the invention, whose scope is clear from all of the description and the claims, to the embodiments mentioned in the examples.

Figure 2:
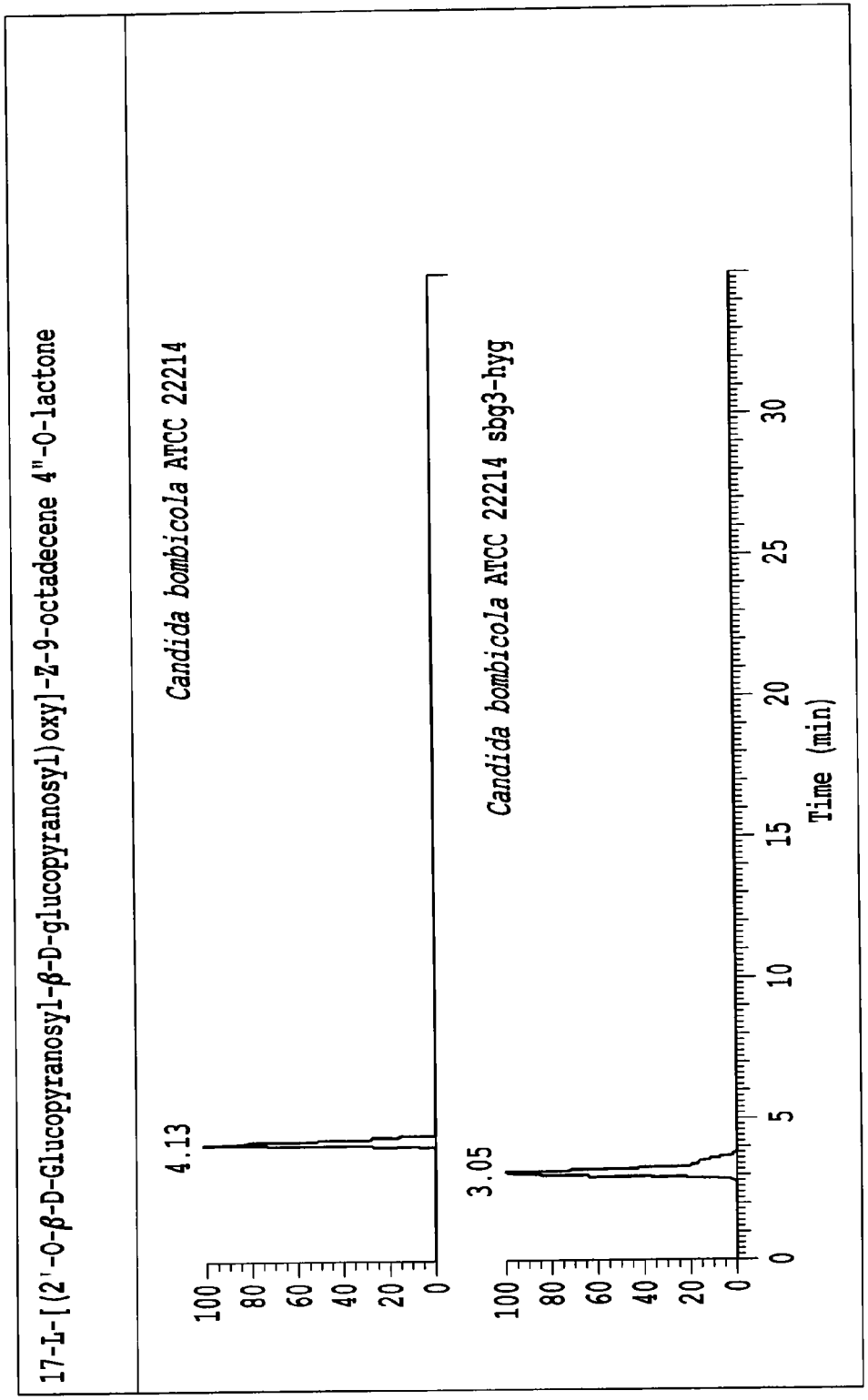

The following figures are part of the examples:

FIG. 1: Accurate mass trajectory for 17-L-[(6'-O-acetyl-2'-O-β-D-glucopyranosyl-6"-O-acetyl-β-D-glucopyranosyl)oxy]-Z-9-octadecene 4"-O-lactone FIG. 2: Accurate mass trajectory for 17-L-[(2'-O-β-D-glucopyranosyl-β-D-glucopyranosyl)oxy]-Z-9-octadecene 4"-O-lactone

EXAMPLES

Example 1

Generation of Uracil-Auxotrophic Mutants of *Candida bombicola* ATCC 22214

A uracil-auxotrophic mutant of *Candida bombicola* ATCC 22214 was generated as described hereinabove (van Bogaert et al. Yeast. 2007. 24(3): 201-8). This strain was named *C. bombicola* ATCC 22214 ura⁻.

Example 2

Inactivation of the Structural Genes of the Enzymes Involved in Sophorolipid Biosynthesis in *Candida bombicola* ATCC 22214

In order to be able to identify enzymes involved in sophorolipid biosynthesis, the genome of *Candida bombicola* ATCC 22214 was first sequenced by means of GLS Flex Titanium technology. Upon inspection of the genetic information of *Candida bombicola* ATCC 22214, a cluster of five genes (SEQ ID NO:01) was identified whose coding regions (SEQ ID NO:02, SEQ ID NO:03, SEQ ID NO:04, SEQ ID NO:05, SEQ ID NO:06) encode gene products (SEQ ID NO:07, SEQ ID NO:08, SEQ ID NO:09, SEQ ID NO:10, SEQ ID NO:11).

The five genes were named SBG1 (SEQ ID NO:02), SBG2 SEQ ID NO:03), SBG3 (SEQ ID NO:04), SBG4 (SEQ ID NO:05) and SBG5 (SEQ ID NO:06) (SBG stands for Sophorolipid Biosynthesis Gene).

They encode the following proteins: Sbg1p (SEQ ID NO:07), Sbg2p (SEQ ID NO:08), Sbg3p (SEQ ID NO:09), Sbg4p (SEQ ID NO:10) and Sbg5p (SEQ ID NO:11).

TABLE 1

Sbg1p, Sbg2p, Sbg3p, Sbg4p and Sbg5p and their functions in the biosynthesis and the export of sophorolipids.

| SEQ ID NO: | Protein | PFAM domain | NCBI conserved domain | Function |
|---|---|---|---|---|
| 07 | Sbg1p | P450 (PFAM PF00067) | cytochrome P450 | monooxygenase which hydroxylates fatty acids [ω, ω-1, ω-2, ω-3] |
| 08 | Sbg2p | UDP glycosyltransferase (PFAM PF00201) | glycosyltransferase | UDP-glucose: [ω, ω-1, ω-2, ω-3]-hydroxy fatty acid glucosyltransferase |
| 09 | Sbg3p | none | Maltose O-acetyltransferase (PRK10092) | acetyl-CoA: sophorolipid acetyltransferase |
| 10 | Sbg4p | ABC transporter (PFAM 00667) | ABC transporter | Sophorolipid export protein |
| 11 | Sbg5p | UDP glycosyltransferase (PFAM PF00201) | glycosyltransferase | UDP-glucose: [ω, ω-1, ω-2, ω-3]-hydroxy fatty acid glucosyltransferase; UDP-glucose: [ω, ω-1, ω-2, ω-3]-(β-D-glucopyranosyl)oxy fatty acid glucosyltransferase |

The genes SBG1, SBG2, SBG3, SBG4 and SBG5 are inactivated individually, and the phenotype of the corresponding mutants is characterized in respect of the sophorolipid biosynthesis. To construct the corresponding mutants in *C. bombicola* ATCC 22214, deletion cassettes are first synthesized by GeneArt AG (Regensburg). These deletion cassettes (SEQ ID NO:12, SEQ ID NO:13, SEQ ID NO:14, SEQ ID NO:15, SEQ ID NO:16) are composed of the above-described gene CbURA3 (van Bogaert et al. Yeast. 2007. 24(3): 201-8) which encodes the *C. bombicola* ATCC 22214 orotidin-5-phosphate decarboxylase and which is flanked upstream and downstream by in each case approximately 1000 bp of the regions flanking the genes to be inactivated. loxP-loci, which optionally permit the deletion of the CbURA3 gene by temporarily introducing the Cre-recombinase-coding gene and permit its functional expression, are inserted in each case between the flanking regions and the CbURA3 gene (for an overview see Kuhn & Torres. Methods Mol Biol. 2002. 180:175-204). In this context, the individual deletion cassettes are constructed as shown in Table 2:

TABLE 2

Structure of the deletion cassettes for the Sbg1p, Sbg2p, Sbg3p, Sbg4p and Sbg5p encoding structural genes of *C. bombicola* ATCC 22214.

| SEQ ID NO: | Gene | 5'-flanking region | loxP-locus 1 | CbURA3 | loxP-locus 2 | 3'-flanking region |
|---|---|---|---|---|---|---|
| 12 | SBG1 | 1-1003 | 1004-1037 | 1038-3106 | 3107-3140 | 3141-4143 |
| 13 | SBG2 | 1-0999 | 1000-1033 | 1034-3102 | 3103-3136 | 3137-4143 |
| 14 | SBG3 | 1-1002 | 1003-1036 | 1037-3105 | 3106-3139 | 3140-4140 |
| 15 | SBG4 | 1-0997 | 0998-1031 | 1032-3100 | 3101-3134 | 3135-4130 |
| 16 | SBG5 | 1-1002 | 1003-1036 | 1037-3105 | 3106-3139 | 3140-4141 |

To provide the deletion cassettes for the subsequent transformation of *C. bombicola* ATCC 22214 ura⁻ in a sufficient amount, the former are amplified by PCR. The following oligonucleotides are used:

Amplification of the deletion cassettes for the inactivation of CbSBG1:

```
SEG1-fw:
                            (SEQ ID NO: 17)
5'- AAT TGT TCG ATG GAT AGC TTT GGA GTC -3'

SBG1-rv:
                            (SEQ ID NO: 18)
5'- TTC GGG GCT CCT GTC GTT GTC -3'
```

Amplification of the deletion cassettes for the inactivation of CbSBG2:

```
SBG2-fw:
                            (SEQ ID NO: 19)
5'- GAA ATC TGA TCA ATT CTG CAA ACC TG -3'

SBG2-rv:
                            (SEQ ID NO: 20)
5'- ATG ACT CCT AGA AAA GAA ATT GAC CAG -3'
```

Amplification of the deletion cassettes for the inactivation of CbSBG3:

```
SBG3-fw:
                            (SEQ ID NO: 21)
5'- TGC AGA CAA GTT CCT GCA GCT G -3'

SBG3-rv:
                            (SEQ ID NO: 22)
5'- ATG CTT TAT TCA GGC ACG CTA CG -3'
```

Amplification of the deletion cassettes for the inactivation of CbSBG4:

```
SBG4-fw:
                                            (SEQ ID NO: 23)
5'- GGA TGA GTC GCA GTC ACG AAC -3'

SBG4-rv:
                                            (SEQ ID NO: 24)
5'- TCA ATC ATT GGC TCA AGA CTA GGA AC -3'
```

Amplification of the deletion cassettes for the inactivation of CbSBG5:

```
SBG5-fw:
                                            (SEQ ID NO: 25)
5'- ATT CTG GTG CTG ACC TCG CCA C -3'

SBG5-rv:
                                            (SEQ ID NO: 26)
5'- ACT CAT GTC GTA CTT GCA AGA ACT

G -3'
```

The following parameters are employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix from New England Biolabs (Frankfurt) is employed for the amplification, following the manufacturer's recommendations. The PCR products are purified using the QIAquick PCR purification kit (Qiagen, Hilden) following the manufacturer's instructions. The procedure of the PCR, the verifying of the successful amplification of the PCR by means of agarose gel electrophoresis, staining the DNA with ethidium bromide, determining the PCR fragment sizes, purification of the PCR products and determining the DNA concentration are all performed in a manner with which the skilled worker is familiar.

The transformation of C. bombicola ATCC 22214 ura⁻ is performed as previously described (van Bogaert et al. Yeast. 2008. 25:273-278); van Bogaert et al. FEMS Yeast Res. 2009. 9:610-617).

To verify the deletion of the genes SBG1, SBG2, SBG3, SBG4 and SBG5 in C. bombicola ATCC 22214 ura⁻ transformants following the transformation with the deletion cassettes for CbSBG1 (SEQ ID NO:12), CbSBG2 (SEQ ID NO:13), CbSBG3 (SEQ ID NO:14), CbSBG4 (SEQ ID NO:15) and CbSBG5 (SEQ ID NO:16), the respective loci of in each case 5 transformants and C. bombicola ATCC 22214 ura⁻ are amplified by means of colony PCR. The following oligonucleotides are employed for this:

Verification of the genomic deletion of CbSBG1:

```
SBG1-KO-fw:
                                            (SEQ ID NO: 27)
5'- GTG TCG ACT CGC CAA ATT CCA TCG GAG -3'

SEG1-KO-rv:
                                            (SEQ ID NO: 28)
5'- GGT TCA TAG CGA GTT TCT TTG CAT GTG

C -3'
```

Verification of the genomic deletion of CbSBG2:

```
SBG2-KO-fw:
                                            (SEQ ID NO: 29)
5'- CTC CTT TAT TAA CTC CGC AGC ATG ACT

G -3'

SBG2-KO-rv:
                                            (SEQ ID NO: 30)
5'- CTC CTC GAA GGA CCC TCA AAA CAA

AGG -3'
```

Verification of the genomic deletion of CbSBG3:

```
SBG3-KO-fw:
                                            (SEQ ID NO: 31)
5'- CAA ATT TAT CTG GGA GCA CAG TTA CAT

TGC -3'

SBG3-KO-rv:
                                            (SEQ ID NO: 32)
5'- CAC ACA TTG CTT TAG TCC AGC AAG AAC

C -3'
```

Verification of the genomic deletion of CbSBG4:

```
SBG4-KO-fw:
                                            (SEQ ID NO: 33)
5'- ATT CTC CTC GCA CGT TTC TCG GGG

C -3'

SBG4-KO-rv:
                                            (SEQ ID NO: 34)
5'- GGT TGA AAT ACT TGT TGC CGC ACT

AAA G -3'
```

Verification of the genomic deletion of CbSBG5:

```
SBG5-KO-fw:
                                            (SEQ ID NO: 35)
5'- CGC TTC CTG AAT TGA GTT GGT ATC GTT AAT

G -3'

SBG5-KO-rv:
                                            (SEQ ID NO: 36)
5'- GAC ATT GTT GGA ATT GGC TGC TTA GTG

G -3'
```

The following parameters are employed in the PCR: 1×: initial denaturation, 94° C., 3 min; 25×: denaturation, 94° C., 1:00 min, annealing, 60° C., 1:00 min; elongation, 72° C., 5:00 min; 1×: terminal elongation, 72° C., 10 min. The Taq PCR Master Mix Kit from Qiagen (Hilden) is employed for the amplification following the manufacturer's recommendations. In each case 10 μl of the PCR reactions are subsequently separated on a 0.8% agarose gel. The procedure of the PCR, of the agarose gel electrophoresis, staining the DNA with ethidium bromide and determining the PCR fragment sizes are all performed in a manner with which the skilled worker is familiar.

The amplification of the corresponding loci should give rise to the PCR fragment sizes specified in Table 3:

TABLE 3

Expected PCR fragment sizes for the amplification of the chromosomal SBG1, SBG2, SBG3, SBG4 and SBG5 loci upon successful deletion and in the wild-type situation.

| Gene | Size of the PCR product upon chromosomal deletion | Size of the PCR product in the wild-type situation |
| --- | --- | --- |
| SBG1 | 4201 bp | 3678 bp |
| SBG2 | 4199 bp | 3451 bp |
| SBG3 | 4199 bp | 2839 bp |
| SBG4 | 4190 bp | 5950 bp |
| SBG5 | 4201 bp | 3360 bp |

Upon amplification of the CbSBG1, CbSBG2, CbSBG3, CbSBG4 and CbSBG5 loci from *C. bombicola* ATCC 22214 ura⁻, only the fragment sizes expected when a wild-type situation is present, i.e. 3.7 kbp, 3.5 kbp, 2.8 kbp, 5.9 kbp and 3.4 kbp, respectively, are obtained.

Upon amplification of the SBG1 locus from transformants following transformation of the deletion cassettes for CbSBG1, only the fragment size to be expected after successful chromosomal deletion of CbSBG1, i.e. approximately 4.2 kbp, is obtained.

Upon amplification of the SBG2 locus from transformants following transformation of the deletion cassettes for CbSBG2, only the fragment size to be expected after successful chromosomal deletion of CbSBG2, i.e. approximately 4.2 kbp, is obtained.

Upon amplification of the SBG3 locus from transformants following transformation of the deletion cassettes for CbSBG3, only the fragment size to be expected after successful chromosomal deletion of CbSBG3, i.e. approximately 4.2 kbp, is obtained.

Upon amplification of the SBG4 locus from transformants following transformation of the deletion cassettes for CbSBG4, only the fragment size to be expected after successful chromosomal deletion of CbSBG4, i.e. approximately 4.2 kbp, is obtained.

Upon amplification of the SBG5 locus from transformants following transformation of the deletion cassettes for CbSBG5, only the fragment size to be expected after successful chromosomal deletion of CbSBG5, i.e. approximately 4.2 kbp, is obtained.

Thus, it is possible to identify in all five cases clones in which the genes CbSBG1, CbSBG2, CbSBG3, CbSBG4 or CbSBG5 have undergone chromosomal deletion. The corresponding strains are hereinbelow referred to as *C. bombicola* ATCC 22214 sbg1, *C. bombicola* ATCC 22214 sbg2, *C. bombicola* ATCC 22214 sbg3, *C. bombicola* ATCC 22214 sbg4 and *C. bombicola* ATCC 22214 sbg5, respectively.

Example 3

Characterization of the Sophorolipid Formation by *C. bombicola* ATCC 22214, *C. bombicola* ATCC 22214 sbg1, *C. bombicola* ATCC 22214 sbg2, *C. bombicola* ATCC 22214 sbg3, *C. bombicola* ATCC 22214 sbg4 and *C. bombicola* ATCC 22214 sbg5

The propagation of strains *C. bombicola* ATCC 22214, *C. bombicola* ATCC 22214 sbg1, *C. bombicola* ATCC 22214 sbg2, *C. bombicola* ATCC 22214 sbg3, *C. bombicola* ATCC 22214 sbg4 and *C. bombicola* ATCC 22214 sbg5 is done on YPD agar plates.

The medium referred to hereinbelow as SL production medium is used for the production of the sophorolipids. It is composed of 0.1% $KH_2PO_4$, 0.5% $MgSO_4 \times 7\ H_2O$, 0.01% $FeCl_3$, 0.01% NaCl, 0.01% uracil, 0.4% yeast extract, 0.1% urea, 10.5% rapeseed oil and 10% glucose. The pH is brought to 4.5 and the medium is then sterilized in an autoclave (121° C., 20 min). It is not necessary to adjust the pH during the cultivation.

To study the sophorolipid production in the shake flask, a preculture is first established. To this end, 10 ml of YPD medium in a 100 ml Erlenmeyer flask are inoculated with one loop of a strain freshly plated onto a YPD agar plate. Cultivation was done overnight at 30° C. and 200 rpm. This preculture is used hereinbelow for inoculating 100 ml of SL medium in a 1000 ml Erlenmeyer flask (starting $OD_{600}$ 0.2). The cultures are grown for 7 days at 200 rpm and 30° C., and a sample of 2 ml of broth is taken every day, good care being taken that the culture medium was mixed thoroughly before sampling.

The samples are prepared for the subsequent chromatographic analyses as follows: using a positive-displacement pipette (Combitip), 800 µl of acetone are placed into a 2-ml reaction vessel and the reaction vessel is sealed immediately to minimize evaporation. 200 µl of broth are added. After vortexing the broth/acetone mixture, the latter is centrifuged for 1 min at 13 000 rpm, and 800 µl of the supernatant are transferred into an HPLC vessel.

An evaporative light scattering detector (ELSD) is used for the detection and quantitative determination of sophorolipids and/or oleic acid. The actual measurement is performed by means of the Agilent Technologies 1200 series (Santa Clara, Calif.) and the Zorbax SB-C8 Rapid Resolution column (4.6× 150 mm, 3.5 µm, Agilent). The injection volume is 5 µl, and the running time of the method is 20 min. The mobile phase used is $H_2O$ and 0.1% of TFA (trifluoroacetic acid, solution A) and methanol (solution B). The column temperature is 40° C. The detectors used were the ELSD (detector temperature 60° C.) and the DAD (diode array, 210 nm). The gradient used in the method is shown in Table 4.

TABLE 4

Description of the gradient profile of the mobile phase to be used for the HPLC-based quantitative determination of sophorolipids.

| t [min] | Solution B % | Flow rate [ml/min] |
| --- | --- | --- |
| 0.00 | 70% | 1.00 |
| 15.00 | 100% | 1.00 |
| 15.01 | 70% | 1.00 |
| 20.00 | 70% | 1.00 |

While *C. bombicola* ATCC 22214 produced sophorolipids, no sophorolipid formation can be detected in the strains *C. bombicola* ATCC 22214 sbg1, *C. bombicola* ATCC 22214 sbg2 and *C. bombicola* ATCC 22214 sbg4. This demonstrates clearly that these genes are involved in sophorolipid formation, where they exert the functions specified above. While strains *C. bombicola* ATCC 22214 sbg3 and *C. bombicola* ATCC 22214 sbg5 are capable of forming sophorolipids, they have a modified retention time in the HPLC analysis.

It can be demonstrated by LC-MS² that, in contrast to the sophorolipids formed by *C. bombicola* ATCC 22214, the sophorolipids formed by *C. bombicola* ATCC 22214 sbg3 correspond exclusively to compounds of the general formulae (Ia) and (Ib) in which $R^1$=H and $R^2$=H.

This proves the function of Sbg3p as acetyltransferase ($E_4$) in sophorolipid biosynthesis.

Likewise, it can be demonstrated by LC-MS that, in contrast to the sophorolipids formed by C. bombicola ATCC 22214, the sophorolipids formed by C. bombicola ATCC 22214 sbg5 exclusively correspond to compounds of the general formula (Ia) in which n=0.

This demonstrates the function of Sbg5p as glycosyltransferase II ($E_3$) in sophorolipid biosynthesis.

Example 4

Construction of Candida bombicola ATCC 22214 Strains which Overproduce Enzymes Involved in Sophorolipid Biosynthesis To make possible the construction of Candida bombicola ATCC 22214 strains which overproduce the enzymes involved in sophorolipid biosynthesis, an integration/overexpression cassette is first synthesized by GeneArt AG (SEQ ID NO:75).

This integration/overexpression cassette comprises the components specified in Table 5:

TABLE 5

Overview over the modules present in the integration/overexpression cassette to be developed for Candida bombicola ATCC 22214, and important restriction cleavage sites.

| Position (bp) | Component |
|---|---|
| 1-8 | NotI recognition site |
| 9-507 | DNA segment upstream of the C. bombicola ATCC 22214 LEU2 gene |
| 508-513 | PciI recognition site |
| 514-1217 | Promoter region of the C. bombicola ATCC 22214 URA3 gene |
| 1217-2005 | Coding region of the C. bombicola ATCC 22214 URA3 gene |
| 2006-2586 | Terminator region of the C. bombicola ATCC 22214 URA3 gene |
| 2587-2592 | PciI recognition site |
| 2593-2600 | AsiSI recognition site |
| 2601-3012 | Promoter region of the C. bombicola ATCC 22214 TSC3 gene |
| 3011-3016 | NdeI recognition site |
| 3025-3032 | FseI recognition site |
| 3033-3210 | Terminator region of the C. bombicola ATCC 22214 TSC3 gene |
| 3211-3218 | AsiSI recognition site |
| 3219-3224 | MluI recognition site |
| 3225-3724 | DNA segment downstream of the C. bombicola ATCC 22214 LEU2 gene |
| 3725-3732 | SbfI recognition site |

This integration/overexpression cassette makes possible the insertion of any desired structural genes from the start codon to the stop codon via NdeI and FseI between the promoter and the terminator region of the C. bombicola ATCC 22214 TSC3 gene, which encodes glyceraldehyde-3-phosphate dehydrogenase (van Bogaert et al.; 2008). Glyceraldehyde-3-phosphate dehydrogenase is a protein which is highly abundant in many yeasts, so that it can be assumed that a strong expression of the inserted gene can be achieved in this manner. The C. bombicola ATCC 22214 URA3 gene is selected as a selection marker so that this integration/overexpression cassette may only be used for the transformation of uracil-auxotrophic strains of C. bombicola ATCC 22214. Its generation, and the C. bombicola ATCC 22214 URA3 gene, have already been described (van Bogaert et al., 2007; van Bogaert et al., 2008). The 5'- and 3'-terminal DNA segments permit the cassette to be inserted at the C. bombicola ATCC 22214 LEU2 locus (SEQ ID NO:37), which inactivates the LEU2 gene. LEU2 encodes the only isopropylmalate dehydrogenase in C. bombicola ATCC 22214. Since isopropylmalate dehydrogenase is an essential component of leucine biosynthesis, transformants with a correct integration of the integration/overexpression cassette can be identified via their leucine auxotrophism. Various unique and redundant recognition sequences (NotI, PciI, AseSI, MluI, SbfI) permit the substitution of individual modules of the integration/overexpression cassette. The cassette is cloned by GeneArt AG into the proprietary vector pMA which comprises none of the above-described cleavage sites so that these cleavage sites may be used to their full extent.

To insert the genes CbSBG1, CbSBG3 and CbSBG5 into the integration/overexpression cassettes described, the genes are amplified by PCR from chromosomal DNA of C. bombicola ATCC 22214 and at the same time an NdeI cleavage site is introduced upstream of the start codon and an FseI cleavage site downstream of the stop codon via the oligonucleotides used. To insert the genes CbSBG2 and CbSBG4 into the integration/overexpression cassette described, the former are first synthesized de novo by GeneArt AG (Regensburg) in order to modify their sequence such that the internal FseI and NotI cleavage sites (CbSBG2) and NdeI cleavage sites (CbSBG4), respectively, are removed without modifying the amino acid sequence of the encoded protein. Thereafter, the modified genes CbSBG2mod and CbSBG4mod provided by GeneArt AG (Regensburg) are amplified by PCR, and an NdeI cleavage site upstream of the start codon and an FseI cleavage site downstream of the stop codon are introduced simultaneously via the oligonucleotides used. The following oligonucleotides are used:

```
CbSBG1:
SBG1-OE-fw:
                                   (SEQ ID NO: 38)
5'- ATA TAT ATA CAT ATG TTA ATC AAA GAC ATT

ATT CTA ACT CCA ATG-3'

SBG1-OE-rv:
                                   (SEQ ID NO: 39)
5'- ATA TAT GGC CGG CCA ACT TAA GAA AAC CGC

ACA ACC ACA CCG-3'

CbSBG2mod:
SBG2-OE-fw:
                                   (SEQ ID NO: 40)
5'- ATA TAT ATA CAT ATG AGC CCT TCA TCA CAC

AAA CCC CTG -3'

SBG2-OE-rv:
                                   (SEQ ID NO: 41)
5'- ATA TAT GGC CGG CCA TTC TAA GAA CTC ACC

GCT AAG GCC -3'

CbSBG3:
SBG3-OE-fw:
                                   (SEQ ID NO: 42)
5'- ATA TAT ATA CAT ATG GTT GTA AAC TCC TCG

AAG GAC CC-3'

SBG3-OE-rv:
                                   (SEQ ID NO: 43)
5'- ATA TAT GGC CGG CCT ACC TAG ACC TTC TGG

TTA GCG GTA TTG -3'
```

```
CbSBG4mod:
SBG4-OE-fw:
                                     (SEQ ID NO: 44)
5'- ATA TAT ATA CAT ATG GTG GAT GAT ATA CAG

GTA GAG AAG C-3'

SBG4-OE-rv:
                                     (SEQ ID NO: 45)
5'- ATA TAT GGC CGG CCA CGT CAA ATC TCT CCG

AGA CCT TGC AAG -3'

CbSBG5:
SBG5-OE-fw:
                                     (SEQ ID NO: 46)
5'- ATA TAT ATA CAT ATG GCC ATC GAG AAA CCA

GTG ATA GTT G -3'

SBG5-OE-rv:
                                     (SEQ ID NO: 47)
5'- ATA TAT GGC CGG CCA GGT TAA GAA GCT AAT

TCA CTA ATT GCC GAC -3'
```

The following parameters are employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix by New England Biolabs (Frankfurt) is employed for the amplification, following the manufacturer's recommendations. In each case 10 μl of the PCR reactions are subsequently separated on a 0.8% agarose gel. The procedure of the PCR, of the agarose gel electrophoresis, staining the DNA with ethidium bromide and determining the PCR fragment sizes are performed in a manner known to a person skilled in the art.

In all cases it is possible to amplify PCR fragments of the expected size. These sizes are: for CbSBG1 1646 bp; for CbSBG2 1421 bp; for CbSBG3 809 bp; for CbSBG4 3929 bp and for CbSBG5 1328 bp. The PCR products are digested with NdeI and FseI following the recommendations of the manufacturer of the restriction endonucleases (New England Biolabs; Frankfurt/Main) and ligated into the NdeI- and FseI-cut vector pMA-ExCat (SEQ ID NO:64). Ligation and the transformation of chemically competent E. coli DH5α cells (New England Biolabs; Frankfurt/Main) are performed in a manner known to the skilled worker. The correct insertion of the CbSBG1, CbSBG2, CbSBG3, CbSBG4 and CbSBG5 fragments into pMA-ExCat is verified and confirmed by a restriction with NdeI and FseI. The resulting vectors are named pMA_ExCat-CbSBG1 (SEQ ID NO:65), pMA_ExCat-CbSBG2 (SEQ ID NO:66), pMA_ExCat-CbSBG3 (SEQ ID NO:67), pMA_ExCat-CbSBG4 (SEQ ID NO:68) and pMAExCat-CbSBG5 (SEQ ID NO:69).

To provide the individual integration/overexpression cassettes and the control cassette ExCat for the subsequent transformation of C. bombicola ATCC 22214 ura⁻ in a sufficient amount, the former are amplified by PCR. The following oligonucleotides are applied:

```
OEx-LEU2-fw:
                                     (SEQ ID NO: 48)
5'- GGA CCT GCG CCC TAA AAT GGG AC -3'

OEx-LEU2-rv:
                                     (SEQ ID NO: 49)
5'- ATC CTA GAA AAC AGC TGG ATA TGG ATA

AAC -3'
```

The PCR products are purified by means of the QIAquick PCR Purification Kit (Qiagen, Hilden) following the manufacturer's information. In the procedure of the PCR, the verification of the successful amplification of the PCR by means of agarose gel electrophoresis, staining the DNA with ethidium bromide, determining the PCR fragment sizes, purification of the PCR products and determination of the DNA concentration are performed in a manner known to the skilled worker.

The resulting integration/overexpression cassettes are given the names IntEx-CbSBG1 (SEQ ID NO:70), IntEx-CbSBG2 (SEQ ID NO:71), IntEx-CbSBG3 (SEQ ID NO:72), IntEx-CbSBG4 (SEQ ID NO:73) and IntEx-CbSBG5 (SEQ ID NO:74). The control cassette ExCat (SEQ ID NO:75) is also obtained.

C. bombicola ATCC 22214 ura⁻ is transformed as previously described (van Bogaert et al. Yeast. 2008. 25:273-278); van Bogaert et al. FEMS Yeast Res. 2009. 9:610-617).

To verify the insertion of the integration/overexpression cassettes for the overexpression CbSBG1, CbSBG2, CbSBG3, CbSBG4 and CbSBG5 and of the control cassette ExCat into the LEU2 locus of C. bombicola ATCC 22214 ura⁻, the LEU2 locus of in each case 5 transformants (after transformation of the integration/overexpression cassettes for CbSBG1, CbSBG2, CbSBG3, CbSBG4 and CbSBG5 and of the control cassette ExCat) and of C. bombicola ATCC 22214 ura⁻ is amplified by colony PCR. The following oligonucleotides are employed:

```
LEU2-KI-fw:
                                     (SEQ ID NO: 50)
5'- GTG CCC GAC CAC CAT GAG CTG TC -3'

LEU2-KI-rv:
                                     (SEQ ID NO: 51)
5'- CCC AAG CAT GAG GGT CGT GCC GG -3'
```

The following parameters are employed in the PCR: 1×: initial denaturation, 94° C., 3 min; 25×: denaturation, 94° C., 1:00 min, annealing, 60° C., 1:00 min; elongation, 72° C., 5:00 min; 1×: terminal elongation, 72° C., 10 min. The Taq PCR Master Mix Kit from Qiagen (Hilden) is employed for the amplification following the manufacturer's recommendations. In each case 10 μl of the PCR reactions are subsequently separated on a 0.8% agarose gel. The procedure of the PCR, of the agarose gel electrophoresis, staining the DNA with ethidium bromide and determining the PCR fragment sizes are all performed in a manner with which the skilled worker is familiar.

The amplification of the corresponding loci should give rise to the PCR fragment sizes specified in Table 6:

TABLE 6

Expected PCR fragment sizes upon amplification of the chromosomal LEU2 locus following homologous recombination of the SBG1, SBG2, SBG3, SBG4 and SBG5 expression cassettes and the control cassette ExCat into the chromosomal C. bombicola LEU2 locus and upon nonhomologous integration.

| Gene | Size of the PCR product upon homologous integration into the CbLEU2 locus | Size of the PCR product upon nonhomologous integration at a different site of the genome |
|---|---|---|
| SBG1 | 5452 bp | 2235 bp |
| SBG2 | 5227 bp | 2235 bp |
| SBG3 | 4615 bp | 2235 bp |
| SBG4 | 7735 bp | 2235 bp |
| SBG5 | 5125 bp | 2235 bp |
| ExCat | 3844 bp | 2235 bp |

Upon amplification of the LEU2 locus from *C. bombicola* ATCC 22214 ura⁻, only the fragment expected when the wild-type situation is present, which has a size of 2.2 kbp, is obtained.

Upon amplification of the LEU2 locus from *C. bombicola* ATCC 22214 transformants after transformation with integration/overexpression cassettes for the overexpression of CbSBG1, CbSBG2 mod, CbSBG3, CbSBG4 mod and CbSBG5, only the fragment sizes expected upon successful chromosomal integration of the integration/overexpression cassettes IntEx-CbSBG1 (SEQ ID NO:70), IntEx-CbSBG2 (SEQ ID NO:71), IntEx-CbSBG3 (SEQ ID NO:72), IntEx-CbSBG4 (SEQ ID NO:73) and IntEx-CbSBG5 (SEQ ID NO:74), which are approximately 5.5 kbp, 5.2 kbp, 4.6 kbp, 7.7 kbp and 5.1 kbp, respectively, are obtained.

Thus, it is possible to identify in all five cases clones in which it was possible to bring the genes CbSBG1, CbSBG2, CbSBG3, CbSBG4 or CbSBG5 under the control of the *C. bombicola* ATCC 22214 TSC3 promoter so that it is possible to postulate the overexpression.

The strains in question are hereinbelow referred to as *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$.

Example 5

Characterization of the Sophorolipid Formation by *C. bombicola* ATCC 22214 ExCat, *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$ The propagation of the strains *C. bombicola* ATCC 22214 ExCat, *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$ is performed on YPD agar plates. The medium referred to hereinbelow as SL production medium is used for producing the sophorolipids. This medium is composed of 0.1% $KH_2PO_4$, 0.5% $MgSO_4 \times 7 H_2O$, 0.01% $FeCl_3$, 0.01% NaCl, 0.01% uracil, 0.4% yeast extract, 0.1% urea, 10.5% rapeseed oil and 10% glucose. The pH is brought to 4.5 and the medium is then sterilized in an autoclave (121° C., 20 min). It is not necessary to adjust the pH during the cultivation.

To study the sophorolipid production in the shake flask, a preculture is first established. To this end, 10 ml of YPD medium in a 100 ml Erlenmeyer flask are inoculated with one loop of a strain freshly plated onto a YPD agar plate. Cultivation was done overnight at 30° C. and 200 rpm. This preculture is used hereinbelow for inoculating 100 ml of SL medium in a 1000 ml Erlenmeyer flask (starting $OD_{600}$ 0.2). The cultures are grown for 7 days at 200 rpm and 30° C., and a sample of 2 ml of broth is taken every day, good care being taken that the culture medium was mixed thoroughly before sampling.

The samples are prepared for the subsequent chromatographic analyses as follows: using a positive-displacement pipette (Combitip), 800 µl of acetone are placed into a 2-ml reaction vessel and the reaction vessel is sealed immediately to minimize evaporation. 200 µl of broth are added. After vortexing the broth/acetone mixture, the latter is centrifuged for 1 min at 13 000 rpm, and 800 µl of the supernatant are transferred into an HPLC vessel.

An evaporative light scattering detector (ELSD) is used for the detection and quantitative determination of sophorolipids and/or oleic acid. The actual measurement is performed by means of the Agilent Technologies 1200 series (Santa Clara, Calif.) and the Zorbax SB-C8 Rapid Resolution column (4.6× 150 mm, 3.5 µm, Agilent). The injection volume is 5 µl, and the running time of the method is 20 min. The mobile phase used is $H_2O$ and 0.1% of TFA (trifluoroacetic acid, solution A) and methanol (solution B). The column temperature is 40° C. The detectors used were the ELSD (detector temperature 60° C.) and the DAD (diode array, 210 nm). The gradient used in the method is shown in Table 3.

Like the control strain *C. bombicola* ATCC 22214 ExCat, all strains produce sophorolipids. However, the strains *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$ show an increased space-time yield of the sophorolipid formation in comparison with *C. bombicola* ATCC 22214 ExCat. While *C. bombicola* ATCC 22214 ExCat produces approximately 2 mg of sophorolipids per liter, hour and $OD_{600}$ under the conditions chosen, these parameters are between 2.5 mg and 6 mg for the strains *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5 $T_{TSC3}$. Thus, it is possible to demonstrate that enhancing the enzymes CbSBG1, CbSBG2, CbSBG3, CbSBG4 and CbSBG5 in *C. bombicola* ATCC 22214 results in an increased sophorolipid formation.

Example 6

Vector pTZ_E02-His-GlcTrI for Overexpressing the *Candida bombicola* Gene SBG2 with N-Terminal His-Tag To overexpress the *Candida bombicola* ATCC22214 gene SBG2 SEQ ID NO:03) in *Escherichia coli*, the plasmid pTZ_E02-His-GlcTrI was constructed. Chromosomal DNA from *Candida bombicola* ATCC22214 was used as the template for a PCR with the "Expand™ High Fidelity" PCR kit from Roche Diagnostics (Mannheim), following the manufacturer's information. The SBG2 gene was amplified from the chromosomal DNA with the aid of oligonucleotides 1373_GlcTrI_BsmBI_His_fp (SEQ ID NO:76) and 1373_GlcTrI_AscI_rp (SEQ ID NO:77) ("PCR protocols. A guide to methods and applications", 1990, Academic Press) and in this manner provided at the 5' end with a 6-fold N-terminal histidine tag. In addition, the cleavage sites BsmBI and AscI were introduced. The following oligonucleotides were employed:

1373_GlcTrI_BsmBI_His_fp (SEQ ID NO: 76):
5'-AAACGTCTCAGATGCACCACCACCACCACCACATGGTTGTAAACTCC
TCG-3'

1373_GlcTrI_AscI_rp (SEQ ID NO: 77):
5'-AAAGGCGCGCCCTAGACCTTCTGGTTAGCG-3'

The PCR product (1435 bp) was purified by means of the QIAquick PCR purification kit (Qiagen, Hilden) following the manufacturer's instructions, cleaved with BsmBI and AscI and subsequently ligated into the expression vector pTZ_E02 (pET24d-based vector; Merck Chemicals, Darmstadt) from Trenzyme GmbH, Konstanz, which had been cleaved in the same manner. The resulting plasmid pTZ_E02_His-GlcTrI (SEQ ID NO:78) is 6700 base pairs in size. The ligation and the transformation of chemically competent *E. coli* DH5α cells (Gibco-BRL, Karlsruhe) were performed in the manner known to the skilled worker.

The authenticity of the insert was verified by a DNA sequence analysis.

The plasmid pTZ_E02-His-GlcTrI was introduced into the strains *Escherichia coli* BL21 (DE3) and *Escherichia coli* Rosetta (DE3) (both from Merck Chemicals, Darmstadt) by means of transformation. The resulting strains were named *E. coli* BL21 (DE3)/pTZ_E02-His-GlcTrI and *E. coli* Rosetta (DE3)/pTZ_E02-His-GlcTrI.

Example 7

Vector pTZ_E02-His-GlcTrII for Overexpressing the *Candida bombicola* Gene SBG5 with N-Terminal His-Tag To overexpress the *Candida bombicola* ATCC22214 gene SBG5 SEQ ID NO:06) in *Escherichia coli*, the plasmid pTZ_E02-His-GlcTrII was constructed. Chromosomal DNA from *Candida bombicola* ATCC22214 was used as the template for a PCR with the "Expand™ High Fidelity" PCR kit from Roche Diagnostics (Mannheim), following the manufacturer's information. The SBG5 gene was amplified from the chromosomal DNA with the aid of oligonucleotides 1373_GlcTrII_BsmBI_His_fp (SEQ ID NO:79) and 1373_GlcTrII_AscI_rp (SEQ ID NO:80) ("PCR protocols. A guide to methods and applications", 1990, Academic Press) and in this manner provided at the 5' end with a 6-fold N-terminal histidine tag. In addition, the cleavage sites BsmBI and AscI were introduced. The following oligonucleotides were employed:

```
1373_GlcTrII_BsmBI_His_fp (SEQ ID NO: 79):
5'-AAACGTCTCAGATGCACCACCACCACCACCACATGGCCATCGAGAAA
CCAG-3'

1373_GlcTrII_AscI_rp (SEQ ID NO: 80):
5'-AAAGGCGCGCCTTAAGAAGCTAATTCACTAATTGCC-3'
```

The PCR product (1342 bp) was purified by means of the QIAquick PCR purification kit (Qiagen, Hilden) following the manufacturer's instructions, cleaved with BsmBI and AscI and subsequently ligated into the expression vector pTZ_E02 (pET24d-based vector; Merck Chemicals, Darmstadt) from Trenzyme GmbH, Konstanz, which had been cleaved in the same manner. The resulting plasmid pTZ_E02-His-GlcTrII SEQ ID NO:81) is 6607 base pairs in size. The ligation and the transformation of chemically competent *E. coli* DH5α cells (Gibco-BRL, Karlsruhe) were performed in the manner known to the skilled worker.

The authenticity of the insert was verified by a DNA sequence analysis.

The plasmid pTZ_E02-His-GlcTrII was introduced into the strains *Escherichia coli* BL21 (DE3) and *Escherichia coli* Rosetta (DE3) (both from Merck Chemicals, Darmstadt) by means of transformation. The resulting strains were named *E. coli* BL21 (DE3)/pTZ_E02-His-GlcTrII and *E. coli* Rosetta (DE3)/pTZ_E02-His-GlcTrII.

Example 8

Vector pTZ_E02-His-AcTr for Overexpressing the *Candida bombicola* Gene SBG3 with N-Terminal His-Tag To overexpress the *Candida bombicola* ATCC22214 gene SBG3 SEQ ID NO:04) in *Escherichia coli*, the plasmid pTZ_E02-His-AcTr was constructed. Chromosomal DNA from *Candida bombicola* ATCC22214 was used as the template for a PCR with the "Expand™ High Fidelity" PCR kit from Roche Diagnostics (Mannheim), following the manufacturer's information. The SBG3 gene was amplified from the chromosomal DNA with the aid of oligonucleotides 1373_AcTr_BsmBI_His_fp (SEQ ID NO:82) and 1373_AcTr_AscI_rp (SEQ ID NO:83) ("PCR protocols. A guide to methods and applications", 1990, Academic Press) and in this manner provided at the 5' end with a 6-fold N-terminal histidine tag. In addition, the cleavage sites BsmBI and AscI were introduced. The following oligonucleotides were employed:

```
1373_AcTr_BsmBI_His_fp (SEQ ID NO: 82):
5'-AAACGTCTCAGATGCACCACCACCACCACCACATGGTTGTAAACTCC
TCG-3'

1373_AcTr_AscI_rp (SEQ ID NO: 83):
5'-AAAGGCGCGCCCTAGACCTTCTGGTTAGCG-3'
```

The PCR product (823 bp) was purified by means of the QIAquick PCR purification kit (Qiagen, Hilden) following the manufacturer's instructions, cleaved with BsmBI and AscI and subsequently ligated into the expression vector pTZ_E02 (pET24d-based vector; Merck Chemicals, Darmstadt) from Trenzyme GmbH, Konstanz, which had been cleaved in the same manner. The resulting plasmid pTZ_E02-His-AcTr (SEQ ID NO:84) is 6088 base pairs in size. The ligation and the transformation of chemically competent *E. coli* DH5α cells (Gibco-BRL, Karlsruhe) were performed in the manner known to the skilled worker.

The authenticity of the insert was verified by a DNA sequence analysis.

The plasmid pTZ_E02 His-AcTr was introduced into the strains *Escherichia coli* BL21 (DE3) and *Escherichia coli* Rosetta (DE3) (both from Merck Chemicals, Darmstadt) by means of transformation. The resulting strains were named *E. coli* BL21 (DE3)/pTZ_E02-His-AcTr and *E. coli* Rosetta (DE3)/pTZ_E02_His-AcTr.

Example 9

Heterologous Expression of the Enzymes SBG2, SBG3 and SBG5 Involved in Sophorolipid Biosynthesis In each case one single colony of the *E. coli* strains constructed under item 1-3 was first grown for 8 hours in 5 ml of LB medium (10 g/l tryptone, 5 g/l yeast extract, 10 g/l NaCl) with 50 μg/ml kanamycin at 37° C. and 175 rpm. Thereafter, 100 ml of LB medium in 500 ml shake flasks were inoculated with the first preculture and grown overnight at 37° C. and 175 rpm. On the next morning, 1 l of LB medium with a starting $OD_{600}$ of 0.1 were inoculated with the second preculture (5-1 shake flask). All cultures were incubated at 37° C. and 175 rpm. The growth of the cultures was monitored with reference to the apparent optical density ($OD_{600}$). When an $OD_{600}$ of ~0.3 was reached, the culture temperature was reduced from 37° C. to 20° C. The expression of the target genes in question was induced at an $OD_{600}$ of 0.6 by adding 0.5 mM IPTG (final concentration). During all of the culture steps, the relevant antibiotics were added (kanamycin 50 µg/ml). Samples for analyses were taken both before the addition of IPTG and 24 h after the induction. The cells were disrupted by Bugbuster (Merck Chemicals, Darmstadt) following the manufacturer's instructions in order to separate soluble and insoluble proteins from each other. Comparable amounts of the cell extracts were separated by means of SDS-PAGE and the gels were subsequently stained with colloidal Coomassie. An overproduction in the soluble cell extract fraction was detected for all three recombinantly produced proteins Sbg2p, Sbg3p and Sbg5p with His tags.

Example 10

Purification of the Enzymes Sbg2p, Sbg3p and Sbg5p Involved in Sophorolipid Biosynthesis 24 h after induction of the gene expression the cells were harvested by centrifugation (8000 g, 20 min, 4° C.). 1 liter of culture resulted in ~5 g fresh biomass. The cell pellets were resuspended in 100 ml of buffer A (100 mM Tris, pH 7.8, 50 mM NaCl, 20 mM imidazole) which additionally comprised a protease inhibitor (Roche, Order No. 11 873 580 001). The resuspended cells were disrupted by six passages through a Microfluidizer. After a further centrifugation step (10 000 g, 20 min, 4° C.), the supernatant was filtered (pore diameter: 0.45 µm) to give the soluble protein fraction. The target proteins were purified via a his-tag affinity chromatography column (GE, HisTrap FF 1 ml columns, Order No. 17-5319-01). The flow rate was 1 ml/min. A linear elution from 0-100% with buffer B (100 mM Tris, pH 7.8, 50 mM NaCl, 500 mM imidazole) was performed. To this end, 20-fold column volume of buffer B was employed, and 2 ml fractions were collected. The eluate fractions with protein were pooled and concentrated by means of a filtration unit (Amicon Ultra-15, NMWL 10 kDa Centricons, Millipore, Order No. UFC901024). Thereafter, the respective protein fractions were subjected to a buffer exchange into the final buffer (100 mM Tris, pH 7.8, 50 mM NaCl) by gel filtration with Sephadex 25 (PD-10 columns, GE, Order No. 17-0851-01). The protein purification was verified by SDS-PAGE. 3.3 mg of Sbg2p (protein concentration 1.0 µg/µl), 7.3 mg of Sbg5p (protein concentration 2.2 µg/µl) and 6.9 mg of Sbg3p (protein concentration 2.1 µg/µl) were isolated from 1 l of culture.

Example 11

Characterization of the Enzymes Sbg2p, Sbg3p and Sbg5p Involved in Sophorolipid Biosynthesis To detect the function of the enzymes Sbg2p, Sbg3p and Sbg5p which are involved in sophorolipid biosynthesis, enzyme assays were performed with the three isolated enzymes Sbg2p, Sbg3p and Sbg5p, in each case individually and in all possible combinations. This was done in a total volume of 350 µl, following the scheme hereinbelow:

TABLE 7

Composition of the enzyme assay mixtures in µl

| | 1 | 2 | 3 | 4 | 5 | 6 | 7 | 8 |
|---|---|---|---|---|---|---|---|---|
| 10 mM Tris—HCl (pH 7.5) | 327.5 | 277.5 | 227.5 | 277.5 | 177.5 | 227.5 | 177.5 | 227.5 |
| 125 mM UDP—glucose | 5 | 5 | 5 | 5 | 5 | 5 | 5 | 5 |
| 100 mM Acetyl—CoA | 3.5 | 3.5 | 3.5 | 3.5 | 3.5 | 3.5 | 3.5 | 3.5 |
| Sbg3p (2.1 µg/µl) | — | 50 | — | — | 50 | 50 | — | 50 |
| Sbg2p (1 µg/µl) | — | — | 100 | — | 100 | — | 100 | 100 |
| Sbg5p (2.2 µg/µl) | — | — | — | 50 | — | 50 | 50 | 50 |
| 13.4 mM 18-hydroxy-Z-9-octadecenoic acid | 14 | 14 | 14 | 14 | 14 | 14 | 14 | 14 |
| Σ | 350 | 350 | 350 | 350 | 350 | 350 | 350 | 350 |

The reaction was started by adding 14 µl of 13.4 mM solution of the substrate (18-hydroxy-Z-9-octadecenoic acid) in ethanol and incubated for 6 h at 30° C., with shaking (600 rpm). Thereafter, the reaction was stopped by adding 1.4 ml of acetone. Undissolved components were sedimented by centrifugation (16 100 g, 5 min, RT). The supernatant was subsequently transferred into a fresh container and concentrated by vacuum evaporator (25° C.) to the original reaction volume (350 µl). The samples were analyzed by LC-ESI-MS, and the products were identified by analyzing the corresponding mass trajectories and the MS spectra.

To identify the products formed, 5 µl were injected into a UPLC system Accela (Thermo Scientific, Dreieich). The substances to be studied were analyzed with a semi-UPLC column "Pursuit XRs ULTRA" (C8, 2.8 µm, 2.1×100 mm) (Varian, Darmstadt). The separation was performed within 25 min using a gradient composed of the mobile phase A1 ($H_2O$, 0.1% (v/v) TFA) and the mobile phase B1 (methanol, 0.1% (v/v) TFA) with a flow rate of 0.3 ml/min at 40° C. The course of the gradient over time is shown in Table 8.

TABLE 8

Course of the HPLC gradient

| Time [min] | Mobile phase A1 [%] | Mobile phase B1 [%] |
|---|---|---|
| 0 | 30 | 70 |
| 15 | 0 | 100 |
| 25 | 0 | 100 |
| 25.01 | 30 | 70 |
| 32 | 30 | 70 |

The detection was by DAD detector in the wavelength range of 200-600 nm and mass-selectively with a highly-resolving FT-ICR mass spectrometer LTQ-FT (Thermo Scientific, Dreieich) in the scanning range m/z 100-1000. Ionization was by ESI (electrospray ionization). The precise masses and the empirical chemical formulae were determined with the aid of the FT-ICR mass analyzer with a resolution of R=100 000 and a mass accuracy of 2 ppm.

The control reaction used was a mixture which only comprised the substrates UDP-glucose, acetyl-CoA and 18-hydroxy-Z-9-octadecenoic acid, but no enzymes (see Table 7). In this sample, only the substrate 18-hydroxy-Z-9-octadecenoic acid ($C_{18}H_{34}O_3$; 298.2502 g/mol) was detected by MS.

Mixture 2 (see Table 7) comprised, besides the substrates, 105 µg of Sbg3p. As in mixture 1, only 18-hydroxy-Z-9-octadecenoic acid was detected in this sample.

Mixture 3 (see Table 7) comprised, besides the substrates, 100 μg of Sbg2p. Besides the substrate 18-hydroxy-Z-9-octadecenoic acid, 18-(β-D-glucopyranosyloxy)-Z-9-octadecenoic acid (empirical formula $C_{24}H_{44}O_8$; molecular weight 460.3031 g/mol) was detected. This proves that Sbg2p is capable of converting UDP-glucose and 18-hydroxy-Z-9-octadecenoic acid into 18-(β-D-glucopyranosyloxy)-Z-9-octadecenoic acid.

Mixture 4 (see Table 7) comprised, besides the substrates, in addition 110 μg of Sbg5p. Besides the substrate 18-hydroxy-Z-9-octadecenoic acid, 18-(β-D-glucopyranosyloxy)-Z-9-octadecenoic acid and 18-L-[(2'-O-β-D-glucopyranosyl-β-D-glucopyranosyl)oxy]-Z-9-octadecenoic acid (empirical formula $C_{30}H_{54}O_{13}$; molecular weight 622.3559 g/mol) were detected. This proves that Sbg5p is capable of converting UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid.

Mixture 5 (see Table 7) comprised, besides the substrates, additionally 100 μg of Sbg2p and 105 μg of Sbg3p. Besides the substrate 18-hydroxy-Z-9-octadecenoic acid, 18-(β-D-glucopyranosyloxy)-Z-9-octadecenoic acid and 18-(6-O-acetyl-β-D-glucopyranosyloxy)-Z-9-octadecenoic acid (empirical formula $C_{26}H_{46}O_9$; molecular weight 502.3136 g/mol) were detected. This confirms that, as has already been demonstrated for mixture 3, Sbg2p is capable of converting UDP-glucose and 18-hydroxy-Z-9-octadecenoic acid into 18-(β-D-glucopyranosyloxy)-Z-9-octadecenoic acid and it proves furthermore that Sbg3p is capable of acetylating 18-(β-D-glucopyranosyloxy)-Z-9-octadecenoic acid in the presence of acetyl-CoA to give 18-(6-O-acetyl-β-D-glucopyranosyloxy)-Z-9-octadecenoic acid.

Mixture 6 (see Table 7) comprised, besides the substrates, additionally 110 μg of Sbg5p and 105 μg of Sbg3p. Besides the substrate 18-hydroxy-Z-9-octadecenoic acid, 18-(β-D-glucopyranosyloxy)-Z-9-octadecenoic acid, 18-(6-O-acetyl-β-D-glucopyranosyloxy)-Z-9-octadecenoic acid, 18-L-[(2'-O-β-D-glucopyranosyl-β-D-glucopyranosyl)oxy]-Z-9-octadecenoic acid, 18-L-[(6'-O-acetyl-2'-O-β-D-glucopyranosyl-β-D-glucopyranosyl)oxy]-Z-9-octadecenoic acid (empirical formula $C_{32}H_{56}O_{14}$; molecular weight 664.3665 g/mol) and 18-L-[(6'-O-acetyl-2'-O-β-D-glucopyranosyl-6"-O-acetyl-β-D-glucopyranosyl)oxy]-Z-9-octadecenoic acid (empirical formula $C_{34}H_{58}O_{15}$; molecular weight 706.3770 g/mol) were detected. This confirms that, as has already been demonstrated for mixture 4, Sbg5p is capable of converting UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid and furthermore proves that the formed products can be acetylated by Sb3gp in the presence of acetyl-CoA to give 18-L-[(6'-O-acetyl-2'-O-β-D-glucopyranosyl-β-D-glucopyranosyl)oxy]-Z-9-octadecenoic acid and/or 18-L-[(2'-O-β-D-glucopyranosyl-6"-O-acetyl-β-D-glucopyranosyl)oxy]-Z-9-octadecenoic acid and also 18-L-[(6'-O-acetyl-2'-O-β-D-glucopyranosyl-6"-O-acetyl-β-D-glucopyranosyl)oxy]-Z-9-octadecenoic acid.

Mixture 7 (see Table 7) comprised, besides the substrates, additionally 100 μg of Sbg2p and 110 μg of Sbg5p. Besides the substrate 18-hydroxy-Z-9-octadecenoic acid, 18-(β-D-glucopyranosyloxy)-Z-9-octadecenoic acid and 18-L-[(2'-O-β-D-glucopyranosyl-β-D-glucopyranosyl)oxy]-Z-9-octadecenoic acid were detected. This proves that Sbg2p and Sbg5p are capable of converting, in one mixture, UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid.

Mixture 8 (see Table 7) comprised, besides the substrates, additionally 100 μg of Sbg2p, 105 μg of Sbg3p and 110 μg of Sbg5p. Besides the substrate 18-hydroxy-Z-9-octadecenoic acid, 18-(β-D-glucopyranosyloxy)-Z-9-octadecenoic acid, 18-(6-O-acetyl-β-D-glucopyranosyloxy)-Z-9-octadecenoic acid, 18-L-[(2'-O-β-D-glucopyranosyl-β-D-glucopyranosyl)oxy]-Z-9-octadecenoic acid, 18-L-[(6'-O-acetyl-2'-O-β-D-glucopyranosyl-β-D-glucopyranosyl)oxy]-Z-9-octadecenoic acid and 18-L-[(6'-O-acetyl-2'-O-β-D-glucopyranosyl-6"-O-acetyl-β-D-glucopyranosyl)oxy]-Z-9-octadecenoic acid were detected. This confirms that, as has already been mentioned for mixture 7, Sbg2p and Sbg5p together are capable of converting UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid and also proves that, as has already been demonstrated for mixtures 5 and 6, the formed products are capable of being acetylated by Sbg3p in the presence of acetyl-CoA to give 18-L-[(6'-β-acetyl-2'-O-β-D-glucopyranosyl-β-D-glucopyranosyl)oxy]-Z-9-octadecenoic acid and/or 18-L-[(2'-O-β-D-glucopyranosyl-6"-O-acetyl-β-D-glucopyranosyl)oxy]-Z-9-octadecenoic acid and also 18-L-[(6'-O-acetyl-2'-O-β-D-glucopyranosyl-6"-O-acetyl-β-D-glucopyranosyl)oxy]-Z-9-octadecenoic acid.

Example 12

Alternative Route to Inactivating Acetyltransferase (SBG3) in *Candida bombicola* ATCC 22214

In an alternative route, the gene SBG3 was inactivated individually, and the phenotype of the corresponding mutant was characterized in terms of the sophorolipid biosynthesis. To construct the corresponding mutant in *C. bombicola* ATCC 22214, a deletion cassette for CbSBG3 was first synthesized by GeneArt AG (Regensburg) (SEQ ID NO:14; cf. Example 2). Thereafter, the gene CbURA3, from Trenzyme GmbH (Konstanz), which encodes the *C. bombicola* ATCC 22214 orotidine-5-phosphate decarboxylase (van Bogaert et al. Yeast. 2007. 24(3): 201-8) was substituted by a hygromycin resistance cassette. To this end, the hygromycin cassette was amplified from the DNA of the vector p-Col-5 (SEQ ID NO:85) using the following oligonucleotides:

```
1390_hygR_fp_EcoRV:
                                  (SEQ ID NO: 86)
5'- AAA GAT ATC TCT ATG CGC ACC

CGT TCT C -3'

1390_hygR_rp_Hind/Bgl:
                                  (SEQ ID NO: 87)
5'- TTT AGA TCT AAG CTT GAG ACA

CCT CAG CAT GCA CCA TTC -3'
```

The following parameters were employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix from New England Biolabs (Frankfurt) was used for the amplification following the manufacturer's recommendations. The PCR product was purified by means of the QIAquick PCR purification kit (Qiagen, Hilden) following the manufacturer's instructions. The PCR product obtained had a size of 1831 bp. The PCR procedure, the verification of the successful amplification of the PCR by means of agarose gel electrophoresis, the staining of the DNA with ethidium bromide, the determination of the PCR fragment sizes, the purification of the PCR products and the determination of the DNA concentration were carried out in a manner known to the skilled worker. The hygromycin cassette was cloned into the vector pCR4_AcTr_URA (SEQ ID NO:88) by linearizing the vector with the restriction endonucleases BglII and PmlI. The insert was prepared for the subsequent ligation using the restriction endonucleases EcoRV and BglII. The ligation and the subsequent transformation into *E. coli* DH5α cells were carried out in a manner known to the skilled worker. The authenticity of the insert was verified by DNA sequence analysis.

The plasmid generated was named pCR4_AcTr_HygR (SEQ ID NO:89) and has a size of 8578 bp.

The deletion cassette CbSbg3-hyg (SEQ ID NO:90) is composed of the *Klebsiella pneumoniae* hygromycin resistance gene (hph), which encodes the hygromycin B phosphatase (Gritz L and Davies J 1983 Plasmid-encoded hygromycin B resistance: the sequence of hygromycin B phosphotransferase gene and its expression in *Escherichia coli* and *Saccharomyces cerevisiae*. Gene 25 (2-3): 179-188). The promoter for the resistance gene is the constitutive hybrid promoter hp4d (Madzak et al. 2000, Strong hybrid promoters and integrative expression/secretion vectors for quasi-constitutive expression of heterologous proteins in the yeast *Yarrowia lipolytica*. J. Mol. Microbiol. Biotechnol. 2, 207-216). The resistance gene is flanked by the terminator of the XPR2 gene, which encodes an extracellular protease from *Y. lipolytica* (Nicaud et al. 1989a. Cloning, sequencing and amplification of the alkaline extracellular protease (XPR2) gene of the yeast *Yarrowia lipolytica*. J. Biotechnol. 12, 285-298). The resistance gene is flanked upstream and downstream by approximately 1000 bp of the adjoining region of the gene to be inactivated.

loxP-Loci which optionally permit the deletion of the hph gene by temporarily producing the Cre-recombinase-encoding gene and permit its functional expression (for an overview, see Kuhn & Torres. Methods Mol. Biol. 2002. 180:175-204) were introduced in each case between the flanking regions and the hph gene. The deletion cassette is constructed following the information in Table 9 hereinbelow:

TABLE 9

Structure of the deletion cassette for the Sbg3p-encoding structural gene of *C. bombicola* ATCC 22214.

| SEQ ID NO: | Gene | 5'-flanking region | loxP locus 1 | hph | loxP locus 2 | 3'-flanking region |
|---|---|---|---|---|---|---|
| 90 | SBG3 | 1-1033 | 1034-1066 | 1067-3599 | 3600-3633 | 3634-4635 |

To provide the deletion cassette for the subsequent transformation of *C. bombicola* ATCC 22214 in a sufficient amount, it was amplified by PCR. The following oligonucleotides were used:

Amplification of the deletion cassette for the inactivation of CbSBG3:

```
SBG3-fw:
                                    (SEQ ID NO: 21)
5'- TGC AGA CAA GTT CCT GCA GCT G -3'
```

-continued

```
SBG3-rv:
                                    (SEQ ID NO: 22)
5'- ATG CTT TAT TCA GGC ACG CTA CG -3'
```

The following parameters were employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix from New England Biolabs (Frankfurt) was used for the amplification following the manufacturer's recommendations. The PCR product was purified by means of the QIAquick PCR purification kit (Qiagen, Hilden) following the manufacturer's instructions. The PCR procedure, the verification of the successful amplification of the PCR by means of agarose gel electrophoresis, the staining of the DNA with ethidium bromide, the determination of the PCR fragment sizes, the purification of the PCR products and the determination of the DNA concentration were carried out in a manner known to the skilled worker.

Transformation of *C. bombicola* ATCC 22214 was as described before (van Bogaert et al. Yeast. 2008. 25:273-278); van Bogaert et al. FEMS Yeast Res. 2009. 9:610-617).

To verify the deletion of the gene SBG3 in *C. bombicola* ATCC 22214 transformants following transformation with the deletion cassette for CbSBG3 (SEQ ID NO:90), the respective locus was amplified from in each case 5 transformants and *C. bombicola* ATCC 22214 by means of colony PCR. The following oligonucleotides were used:

Verification of the genomic deletion of CbSBG3:

```
SBG3-KO-fw:
                                    (SEQ ID NO: 31)
5'- CAA ATT TAT CTG GGA GCA CAG TTA CAT

TGC -3'

SBG3-KO-rv:
                                    (SEQ ID NO: 32)
5'- CAC ACA TTG CTT TAG TCC AGC AAG AAC

C -3'
```

The following parameters were employed for the PCR: 1×: initial denaturation, 94° C., 3 min; 25×: denaturation, 94° C., 1:00 min, annealing, 60° C., 1:00 min; elongation, 72° C., 5:00 min; 1×: terminal elongation, 72° C., 10 min. The Taq PCR Master Mix Kit from Qiagen (Hilden) was used for the amplification following the manufacturer's recommendations. In each case 10 μl of the PCR reactions were subsequently separated on a 0.8% agarose gel. The procedure of the PCR, of the agarose gel electrophoresis, the staining of the DNA with ethidium bromide and the determination of the PCR fragment sizes were performed in a manner known to the skilled worker.

Upon amplification of the CbSBG3 locus from *C. bombicola* ATCC 22214, only the fragment sizes to be expected when the wild-type situation is present, i.e. 2839 bp, were determined.

Upon amplification of the SBG3 locus from transformants following the transformation of the deletion cassette CbSBG3-hyg, only the fragment size to be expected after the successful deletion of CbSBG3 from the chromosome, i.e. 4693 bp, was obtained.

In this manner, it was possible to identify clones in which the gene CbSBG3 had been deleted from the chromosome. The strain in question was henceforth referred to as *C. bombicola* ATCC 22214 sbg3-hyg.

Example 13

Characterization of the Sophorolipid Formation by C. bombicola ATCC 22214 sbg3-hyg The strains *C. bombicola* ATCC 22214 and *C. bombicola* ATCC 22214 sbg3-hyg were propagated on YPD agar plates. The medium referred to hereinbelow as SL production medium was used for producing the sophorolipids. This medium is composed of 0.1% $KH_2PO_4$, 0.5% $MgSO_4 \times 7 H_2O$, 0.01% $FeCl_3$, 0.01% NaCl, 0.4% yeast extract, 0.1% urea, 10.5% rapeseed oil and 10% glucose. The pH is brought to 4.5 and the medium is then sterilized in an autoclave (121° C., 20 min). It is not necessary to adjust the pH during the cultivation.

To study the sophorolipid production in the shake flask, a preculture was first established. To this end, 10 ml of YPD medium in a 100 ml Erlenmeyer flask were inoculated with one loop of a strain freshly plated onto a YPD agar plate. Cultivation was done overnight at 30° C. and 200 rpm. This preculture was used hereinbelow for inoculating 100 ml of SL medium in a 1000 ml Erlenmeyer flask (starting $OD_{600}$ 0.2). The cultures were grown for 7 days at 200 rpm and 30° C., and a sample of 2 ml of broth was taken every day, good care being taken that the culture medium was mixed thoroughly before sampling.

The samples were prepared for the subsequent chromatographic analyses as follows: using a positive-displacement pipette (Combitip), 800 µl of acetone were placed into a 2-ml reaction vessel and the reaction vessel was sealed immediately to minimize evaporation. 200 µl of broth were added. After vortexing the broth/acetone mixture, the latter was centrifuged for 1 min at 13 000 rpm, and 800 µl of the supernatant were transferred into an HPLC vessel.

An evaporative light scattering detector (ELSD) was used for the detection and quantitative determination of sophorolipids and/or oleic acid. The actual measurement was performed by means of the Agilent Technologies 1200 series (Santa Clara, Calif.) and the Zorbax SB-C8 Rapid Resolution column (4.6×150 mm, 3.5 µm, Agilent). The injection volume was 5 µl, and the running time of the method was 20 min. The mobile phase used was $H_2O$ and 0.1% of TFA (trifluoroacetic acid, solution A) and methanol (solution B). The column temperature was 40° C. The detectors used were the ELSD (detector temperature 60° C.) and the DAD (diode array, 210 nm). The gradient used in the method is shown in Table 10 hereinbelow.

TABLE 10

Description of the gradient profile of the mobile phase to be used for the HPLC-based quantification of sophorolipids.

| t [min] | Solution B % | Flow rate [ml/min] |
| --- | --- | --- |
| 0.00 | 70% | 1.00 |
| 15.00 | 100% | 1.00 |
| 15.01 | 70% | 1.00 |
| 20.00 | 70% | 1.00 |

The analysis showed that both *C. bombicola* ATCC 22214 and *C. bombicola* ATCC 22214 sbg3-hyg produce sophorolipids. It was confirmed by LC-$MS^2$ that, in contrast to the sophorolipids formed by *C. bombicola* ATCC 22214, the sophorolipids formed by *C. bombicola* ATCC 22214 sbg3-hyg exclusively correspond to compounds of the general formulae (Ia) and (Ib) in which $R^1$=H and $R^2$=H (see FIGS. 1 and 2) and that the concentration of these compounds is increased by the factor 10 in comparison with *C. bombicola* ATCC 22214. This proves the function of Sbg3p as acetyltransferase in sophorolipid biosynthesis.

Embodiments

1. A sophorolipid-forming cell which is genetically modified in such a way that it has an activity, as specified in each case hereinbelow, of at least one of the enzymes selected from the group hereafter, which activity is modified in comparison with its wild type:

at least one enzyme $E_1$ with the polypeptide sequence SEQ ID NO: 7, SEQ ID NO: 53, SEQ ID NO: 55, SEQ ID NO: 57, SEQ ID NO: 59, SEQ ID NO: 61 or SEQ ID NO: 63 or with a polypeptide sequence where up to 25% of the amino acid residues are modified over SEQ ID NO: 7, SEQ ID NO: 53, SEQ ID NO: 55, SEQ ID NO: 57, SEQ ID NO: 59, SEQ ID NO: 61 or SEQ ID NO: 63 by deletion, insertion, substitution or a combination of these and which retains at least 50% of the enzymatic activity of the enzyme with the respective reference sequence SEQ ID NO: 7, SEQ ID NO: 53, SEQ ID NO: 55, SEQ ID NO: 57, SEQ ID NO: 59, SEQ ID NO: 61 or SEQ ID NO: 63, where enzymatic activity for an enzyme $E_1$ is understood as meaning the ability to convert Z-9-octadecenoic acid into 17-hydroxy-Z-9-octadecenoic acid, at least one enzyme $E_2$ with the polypeptide sequence SEQ ID NO: 8 or SEQ ID NO: 11 or with a polypeptide sequence where up to 60% of the amino acid residues are modified over SEQ ID NO: 8 or SEQ ID NO: 11 by deletion, insertion, substitution or a combination of these and which retains at least 50% of the enzymatic activity of the enzyme with the respective reference sequence SEQ ID NO: 8 or SEQ ID NO: 11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid, at least one enzyme $E_3$ with the polypeptide sequence SEQ ID NO: 11 or with a polypeptide sequence where up to 60% of the amino acid residues are modified over SEQ ID NO: 11 by deletion, insertion, substitution or a combination of these and which retains at least 50% of the enzymatic activity of the enzyme with the reference sequence SEQ ID NO: 11, where enzymatic activity for an enzyme $E_3$ is understood as meaning the ability to convert 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, at least one enzyme $E_4$ with the polypeptide sequence SEQ ID NO: 9 or with a polypeptide sequence where up to 50% of the amino acid residues are modified over SEQ ID NO: 9 by deletion, insertion, substitution or a combination of these and which retains at least 50% of the enzymatic activity of the enzyme with SEQ ID NO: 9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, at least one enzyme $E_5$ with the polypeptide sequence SEQ ID NO: 10 or with a polypeptide sequence where up to 45% of the amino acid residues are modified over SEQ ID NO: 10 by deletion, insertion, substitution or a combination of these and which retains at least 50% of the enzymatic activity of the enzyme with SEQ ID NO: 10, where enzymatic activity for an enzyme $E_5$ is understood as meaning the ability to transfer a sophorolipid out of a cell into the surrounding medium.

2. The cell as embodied in embodiment 1, characterized in that it is at least partially blocked in its β-oxidation.
3. The cell as embodied in embodiment 1 or 2, characterized in that the modified activity is an increased activity.
4. The cell as embodied in embodiment 3, characterized in that it has increased activities of the following enzyme combinations:
   $E_1E_2$, $E_1E_3$, $E_1E_4$, $E_1E_5$, $E_2E_3$, $E_2E_4$, $E_2E_5$, $E_3E_4$, $E_3E_5$, $E_4E_5$, $E_1E_2E_3$, $E_1E_2E_4$, $E_1E_2E_5$, $E_1E_3E_4$, $E_1E_3E_5$, $E_1E_4E_5$, $E_2E_3E_4$, $E_2E_4E_5$, $E_3E_4E_5$, $E_1E_2E_3E_4$, $E_2E_3E_4E_5$, $E_1E_3E_4E_5$, $E_1E_2E_4E_5$, $E_1E_2E_3E_5$, $E_1E_2E_3E_4$ and $E_1E_2E_3E_4E_5$.
5. The cell as embodied in embodiment 1 or 2, characterized in that it has a reduced activity of the enzyme $E_3$ and optionally an increased activity of the following enzyme combinations:
   $E_1E_2$, $E_1E_4$, $E_1E_5$, $E_2E_4$, $E_2E_5$, $E_4E_5$, $E_1E_2E_4$, $E_1E_2E_5$, $E_1E_4E_5$ and $E_1E_2E_4E_5$.
6. The cell as embodied in embodiment 1 or 2, characterized in that it has a reduced activity of the enzyme $E_4$ and optionally an increased activity of the following enzyme combinations:
   $E_1E_2$, $E_1E_3$, $E_1E_5$, $E_2E_3$, $E_2E_5$, $E_3E_5$, $E_1E_2E_3$, $E_1E_2E_5$, $E_1E_3E_5$ and $E_1E_2E_3E_5$.
7. The cell as embodied in embodiment 1 or 2, characterized in that it has a reduced activity of the enzymes $E_3$ and $E_4$ and optionally an increased activity of the following enzyme combinations:
   $E_1E_2$, $E_1E_5$, $E_2E_5$, $E_1E_2E_5$.
8. The cell as embodied in at least one of embodiments 1 to 7, characterized in that it is transformed with at least one nucleic acid as embodied in embodiment 10 or 11.
9. A process for the production of sophorolipids, comprising the process steps:
   I) bringing a cell as embodied in at least one of embodiments 1 to 8 into contact with a medium comprising a carbon source,
   II) culturing the cell under conditions which allow the cell to form a sophorolipid from the carbon source, and
   III) optionally isolating the formed sophorolipids.
10. The use of the sophorolipids obtained by the process as embodied in embodiment 9 for the preparation of cosmetic, dermatological or pharmaceutical formulations, crop protection formulations and care and cleaning compositions and surfactant concentrates.
11. An isolated DNA which is selected from among the following sequences:
    A) a sequence according to SEQ ID NO: 2, SEQ ID NO: 3, SEQ ID NO: 4, SEQ ID NO: 5, SEQ ID NO: 6, SEQ ID NO: 52, SEQ ID NO: 54, SEQ ID NO: 56, SEQ ID NO: 58, SEQ ID NO: 60 or SEQ ID NO: 62, where the sequence according to SEQ ID NO: 2, SEQ ID NO: 52, SEQ ID NO: 54, SEQ ID NO: 56, SEQ ID NO: 58, SEQ ID NO: 60 or SEQ ID NO: 62 encodes a protein which is capable of converting Z-9-octadecenoic acid into 17-hydroxy-Z-9-octadecenoic acid,
    where the sequence SEQ ID NO: 3 encodes a protein which is capable of converting
    UDP-glucose and 17-hydroxy-Z-9-octadecenoic acid into 17-(β-D-glucopyranosyloxy)-Z-9-octadecenoic acid,
    where the sequence SEQ ID NO: 4 encodes a protein which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate
    or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate,
    where the sequence SEQ ID NO: 5 encodes a protein which is capable of transferring a sophorolipid out of a cell into the surrounding medium,
    where the sequence SEQ ID NO: 6 encodes a protein which is capable of converting
    UDP-glucose and 17-hydroxy-Z-9-octadecenoic acid into 17-(β-D-glucopyranosyloxy)-Z-9-octadecenoic acid or
    17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid,
    B) an intron-free sequence which is derived from a sequence according to A) and which encodes the same protein or peptide as the sequence according to SEQ ID NO: 2, SEQ ID NO: 3, SEQ ID NO: 4, SEQ ID NO: 5, SEQ ID NO: 6, SEQ ID NO: 52, SEQ ID NO: 54, SEQ ID NO: 56, SEQ ID NO: 58, SEQ ID NO: 60 or SEQ ID NO: 62,
    C) a sequence which encodes a protein or peptide which comprises the amino acid sequence according to SEQ ID NO: 7, SEQ ID NO: 8, SEQ ID NO: 9, SEQ ID NO: 10, SEQ ID NO: 11, SEQ ID NO: 53, SEQ ID NO: 55, SEQ ID NO: 57, SEQ ID NO: 59, SEQ ID NO: 61 or SEQ ID NO: 63, where the protein or peptide which comprises the amino acid sequence according to SEQ ID NO: 7, SEQ ID NO: 53, SEQ ID NO: 55, SEQ ID NO: 57, SEQ ID NO: 59, SEQ ID NO: 61 or SEQ ID NO: 63 is capable of converting
    Z-9-octadecenoic acid into 17-hydroxy-Z-9-octadecenoic acid,
    D) a sequence which is to at least 80% identical to a sequence according to one of groups A) to C),
    E) a sequence which hybridizes or, taking into consideration the degeneracy of the genetic code, would hybridize to the counterstrand of a sequence according to one of groups A) to D),
    F) a derivative of a sequence according to one of groups A) to E) which is obtained by substitution, addition, inversion and/or deletion of one or more bases, and G) a complementary sequence to a sequence according to one of groups A) to F).
12. A vector comprising a DNA sequence according to one of groups A) to G) as defined in embodiment 11.
13. The use of the vector as embodied in embodiment 12 for transforming a cell.
14. An isolated polypeptide selected from the group consisting of an enzyme $E_1$ with the polypeptide sequence SEQ ID NO: 7, SEQ ID NO: 53, SEQ ID NO: 55, SEQ ID NO: 57, SEQ ID NO: 59, SEQ ID NO: 61 or SEQ ID NO: 63, especially SEQ ID NO: 7, or with a polypeptide sequence where up to 25% of the amino acid residues are modified over the respective reference sequence SEQ ID NO: 7, SEQ ID NO: 53, SEQ ID NO: 55, SEQ ID NO: 57, SEQ ID NO: 59, SEQ ID NO: 61 or SEQ ID NO: 63, especially SEQ ID NO: 7, by deletion, insertion, substitution or a combination of these and which retains at least 50% of the enzymatic activity of the enzyme with the respective reference sequence, where enzymatic activity for an enzyme $E_1$ is understood as meaning the ability to convert Z-9-octadecenoic acid into 17-hydroxy-Z-9-octadecenoic acid, an enzyme $E_2$ with the polypeptide sequence SEQ ID NO: 8 or SEQ ID NO: 11 or with a polypeptide sequence where up to 60% of the amino acid residues are modified over SEQ ID NO: 8 or SEQ ID NO: 11 by deletion, insertion, substitution or a combination of these and which retains at least 50% of the enzymatic activity of the enzyme with the respective reference sequence No. 8 or 11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid, an enzyme $E_3$ with the polypeptide sequence SEQ ID NO: 11 or with a polypeptide sequence where up to 60% of the amino acid residues are modified over SEQ ID NO: 11 by deletion, insertion, substitution or a combination of these and which retains at least 50% of the enzymatic activity of the enzyme with the respective reference sequence 11, where enzymatic activity for an enzyme $E_3$ is understood as meaning the ability to convert 17-(β-D-glucopyranosyloxy)-Z-9-octadecenoic acid and UDP-glucose into 17-L-[(2'-O-3-D-glucopyranosyl-β-D-glucopyranosyl)oxy]-Z-9-octadecenoic acid, an enzyme $E_4$ with the polypeptide sequence SEQ ID NO: 9 or with a polypeptide sequence where up to 50% of the amino acid residues are modified over SEQ ID NO: 9 by deletion, insertion, substitution or a combination of these and which retains at least 50% of the enzymatic activity of the enzyme with SEQ ID NO: 9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate and an enzyme $E_5$ with the polypeptide sequence SEQ ID NO: 10 or with a polypeptide sequence where up to 45% of the amino acid residues are modified over SEQ ID NO: 10 by deletion, insertion, substitution or a combination of these and which retains at least 50% of the enzymatic activity of the enzyme with SEQ ID NO: 10, where enzymatic activity for an enzyme $E_5$ is understood as meaning the ability to transfer a sophorolipid out of a cell into the surrounding medium.

We claim:

1. An isolated or purified sophorolipid-producing cell transformed with a nucleic acid encoding an $E_1$ polypeptide;

wherein the $E_1$ polypeptide comprises (a) an amino acid sequence selected from the group consisting of SEQ ID NO: 53, 55, 57, 59, 61 and 63; or (b) a variant of the amino acid sequence of SEQ ID NO: 53, 55, 57, 59, 61 or 63 which is identical to SEQ ID NO: 53, 55, 57, 59, 61 or 63 except that at least one residue up to 5% of the amino acid residues of SEQ ID NO: 53, 55, 57, 59, 61 or 63 have been modified by deletion, substitution, and/or insertion, wherein the $E_1$ polypeptide catalyzes the conversion of Z-9-octadecenoic acid into 17-hydroxy-Z-9-octadecenoic acid;

wherein said cell may optionally contain a nucleic acid encoding at least one $E_2$, $E_3$, $E_4$ or $E_5$ polypeptide or wherein said cell may optionally have a disruption in an endogenous gene encoding an $E_3$ and/or $E_4$ polypeptide; wherein:

$E_2$ comprises (a) an amino acid sequence selected from the group consisting of SEQ ID NO: 8 and 11; or (b) a variant of the amino acid sequence of SEQ ID NO: 8 or 11 which is identical to the amino acid sequence of SEQ ID NO: 8 or 11 except that at least one residue up to 5% of the amino acid residues of SEQ ID NO: 8 or 11 have been modified by deletion, substitution, and/or insertion, wherein the $E_2$ polypeptide catalyzes the conversion of UDP-glucose and 17-hydroxy-Z-9-octadecenoic acid into 17-(β-D-glucopyranosyloxy)-Z-9-octadecenoic acid;

$E_3$ comprises (a) the amino acid sequence of SEQ ID NO: 11; or (b) a variant of the amino acid sequence of SEQ ID NO: 11 which is identical to the amino acid sequence of SEQ ID NO: 11 except that at least one residue up to 5% of the amino acid residues of SEQ ID NO: 11 have been modified by deletion, substitution, and/or insertion, wherein the $E_3$ polypeptide has the ability to catalyze the conversion of 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid;

$E_4$ comprises (a) the amino acid sequence of SEQ ID NO: 9; or (b) a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:
(i) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone monoacetate;
(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate; or
(iii) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone diacetate; and $E_5$ comprises (a) the amino acid sequence of SEQ ID NO: 10; or (b) a variant of the amino acid sequence of SEQ ID NO: 10 which is identical to the amino acid sequence of SEQ ID NO: 10 except that at least one residue up to 5% of the amino acid residues of SEQ ID NO: 10 have been modified by deletion, substitution, and/or insertion, wherein the $E_5$ polypeptide has the ability to transfer a sophorolipid out of the sophorolipid-producing cell into the surrounding medium.

2. The isolated or purified sophorolipid-producing cell of claim 1, wherein said sophorolipid-producing cell has been transformed with at least one extrachromosomally replicating vector carrying said nucleic acid(s).

3. The isolated or purified sophorolipid-producing cell of claim 1, wherein said nucleic acid(s) are operably linked to a promoter, a regulation region, a ribosome binding site, an expression cassette or an enhancer that increases the expression of said polypeptide.

4. The isolated or purified sophorolipid-producing cell of claim 1, wherein said transformed sophorolipid-producing cell expresses more of the polypeptide of SEQ ID NO: 53, 55, 57, 59, 61 or 63 than the identical non-transformed cell.

5. The isolated or purified sophorolipid-producing cell of claim 1, wherein said sophorolipid-producing cell produces a greater yield of sophorolipids than the identical non-transformed cell.

6. The isolated or purified sophorolipid-producing cell of claim 1, wherein said sophorolipid-producing cell has been transformed with a nucleic acid encoding the polypeptide of SEQ ID NO: 53, 55, 57, 59, 61 or 63.

7. The isolated or purified sophorolipid-producing cell of claim 1, wherein said sophorolipid-producing cell has been transformed with a nucleic acid encoding an $E_1$ polypeptide that comprises a variant of the amino acid sequence of SEQ ID NO: 53, 55, 57, 59, 61 or 63 which is identical to the amino acid sequence of SEQ ID NO: 53, 55, 57, 59, 61 or 63 except that at least one residue up to 5% of the amino acid residues of SEQ ID NO: 53, 55, 57, 59, 61 or 63 have been modified by deletion, substitution, and/or insertion, wherein the $E_1$ polypeptide catalyzes the conversion of Z-9-octadecenoic acid into 17-hydroxy-Z-9-octadecenoic acid.

8. The isolated or purified sophorolipid-producing cell of claim 1, wherein said sophorolipid-producing cell is a yeast or fungal cell.

9. The isolated or purified sophorolipid-producing cell of claim 1, wherein said sophorolipid-producing cell is selected from the group consisting of *Candida bombicola*, *Candida bogoriensis*, *Candida batistae*, *Candida apicola* and *Wickerhamiella domericqiae*.

10. The isolated or purified sophorolipid-producing cell of claim 1, wherein said sophorolipid-producing cell has been further modified to block or partially block β-oxidation in said cell.

11. The isolated or purified sophorolipid-producing cell of claim 1, wherein said sophorolipid-producing cell has been further transformed with a nucleic acid encoding at least one $E_2$ polypeptide.

12. The isolated or purified sophorolipid-producing cell of claim 1, wherein said sophorolipid-producing cell has been further transformed with a nucleic acid encoding at least one $E_3$ polypeptide.

13. The isolated or purified sophorolipid-producing cell of claim 1, wherein said sophorolipid-producing cell has been further transformed with a nucleic acid encoding at least one $E_4$ polypeptide.

14. The isolated or purified sophorolipid-producing cell of claim 1, wherein said sophorolipid-producing cell has been further transformed with a nucleic acid encoding at least one $E_5$ polypeptide.

15. The isolated or purified sophorolipid-producing cell of claim 1, wherein said sophorolipid-producing cell has been transformed with nucleic acid(s) encoding a combination of polypeptides selected from the group consisting of $E_1E_2$, $E_1E_3$, $E_1E_4$, $E_1E_5$, $E_1E_2E_3$, $E_1E_2E_4$, $E_1E_2E_5$, $E_1E_3E_4$, $E_1E_3E_5$, $E_1E_4E_5$, $E_1E_2E_3E_4$, $E_1E_3E_4E_5$, $E_1E_2E_4E_5$, $E_1E_2E_3E_5$, and $E_1E_2E_3E_4E_5$ polypeptides.

16. The isolated or purified sophorolipid-producing cell of claim 1, wherein said sophorolipid-producing cell has been further modified to disrupt at least one endogenous gene encoding an $E_3$ polypeptide and optionally further transformed with one or more nucleic acids encoding an $E_2$, $E_4$ or $E_5$ polypeptide.

17. The isolated or purified sophorolipid-producing cell of claim 1, wherein said sophorolipid-producing cell has been further modified to disrupt at least one endogenous gene encoding an $E_4$ polypeptide and optionally further transformed with one or more nucleic acids encoding an $E_2$, $E_3$ or $E_5$ polypeptide.

18. The isolated or purified sophorolipid-producing cell of claim 1, wherein said sophorolipid-producing cell has been further modified to disrupt at least one endogenous gene encoding an $E_3$ polypeptide and at least one endogenous gene encoding an $E_4$ polypeptide, and optionally further transformed with one or more nucleic acids encoding an $E_2$ or $E_5$ polypeptide.

19. A process for producing a sophorolipid comprising:
culturing the cell of claim 1 on a medium containing a carbon source under conditions suitable for producing a sophorolipid from the carbon source and, optionally, isolating or recovering the sophorolipid;
wherein said cell may optionally contain a nucleic acid encoding at least one $E_2$, $E_3$, $E_3$ or $E_5$ polypeptide or wherein said cell may optionally have a disruption in an endogenous gene encoding an $E_3$ and/or $E_4$ polypeptide; wherein:
$E_2$ comprises (a) an amino acid sequence selected from the group consisting of SEQ ID NO: 8 and 11; or (b) a variant of the amino acid sequence of SEQ ID NO: 8 or 11 which is identical to the amino acid sequence of SEQ ID NO: 8 or 11 except that at least one residue up to 5% of the amino acid residues of SEQ ID NO: 8 or 11 have been modified by deletion, substitution, and/or insertion, wherein the $E_2$ polypeptide catalyzes the conversion of UDP-glucose and 17-hydroxy-Z-9-octadecenoic acid into 17-(β-D-glucopyranosyloxy)-Z-9-octadecenoic acid;

$E_3$ comprises (a) the amino acid sequence of SEQ ID NO: 11; or (b) a variant of the amino acid sequence of SEQ ID NO: 11 which is identical to the amino acid sequence of SEQ ID NO: 11 except that at least one residue up to 5% of the amino acid residues of SEQ ID NO: 11 have been modified by deletion, substitution, and/or insertion, wherein the $E_3$ polypeptide has the ability to catalyze the conversion of 17-(β-D-glucopyranosyloxy)-Z-9-octadecenoic acid and UDP-glucose into 17-L-[(2'-O-β-D-glucopyranosyl-(-D-glucopyranosyl)oxy]-Z-9-octadecenoic acid;

$E_4$ comprises (a) the amino acid sequence of SEQ ID NO: 9; or (b) a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:

(i) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone monoacetate;

(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate; or (iii) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone diacetate; and $E_5$ comprises (a) the amino acid sequence of SEQ ID NO: 10; or (b) a variant of the amino acid sequence of SEQ ID NO: 10 which is identical to the amino acid sequence of SEQ ID NO: 10 except that at least one residue up to 5% of the amino acid residues of SEQ ID NO: 10 have been modified by deletion, substitution, and/or insertion, wherein the $E_5$ polypeptide has the ability to transfer a sophorolipid out of the sophorolipid-producing cell into the surrounding medium.

20. The process of claim 19, wherein said sophorolipid-producing cell has been transformed with a nucleic acid encoding the polypeptide of SEQ ID NO: 53, 55, 57, 59, 61 or 63.

21. The process of claim 19, wherein said sophorolipid-producing cell has been transformed with a nucleic acid encoding an $E_1$ polypeptide that comprises a variant of the amino acid sequence of SEQ ID NO: 53, 55, 57, 59, 61 or 63 which is identical to the amino acid sequence of SEQ ID NO: 53, 55, 57, 59, 61 or 63 except that at least one residue up to 5% of the amino acid residues of SEQ ID NO: 53, 55, 57, 59, 61 or 63 have been modified by deletion, substitution, and/or insertion, wherein the $E_1$ polypeptide catalyzes the conversion of Z-9-octadecenoic acid into 17-hydroxy-Z-9-octadecenoic acid.

22. The process of claim 19, wherein said sophorolipid-producing cell has been transformed with nucleic acid(s) encoding a combination of polypeptides selected from the group consisting of $E_1E_2$, $E_1E_3$, $E_1E_4$, $E_1E_5$, $E_1E_2E_3$, $E_1E_2E_4$, $E_1E_2E_5$, $E_1E_3E_4$, $E_1E_3E_5$, $E_1E_4E_5$, $E_1E_2E_3E_4$, $E_1E_3E_4E_5$, $E_1E_2E_4E_5$, $E_1E_2E_3E_5$, and $E_1E_2E_3E_4E_5$ polypeptides.

23. The process of claim 19, wherein said sophorolipid-producing cell:
(a) has been modified to disrupt endogenous gene(s) encoding $E_3$ polypeptide(s); and
(b) has been further transformed with a nucleic acid(s) encoding $E_2$, $E_4$, and/or $E_5$ polypeptides.

24. The process of claim 19, wherein said sophorolipid-producing cell:
(a) has been modified to disrupt endogenous gene(s) encoding $E_4$ polypeptide(s); and
(b) has been further transformed with a nucleic acid(s) encoding $E_2$, $E_3$, and/or $E_5$ polypeptides.

25. The process of claim 19, wherein said sophorolipid-producing cell:
(a) has been further modified to disrupt endogenous gene(s) encoding $E_3$ and $E_4$ polypeptide(s); and
(b) has been further transformed with a nucleic acid(s) encoding $E_2$ and/or $E_5$.

26. An isolated or purified sophorolipid-producing cell transformed with a nucleic acid encoding an $E_1$ polypeptide; wherein the $E_1$ polypeptide comprises (a) the amino acid sequence of SEQ ID NO: 7; or (b) a variant of the amino acid sequence of SEQ ID NO: 7 which is identical to SEQ ID NO: 7 except that at least one residue up to 5% of the amino acid residues of SEQ ID NO: 7 have been modified by deletion, substitution, and/or insertion, wherein the $E_1$ polypeptide catalyzes the conversion of Z-9-octadecenoic acid into 17-hydroxy-Z-9-octadecenoic acid;

wherein said cell also contains a nucleic acid encoding at least one $E_2$, $E_3$, $E_4$ or $E_5$ polypeptide or wherein said cell also has a disruption in an endogenous gene encoding an $E_3$ and/or $E_4$ polypeptide; wherein:

$E_2$ comprises (a) an amino acid sequence selected from the group consisting of SEQ ID NO: 8 and 11; or (b) a variant of the amino acid sequence of SEQ ID NO: 8 or 11 which is identical to the amino acid sequence of SEQ ID NO: 8 or 11 except that at least one residue up to 5% of the amino acid residues of SEQ ID NO: 8 or 11 have been modified by deletion, substitution, and/or insertion, wherein the $E_2$ polypeptide catalyzes the conversion of UDP-glucose and 17-hydroxy-Z-9-octadecenoic acid into 17-(β-D-glucopyranosyloxy)-Z-9-octadecenoic acid;

$E_3$ comprises (a) the amino acid sequence of SEQ ID NO: 11; or (b) a variant of the amino acid sequence of SEQ ID NO: 11 which is identical to the amino acid sequence of SEQ ID NO: 11 except that at least one residue up to 5% of the amino acid residues of SEQ ID NO: 11 have been modified by deletion, substitution, and/or insertion, wherein the $E_3$ polypeptide has the ability to catalyze the conversion of 17-(β-D-glucopyranosyloxy)-Z-9-octadecenoic acid and UDP-glucose into 17-L-[(2'-O-β-D-glucopyranosyl-(-D-glucopyranosyl)oxy]-Z-9-octadecenoic acid;

$E_4$ comprises (a) the amino acid sequence of SEQ ID NO: 9; or (b) a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:

(i) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone monoacetate;
(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate; or
(iii) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone diacetate; and
$E_5$ comprises (a) the amino acid sequence of SEQ ID NO: 10; or (b) a variant of the amino acid sequence of SEQ ID NO: 10 which is identical to the amino acid sequence of SEQ ID NO: 10 except that at least one residue up to 5% of the amino acid residues of SEQ ID NO: 10 have been modified by deletion, substitution, and/or insertion, wherein the $E_5$ polypeptide has the ability to transfer a sophorolipid out of the sophorolipid-producing cell into the surrounding medium.

27. A process for producing a sophorolipid comprising:
culturing the cell of claim 26 on a medium containing a carbon source under conditions suitable for producing a sophorolipid from the carbon source and, optionally, isolating or recovering the sophorolipid;
wherein said cell also contains a nucleic acid encoding at least one $E_2$, $E_3$, $E_3$ or $E_5$ polypeptide or wherein said cell also has a disruption in an endogenous gene encoding an $E_3$ and/or $E_4$ polypeptide; wherein:
$E_2$ comprises (a) an amino acid sequence selected from the group consisting of SEQ ID NO: 8 and 11; or (b) a variant of the amino acid sequence of SEQ ID NO: 8 or 11 which is identical to the amino acid sequence of SEQ ID NO: 8 or 11 except that at least one residue up to 5% of the amino acid residues of SEQ ID NO: 8 or 11 have been modified by deletion, substitution, and/or insertion, wherein the $E_2$ polypeptide catalyzes the conversion of UDP-glucose and 17-hydroxy-Z-9-octadecenoic acid into 17-(β-D-glucopyranosyloxy)-Z-9-octadecenoic acid;
$E_3$ comprises (a) the amino acid sequence of SEQ ID NO: 11; or (b) a variant of the amino acid sequence of SEQ ID NO: 11 which is identical to the amino acid sequence of SEQ ID NO: 11 except that at least one residue up to 5% of the amino acid residues of SEQ ID NO: 11 have been modified by deletion, substitution, and/or insertion, wherein the $E_3$ polypeptide has the ability to catalyze the conversion of 17-(β-D-glucopyranosyloxy)-Z-9-octadecenoic acid and UDP-glucose into 17-L-[(2'-O-β-D-glucopyranosyl-(-D-glucopyranosyl)oxy]-Z-9-octadecenoic acid;
$E_4$ comprises (a) the amino acid sequence of SEQ ID NO: 9; or (b) a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:
(i) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone monoacetate;
(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate; or
(iii) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-(-D-glucopyranosyl)oxy]-Z-9-octadecenoic acid 1',4"-lactone diacetate; and
$E_5$ comprises (a) the amino acid sequence of SEQ ID NO: 10; or (b) a variant of the amino acid sequence of SEQ ID NO: 10 which is identical to the amino acid sequence of SEQ ID NO: 10 except that at least one residue up to 5% of the amino acid residues of SEQ ID NO: 10 have been modified by deletion, substitution, and/or insertion, wherein the $E_5$ polypeptide has the ability to transfer a sophorolipid out of the sophorolipid-producing cell into the surrounding medium.

* * * * *

SEQUENCE LISTING

```
<160> NUMBER OF SEQ ID NOS: 90

<210> SEQ ID NO 1
<211> LENGTH: 18013
<212> TYPE: DNA
<213> ORGANISM: Candida bombicola

<400> SEQUENCE: 1
caaactcgac gctaaacaga ccttaaatga caccaatcaa tgtgaaaaaa tcaagttttt      60
ttgttcactc tatattgact gtttccgatg tgtgctatgc agccctcttt gaatcggtgg     120
aagcatgtag ttgaagaaag atggacgtag gagaaacatc aaactgaaca atagtaactt     180
aaacgtggtt tagaatgcaa gagcaggctc gctgctatgg cattcatagc caggaaagaa     240
acacggatga tctcacactt tgttggatcg acagtcggat ttttttgaaa atttatactt     300
ggcatacatc ttaatacagg ggtagaagga gaagtcgcga gagcgatttc tccgtcattt     360
attcgccgac aaatgtggat ccgtatttag cagattcgaa gtaaattgca ctcgacacca     420
cccacgtgat cgacactgtc gcgtcgatct ccatatatgt acgtgcctat ataaacaagc     480
aacacgcaga ttttgaaatc acataggaag ttgcccgtat gaatccggtt caaataataa     540
tactttgttt tcagatagga gaaacaaaac acccttggta ctcagaagac aaataacgat     600
ccattgtttt caactggaag aaataataca cattgatatt cagaagacaa ataactatcc     660
```

-continued

```
catttctttta gtatgtgcga aggtaaacag ttctatttca ccttaaaaac actactgaaa    720
gtgcgacata ctgtcgtacg taaaatataa aagcaatcac tatcatttcg ccattatcct    780
tgtcttgtaa taatccaaaa ctgagatcgg gaacggttcc cgttcttgac ataagcagga    840
gctgagaaca ggaacggttc ctggtcttga aatcagcagt aatagagaac gggattggtt    900
cccgttcttg acataagcag gaattggaaa caggaacggt tcccggtctt gacatcagca    960
gggatcgaaa acaggagcgg tttccggtct tgacatgata caaagaatga ttctttgtat   1020
cgggtctatg ggaggaaaaa cagctcattt tcacagaaaa tacagagaac aaaataattg   1080
aaagcgcgac ataatgtcgt acgtagaatt tagaagcaat tactcttatt tttccattat   1140
ccgcgctatt gtacacacac ccaaaccaga acgcgacttg agtgcaatgc ttactaacgc   1200
gcacattaat aagcaaatat agatacgcgg agagcacgcg aaatttgttt accagtacac   1260
tagtgcttag cacaatgaaa tagaccgtac tccggctgag gctcaaagtc cagaagttag   1320
agatttgcca gtttcgttac tagacggttc gttgtgccag gtatgtcgta cagcgcattt   1380
atcagggacg gaaatgggtc ttccatccct gttttggaat gcgctgtcga tccggacgca   1440
gcctcagccg cgtctatttc aaccccccat tagacaggcg gtacattagc tgtttggcct   1500
tcacgctaca gcataattct ccgtcatgtg tgtttccatg accaagaatt gttttggccc   1560
acgaaccaag atcatcgccg tcatataaac ccacattgga gtgttgactc tccatagctt   1620
gtcgttgaat gcaaacttga tgcccgcaaa agtgcttatt agcctacgca ctgattcgcc   1680
ccactctgcg agccacattt ccgctagctt aacatcaggc accgcaatcg gtgcctggac   1740
tgtctccggg ctcggccgag cccggttgag accatcttct tcaaattcat cttctgatag   1800
ctcatctaac atcctagagc tgttcctctt tttccttctt tttgttaatt ggtatttaaa   1860
ccaccaagtg tgtaaacttg tatttttgtc atccgagaga tatctaatag caagtttgcg   1920
attagttaca aatttgttgc gctcttgttc ggtactctta ttgaaacaag ggtgtcgact   1980
cgccaaattc catcggagaa aattgttcga tggatagctt tggagtctgt cccatcatga   2040
tacgaaaagc gtgaagctcc tctgacaatc aaaactttgt ttcaatgggg tgtaggatgg   2100
accccggatc caaacgaccg cgagtcaaaa aacctacggg tgcatttacc cgtagttgat   2160
ctggaaagtc gagatcaact ttttgtagtt tagttacatt catttcacgg tcgaaaaact   2220
cacacacaac gattgcagta tatttaccaa aatcgtctga agagaagcat ctgattgaga   2280
gttcaccatg acgaatccca taaacgacta ctccactgga cacaccgaca gacgccctgg   2340
ggatagtgaa actgaatttg tcggtataat ggcccgtctc acaggccggg cagaacactt   2400
tcatgtcctt tcgcaggtct cgacattgga caagtatgtt gtcgtgggtg acgacaaatt   2460
ggtcctcatc cttgaataag atgctccctt tgttctcagg aactggcacc attccattat   2520
gggcgaataa tttctgctca tcttcgggac tgatgccata ttcttctaac agaagacggc   2580
gctcacatgg gacctggtgc tctcgccggc ctctcaaatc gccggtgcat ctccacacgc   2640
aaattcacgg gtgtataccc ctgatcaaac gtatcttgcg cgttctgtta ttcattggag   2700
cgagggcccg atcctgtcct atcaaatgat ttcatgtggg aataatccat caattgttct   2760
ggattgaggt atacttcgag ctgtaaagat gtcgcttcta tgtcaagaat agtcggttaa   2820
acgcactcct tcaagattta catgatttac atgattcttc ataaagagca taaataaaga   2880
actgcagcca ttcttgagta aagtgctcag aataataaaa aggttgccac aggttgagtt   2940 aacatggggtt gattgaacca attaaggagg gaacgtttct tccatgggag gctaagaaac   3000
ttaagaaaac cgcacaacca caccgggagg agcgtgttga gctgtaagcg ttgttgagaa   3060
```

```
acgagggggac tctgggaagt cgggacccat ctcaatcttg gaatactcct gtaagagtct   3120
caccagagtt agcgaaagct ctgtcagggc gaattgttgg ccgagacaaa ttcggggacc   3180
gccattgaag ggcaagaatg cccacacatt atctagcttc aagttctccc atcgattggg   3240
attgaattcg tgggcgtcag gaccccaata cttgatgtcc ctgtggacca tgtaaattga   3300
atagtaaact gcggtgccct taggaacgaa gatcggatcc ttctgctcgg gaccaccacc   3360
tatgggtaga gttgtatctc tcacagcagt acggaagttc aatggcaata ccggcgcaag   3420
acgcaagact tcatttataa cttgcttcaa ataaggtgct tgcttcagaa gttcgaatga   3480
taaaggcctt tgctcctcct tggttccaaa atgatcgagg acctcctcac gtagtttgtt   3540
gaatacgtca ggatttctgg caaggaaatg aatagcgaag ctcaacgtag cagctgttgt   3600
atctctacca gcaatgagaa tgttgaaaat ttgatcacgt atcgtcactg ggtctcgggt   3660
aactttagcc atctcaagcg agaacacata gatgccacta gactctgcag cagcatcctt   3720
ctctgcaata gagttctcag cagcgaaaga tgtggcgtaa agagccttat caacgtagta   3780
gtcaatatag gactgagcac gtttcttgtg atctcggaat tccttagagt tgaacaacca   3840
gtagactttg cttgatagggg tccgtttgaa agcgtaattc agtagaaagt tgtaggactc   3900
cacgaattgt tcggcagtaa tctccgaacc atcacgggct acaatacatg actgattctc   3960
agggttcaag ctctcgcagg actcccaaa taggaattca gtcgctgtat ccagcgtaag   4020
tttgtggaaa taatgttgaa catcaataaa ttggtccact ttcattgcac ggttcatctc   4080
ctttattaac tccgcagcat gactggaaat ctgatcaatt ctgcaaacct gatctttagt   4140
gaactgaggt ctcaacatcg atcgagactg tttccatcca tttccgctga gtgtaaatat   4200
cccttggcca aacactttc ccactgtgtg gaaacgtgct ccaagaccaa atcattgaa    4260 tttggttgcc aggattgtct taatgttttc tggctcgatt gtgaagattt ggtattgaag   4320
gggagcttgt cgaagatacg tccgtgcttt gaacttattg aagactctgt cgtattgaac   4380
ttccagtaag gtgtatgact tggccgtctt gatcatgtcc atggttcttt gtattcccag   4440
tgggaacgat ttctcaatga agcgaggcat actacacttg tgcctacgtg ctgcatagcg   4500
gtaccatagg agccagatag gctcgtgtag aactaagaaa gctacgaaga gcagtggcaa   4560
caagccagca acagcggata aactcattgg agttagaata atgtctttga ttaacatata   4620
tgtacttttc aatatgataa acggagaaat aacgcccggc tctatatgca agctgcatca   4680
accctaatat atattagcga gtttctcatg caggctgtag tttgagtcgc tgtaacctca   4740
gcctcaagac tcttacacca taggtagagt ttcgtcactg ggaaactcag ttactatcta   4800
aaccaaactg tgctaatgct caaacctatc actcagaatt tagattgaat caatctaagt   4860
ctgttgagaa acagatatgc atcaggggca cagactaaaa gctgctctca gcgagtaccc   4920
ttacctcttg agaaccctca aaatttaccc agcctgcagc atatcatgca ccatggttaa   4980
attcggaaat gaatttaccg gtggccttga accacgttcc tccaattatt taaggcaata   5040
acctgccact ctcttgattt gattaagaaa gactttcaat ttagcttctc cctacgaata   5100
ttcaatgagc ccttcatcac acaaaccccct gattctcgct tgcggcttgc ctctttcagg   5160
ccatataatg cccgttttga gtctggtaca cggccttacg gacgacggat acgaagctac   5220
tgttgtgaca ggcagagcgt ttgaacaaaa agttcgagat gtgggtgcag actttgttcc   5280
tttagaaggg aacgcagatt ttgatgacca caccttagac gatctggtcc cgggccgtaa   5340
agacatggcc ccaagcttcg atcgtacagt tcaagatgtg gagcacatga tggtagctac   5400
```

```
tcttcctgag cagtttgccg ctattcagag ggctttcaaa aagctcagcg caagcggccg   5460
ccctgtcgtt cttgtcagtg aagtgctgtt tttcggtgca caccctatca gcctcggtgc   5520
tcctggtttc aaacccgctg gctggatttg tttaggggtt ttgcctcttt tgatccgcag   5580
tgatcatacc ttaggacttg acaacgacag gagccccgaa gcacatgcaa agaaactcgc   5640
tatgaaccac gctcttgagc accaaatttt cgttaaagcc actgctaagc acaaggaaat   5700
ctgccgagag ttaggttgca ctgaagatcc caaatttatc tgggagcaca gttacattgc   5760
tgcagacaag ttcctgcagc tgtgcccgcc ttctcttgag ttcagcagag accatctgcc   5820
tagcaacttc aaattcgccg gctcaacgcc caagcaccga actcaattca cccctccttc   5880
ctggtggggg gatgttctga gtgccaagcg agtcatcatg gtcactcaag aacttttgc    5940 tgtcagttac aagcatctta ttgtgcctac tcttgaggcc ttgaaggacg agcctgacac   6000
tttaacagta gccatattgg gccgccgcgg tgccaagcta ccggatgatg ttgtggttcc   6060
tgagaatgct cgcgtgatcg actacttcaa ctacgatgct ctacttcctc acgttgatgc   6120
tcttgtctac aatggtggat atggcggact tcagcacagc ttaagccact ctgttccagt   6180
tgttattgct ggtgactctg aagacaagcc aatggtggca tcgagagctg aggccgctgg   6240
cgtggcaatt gatttgaaaa ctggcttgcc tacagtggag caaatcaaag aagctgttga   6300
ttcgataatt ggaaatccga aattccacga agcctcgaag aaggttcaaa tggagttgga   6360
aagccacaac tccttgaaaa ttcttgagga aagcatcgag gaaatcgcca gccatgactt   6420
tggtcttttg accaagagtg acgaggaaac tgaagatata cctgtcaaag gccggccctt   6480
agcggtgagt tcttagaatc gtacgatcaa atcagatcag ggaagagagg tagggttttt   6540
tttatttatg tctttgtttt tattgattga aatttacaat acaacaacca tcaaattaat   6600
ttgaacaaac aacaacacac acacacactg caactttcaa aaaaataagt aaaaggaaga   6660
gaggagtttg ccaatatatt taccttcttc taattctgtt attttttttta attgttttgt   6720 ggaaagaaag aagaaaaggc tgtcatgaat ttagtttacc tagaccttct ggttagcggt   6780
attgacgttc atttcaactg gaagaaggaa ttccagttcc tctccttcag cctcgtcggg   6840
atcctcctct ggaatatgct tgaggattcg cgcagggact cctccccacca cagtacgagg   6900 aggaacatct tctcgaacga cagcaccagc cgcaattgtt gagccatctc caatcgtaac   6960
acccggcagg acagtcacat tcgcaccaat ccatacatta ttccccacct tgataggaag   7020
agcatacaca attctcctcg cacgtttctc ggggctaata ggatgagtcg cagtcacgaa   7080
cgttgtattg ggccctacaa tcacctcatc accaaagatt attggagccg agtccaagaa   7140
gcaaacgttg aagttggcgt aaaagtgctc gcctacgctg atgttgaatc caaaatcaac   7200
tgagaatgga gcggtcagcc agacaatatc ctttgtttga ccaaaagtgt ctttgagaat   7260
ctcgaccttc ttgatataag cagcgtgatt tgactcaaaa gtacgacttt cacttgcaat   7320
ggtattgaac tccctaactt tctcactagt agccagggct ctaaacataa gatctggatc   7380
gtatggattg taaggaactc ctgagaccat cttctcatag ttttcattgc caggggtgtt   7440
tttgaggttt ttttttggccc aagagaccat ttcctggtca atttcttttc taggagtcat   7500
tcctttgttt tgagggtcct tcgaggagtt tacaaccatt gaattctaga atgtgaggtg   7560
gaatgaggca aggaaggagg aacgtattga gttgtaccct aagatatctc aaagtgctta   7620
tctccgacta ccggaatatg ctccgggtaa tgcaagtcag tgtgcatatg gtaaggtga   7680 tgcaagctaa ccctcagggc atatctaatt cgcgtgaggg ttattattgg tctacattac   7740
ctcagtcata gcccgtcaaa gcaaaagccc aaaatcagca cgaaatccca gagatagatt   7800
```

```
gttgctgtct cttcaagtac tacgacagtt ccctatatct acagattatc gtcacgagtg   7860
aattatgcag gataggtgac tcaggggtca taatcagagg aatccaatgt gctatttcaa   7920
ttaacgagtc cctttaatca gacaatgtat ggtgactcag gggccataac tagagaaatt   7980
cgatatgcta tttcaattaa tgagtgcctt taatcaaata atgtatgcaa gcagtggcca   8040
aaaataaatg aacgtcaaat ctctccgaga ccttgcaagt tcaccaattc agcgtaccat   8100
ccattgagtt caaggaggct ctgatggtcg ccctgctcca cgatgcgccc tcctgagaac   8160
acatatatga catctgcttt ctgaattgtt gataatctat gcgcaacggc gattgtagta   8220
cggcccttcg ctgctgcgtc gagtgctgct tgaactactt tctcagattc ggaatccaga   8280
gctgaggtgg cctcatcgag gaggagtacc tttggatttc tgatcagggc ccttgcaatt   8340
gcaattcgct gcttttgccc cccagatagc aacgatcccc tagatccgct gagcgtttcg   8400
tagccatcag gcaacgacat gatgaattcg tgaatgttcg ctttgcgagc ggcatcctca   8460
atcatctcct gcgttacttc agactcaggg ccagaccatc ccattagaat attctcacgt   8520
agcgtgcctg aataaagcat tggttcttgc tggactaaag caatgtgtga tctcaatgca   8580
ttcaggttat attcgcgtaa atctttccca tcgaaaagta cttgacctgc taatggatca   8640
taaaatcttt ccaccagtcc aatagtagta gacttaccgc atccactggc tccaactaga   8700
gcgatgtatt ggccctttt gactgttaag ttgagatctt gtaaaactgg tacttgaggt   8760
cgagtaggat atcggaaatt cacatgacgg aactcaatat ctcctctcac cgactcctcg   8820
ggagcaacgt aaccttcctc actccataca tctatagaag gagtggcagt caagattctg   8880
taaatgttac gcgctgcatc tttggctgag ttcatgtttg gagcatagct gaaaatttgg   8940
ccagcggctt gagaacctgt aataatagcc atgaagacag tcatatatcc tgcgaccgaa   9000
gcttcacctc gtctcattac agtgcttccc caccaaaaaa cgagggctac cacccagggt   9060
gtcattcctt ccgagagtgc gtagtacaat gctgagcggg caatggcaat tctggagctg   9120
aaaatctgag agtctactgt ctttgtgtat tttacgacca cgtctaactc acgagttaag   9180
gactggactg tgcggacagc acttgtatac tcagatgcca tggagccact tcgttcgtaa   9240
acttctctcg cacgatccga taattgggta agaacccaga ctctgacgaa gccacacacc   9300
aacatgacag gaacaacaga cgtagccacg agtccaattc tccaattgaa aggtatacca   9360
gtaactatgc cgccaatcaa ggtcaccaga ctctgttgaa tttgaccgag ggtggcccca   9420
ctcaaaccct cgatcatttt agcttccttc gccaaaattg aggttagcgc acccggcgtg   9480 ttgttttgt ggtcgaagaa tgcaatatcc attcgcatca attggcggaa caaagctaat   9540
ctgatatttt tgaccaactt atcagatgca agtgataaag cagctatagt gataaaagcc   9600
gtcatgaatg aaatgcagcc tacgaaaaaa taccaccatc ccatgatatt cacccacatgc   9660 cgcatttttc cgtattcact gggaggtaga accatgcttc cagtggtttg gccagttatt   9720
attgccattg caggatagca atagcccaaa ataatggagg ctaaactacc aatgagaatg   9780 taacccatt ctttcctatt cagcccccaa accagtttgg tattggtcat caacgtgcta   9840 tgtgggggt tgcgcacacc agggatgtca ttttcttgat attcaggagg ttgagtggtc   9900
tgagtacctg cactgtgaac actcaatgtg ctcacatcct tgggattgaa cttttcgttc   9960
agtgagtcca gaggcgaaat gtctagagct tcaatatcga ggacctcaac gttagtgctc  10020
tttgctttag ttactctttg agcatcaacc aaagctttat aaggcccttc tcgctgtatg  10080
agctcattgt gagtaccctg ctctatgacg ttacctttag acatgacaac tatcttgttg  10140
```

```
gcatccttga tcgtagagag tctgtgtgca acgactatag tggtacgacc ttcggccgct    10200
ttgtcgagcg catcttgaac gatacettca gatttggtat ccagagcaga agtcgcttca    10260
tcgagcagca gaattttagg gtctgagacg attgctcttg ctattgcaat gcgttgtttc    10320
tgaccaccgc tgagaagaaa tcctcgatct ccaacattgg tttggatgcc ttctgagaga    10380
gtctgaatga atcccaggc attggcatct ttacaagctt gaatgatttt agcttcctta     10440
acatgctcgt cagcgaactc aatgtcagtg ccaatcaaac catagctgat attctcatat    10500
attgactctg aaaagagtac tggttcctgc tgaacataac caatttgttg acggagccat    10560
cttgtgttca ggtcgctaat ctcctggcca tccagagtaa cgcttccttc gagaggtaaa    10620
tagaacctct caagaatacc tacaattgta gacttccctg atcccgaggc acctaccagt    10680
gccacagtag atccagcagg aacttcaagg ctaaaatcgg agaggaccaa aacgtctggg    10740
cgactaggat atcggaactt gacatttttg agctcaattc tgccaacggc cttagtttgg    10800
gggacaattc ctttatctat ggactggcca tcgatgactg ggacacgatc aatggcctca    10860
ttgagaatgc tcgcggcagt gagacccttg acaagaaacc tcacgtttgg cgcgatattc    10920
ccaagctgga agcttccaag taacatagct gtgattacaa ctattatctt tccaacgtca    10980
gcactcccac taacgatttc tctggaaccc tgccacagag ctaaggcata cacccaaaaa    11040
gtactagccc atatgcacgc taacatgacc cccaatgagt aactgctccg cttcgattcc    11100 ttcacaaac gatcaagtac cttttcatac ttgacggcga gatgaggttg agcgccaaat     11160
gctactgtag tcctgacagc actgagagcc tcctccgcaa cggtagctcc agactgcgaa    11220
tatatcgcgt cagatctgag ctgatatttg gccatgaagg tggcgccagt tcccattgtg    11280
attaccatga accctacagc actcaggagg atgcaagcca gtttccattg cgaagcaaaa    11340
cttataacgg tggccgcaat gaaggaagct attccctgta cgacgttttcc aagcttgtcg   11400 ctgatcgctt cctgaattga gttggtatcg ttaatgattc tggtgctgac ctcgccacca    11460
cctagtttgt cgtaaaacgc gatattctgg cgaataacag cactcagata atgctttcgg    11520
taacgtcctg ccaacacttc gcctctgtcc acaagcagga agctctcgag aaacgcactg    11580
ccgagcatac caatgccaat atagacaaaa tagagagaca ggtgattcac cttatgctgg    11640
aactcattgc ccttgaggtc atatgaagtg aagtctctga atgtgttgaa gatggcgccc    11700
actactaacg tgaacattgg aagcgcggct ccatgcaccg ctgcaaaaaa aagcgcaagt    11760
atctccaaga aaacgtcaag gggagtgcaa aatctgaaca acctgaaaaa gcttgtggcg    11820
actctctttg tttcaagctg acttcgcaat acattggcct catgtggatc taacgcagag    11880
agcttctcct cgagaagctt gtccttagtc tcgatgagtt tctcacgctt ctctacctgt    11940
atatcatcca ccataagcca aaatcagaga gtgggacctg attcagaatc acacggaccc    12000
gtatatataa caatcacttt ccaacaatat agcgagtatt aatatatttc cgggtaaggg    12060
ttgttccgga cttatgcatt taatcacagg ttgcatcagc taaatatgtc agggccgacg    12120
gcgtaaattt agaaggttag gtcaagatcc atcggtcagg ccaatggagc tctactatga    12180
taggcagctg aagcgagaca agatatactt cagttgcgct ctctgaaaaa attattttgt    12240
gattctcact cagtggatgt ggcgacacac ggaaccaata atctcgccgg aaaggcggct    12300
gaacatcagt cttgcataag tgtgcaagtg gcctgagcac agcgtgcatt acccttacca    12360
tacattcggg gcaagttaaa tccagcatta tataaacttg attgacacaa atgggcataa    12420
aacaataaag tctcctatat ggccatcgag aaaccagtga tagttgcttg tgcctgccca    12480
ctagcggggc acgtgggccc agtgctcagc ctggtccgcg gtctactcaa tagaggatat    12540
```

```
gaggtgactt tcgtaacagg gaacgcattc aaggagaaag ttattgaggc aggatgcact   12600
ttcgtccctc tccaaggacg agctgactac catgaataca atctccctga aatcgctcca   12660
ggattgctca cgattcctcc aggccttgag cagaccggtt actcaatgaa tgagattttt   12720
gtgaaggcga ttcctgagca gtacgatgca cttcaaactg ctctaaaaca ggttgaggct   12780
gaaaataaat cagctgtggt gattggcgag accatgtttc tagggtgcat ccgatatca   12840 ctgggtgccc caggtctcaa gcccaaggc gtaatcacgt taggaactat tccgtgcatg   12900
ctgaaagcag agaaggcgcc tggagttcct agtcttgagc aatgattga tactttagtg   12960 cggcaacaag tatttcaacc aggaactgac tctgagaagg agatcatgaa gacgctcggg   13020
gccacgaagg agcccgaatt tctcctggag aatatataca gcagccctga cagattttg   13080 caactgtgcc ctccatctct gaatttcac ttgacttcgc ctcctcctgg cttctcgttc   13140
gctggtagtg caccgcatgt aaagtctgct ggattagcaa ctccacctca cctgccgtct   13200
tggtggcctg atgtgctgag tgcgaagcgt ctgattgttg ttacacaagg aacagcagcc   13260
atcaactatg aagatctgct cattccagca ttgcaggcct ttgctgacga agaagacact   13320
ctcgtagttg gtatatggg cgtcaaaggg gcgtcacttc ctgatagcgt taaagttcct   13380
gcaaacgctc gaattgttga ttatttcct tacgatgagc tactaccgca tgcctctgtt   13440
ttcatataca acgtggata cggaggtctg cagcacagtt tgagccatgg cgttcccgtc   13500
atcatcggag gaggaatgtt ggtagacaag ccagctgttg cttcacgagc tgtatgggct   13560
ggtgttggtt atgatcttca aaccttgcag gcaacttctg agctagtctc cacggccgtt   13620
aaggaggtgt tggctactcc ctcgtatcac gagaaagcca tggcagtcaa gaaagagctt   13680
gaaaaataca agtctcttga tattctagag tcggcaatta gtgaattagc ttcttaacct   13740 ggctctttt ctagatatgt ctgcgccctg ctcactgctt actggcctaa gctggtatta   13800
cggaccttaa tcaagtatca ccccaaggca atcgagagtc ttatcgagtc tctaggtaga   13860
tagatacacg ttttgatttt tcggcccact ttgtagaaaa atctcagtga tttcatggaa   13920
ttcagttaca aatactaatc tgataaacca agaactacac tcggtgttga gagcagaatt   13980
aaagggactt ggcgtctagc acaaaacgat acttgacgtc accactgtga acgcgcttcc   14040
aagcttcggc gatatagctg tactcaatca gctcaacatc acaggtgatg ttatttcac   14100 cacagaagtc cagcatctcc tgagtctctg gcaagccacc aatgtttgag taagtgatag   14160
atttatttcc agccaaatga gaggtcagaa ccttgagggg tccaatttga ccaacaacaa   14220
cgagacaccc accaatatca agggactga ggtatggctc gaagtcgtgt tcaaagggaa   14280
tggtgtcgat gatcaggtca aatgtgccag cgaccgcctc gagctcattc ggatcagagg   14340
aagcaactac gcggctagca ccttgtgctt tcgctcctgc ggctttggcg tgactcctgc   14400
tgaacagtgt gacttcagag cccatggctg aggcaaattt gatagccatg gaaccaaggc   14460
ctccgagacc aactacaccg actctttttc caggtccggc gccgtgagcc ctcagaggag   14520
agtaggtagt gataccagca cagagaaggg gcgcagaagc tgccaagtcg aggttggagg   14580
ggattttgag cacaaactcc tcgcgagcaa gaatgtgttg cgaataccct cccttcgtga   14640
cttccccgtt ctttccgctg gaattgtaag tttgagtgcg tgaaacacac caattttctt   14700
tgcctaattt acagttcttg caagtacgac atgagtccac taagcagcca attccaacaa   14760
tgtcgccagc ttgaacttc ttgacggccg ggccgacagc agtggccctt ccaataatct   14820
catgcccacc aacaaaggga aattttgcat tgttccagtc gttgtgcgct gtatggagtt   14880
```

```
cactgtgaca aattccacaa taaaggatct cgatgcttac gtcgttgggt cggggatcgc   14940
gacgctcaat agtgccagga actgggtcgc tagttgtatc gtggactatg taggccttgc   15000
aagttgaagg catcgtgaat tttgactgat ccgagcgcag tactctacgt ttagcttgaa   15060
gtcgggagaa gggtccggat tagaagataa gcggcatcct gtgacaagca gtaaaaaaat   15120
gcacccaaaa taaagttgt gctaaggacc aagagttaga ttaaattcac tacctgatta    15180
tgagctgttt agttttagaa ctttgttgct aaacaattat acgtggctat acaacctacc   15240
caaaatttac aacgccgctt agctaatgac tacgcaaccc tactggatta ggctagggct   15300
ccgagatagc gaaacgtggg gtagcgggcg acaggtcata tagagcccct accctactcg   15360
gtgcaggtta ccgacggacg acatttggag tagtgatttt gactttccaa agatggaatt   15420
tcctctgtag tgaaagatta ctgtatatat ttattggtcg catcgcttgc tcagtttgtg   15480
atccaaccca gggttaatag tggtttaagc tgaactgcgg tgggaagccc agccggtgaa   15540
aggagctttc tggagagcat acggcactaa tgagagcctc tgacaggctg cattccttt    15600 cccgcacgta cctgatatcc catcatgcgg gaccaggtta gggagtgggt tcagggttta   15660
gatagtggag ctcattggta gctcaccagc gagctctgag tagatggctg tgtcacacat   15720
tgaggcagaa gttttctgt ctgaagtact gaagatttct tgctttggca acagtaatgg    15780
ggccaggtcc gaaggctcgg caaacttaag ctcgaaatta gatgagcgta agattcactt   15840
aacaacaaat tcgcgaagtc ctaggaagcg cgactgacag aggagtgttt cgttcaacaa   15900
tttcgcgaag gattgcacta ctcaccaact catattaatt cagctaatgt ttctaatttt   15960
caaaactagt acgaagtct gcagttagac agctcttgcg tttgaagaac ttaggcgcga    16020
gatttctcag ctgtatctac acgtcttggg tcgacgcagc tgttggagcg aaccaacgca   16080
caactaacaa caaatcaagt agactaggga tacaagatta aaatcatacg taaagcatca   16140
tttatcatta ttgacaggca ctcaacaagc acaacggctc ggagatgaaa gcacactgct   16200
ctctgcattt taaagggac atctagatga ggagggcagc agcagcaata gcaccgacag    16260
caacagggac ttggaggacc gaagcagcat taggggcagc tgacgcagtg cccttgctag   16320
agccagaagc cttaggagtg ccagaactct tagagttgcc agaagcagaa gatttgccgg   16380
atgcgctagc atcagcagca gaactcagag aagatgagga accggagtca gtggaggtcg   16440
attttatggg agtgaacttg tagagcatgt tcttagaact cttgtcagtg acaaagacgt   16500
ctccattggg ggcaacctcg atgtggttgg gagttgtgac gttgagctga gtgataatac   16560
tatagtcttc aggatcaata acaaccacg agtggcccgc acggcaggca acgtaaacaa    16620
cgtcataaac gggatcgtaa cgagcgttga gaggacgtcc aggcatatcg atgctcttca   16680
caaccttgcc ggacttgggg ttgacaataa cagtattgtt ggagccttgg ttcgtaacga   16740
aaagttgctc acgtcgggag tcccaagcaa caccacttga aaacttgaca ttgtccccga   16800
gatcgaagga tttgacagag tagtcgttga ggtcgatggc tgcggcaagg ggctgtttca   16860
aagccaccgt gtagagtact ttgttgacct cgtcagcaac aagactcata ctgctggaga   16920
aattcttgcc gagagactca gatatattga tactcttggc ggatttgtca gtggtgctag   16980
catcgaatac ggctatgaca ctagacctcg cagaagagac gtaagcaagc ccagtgctct   17040
ggtcaacata gacatcacgc ggatgcggct gaatgtcatc ggggtactga acaccaaggc   17100
tgaggtcctt accattataa taggaaacag tgccctggcg ggtgttggta acccaaaacac  17160 ggttgttatc gtagtcgcta tcaacgccat aaactgcgta gcgttgggta acatttccag   17220
tggtaccgat ggcaggctga acgtccctga caacagccag gctcttaggg tcaacctcga   17280
```

-continued

```
taaggtcgga ctggttcaca gggggacgac aacagagtt ggtaaggaaa agcctgtcat    17340
tggttctgtc ataagtgctt tggtagagac cgccgtactt actaaagtca gcgctttgag    17400
tctcgtaaga gagggtgcga gcatcaatcc cgacggcgag gagaagaaca gcaagagagt    17460
ggatagcaat cattagagct cagtaaaaac gctgttatgg tcaaataac atttgtgaga    17520 tagtttccct atttatattt ctcgagaaag agccgtttgc gaaaatgggc gccaggcata    17580
attggccaag ggtaaatatg ggtcagggta tctttgggct cgggcggatt ctgcagatgg    17640
cccagagaga ttttcatcat cgaggcaagt tcaaagctcg aaactggcca cattgagcac    17700
cgtggtaaag attgaacgac tatatagtga tttcaattat gtcctgcatt agggcttggt    17760 ttttttctg actgcagcag tgcctattga ggaattcgca atgagagagc cctacggtct    17820
gtgctagatg taaagatac gatcgagact tagatgcatc taccccagcc cttaccatct    17880
tatatgaggt tgagagattt attttgttt ttagagatga ttcttcagca aaccagaagg    17940
gaatccggaa ggagttaggg ttaatgatcc agttagtgtt tgtagatatt atccagctcg    18000
tagatgagaa gcg                                                       18013

<210> SEQ ID NO 2
<211> LENGTH: 1617
<212> TYPE: DNA
<213> ORGANISM: Candida bombicola

<400> SEQUENCE: 2
atgttaatca aagacattat tctaactcca atgagtttat ccgctgttgc tggcttgttg       60
ccactgctct tcgtagcttt cttagttcta cacgagccta tctggctcct atggtaccgc      120
tatgcagcac gtaggcacaa gtgtagtatg cctcgcttca ttgagaaatc gttcccactg      180
ggaatacaaa gaaccatgga catgatcaag acggccaagt catacacctt actggaagtt      240
caatacgaca gagtcttcaa taagttcaaa gcacggacgt atcttcgaca agctcccctt      300
caataccaaa tcttcacaat cgagccagaa acattaaga caatcctggc aaccaaattc      360
aatgattttg gtcttggagc acgtttccac acagtgggaa aagtgtttgg ccaagggata      420
tttacactca gcggaaatgg atggaaacag tctcgatcga tgttgagacc tcagttcact      480
aaagatcagg tttgcagaat tgatcagatt ccagtcatg ctgcggagtt aataaaggag      540
atgaaccgtg caatgaaagt ggaccaattt attgatgttc aacattattt ccacaaactt      600
acgctggata cagcgactga attcctattt ggggagtcct gcgagagctt gaaccctgag      660
aatcagtcat gtattgtagc ccgtgatggt tcggagatta ctgccgaaca attcgtggag      720
tcctacaact ttctactgaa ttacgctttc aaacggaccc tatcaagcaa agtctactgg      780
ttgttcaact ctaaggaatt ccgagatcac aagaaacgtg ctcagtccta tattgactac      840
tacgttgata aggctcttta cgccacatct ttcgctgctg agaactctat tgcagagaag      900
gatgctgctg cagagtctag tggcatctat gtgttctcgc ttgagatggc taaagttacc      960
cgagacccag tgacgatacg tgatcaaatt ttcaacattc tcattgctgg tagagataca     1020
acagctgcta cgttgagctt cgctattcat ttccttgcca gaaatcctga cgtattcaac     1080
aaactacgtg aggaggtcct cgatcatttt ggaaccaagg aggagcaaag gcctttatca     1140
ttcgaacttc tgaagcaagc accttatttg aagcaagtta taatgaagt cttgcgtctt     1200 gcgccggtat tgccattgaa cttccgtact gctgtgagag atacaactct acccataggt     1260
ggtggtcccg agcagaagga tccgatcttc gttcctaagg gcaccgcagt ttactattca     1320
```

-continued

| | |
|---|---|
| atttacatgg tccacaggga catcaagtat tggggtcctg acgcccacga attcaatccc | 1380 |
| aatcgatggg agaacttgaa gctagataat gtgtgggcat tcttgcccct caatggcggt | 1440 |
| ccccgaattt gtctcggcca acaattcgcc ctgacagagc tttcgctaac tctggtgaga | 1500 |
| ctcttacagg agtattccaa gattgagatg ggtcccgact tcccagagtc ccctcgtttc | 1560 |
| tcaacaacgc ttacagctca acacgctcct cccggtgtgg ttgtgcggtt ttcttaa | 1617 |

<210> SEQ ID NO 3
<211> LENGTH: 1392
<212> TYPE: DNA
<213> ORGANISM: Candida bombicola

<400> SEQUENCE: 3

| | |
|---|---|
| atgagccctt catcacacaa acccctgatt ctcgcttgcg gcttgcctct ttcaggccat | 60 |
| ataatgcccg ttttgagtct ggtacacggc cttacggacg acggatacga agctactgtt | 120 |
| gtgacaggca gagcgtttga acaaaaagtt cgagatgtgg gtgcagactt tgttccttta | 180 |
| gaagggaacg cagattttga tgaccacacc ttagacgatc tggtcccggg ccgtaaagac | 240 |
| atggccccaa gcttcgatcg tacagttcaa gatgtggagc acatgatggt agctactctt | 300 |
| cctgagcagt ttgccgctat tcagagggct ttcaaaaagc tcagcgcaag cggccgccct | 360 |
| gtcgttcttg tcagtgaagt gctgtttttc ggtgcacacc tatcagcct cggtgctcct | 420 |
| ggtttcaaac ccgctggctg gatttgttta ggggttttgc ctcttttgat ccgcagtgat | 480 |
| catacccttag gacttgacaa cgacaggagc cccgaagcac atgcaaagaa actcgctatg | 540 |
| aaccacgctc ttgagcacca aattttcgtt aaagccactg ctaagcacaa ggaaatctgc | 600 |
| cgagagttag gttgcactga agatcccaaa tttatctggg agcacagtta cattgctgca | 660 |
| gacaagttcc tgcagctgtg cccgccttct cttgagttca gcagagacca tctgcctagc | 720 |
| aacttcaaat tcgccggctc aacgcccaag caccgaactc aattcacccc tccttcctgg | 780 |
| tgggggggatg ttctgagtgc caagcgagtc atcatggtca ctcaaggaac ttttgctgtc | 840 |
| agttacaagc atcttattgt gcctactctt gaggcttga aggacgagcc tgacactta | 900 |
| acagtagcca tattgggccg ccgcggtgcc aagctaccgg atgatgttgt ggttcctgag | 960 |
| aatgctcgcg tgatcgacta cttcaactac gatgctctac ttcctcacgt tgatgctctt | 1020 |
| gtctacaatg tggatatagg cggacttcag cacagcttaa gccactctgt tccagttgtt | 1080 |
| attgctggtg actctgaaga caagccaatg gtggcatcga gagctgaggc cgctggcgtg | 1140 |
| gcaattgatt tgaaaactgg cttgcctaca gtggagcaaa tcaaagaagc tgttgattcg | 1200 |
| ataattggaa atccgaaatt ccacgaagcc tcgaagaagg ttcaaatgga gttggaaagc | 1260 |
| cacaactcct tgaaaattct tgaggaaagc atcgaggaaa tcgccagcca tgactttggt | 1320 |
| cttttgacca agagtgacga ggaaactgaa gatatacctg tcaaagggcc ggccttagcg | 1380 |
| gtgagttctt ag | 1392 |

<210> SEQ ID NO 4
<211> LENGTH: 780
<212> TYPE: DNA
<213> ORGANISM: Candida bombicola

<400> SEQUENCE: 4

| | |
|---|---|
| atggttgtaa actcctcgaa ggaccctcaa aacaaggaa tgactcctag aaaagaaatt | 60 |
| gaccaggaaa tggtctcttg ggccaaaaaa aacctcaaaa acaccctggg caatgaaaac | 120 |
| tatgagaaga tggtctcagg agttccttac aatccatacg atccagatct tatgtttaga | 180 |

```
gccctggcta ctagtgagaa agttagggag ttcaatacca ttgcaagtga aagtcgtact    240
tttgagtcaa atcacgctgc ttatatcaag aaggtcgaga ttctcaaaga cacttttggt    300
caaacaaagg atattgtctg gctgaccgct ccattctcag ttgattttgg attcaacatc    360
agcgtaggcg agcactttta cgccaacttc aacgtttgct tcttggactc ggctccaata    420
atctttggtg atgaggtgat tgtagggccc aatacaacgt tcgtgactgc gactcatcct    480
attagccccg agaaacgtgc gaggagaatt gtgtatgctc ttcctatcaa ggtgggaat    540 aatgtatgga ttggtgcgaa tgtgactgtc ctgccgggtg ttacgattgg agatggctca    600
acaattgcgg ctggtgctgt cgttcgagaa atgttcctc ctcgtactgt ggtgggagga    660
gtccctgcgc gaatcctcaa gcatattcca gaggaggatc ccgacgaggc tgaaggagag    720
gaactggaat tccttcttcc agttgaaatg aacgtcaata ccgctaacca gaaggtctag    780
```

```
<210> SEQ ID NO 5
<211> LENGTH: 3900
<212> TYPE: DNA
<213> ORGANISM: Candida bombicola

<400> SEQUENCE: 5
```

```
atggtggatg atatacaggt agagaagcgt gagaaactca tcgagactaa ggacaagctt     60
ctcgaggaga agctctctgc gttagatcca catgaggcca atgtattgcg aagtcagctt    120
gaaacaaaga gagtcgccac aagcttttc aggttgttca gattttgcac tccccttgac    180
gttttcttgg agatacttgc gcttttttt gcagcggtgc atggagccgc gcttccaatg    240
ttcacgttag tagtgggcgc catcttcaac acattcagag acttcacttc atatgacctc    300
aagggcaatg agttccagca taaggtgaat cacctgtctc tctattttgt ctatattggc    360
attggtatgc tcggcagtgc gtttctcgag agcttcctgc ttgtggacag aggcgaagtg    420
ttggcaggac gttaccgaaa gcattatctg agtgctgtta ttcgccagaa tatcgcgttt    480
tacgacaaac taggtggtgg cgaggtcagc accagaatca ttaacgatac caactcaatt    540
caggaagcga tcagcgacaa gcttggaaac gtcgtacagg gaatagcttc cttcattgcg    600
gccaccgtta taagttttgc ttcgcaatgg aaactggctt gcatcctcct gagtgctgta    660
gggttcatgg taatcacaat gggaactggc gccaccttca tggccaaata tcagctcaga    720
tctgacgcga tatattcgca gtctggagct accgttgcgg aggaggctct cagtgctgtc    780
aggactacag tagcatttgg cgctcaacct catctcgccg tcaagtatga aaaggtactt    840
gatcgtgttg tgaaggaatc gaagcggagc agttactcat gggggtcat gttagcgtgc    900 atatgggcta gtacttttg ggtgtatgcc ttagctctgt ggcagggttc cagagaaatc    960
gttagtggga gtgctgacgt tggaaagata atagttgtaa tcacagctat gttacttgga   1020
agcttccagc ttgggaatat cgcgccaaac gtgaggtttc ttgtcaaggg tctcactgcc   1080
gcgagcattc tcaatgaggc cattgatcgt gtcccagtca tcgatggcca gtccatagat   1140
aaaggaattg tcccccaaac taaggccgtt ggcagaattg agctcaaaaa tgtcaagttc   1200
cgatatccta gtcgcccaga cgttttggtc ctctccgatt ttagccttga agttcctgct   1260
ggatctactg tggcactggt aggtgcctcg ggatcaggga gtctacaat tgtaggtatt   1320 cttgagaggt tctatttacc tctcgaagga agcgttactc tggatggcca ggagattagc   1380
gacctgaaca agatggct ccgtcaacaa attggttatg ttcagcagga accagtactc   1440 tttcagagt caatatatga gaatatcagc tatggttga ttgcactga cattgagttc   1500
```

```
gctgacgagc atgttaagga agctaaaatc attcaagctt gtaaagatgc caatgcctgg       1560
gatttcattc agactctctc agaaggcatc caaaccaatg ttggagatcg aggatttctt       1620
ctcagcggtg gtcagaaaca acgcattgca atagcaagag caatcgtctc agaccctaaa       1680
attctgctgc tcgatgaagc gacttctgct ctggatacca aatctgaagg tatcgttcaa       1740
gatgcgctcg acaaagcggc cgaaggtcgt accactatag tcgttgcaca cagactctct       1800
acgatcaagg atgccaacaa atagttgtc atgtctaaag gtaacgtcat agagcagggt        1860
actcacaatg agctcataca gcgagaaggg ccttataaag ctttggttga tgctcaaaga       1920
gtaactaaag caaagagcac taacgttgag gtcctcgata ttgaagctct agacatttcg       1980
cctctggact cactgaacga aaagttcaat cccaaggatg tgagcacatt gagtgttcac       2040
agtgcaggta ctcagaccac tcaacctcct gaatatcaag aaaatgacat ccctggtgtg       2100 cgcaacccc cacatagcac gttgatgacc aataccaaac tggtttgggg gctgaatagg         2160
aaagaatggg gttacattct cattggtagt ttagcctcca ttattttggg ctattgctat       2220
cctgcaatgg caataataac tggccaaacc actggaagca tggttctacc tcccagtgaa       2280
tacgaaaaaa tgcggcatgt ggtgaatatc atgggatggt ggtattttt cgtaggctgc        2340 atttcattca tgacggcttt tatcactata gctgctttat cacttgcatc tgataagttg       2400
gtcaaaaata tcagattagc tttgttccgc caattgatgc gaatggatat tgcattcttc       2460
gaccacaaaa acaacacgcc gggtgcgcta acctcaattt tggcgaagga agctaaaatg       2520
atcgagggtt tgagtggggc caccctcggt caaattcaac agagtctggt gaccttgatt       2580
ggcggcatag ttactggtat acctttcaat tggagaattg gactcgtggc tacgtctgtt       2640
gttcctgtca tgttggtgtg tggcttcgtc agagtctggg ttcttaccca attatcggat       2700
cgtgcgagag aagtttacga acgaagtggc tccatggcat ctgagtatac aagtgctgtc       2760
cgcacagtcc agtccttaac tcgtgagtta gacgtggtcg taaaatacac aaagacagta       2820
gactctcaga ttttcagctc cagaattgcc attgcccgct cagcattgta ctacgcactc       2880
tcggaaggaa tgacaccctg ggtggtagcc ctcgtttttt ggtggggaag cactgtaatg       2940
agacgaggtg aagcttcggt cgcaggatat atgactgtct tcatggctat tattacaggt       3000
tctcaagccg ctggccaaat tttcagctat gctccaaaca tgaactcagc caaagatgca       3060
gcgcgtaaca tttacagaat cttgactgcc actccttcta tagatgtatg gagtgaggaa       3120
ggttacgttg ctcccgagga gtcggtgaga ggagatattg agttccgtca tgtgaatttc       3180
cgatatccta ctcgacctca gtaccagtt ttacaagatc tcaacttaac agtcaaaaag         3240
ggccaataca tcgctctagt tggagccagt ggatgcggta agtctactac tattggactg       3300
gtggaaagat tttatgatcc attagcaggt caagtacttt tcgatgggaa agatttacgc       3360
gaatataacc tgaatgcatt gagatcacac attgctttag tccagcaaga accaatgctt       3420
tattcaggca cgctacgtga gaatattcta atgggatggt ctggccctga gtctgaagta       3480
acgcaggaga tgattgagga tgccgctcgc aaagcgaaca ttcacgaatt catcatgtcg       3540
ttgcctgatg gctacgaaac gctcagcgga tctaggggat cgttgctatc tgggggcaa       3600 aagcagcgaa ttgcaattgc aagggccctg atcagaaatc caaggtact cctcctcgat       3660 gaggccacct cagctctgga ttccgaatct gagaagtag ttcaagcagc actcgacgca       3720
gcagcgaagg gccgtactac aatcgccgtt gcgcatagat tatcaacaat tcagaaagca       3780
gatgtcatat atgtgttctc aggagggcgc atccgtgagc agggcgacca tcagagcctc       3840
cttgaactca atggatggta cgctgaattg gtgaacttgc aaggtctcgg agagatttga       3900
```

<210> SEQ ID NO 6
<211> LENGTH: 1299
<212> TYPE: DNA
<213> ORGANISM: Candida bombicola

<400> SEQUENCE: 6

```
atggccatcg agaaaccagt gatagttgct tgtgcctgcc cactagcggg gcacgtgggc      60
ccagtgctca gcctggtccg cggtctactc aatagaggat atgaggtgac tttcgtaaca     120
gggaacgcat tcaaggagaa agttattgag gcaggatgca ctttcgtccc tctccaagga     180
cgagctgact accatgaata caatctccct gaaatcgctc caggattgct cacgattcct     240
ccaggccttg agcagaccgg ttactcaatg aatgagattt tgtgaaggc gattcctgag      300
cagtacgatg cacttcaaac tgctctaaaa caggttgagg ctgaaaataa atcagctgtg     360
gtgattggcg agaccatgtt tctaggggtg catccgatat cactgggtgc cccaggtctc     420
aagccccaag gcgtaatcac gttaggaact attccgtgca tgctgaaagc agagaaggcg     480
cctggagttc ctagtcttga gccaatgatt gatactttag tgcggcaaca agtatttcaa     540
ccaggaactg actctgagaa ggagatcatg aagacgctcg gggccacgaa ggagcccgaa     600
tttctcctgg agaatatata cagcagccct gacagatttt tgcaactgtg ccctccatct     660
cttgaatttc acttgacttc gcctcctcct ggcttctcgt tcgctggtag tgcaccgcat     720
gtaaagtctg ctggattagc aactccacct cacctgccgt cttggtggcc tgatgtgctg     780
agtgcgaagc gtctgattgt tgttacacaa ggaacagcag ccatcaacta tgaagatctg     840
ctcattccag cattgcaggc ctttgctgac gaagaagaca ctctcgtagt tggtatattg     900
ggcgtcaaag gggcgtcact tcctgatagc gttaaagttc ctgcaaacgc tcgaattgtt     960
gattattttc cttacgatga gctactaccg catgcctctg ttttcatata caacggtgga    1020
tacggaggtc tgcagcacag tttgagccat ggcgttcccg tcatcatcgg aggaggaatg    1080
ttggtagaca agccagctgt tgcttcacga gctgtatggg ctggtgttgg ttatgatctt    1140
caaaccttgc aggcaacttc tgagctagtc tccacggccg ttaaggaggt gttggctact    1200
ccctcgtatc acgagaaagc catggcagtc aagaaagagc ttgaaaaata caagtctctt    1260
gatattctag agtcggcaat tagtgaatta gcttcttaa                           1299
```

<210> SEQ ID NO 7
<211> LENGTH: 538
<212> TYPE: PRT
<213> ORGANISM: Candida bombicola

<400> SEQUENCE: 7

```
Met Leu Ile Lys Asp Ile Ile Leu Thr Pro Met Ser Leu Ser Ala Val
1               5                   10                  15

Ala Gly Leu Leu Pro Leu Leu Phe Val Ala Phe Leu Val Leu His Glu
            20                  25                  30

Pro Ile Trp Leu Leu Trp Tyr Arg Tyr Ala Ala Arg Arg His Lys Cys
        35                  40                  45

Ser Met Pro Arg Phe Ile Glu Lys Ser Phe Pro Leu Gly Ile Gln Arg
    50                  55                  60

Thr Met Asp Met Ile Lys Thr Ala Lys Ser Tyr Thr Leu Leu Glu Val
65                  70                  75                  80

Gln Tyr Asp Arg Val Phe Asn Lys Phe Lys Ala Arg Thr Tyr Leu Arg
                85                  90                  95
```

```
Gln Ala Pro Leu Gln Tyr Gln Ile Phe Thr Ile Glu Pro Glu Asn Ile
                100                 105                 110
Lys Thr Ile Leu Ala Thr Lys Phe Asn Asp Phe Gly Leu Gly Ala Arg
            115                 120                 125
Phe His Thr Val Gly Lys Val Phe Gly Gln Gly Ile Phe Thr Leu Ser
        130                 135                 140
Gly Asn Gly Trp Lys Gln Ser Arg Ser Met Leu Arg Pro Gln Phe Thr
145                 150                 155                 160
Lys Asp Gln Val Cys Arg Ile Asp Gln Ile Ser Ser His Ala Ala Glu
                165                 170                 175
Leu Ile Lys Glu Met Asn Arg Ala Met Lys Val Asp Gln Phe Ile Asp
            180                 185                 190
Val Gln His Tyr Phe His Lys Leu Thr Leu Asp Thr Ala Thr Glu Phe
        195                 200                 205
Leu Phe Gly Glu Ser Cys Glu Ser Leu Asn Pro Glu Asn Gln Ser Cys
    210                 215                 220
Ile Val Ala Arg Asp Gly Ser Glu Ile Thr Ala Glu Gln Phe Val Glu
225                 230                 235                 240
Ser Tyr Asn Phe Leu Leu Asn Tyr Ala Phe Lys Arg Thr Leu Ser Ser
                245                 250                 255
Lys Val Tyr Trp Leu Phe Asn Ser Lys Glu Phe Arg Asp His Lys Lys
            260                 265                 270
Arg Ala Gln Ser Tyr Ile Asp Tyr Val Asp Lys Ala Leu Tyr Ala
        275                 280                 285
Thr Ser Phe Ala Ala Glu Asn Ser Ile Ala Glu Lys Asp Ala Ala Ala
    290                 295                 300
Glu Ser Ser Gly Ile Tyr Val Phe Ser Leu Glu Met Ala Lys Val Thr
305                 310                 315                 320
Arg Asp Pro Val Thr Ile Arg Asp Gln Ile Phe Asn Ile Leu Ile Ala
                325                 330                 335
Gly Arg Asp Thr Thr Ala Ala Thr Leu Ser Phe Ala Ile His Phe Leu
            340                 345                 350
Ala Arg Asn Pro Asp Val Phe Asn Lys Leu Arg Glu Glu Val Leu Asp
        355                 360                 365
His Phe Gly Thr Lys Glu Glu Gln Arg Pro Leu Ser Phe Glu Leu Leu
    370                 375                 380
Lys Gln Ala Pro Tyr Leu Lys Gln Val Ile Asn Glu Val Leu Arg Leu
385                 390                 395                 400
Ala Pro Val Leu Pro Leu Asn Phe Arg Thr Ala Val Arg Asp Thr Thr
                405                 410                 415
Leu Pro Ile Gly Gly Pro Glu Gln Lys Asp Pro Ile Phe Val Pro
            420                 425                 430
Lys Gly Thr Ala Val Tyr Tyr Ser Ile Tyr Met Val His Arg Asp Ile
        435                 440                 445
Lys Tyr Trp Gly Pro Asp Ala His Glu Phe Asn Pro Asn Arg Trp Glu
    450                 455                 460
Asn Leu Lys Leu Asp Asn Val Trp Ala Phe Leu Pro Phe Asn Gly Gly
465                 470                 475                 480
Pro Arg Ile Cys Leu Gly Gln Gln Phe Ala Leu Thr Glu Leu Ser Leu
                485                 490                 495
Thr Leu Val Arg Leu Leu Gln Glu Tyr Ser Lys Ile Glu Met Gly Pro
            500                 505                 510
Asp Phe Pro Glu Ser Pro Arg Phe Ser Thr Thr Leu Thr Ala Gln His
```

```
                515                 520                 525

Ala Pro Pro Gly Val Val Arg Phe Ser
    530                 535

<210> SEQ ID NO 8
<211> LENGTH: 463
<212> TYPE: PRT
<213> ORGANISM: Candida bombicola

<400> SEQUENCE: 8

Met Ser Pro Ser Ser His Lys Pro Leu Ile Leu Ala Cys Gly Leu Pro
1               5                   10                  15

Leu Ser Gly His Ile Met Pro Val Leu Ser Leu Val His Gly Leu Thr
            20                  25                  30

Asp Asp Gly Tyr Glu Ala Thr Val Val Thr Gly Arg Ala Phe Glu Gln
        35                  40                  45

Lys Val Arg Asp Val Gly Ala Asp Phe Val Pro Leu Glu Gly Asn Ala
    50                  55                  60

Asp Phe Asp Asp His Thr Leu Asp Asp Leu Val Pro Gly Arg Lys Asp
65                  70                  75                  80

Met Ala Pro Ser Phe Asp Arg Thr Val Gln Asp Val Glu His Met Met
                85                  90                  95

Val Ala Thr Leu Pro Glu Gln Phe Ala Ala Ile Gln Arg Ala Phe Lys
            100                 105                 110

Lys Leu Ser Ala Ser Gly Arg Pro Val Val Leu Val Ser Glu Val Leu
        115                 120                 125

Phe Phe Gly Ala His Pro Ile Ser Leu Gly Ala Pro Gly Phe Lys Pro
130                 135                 140

Ala Gly Trp Ile Cys Leu Gly Val Leu Pro Leu Leu Ile Arg Ser Asp
145                 150                 155                 160

His Thr Leu Gly Leu Asp Asn Asp Arg Ser Pro Glu Ala His Ala Lys
                165                 170                 175

Lys Leu Ala Met Asn His Ala Leu Glu His Gln Ile Phe Val Lys Ala
            180                 185                 190

Thr Ala Lys His Lys Glu Ile Cys Arg Glu Leu Gly Cys Thr Glu Asp
        195                 200                 205

Pro Lys Phe Ile Trp Glu His Ser Tyr Ile Ala Ala Asp Lys Phe Leu
    210                 215                 220

Gln Leu Cys Pro Pro Ser Leu Glu Phe Ser Arg Asp His Leu Pro Ser
225                 230                 235                 240

Asn Phe Lys Phe Ala Gly Ser Thr Pro Lys His Arg Thr Gln Phe Thr
                245                 250                 255

Pro Pro Ser Trp Trp Gly Asp Val Leu Ser Ala Lys Arg Val Ile Met
            260                 265                 270

Val Thr Gln Gly Thr Phe Ala Val Ser Tyr Lys His Leu Ile Val Pro
        275                 280                 285

Thr Leu Glu Ala Leu Lys Asp Glu Pro Asp Thr Thr Val Ala Ile
    290                 295                 300

Leu Gly Arg Arg Gly Ala Lys Leu Pro Asp Asp Val Val Pro Glu
305                 310                 315                 320

Asn Ala Arg Val Ile Asp Tyr Phe Asn Tyr Asp Ala Leu Leu Pro His
                325                 330                 335

Val Asp Ala Leu Val Tyr Asn Gly Gly Tyr Gly Gly Leu Gln His Ser
            340                 345                 350
```

Leu Ser His Ser Val Pro Val Val Ile Ala Gly Asp Ser Glu Asp Lys
            355                 360                 365

Pro Met Val Ala Ser Arg Ala Glu Ala Ala Gly Val Ala Ile Asp Leu
    370                 375                 380

Lys Thr Gly Leu Pro Thr Val Glu Gln Ile Lys Glu Ala Val Asp Ser
385                 390                 395                 400

Ile Ile Gly Asn Pro Lys Phe His Glu Ala Ser Lys Lys Val Gln Met
                405                 410                 415

Glu Leu Glu Ser His Asn Ser Leu Lys Ile Leu Glu Gly Ser Ile Glu
            420                 425                 430

Glu Ile Ala Ser His Asp Phe Gly Leu Leu Thr Lys Ser Asp Glu Glu
            435                 440                 445

Thr Glu Asp Ile Pro Val Lys Gly Pro Ala Leu Ala Val Ser Ser
    450                 455                 460

<210> SEQ ID NO 9
<211> LENGTH: 259
<212> TYPE: PRT
<213> ORGANISM: Candida bombicola

<400> SEQUENCE: 9

Met Val Val Asn Ser Ser Lys Asp Pro Gln Asn Lys Gly Met Thr Pro
1               5                   10                  15

Arg Lys Glu Ile Asp Gln Glu Met Val Ser Trp Ala Lys Lys Asn Leu
            20                  25                  30

Lys Asn Thr Pro Gly Asn Glu Asn Tyr Glu Lys Met Val Ser Gly Val
        35                  40                  45

Pro Tyr Asn Pro Tyr Asp Pro Asp Leu Met Phe Arg Ala Leu Ala Thr
50                  55                  60

Ser Glu Lys Val Arg Glu Phe Asn Thr Ile Ala Ser Glu Ser Arg Thr
65                  70                  75                  80

Phe Glu Ser Asn His Ala Ala Tyr Ile Lys Lys Val Glu Ile Leu Lys
                85                  90                  95

Asp Thr Phe Gly Gln Thr Lys Asp Ile Val Trp Leu Thr Ala Pro Phe
            100                 105                 110

Ser Val Asp Phe Gly Phe Asn Ile Ser Val Gly Glu His Phe Tyr Ala
        115                 120                 125

Asn Phe Asn Val Cys Phe Leu Asp Ser Ala Pro Ile Ile Phe Gly Asp
130                 135                 140

Glu Val Ile Val Gly Pro Asn Thr Thr Phe Val Thr Ala Thr His Pro
145                 150                 155                 160

Ile Ser Pro Glu Lys Arg Ala Arg Ile Val Tyr Ala Leu Pro Ile
                165                 170                 175

Lys Val Gly Asn Asn Val Trp Ile Gly Ala Asn Val Thr Val Leu Pro
            180                 185                 190

Gly Val Thr Ile Gly Asp Gly Ser Thr Ile Ala Ala Gly Ala Val Val
        195                 200                 205

Arg Glu Asp Val Pro Pro Arg Thr Val Val Gly Gly Val Pro Ala Arg
210                 215                 220

Ile Leu Lys His Ile Pro Glu Glu Asp Pro Asp Glu Ala Glu Gly Glu
225                 230                 235                 240

Glu Leu Glu Phe Leu Leu Pro Val Glu Met Asn Val Asn Thr Ala Asn
                245                 250                 255

Gln Lys Val

<210> SEQ ID NO 10
<211> LENGTH: 1299
<212> TYPE: PRT
<213> ORGANISM: Candida bombicola

<400> SEQUENCE: 10

```
Met Val Asp Asp Ile Gln Val Glu Lys Arg Glu Lys Leu Ile Glu Thr
1               5                   10                  15

Lys Asp Lys Leu Leu Glu Glu Lys Leu Ser Ala Leu Asp Pro His Glu
            20                  25                  30

Ala Asn Val Leu Arg Ser Gln Leu Glu Thr Lys Arg Val Ala Thr Ser
        35                  40                  45

Phe Phe Arg Leu Phe Arg Phe Cys Thr Pro Leu Asp Val Phe Leu Glu
    50                  55                  60

Ile Leu Ala Leu Phe Phe Ala Ala Val His Gly Ala Ala Leu Pro Met
65                  70                  75                  80

Phe Thr Leu Val Val Gly Ala Ile Phe Asn Thr Phe Arg Asp Phe Thr
                85                  90                  95

Ser Tyr Asp Leu Lys Gly Asn Glu Phe Gln His Lys Val Asn His Leu
            100                 105                 110

Ser Leu Tyr Phe Val Tyr Ile Gly Ile Gly Met Leu Gly Ser Ala Phe
        115                 120                 125

Leu Glu Ser Phe Leu Leu Val Asp Arg Gly Glu Val Leu Ala Gly Arg
    130                 135                 140

Tyr Arg Lys His Tyr Leu Ser Ala Val Ile Arg Gln Asn Ile Ala Phe
145                 150                 155                 160

Tyr Asp Lys Leu Gly Gly Gly Glu Val Ser Thr Arg Ile Ile Asn Asp
                165                 170                 175

Thr Asn Ser Ile Gln Glu Ala Ile Ser Asp Lys Leu Gly Asn Val Val
            180                 185                 190

Gln Gly Ile Ala Ser Phe Ile Ala Ala Thr Val Ile Ser Phe Ala Ser
        195                 200                 205

Gln Trp Lys Leu Ala Cys Ile Leu Leu Ser Ala Val Gly Phe Met Val
    210                 215                 220

Ile Thr Met Gly Thr Gly Ala Thr Phe Met Ala Lys Tyr Gln Leu Arg
225                 230                 235                 240

Ser Asp Ala Ile Tyr Ser Gln Ser Gly Ala Thr Val Ala Glu Glu Ala
                245                 250                 255

Leu Ser Ala Val Arg Thr Thr Val Ala Phe Gly Ala Gln Pro His Leu
            260                 265                 270

Ala Val Lys Tyr Glu Lys Val Leu Asp Arg Val Val Lys Glu Ser Lys
        275                 280                 285

Arg Ser Ser Tyr Ser Leu Gly Val Met Leu Ala Cys Ile Trp Ala Ser
    290                 295                 300

Thr Phe Trp Val Tyr Ala Leu Ala Leu Trp Gln Gly Ser Arg Glu Ile
305                 310                 315                 320

Val Ser Gly Ser Ala Asp Val Gly Lys Ile Ile Val Val Ile Thr Ala
                325                 330                 335

Met Leu Leu Gly Ser Phe Gln Leu Gly Asn Ile Ala Pro Asn Val Arg
            340                 345                 350

Phe Leu Val Lys Gly Leu Thr Ala Ala Ser Ile Leu Asn Glu Ala Ile
        355                 360                 365

Asp Arg Val Pro Val Ile Asp Gly Gln Ser Ile Asp Lys Gly Ile Val
    370                 375                 380
```

-continued

```
Pro Gln Thr Lys Ala Val Gly Arg Ile Glu Leu Lys Asn Val Lys Phe
385                 390                 395                 400

Arg Tyr Pro Ser Arg Pro Asp Val Leu Val Leu Ser Asp Phe Ser Leu
            405                 410                 415

Glu Val Pro Ala Gly Ser Thr Val Ala Leu Val Gly Ala Ser Gly Ser
            420                 425                 430

Gly Lys Ser Thr Ile Val Gly Ile Leu Glu Arg Phe Tyr Leu Pro Leu
        435                 440                 445

Glu Gly Ser Val Thr Leu Asp Gly Gln Glu Ile Ser Asp Leu Asn Thr
    450                 455                 460

Arg Trp Leu Arg Gln Gln Ile Gly Tyr Val Gln Glu Pro Val Leu
465                 470                 475                 480

Phe Ser Glu Ser Ile Tyr Glu Asn Ile Ser Tyr Gly Leu Ile Gly Thr
            485                 490                 495

Asp Ile Glu Phe Ala Asp Glu His Val Lys Glu Ala Lys Ile Ile Gln
            500                 505                 510

Ala Cys Lys Asp Ala Asn Ala Trp Asp Phe Ile Gln Thr Leu Ser Glu
        515                 520                 525

Gly Ile Gln Thr Asn Val Gly Asp Arg Gly Phe Leu Leu Ser Gly Gly
    530                 535                 540

Gln Lys Gln Arg Ile Ala Ile Ala Arg Ala Ile Val Ser Asp Pro Lys
545                 550                 555                 560

Ile Leu Leu Leu Asp Glu Ala Thr Ser Ala Leu Asp Thr Lys Ser Glu
            565                 570                 575

Gly Ile Val Gln Asp Ala Leu Asp Lys Ala Ala Glu Gly Arg Thr Thr
            580                 585                 590

Ile Val Val Ala His Arg Leu Ser Thr Ile Lys Asp Ala Asn Lys Ile
        595                 600                 605

Val Val Met Ser Lys Gly Asn Val Ile Glu Gln Gly Thr His Asn Glu
    610                 615                 620

Leu Ile Gln Arg Glu Gly Pro Tyr Lys Ala Leu Val Asp Ala Gln Arg
625                 630                 635                 640

Val Thr Lys Ala Lys Ser Thr Asn Val Glu Val Leu Asp Ile Glu Ala
            645                 650                 655

Leu Asp Ile Ser Pro Leu Asp Ser Leu Asn Glu Lys Phe Asn Pro Lys
            660                 665                 670

Asp Val Ser Thr Leu Ser Val His Ser Ala Gly Thr Gln Thr Thr Gln
        675                 680                 685

Pro Pro Glu Tyr Gln Glu Asn Asp Ile Pro Gly Val Arg Asn Pro Pro
    690                 695                 700

His Ser Thr Leu Met Thr Asn Thr Lys Leu Val Trp Gly Leu Asn Arg
705                 710                 715                 720

Lys Glu Trp Gly Tyr Ile Leu Ile Gly Ser Leu Ala Ser Ile Ile Leu
            725                 730                 735

Gly Tyr Cys Tyr Pro Ala Met Ala Ile Ile Thr Gly Gln Thr Thr Gly
            740                 745                 750

Ser Met Val Leu Pro Pro Ser Glu Tyr Gly Lys Met Arg His Val Val
        755                 760                 765

Asn Ile Met Gly Trp Trp Tyr Phe Val Gly Cys Ile Ser Phe Met
    770                 775                 780

Thr Ala Phe Ile Thr Ile Ala Ala Leu Ser Leu Ala Ser Asp Lys Leu
785                 790                 795                 800
```

Val Lys Asn Ile Arg Leu Ala Leu Phe Arg Gln Leu Met Arg Met Asp
            805                 810                 815

Ile Ala Phe Phe Asp His Lys Asn Asn Thr Pro Gly Ala Leu Thr Ser
            820                 825                 830

Ile Leu Ala Lys Glu Ala Lys Met Ile Glu Gly Leu Ser Gly Ala Thr
            835                 840                 845

Leu Gly Gln Ile Gln Gln Ser Leu Val Thr Leu Ile Gly Gly Ile Val
850                 855                 860

Thr Gly Ile Pro Phe Asn Trp Arg Ile Gly Leu Val Ala Thr Ser Val
865                 870                 875                 880

Val Pro Val Met Leu Val Cys Gly Phe Val Arg Val Trp Val Leu Thr
            885                 890                 895

Gln Leu Ser Asp Arg Ala Arg Glu Val Tyr Glu Arg Ser Gly Ser Met
            900                 905                 910

Ala Ser Glu Tyr Thr Ser Ala Val Arg Thr Val Gln Ser Leu Thr Arg
            915                 920                 925

Glu Leu Asp Val Val Lys Tyr Thr Lys Thr Val Asp Ser Gln Ile
930                 935                 940

Phe Ser Ser Arg Ile Ala Ile Ala Arg Ser Ala Leu Tyr Tyr Ala Leu
945                 950                 955                 960

Ser Glu Gly Met Thr Pro Trp Val Val Ala Leu Val Phe Trp Trp Gly
            965                 970                 975

Ser Thr Val Met Arg Arg Gly Glu Ala Ser Val Ala Gly Tyr Met Thr
            980                 985                 990

Val Phe Met Ala Ile Ile Thr Gly Ser Gln Ala Ala Gly Gln Ile Phe
            995                 1000                1005

Ser Tyr Ala Pro Asn Met Asn Ser Ala Lys Asp Ala Ala Arg Asn
    1010                1015                1020

Ile Tyr Arg Ile Leu Thr Ala Thr Pro Ser Ile Asp Val Trp Ser
    1025                1030                1035

Glu Glu Gly Tyr Val Ala Pro Glu Glu Ser Val Arg Gly Asp Ile
    1040                1045                1050

Glu Phe Arg His Val Asn Phe Arg Tyr Pro Thr Arg Pro Gln Val
    1055                1060                1065

Pro Val Leu Gln Asp Leu Asn Leu Thr Val Lys Lys Gly Gln Tyr
    1070                1075                1080

Ile Ala Leu Val Gly Ala Ser Gly Cys Gly Lys Ser Thr Thr Ile
    1085                1090                1095

Gly Leu Val Glu Arg Phe Tyr Asp Pro Leu Ala Gly Gln Val Leu
    1100                1105                1110

Phe Asp Gly Lys Asp Leu Arg Glu Tyr Asn Leu Asn Ala Leu Arg
    1115                1120                1125

Ser His Ile Ala Leu Val Gln Gln Glu Pro Met Leu Tyr Ser Gly
    1130                1135                1140

Thr Leu Arg Glu Asn Ile Leu Met Gly Trp Ser Gly Pro Glu Ser
    1145                1150                1155

Glu Val Thr Gln Glu Met Ile Glu Asp Ala Ala Arg Lys Ala Asn
    1160                1165                1170

Ile His Glu Phe Ile Met Ser Leu Pro Asp Gly Tyr Glu Thr Leu
    1175                1180                1185

Ser Gly Ser Arg Gly Ser Leu Leu Ser Gly Gly Gln Lys Gln Arg
    1190                1195                1200

Ile Ala Ile Ala Arg Ala Leu Ile Arg Asn Pro Lys Val Leu Leu

```
                  1205                1210                1215

Leu Asp Glu Ala Thr Ser Ala Leu Asp Ser Ser Glu Lys Val
            1220                1225            1230

Val Gln Ala Ala Leu Asp Ala Ala Lys Gly Arg Thr Thr Ile
    1235                1240                1245

Ala Val Ala His Arg Leu Ser Thr Ile Gln Lys Ala Asp Val Ile
            1250                1255                1260

Tyr Val Phe Ser Gly Gly Arg Ile Val Glu Gln Gly Asp His Gln
        1265                1270                1275

Ser Leu Leu Glu Leu Asn Gly Trp Tyr Ala Glu Leu Val Asn Leu
            1280                1285                1290

Gln Gly Leu Gly Glu Ile
        1295

<210> SEQ ID NO 11
<211> LENGTH: 432
<212> TYPE: PRT
<213> ORGANISM: Candida bombicola

<400> SEQUENCE: 11

Met Ala Ile Glu Lys Pro Val Ile Val Ala Cys Ala Cys Pro Leu Ala
1               5                   10                  15

Gly His Val Gly Pro Val Leu Ser Leu Val Arg Gly Leu Leu Asn Arg
            20                  25                  30

Gly Tyr Glu Val Thr Phe Val Thr Gly Asn Ala Phe Lys Glu Lys Val
        35                  40                  45

Ile Glu Ala Gly Cys Thr Phe Val Pro Leu Gln Gly Arg Ala Asp Tyr
    50                  55                  60

His Glu Tyr Asn Leu Pro Glu Ile Ala Pro Gly Leu Leu Thr Ile Pro
65                  70                  75                  80

Pro Gly Leu Glu Gln Thr Gly Tyr Ser Met Asn Glu Ile Phe Val Lys
                85                  90                  95

Ala Ile Pro Glu Gln Tyr Asp Ala Leu Gln Thr Ala Leu Lys Gln Val
            100                 105                 110

Glu Ala Glu Asn Lys Ser Ala Val Val Ile Gly Glu Thr Met Phe Leu
        115                 120                 125

Gly Val His Pro Ile Ser Leu Gly Ala Pro Gly Leu Lys Pro Gln Gly
    130                 135                 140

Val Ile Thr Leu Gly Thr Ile Pro Cys Met Leu Lys Ala Glu Lys Ala
145                 150                 155                 160

Pro Gly Val Pro Ser Leu Glu Pro Met Ile Asp Thr Leu Val Arg Gln
                165                 170                 175

Gln Val Phe Gln Pro Gly Thr Asp Ser Glu Lys Glu Ile Met Lys Thr
            180                 185                 190

Leu Gly Ala Thr Lys Glu Pro Glu Phe Leu Leu Glu Asn Ile Tyr Ser
        195                 200                 205

Ser Pro Asp Arg Phe Leu Gln Leu Cys Pro Pro Ser Leu Glu Phe His
    210                 215                 220

Leu Thr Ser Pro Pro Gly Phe Ser Phe Ala Gly Ser Ala Pro His
225                 230                 235                 240

Val Lys Ser Ala Gly Leu Ala Thr Pro Pro His Leu Pro Ser Trp Trp
                245                 250                 255

Pro Asp Val Leu Ser Ala Lys Arg Leu Ile Val Val Thr Gln Gly Thr
            260                 265                 270
```

```
Ala Ala Ile Asn Tyr Glu Asp Leu Leu Ile Pro Ala Leu Gln Ala Phe
            275                 280                 285

Ala Asp Glu Glu Asp Thr Leu Val Val Gly Ile Leu Gly Val Lys Gly
290                 295                 300

Ala Ser Leu Pro Asp Ser Val Lys Val Pro Ala Asn Ala Arg Ile Val
305                 310                 315                 320

Asp Tyr Phe Pro Tyr Asp Glu Leu Leu Pro His Ala Ser Val Phe Ile
            325                 330                 335

Tyr Asn Gly Gly Tyr Gly Gly Leu Gln His Ser Leu Ser His Gly Val
            340                 345                 350

Pro Val Ile Ile Gly Gly Gly Met Leu Val Asp Lys Pro Ala Val Ala
            355                 360                 365

Ser Arg Ala Val Trp Ala Gly Val Gly Tyr Asp Leu Gln Thr Leu Gln
370                 375                 380

Ala Thr Ser Glu Leu Val Ser Thr Ala Val Lys Glu Val Leu Ala Thr
385                 390                 395                 400

Pro Ser Tyr His Glu Lys Ala Met Ala Val Lys Lys Glu Leu Glu Lys
            405                 410                 415

Tyr Lys Ser Leu Asp Ile Leu Glu Ser Ala Ile Ser Glu Leu Ala Ser
            420                 425                 430

<210> SEQ ID NO 12
<211> LENGTH: 4143
<212> TYPE: DNA
<213> ORGANISM: Artificial
<220> FEATURE:
<223> OTHER INFORMATION: IntegrationConstruct

<400> SEQUENCE: 12
aattgttcga tggatagctt tggagtctgt cccatcatga tacgaaaagc gtgaagctcc      60
tctgacaatc aaaactttgt tcaatgggg tgtaggatgg accccggatc caaacgaccg     120
cgagtcaaaa aacctacggg tgcatttacc cgtagttgat ctggaaagtc gagatcaact     180
ttttgtagtt tagttacatt catttcacgg tcgaaaaact cacacacaac gattgcagta     240
tatttaccaa aatcgtctga agagaagcat ctgattgaga gttcaccatg acgaatccca     300
taaacgacta ctccactgga cacaccgaca gacgccctgg ggatagtgaa actgaatttg     360
tcggtataat ggcccgtctc acaggccggg cagaacactt tcatgtcctt cgcaggtct     420
cgacattgga caagtatgtt gtcgtgggtg acgacaaatt ggtcctcatc cttgaataag     480
atgctccctt tgttctcagg aactggcacc attccattat gggcgaataa tttctgctca     540
tcttcgggac tgatgccata ttcttctaac agaagacggc gctcacatgg gacctggtgc     600
tctcgccggc ctctcaaatc gccggtgcat ctccacacgc aaattcacgg tgtatacccc    660
ctgatcaaac gtatcttgcg cgttctgtta ttcattggag cgagggcccg atcctgtcct     720
atcaaatgat ttcatgtggg aataatccat caattgttct ggattgaggt atacttcgag     780
ctgtaaagat gtcgcttcta tgtcaagaat agtcggttaa acgcactcct tcaagattta     840
catgatttac atgattcttc ataaagagca taaataaga actgcagcca ttcttgagta     900
aagtgctcag aataataaaa aggttgccac aggttgagtt aacatgggtt gattgaacca     960
attaaggagg gaacgtttct tccatgggag gctaagaaac ttaataactt cgtataatgt    1020
atgctatacg aagttattaa ttaactgacg ggcggatagt acaggctttg ccaaaagcct    1080
ataaggctaa agaaagtaaa caagtgaggt tgaaccatga tggcagtgtt cgaattctga    1140
tcaatgaagt acactgcgaa gggaatcccc gaaacggcga acaaaaagaa catcagagga    1200
```

```
ggaacgccct cgcaatcccg aacataccag tttcgcagaa cctggggtat caactggatg   1260
caccagcata ctgttcccac tgttgccaat gctgtagacg ctccattgtt gtcagtcatt   1320
ttagcatttt acagtaacca actccaaaaa acagcccgct ctgctgggaa gacttcgcaa   1380
ttatttatcc actactgctg cggttatata cttctcgatc tcagtctcgg ttataattgc   1440
cgcttgacag cctggagaaa ttcggatact ccacgtgata attgccatag gcataatttt   1500
tcgaaacagc tcgcaacgat ctcggctagt tttccccttt tttgacccat atcgacgctg   1560
agactcactc acttgatgcc taccgttagg gtaaattttt caagcctgca gaatatcgcg   1620
ggacgcagtc tcctgcacgc gcgtgacttc atcttactta catcaaacag cccgattaat   1680
ttgaaaagtc ctagctgatc gagggcacgg gcactactgt agagaaataa tatgaagctg   1740
agctatgagg agcgccgaga gaggctgccg gctgtagcag cccggctatt cgacatcatt   1800
gtgagcaagc aaacaaatct tgcgcaagc ttggatgtgc gaactacctc tgagttactg   1860
agtatcctgg accgcattgg accttacatt tgtatggtta agaccacat tgacataatt   1920 gacgacttcg aatacgacac aactgtcagc ggtttgaaac agctttcaac gaagcacaat   1980
tttctcattt ttgaagaccg aaagttcgca gacatcggtt ccactgttaa ggcccaatat   2040
gcaggtggag tgtttaagat cgctcaatgg gctgatataa caaatgctca cggtgttcct   2100
gggccgggaa ttgtgagcgg actagaagag gctgcgaagg aaactacgga tgaacctcgc   2160
ggccttgtca tgcttgcaga actgagttcg aagggcacac tggctcacgg cgaatactcg   2220
caagcgacag tagacatcgc tcgcagtaac cgcgcatttg tgtttggttt catcgctcag   2280
caaaaagtcg gaaagccaga ggaagactgg gtcattatga ctcctggggt gggcctggac   2340
gacaaaggtg atggattggg gcagcagtat cgtactgtgg acgacgtcat agagaccggc   2400
acagacgtta ttatcgtcgg acgcgggctc tatagcaagg gacgagatcc tgtgcacgaa   2460
gctcagcgtt accaaaaggc gggctggaat gcatatctga gaaaagttca gtcaagatga   2520
ttttctcaaa cagttccttc aatgcaactt gcacatgaat acctataaaa tctgattaaa   2580
ttaccataaa aggtacagat taaaatatat atgccttcaa tggcatcctt cgcgattctg   2640
attcgtcagc acacttcaac cttcctacta tgagtgacag tgatgatgat ctgctggcat   2700
tggccgacgt tggctccgac tccgaagagg aaatctcgct gccgtcgccg ccaagcaatg   2760
aggtcgtcaa tccctatcct ctagaaggca atatctcga tgctgaagac agggcgaagt   2820
tggacgcgct gccagagatt gagcgagaag agatcttgta tgaccgagct caggagatgc   2880
agcggtacga ggagagaagg tatcttgctc agcgaaggaa gcagatgacg cgggttgctg   2940
acgaggacga agcccctcc gccaagcgtc aacggggtac aacaggcgtc tcttcgggta   3000
cgaagtcatc tcttgaggca ttaaagaaac gaagggccca gcagtctcgg aagtcctcac   3060
gccatggagt tgatgacgat gtgtatagtg acgatgatgt taattaataa cttcgtataa   3120
tgtatgctat acgaagttat atatgtactt ttcaatatga taaacggaga ataacgccc   3180 ggctctatat gcaagctgca tcaaccctaa tatatattag cgagtttctc atgcaggctg   3240
tagtttgagt cgctgtaacc tcagcctcaa gactcttaca ccataggtag agtttcgtca   3300
ctgggaaact cagttactat ctaaaccaaa ctgtgctaat gctcaaacct atcactcaga   3360
atttagattg aatcaatcta agtctgttga gaaacagata tgcatcaggg gcacagacta   3420
aaagctgctc tcagcgagta cccttacctc ttgagaaccc tcaaaattta cccagcctgc   3480
agcatatcat gcaccatggt taaattcgga aatgaattta ccggtggcct tgaaccacgt   3540
```

```
tcctccaatt atttaaggca ataacctgcc actctcttga tttgattaag aaagactttc    3600
aatttagctt ctccctacga atattcaatg agcccttcat cacacaaacc cctgattctc    3660
gcttgcggct tgcctctttc aggccatata atgcccgttt tgagtctggt acacggcctt    3720
acggacgacg gatacgaagc tactgttgtg acaggcagag cgtttgaaca aaaagttcga    3780
gatgtgggtg cagactttgt tcctttagaa gggaacgcag attttgatga ccacaccta    3840 gacgatctgg tcccgggccg taaagacatg gccccaagct tcgatcgtac agttcaagat    3900
gtggagcaca tgatggtagc tactcttcct gagcagtttg ccgctattca gagggctttc    3960
aaaaagctca gcgcaagcgg ccgccctgtc gttcttgtca gtgaagtgct gttttcggt     4020 gcacaccta tcagcctcgg tgctcctggt ttcaaacccg ctggctggat tgtttaggg     4080 gttttgcctc ttttgatccg cagtgatcat accttaggac ttgacaacga caggagcccc    4140
gaa                                                                   4143
```

<210> SEQ ID NO 13
<211> LENGTH: 4143
<212> TYPE: DNA
<213> ORGANISM: Artificial
<220> FEATURE:
<223> OTHER INFORMATION: IntegrationConstruct

<400> SEQUENCE: 13

```
gaaatctgat caattctgca aacctgatct ttagtgaact gaggtctcaa catcgatcga      60
gactgtttcc atccatttcc gctgagtgta aatatccctt ggccaaacac ttttcccact     120
gtgtggaaac gtgctccaag accaaaatca ttgaatttgg ttgccaggat tgtcttaatg     180
ttttctggct cgattgtgaa gatttggtat tgaaggggag cttgtcgaag atacgtccgt     240
gctttgaact tattgaagac tctgtcgtat tgaacttcca gtaaggtgta tgacttggcc     300
gtcttgatca tgtccatggt tctttgtatt cccagtggga acgatttctc aatgaagcga     360
ggcatactac acttgtgcct acgtgctgca tagcggtacc ataggagcca gataggctcg     420
tgtagaacta agaaagctac gaagagcagt ggcaacaagc cagcaacagc ggataaactc     480
attggagtta gaataatgtc tttgattaac atatatgtac ttttcaatat gataaacgga     540
gaaataacgc ccggctctat atgcaagctg catcaaccct aatatatatt agcgagtttc     600
tcatgcaggc tgtagtttga gtcgctgtaa cctcagcctc aagactctta caccataggt     660
agagtttcgt cactgggaaa ctcagttact atctaaacca aactgtgcta atgctcaaac     720
ctatcactca gaatttagat tgaatcaatc taagtctgtt gagaaacaga tatgcatcag     780
gggcacagac taaaagctgc tctcagcgag tacccttacc tcttgagaac cctcaaaatt     840
tacccagcct gcagcatatc atgcaccatg gttaaattcg gaatgaatt taccggtggc     900 cttgaaccac gttcctccaa ttatttaagg caataacctg ccactctctt gatttgatta     960
agaaagactt tcaatttagc ttctccctac gaatattcaa taacttcgta taatgtatgc    1020
tatacgaagt tattaattaa ctgacgggcg gatagtacag gctttgccaa aagcctataa    1080
ggctaaagaa agtaaacaag tgaggttgaa ccatgatggc agtgttcgaa ttctgatcaa    1140
tgaagtacac tgcgaaggga atccccgaaa cggcgaacaa aaagaacatc agaggaggaa    1200
cgccctcgca atcccgaaca taccagtttc gcagaacctg gggtatcaac tggatgcacc    1260
agcatactgt tccccactgtt gccaatgctg tagacgctcc attgttgtca gtcattttag    1320
cattttacag taaccaactc caaaaaacag cccgctctgc tgggaagact tcgcaattat    1380
ttatccacta ctgctgcggt tatatacttc tcgatctcag tctcggttat aattgccgct    1440
```

```
tgacagcctg gagaaattcg gatactccac gtgataattg ccatagggca taattttcga    1500
aacagctcgc aacgatctcg gctagttttc ccctttttg acccatatcg acgctgagac     1560
tcactcactt gatgcctacc gttagggtaa attttcaag cctgcagaat atcgcgggac     1620
gcagtctcct gcacgcgcgt gacttcatct tacttacatc aaacagcccg attaatttga    1680
aaagtcctag ctgatcgagg gcacgggcac tactgtagag aaataatatg aagctgagct    1740
atgaggagcg ccgagagagg ctgccggctg tagcagcccg gctattcgac atcattgtga    1800
gcaagcaaac aaatctttgc gcaagcttgg atgtgcgaac tacctctgag ttactgagta    1860
tcctggaccg cattggacct tacatttgta tggttaagac ccacattgac ataattgacg    1920
acttcgaata cgacacaact gtcagcggtt tgaaacagct ttcaacgaag cacaattttc    1980 tcattttga agaccgaaag ttcgcagaca tcggttccac tgttaaggcc caatatgcag     2040
gtggagtgtt taagatcgct caatgggctg atataacaaa tgctcacggt gttcctgggc    2100
cgggaattgt gagcggacta aagaggctg cgaaggaaac tacggatgaa cctcgcggcc     2160
ttgtcatgct tgcagaactg agttcgaagg gcacactggc tcacggcgaa tactcgcaag    2220
cgacagtaga catcgctcgc agtaaccgcg catttgtgtt tggtttcatc gctcagcaaa    2280
aagtcggaaa gccagaggaa gactgggtca ttatgactcc tggggtgggc ctggacgaca    2340
aaggtgatgg attggggcag cagtatcgta ctgtggacga cgtcatagag accggcacag    2400
acgttattat cgtcggacgc gggctctata gcaagggacg agatcctgtg cacgaagctc    2460
agcgttacca aaaggcgggc tggaatgcat atctgagaaa agttcagtca agatgatttt    2520
ctcaaacagt tccttcaatg caacttgcac atgaatacct ataaaatctg attaaattac    2580
cataaaaggt acagattaaa atatatatgc cttcaatggc atccttcgcg attctgattc    2640
gtcagcacac ttcaaccttc ctactatgag tgacagtgat gatgatctgc tggcattggc    2700
cgacgttggc tccgactccg aagaggaaat ctcgctgccg tcgccgccaa gcaatgaggt    2760
cgtcaatccc tatcctctag aaggcaaata tctcgatgct gaagacaggg cgaagttgga    2820
cgcgctgcca gagattgagc gagaagagat cttgtatgac cgagctcagg agatgcagcg    2880
gtacgaggag agaaggtatc ttgctcagcg aaggaagcag atgacgcggg ttgctgacga    2940
ggacgaagcc ccctccgcca agcgtcaacg gggtacaaca ggcgtctctt cgggtacgaa    3000
gtcatctctt gaggcattaa agaaacgaag ggcccagcag tctcggaagt cctcacgcca    3060
tggagttgat gacgatgtgt atagtgacga tgatgttaat taataacttc gtataatgta    3120
tgctatacga agttattaga atcgtacgat caaatcagat cagggaagag aggtagggtt    3180
ttttttattt atgtctttgt ttttattgat tgaaatttac aatacaacaa ccatcaaatt    3240
aatttgaaca aacaacaaca cacacacaca ctgcaacttt caaaaaaata agtaaaagga    3300
agagaggagt ttgccaatat atttaccttc ttctaattct gttatttttt ttaattgttt    3360
tgtggaaaga aagaagaaaa ggctgtcatg aatttagttt acctagacct tctggttagc    3420
ggtattgacg ttcatttcaa ctggaagaag gaattccagt tcctctcctt cagcctcgtc    3480
gggatcctcc tctggaatat gcttgaggat tcgcgcaggg actcctccca ccacagtacg    3540
aggaggaaca tcttctcgaa cgacagcacc agccgcaatt gttgagccat ctccaatcgt    3600
aacacccggc aggacagtca cattcgcacc aatccataca ttattcccca ccttgatagg    3660
aagagcatac acaattctcc tcgcacgttt ctcggggcta ataggatgag tcgcagtcac    3720
gaacgttgta ttgggcccta caatcacctc atcaccaaag attattggag ccgagtccaa    3780
```

```
gaagcaaacg ttgaagttgg cgtaaaagtg ctcgcctacg ctgatgttga atccaaaatc   3840
aactgagaat ggagcggtca gccagacaat atcctttgtt tgaccaaaag tgtctttgag   3900
aatctcgacc ttcttgatat aagcagcgtg atttgactca aaagtacgac tttcacttgc   3960
aatggtattg aactccctaa cttttctcact agtagccagg gctctaaaca taagatctgg   4020
atcgtatgga ttgtaaggaa ctcctgagac catcttctca tagttttcat tgccaggggt   4080
gtttttgagg ttttttttgg cccaagagac catttcctgg tcaatttctt ttctaggagt   4140
cat                                                                  4143
```

<210> SEQ ID NO 14
<211> LENGTH: 4140
<212> TYPE: DNA
<213> ORGANISM: Artificial
<220> FEATURE:
<223> OTHER INFORMATION: IntegrationConstruct

<400> SEQUENCE: 14

```
tgcagacaag ttcctgcagc tgtgcccgcc ttctcttgag ttcagcagag accatctgcc     60
tagcaacttc aaattcgccg gctcaacgcc caagcaccga actcaattca cccctccttc    120
ctggtggggg gatgttctga gtgccaagcg agtcatcatg gtcactcaag gaacttttgc    180
tgtcagttac aagcatctta ttgtgcctac tcttgaggcc ttgaaggacg agcctgacac    240
tttaacagta gccatattgg gccgccgcgg tgccaagcta ccggatgatg ttgtggttcc    300
tgagaatgct cgcgtgatcg actacttcaa ctacgatgct ctacttcctc acgttgatgc    360
tcttgtctac aatggtggat atggcggact tcagcacagc ttaagccact ctgttccagt    420
tgttattgct ggtgactctg aagacaagcc aatggtggca tcgagagctg aggccgctgg    480
cgtggcaatt gatttgaaaa ctggcttgcc tacagtggac caaatcaaag aagctgttga    540
ttcgataatt ggaaatccga attccacga agcctcgaag aaggttcaaa tggagttgga    600
aagccacaac tccttgaaaa ttcttgagga agcatcgag gaaatcgcca gccatgactt    660
tggtcttttg accaagagtg acgaggaaac tgaagatata cctgtcaaag ggccggcctt    720
agcggtgagt tcttagaatc gtacgatcaa atcagatcag ggaagagagg tagggttttt    780
tttatttatg tctttgtttt tattgattga aatttacaat acaacaacca tcaaattaat    840
ttgaacaaac aacaacacac acacacactg caactttcaa aaaataagt aaaaggaaga    900 gaggagtttg ccaatatatt taccttcttc taattctgtt attttttta attgttttgt    960 ggaaagaaag aagaaaaggc tgtcatgaat ttagtttacc taataacttc gtataatgta   1020
tgctatacga agttattaat taactgacgg gcggatagta caggctttgc caaaagccta   1080
taaggctaaa gaaagtaaac aagtgaggtt gaaccatgat ggcagtgttc gaattctgat   1140
caatgaagta cactgcgaag ggaatccccg aaacggcgaa caaaagaac atcagaggag   1200 gaacgccctc gcaatcccga acataccagt ttcgcagaac ctggggtatc aactggatgc   1260
accagcatac tgttcccact gttgccaatg ctgtagacgc tccattgttg tcagtcattt   1320
tagcatttta cagtaaccaa ctccaaaaaa cagcccgctc tgctgggaag acttcgcaat   1380
tatttatcca ctactgctgc ggttatatac ttctcgatct cagtctcggt tataattgcc   1440
gcttgacagc ctggagaaat tcggatactc cacgtgataa ttgccatagg cataattttt   1500
cgaaacagct cgcaacgatc tcggctagtt ttccccttttt ttgacccata tcgacgctga   1560
gactcactca cttgatgcct accgttaggg taaattttc aagcctgcag aatatcgcgg   1620
gacgcagtct cctgcacgcg cgtgacttca tcttacttac atcaaacagc ccgattaatt   1680
```

```
tgaaaagtcc tagctgatcg agggcacggg cactactgta gagaaataat atgaagctga    1740
gctatgagga gcgccgagag aggctgccgg ctgtagcagc ccggctattc gacatcattg    1800
tgagcaagca aacaaatctt tgcgcaagct tggatgtgcg aactacctct gagttactga    1860
gtatcctgga ccgcattgga ccttacattt gtatggttaa acccacatt gacataattg     1920
acgacttcga atacgacaca actgtcagcg gtttgaaaca gctttcaacg aagcacaatt    1980
ttctcatttt tgaagaccga aagttcgcag acatcggttc cactgttaag gcccaatatg    2040
caggtggagt gtttaagatc gctcaatggg ctgatataac aaatgctcac ggtgttcctg    2100
ggccgggaat tgtgagcgga ctagaagagg ctgcgaagga aactacggat gaacctcgcg    2160
gccttgtcat gcttgcagaa ctgagttcga agggcacact ggctcacggc gaatactcgc    2220
aagcgacagt agacatcgct cgcagtaacc gcgcatttgt gtttggtttc atcgctcagc    2280
aaaaagtcgg aaagccagag gaagactggg tcattatgac tcctggggtg ggcctggacg    2340
acaaggtga tggattgggg cagcagtatc gtactgtgga cgacgtcata gagaccggca     2400
cagacgttat tatcgtcgga cgcgggctct atagcaaggg acgagatcct gtgcacgaag    2460
ctcagcgtta ccaaaaggcg ggctggaatg catatctgag aaaagttcag tcaagatgat    2520
tttctcaaac agttccttca atgcaacttg cacatgaata cctataaaat ctgattaaat    2580
taccataaaa ggtacagatt aaaatatata tgccttcaat ggcatccttc gcgattctga    2640
ttcgtcagca cacttcaacc ttcctactat gagtgacagt gatgatgatc tgctggcatt    2700
ggccgacgtt ggctccgact ccgaagagga aatctcgctg ccgtcgccgc caagcaatga    2760
ggtcgtcaat ccctatcctc tagaaggcaa atatctcgat gctgaagaca gggcgaagtt    2820
ggacgcgctg ccagagattg agcgagaaga gatcttgtat gaccgagctc aggagatgca    2880
gcggtacgag gagagaaggt atcttgctca gcgaaggaag cagatgacgc gggttgctga    2940
cgaggacgaa gcccctccg ccaagcgtca acggggtaca acaggcgtct cttcgggtac     3000
gaagtcatct cttgaggcat aaagaaacg aagggcccag cagtctcgga agtcctcacg     3060
ccatggagtt gatgacgatg tgtatagtga cgatgatgtt aattaataac ttcgtataat    3120
gtatgctata cgaagttatt gaattctaga atgtgaggtg gaatgaggca aggaaggagg    3180
aacgtattga gttgtacctt aagatatctc aaagtgctta tctccgacta ccggaatatg    3240
ctccgggtaa tgcaagtcag tgtgcatatg ggtaaggtga tgcaagctaa ccctcagggc    3300
atatctaatt cgcgtgaggg ttattattgg tctacattac ctcagtcata gcccgtcaaa    3360
gcaaaagccc aaaatcagca cgaaatccca gagatagatt gttgctgtct cttcaagtac    3420
tacgacagtt ccctatatct acagattatc gtcacgagtg aattatgcag gataggtgac    3480
tcaggggtca taatcagagg aatccaatgt gctatttcaa ttaacgagtc cctttaatca    3540
gacaatgtat ggtgactcag gggccataac tagagaaatt cgatatgcta tttcaattaa    3600
tgagtgcctt taatcaaata atgtatgcaa gcagtggcca aaaataaatg aacgtcaaat    3660
ctctccgaga ccttgcaagt tcaccaattc agcgtaccat ccattgagtt caaggaggct    3720
ctgatggtcg ccctgctcca cgatgcgccc tcctgagaac acatatatga catctgcttt    3780
ctgaattgtt gataatctat gcgcaacggc gattgtagta cggcccttcg ctgctgcgtc    3840
gagtgctgct tgaactactt tctcagattc ggaatccaga gctgaggtgg cctcatcgag    3900
gaggagtacc tttggatttc tgatcagggc ccttgcaatt gcaattcgct gcttttgccc    3960
cccagatagc aacgatcccc tagatccgct gagcgtttcg tagccatcag gcaacgacat    4020
```
gatgaattcg tgaatgttcg ctttgcgagc ggcatcctca atcatctcct gcgttacttc    4080
agactcaggg ccagaccatc ccattagaat attctcacgt agcgtgcctg aataaagcat    4140

<210> SEQ ID NO 15
<211> LENGTH: 4130
<212> TYPE: DNA
<213> ORGANISM: Artificial
<220> FEATURE:
<223> OTHER INFORMATION: IntegrationConstruct

<400> SEQUENCE: 15
ggatgagtcg cagtcacgaa cgttgtattg ggccctacaa tcacctcatc accaaagatt      60
attggagccg agtccaagaa gcaaacgttg aagttggcgt aaaagtgctc gcctacgctg     120
atgttgaatc caaatcaac tgagaatgga gcggtcagcc agacaatatc ctttgtttga     180
ccaaaagtgt ctttgagaat ctcgaccttc ttgatataag cagcgtgatt tgactcaaaa     240
gtacgacttt cacttgcaat ggtattgaac tccctaactt tctcactagt agccagggct     300
ctaaacataa gatctggatc gtatggattg taaggaactc ctgagaccat cttctcatag     360
ttttcattgc cagggtgtt tttgaggttt tttttggccc aagagaccat ttcctggtca     420
atttcttttc taggagtcat tcctttgttt tgagggtcct tcgaggagtt tacaaccatt     480
gaattctaga atgtgaggtg gaatgaggca aggaaggagg aacgtattga gttgtacctt     540
aagatatctc aaagtgctta tctccgacta ccggaatatg ctccgggtaa tgcaagtcag     600
tgtgcatatg ggtaaggtga tgcaagctaa ccctcagggc atatctaatt cgcgtgaggg     660
ttattattgg tctacattac ctcagtcata gcccgtcaaa gcaaaagccc aaaatcagca     720
cgaaatccca gagatagatt gttgctgtct cttcaagtac tacgacagtt ccctatatct     780
acagattatc gtcacgagtg aattatgcag gataggtgac tcagggtca taatcagagg     840 aatccaatgt gctatttcaa ttaacgagtc cctttaatca gacaatgtat ggtgactcag     900
gggccataac tagagaaatt cgatatgcta tttcaattaa tgagtgcctt taatcaaata     960
atgtatgcaa gcagtggcca aaaataaatg aacgtcaata acttcgtata atgtatgcta    1020
tacgaagtta ttaattaact gacgggcgga tagtacaggc tttgccaaaa gcctataagg    1080
ctaaagaaag taaacaagtg aggttgaacc atgatggcag tgttcgaatt ctgatcaatg    1140
aagtacactg cgaagggaat ccccgaaacg gcgaacaaaa agaacatcag aggaggaacg    1200
ccctcgcaat cccgaacata ccagtttcgc agaacctggg gtatcaactg gatgcaccag    1260
catactgttc ccactgttgc caatgctgta gacgctccat tgttgtcagt catttttagca    1320 ttttacagta accaactcca aaaacagcc cgctctgctg ggaagacttc gcaattattt    1380
atccactact gctgcggtta tacttctc gatctcagtc tcggttataa ttgccgcttg    1440
acagcctgga gaaattcgga tactccacgt gataattgcc atagggcata attttcgaaa    1500
cagctcgcaa cgatctcggc tagttttccc cttttttgac ccatatcgac gctgagactc    1560
actcacttga tgcctaccgt tagggtaaat ttttcaagcc tgcagaatat cgcgggacgc    1620
agtctcctgc acgcgcgtga cttcatctta cttacatcaa acagcccgat taatttgaaa    1680
agtcctagct gatcgagggc acgggcacta ctgtagagaa ataatatgaa gctgagctat    1740
gaggagcgcc gagagaggct gccggctgta gcagcccggc tattcgacat cattgtgagc    1800
aagcaaacaa atctttgcgc aagcttggat gtgcgaacta cctctgagtt actgagtatc    1860
ctggaccgca ttggacctta catttgtatg gttaagaccc acattgacat aattgacgac    1920
ttcgaatacg acacaactgt cagcggtttg aaacagcttt caacgaagca caattttctc    1980

```
attttttgaag accgaaagtt cgcagacatc ggttccactg ttaaggccca atatgcaggt    2040
ggagtgttta agatcgctca atgggctgat ataacaaatg ctcacggtgt tcctgggccg    2100
ggaattgtga gcggactaga agaggctgcg aaggaaacta cggatgaacc tcgcggcctt    2160
gtcatgcttg cagaactgag ttcgaagggc acactggctc acggcgaata ctcgcaagcg    2220
acagtagaca tcgctcgcag taaccgcgca tttgtgtttg gtttcatcgc tcagcaaaaa    2280
gtcggaaagc cagaggaaga ctgggtcatt atgactcctg gggtgggcct ggacgacaaa    2340
ggtgatggat tggggcagca gtatcgtact gtggacgacg tcatagagac cggcacagac    2400
gttattatcg tcggacgcgg gctctatagc aagggacgag atcctgtgca cgaagctcag    2460
cgttaccaaa aggcgggctg aatgcatat ctgagaaaag ttcagtcaag atgattttct    2520
caaacagttc cttcaatgca acttgcacat gaatacctat aaaatctgat taaattacca    2580
taaaaggtac agattaaaat atatatgcct tcaatggcat ccttcgcgat tctgattcgt    2640
cagcacactt caaccttcct actatgagtg acagtgatga tgatctgctg cattggccg    2700 acgttggctc cgactccgaa gaggaaatct cgctgccgtc gccgccaagc aatgaggtcg    2760
tcaatcccta tcctctagaa ggcaaatatc tcgatgctga agacagggcg aagttggacg    2820
cgctgccaga gattgagcga aagagatct tgtatgaccg agctcaggag atgcagcggt    2880
acgaggagag aaggtatctt gctcagcgaa ggaagcagat gacgcgggtt gctgacgagg    2940
acgaagcccc ctccgccaag cgtcaacggg gtacaacagg cgtctcttcg ggtacgaagt    3000
catctcttga ggcattaaag aaacgaaggg cccagcagtc tcggaagtcc tcacgccatg    3060
gagttgatga cgatgtgtat agtgacgatg atgttaatta ataacttcgt ataatgtatg    3120
ctatacgaag ttataagcca aaatcagaga gtgggacctg attcagaatc acacggaccc    3180
gtatatataa caatcacttt ccaacaatat agcgagtatt aatatatttc cgggtaaggg    3240
ttgttccgga cttatgcatt taatcacagg ttgcatcagc taaatatgtc agggccgacg    3300
gcgtaaattt agaaggttag gtcaagatcc atcggtcagg ccaatggagc tctactatga    3360
taggcagctg aagcgagaca agatatactt cagttgcgct ctctgaaaaa attattttgt    3420
gattctcact cagtggatgt ggcgacacac ggaaccaata atctcgccgg aaaggcggct    3480
gaacatcagt cttgcataag tgtgcaagtg gcctgagcac agcgtgcatt acccttacca    3540
tacattcggg gcaagttaaa tccagcatta tataaacttg attgacacaa atgggcataa    3600
aacaataaag tctcctatat ggccatcgag aaaccagtga tagttgcttg tgcctgccca    3660 ctagcgggc acgtgggccc agtgctcagc ctggtccgcg gtctactcaa tagaggatat    3720
gaggtgactt tcgtaacagg gaacgcattc aaggagaaag ttattgaggc aggatgcact    3780
ttcgtccctc tccaaggacg agctgactac catgaataca atctccctga aatcgctcca    3840
ggattgctca cgattcctcc aggccttgag cagaccggtt actcaatgaa tgagattttt    3900
gtgaaggcga ttcctgagca gtacgatgca cttcaaactg ctctaaaaca ggttgaggct    3960
gaaaataaat cagctgtggt gattggcgag accatgtttc taggggtgca tccgatatca    4020
ctgggtgccc caggtctcaa gccccaaggc gtaatcacgt taggaactat tccgtgcatg    4080
ctgaaagcag agaaggcgcc tggagttcct agtcttgagc caatgattga              4130
```

<210> SEQ ID NO 16
<211> LENGTH: 4141
<212> TYPE: DNA
<213> ORGANISM: Artificial
<220> FEATURE:

<223> OTHER INFORMATION: IntegrationConstruct

<400> SEQUENCE: 16

```
attctggtgc tgacctcgcc accacctagt ttgtcgtaaa acgcgatatt ctggcgaata    60
acagcactca gataatgctt tcggtaacgt cctgccaaca cttcgcctct gtccacaagc   120
aggaagctct cgagaaacgc actgccgagc ataccaatgc caatatagac aaaatagaga   180
gacaggtgat tcaccttatg ctggaactca ttgcccttga ggtcatatga agtgaagtct   240
ctgaatgtgt tgaagatggc gcccactact aacgtgaaca ttggaagcgc ggctccatgc   300
accgctgcaa aaaaagcgc aagtatctcc aagaaacgt caaggggagt gcaaaatctg     360
aacaacctga aaaagcttgt ggcgactctc tttgtttcaa gctgacttcg caatacattg   420
gcctcatgtg gatctaacgc agagagcttc tcctcgagaa gcttgtcctt agtctcgatg   480
agtttctcac gcttctctac ctgtatatca tccaccataa gccaaaatca gagagtggga   540
cctgattcag aatcacacgg acccgtatat ataacaatca ctttccaaca atatagcgag   600
tattaatata tttccgggta agggttgttc cggacttatg catttaatca caggttgcat   660
cagctaaaata tgtcagggcc gacggcgtaa atttagaagg ttaggtcaag atccatcggt   720
caggccaatg gagctctact atgataggca gctgaagcga gacaagatat acttcagttg   780
cgctctctga aaaattatt ttgtgattct cactcagtgg atgtggcgac acacggaacc    840
aataatctcg ccggaaaggc ggctgaacat cagtcttgca taagtgtgca agtggcctga   900
gcacagcgtg cattacccct accatacatt cgggcaagt taaatccagc attatataaa    960
cttgattgac acaaatgggc ataaaacaat aaagtctcct atataacttc gtataatgta  1020
tgctatacga agttattaat taactgacgg gcggatagta caggctttgc caaaagccta  1080
taaggctaaa gaaagtaaac aagtgaggtt gaaccatgat ggcagtgttc gaattctgat  1140
caatgaagta cactgcgaag ggaatccccg aaacggcgaa caaaaagaac atcagaggag  1200
gaacgccctc gcaatcccga acataccagt ttcgcagaac ctggggtatc aactggatgc  1260
accagcatac tgttcccact gttgccaatg ctgtagacgc tccattgttg tcagtcattt  1320
tagcatttta cagtaaccaa ctccaaaaaa cagcccgctc tgctgggaag acttcgcaat  1380
tatttatcca ctactgctgc ggttatatac ttctcgatct cagtctcggt tataattgcc  1440
gcttgacagc ctggagaaat tcggatactc acgtgataa ttgccatagg gcataatttt    1500
cgaaacagct cgcaacgatc tcggctagtt ttcccctttt ttgacccata tcgacgctga  1560
gactcactca cttgatgcct accgttaggg taaattttc aagcctgcag aatatcgcgg    1620
gacgcagtct cctgcacgcg cgtgacttca tcttacttac atcaaacagc ccgattaatt  1680
tgaaaagtcc tagctgatcg agggcacggg cactactgta gagaaataat atgaagctga  1740
gctatgagga gcgccgagag aggctgccgg ctgtagcagc ccggctattc gacatcattg  1800
tgagcaagca aacaaatctt tgcgcaagct tggatgtgcg aactacctct gagttactga  1860
gtatcctgga ccgcattgga ccttacattt gtatggttaa gacccacatt gacataattg  1920
acgacttcga atacgacaca actgtcagcg gtttgaaaca gctttcaacg aagcacaatt  1980
ttctcatttt tgaagaccga agttcgcag acatcggttc cactgttaag gcccaatatg    2040
caggtggagt gtttaagatc gctcaatggg ctgatataac aaatgctcac ggtgttcctg  2100
ggccgggaat tgtgagcgga ctagaagagg ctgcgaagga aactacggat gaacctcgcg  2160
gccttgtcat gcttgcagaa ctgagttcga agggcacact ggctcacggc gaatactcgc  2220
aagcgacagt agacatcgct cgcagtaacc gcgcatttgt gtttggtttc atcgctcagc  2280
```

```
aaaaagtcgg aaagccagag gaagactggg tcattatgac tcctggggtg ggcctggacg   2340
acaaaggtga tggattgggg cagcagtatc gtactgtgga cgacgtcata gagaccggca   2400
cagacgttat tatcgtcgga cgcgggctct atagcaaggg acgagatcct gtgcacgaag   2460
ctcagcgtta ccaaaggcg ggctggaatg catatctgag aaaagttcag tcaagatgat    2520
tttctcaaac agttccttca atgcaacttg cacatgaata cctataaaat ctgattaaat   2580
taccataaaa ggtacagatt aaaatatata tgccttcaat ggcatccttc gcgattctga   2640
ttcgtcagca cacttcaacc ttcctactat gagtgacagt gatgatgatc tgctggcatt   2700
ggccgacgtt ggctccgact ccgaagagga aatctcgctg ccgtcgccgc caagcaatga   2760
ggtcgtcaat ccctatcctc tagaaggcaa atatctcgat gctgaagaca gggcgaagtt   2820
ggacgcgctg ccagagattg agcgagaaga gatcttgtat gaccgagctc aggagatgca   2880
gcggtacgag gagagaaggt atcttgctca gcgaaggaag cagatgacgc gggttgctga   2940
cgaggacgaa gcccctccg ccaagcgtca acggggtaca acaggcgtct cttcgggtac    3000
gaagtcatct cttgaggcat taagaaacg aagggcccag cagtctcgga agtcctcacg    3060
ccatggagtt gatgacgatg tgtatagtga cgatgatgtt aattaataac ttcgtataat   3120
gtatgctata cgaagttatt aacctggctc tttttctaga tatgtctgcg ccctgctcac   3180
tgcttactgg cctaagctgg tattacggac cttaatcaag tatcacccca aggcaatcga   3240
gagtcttatc gagtctctag gtagatagat acacgttttg atttttcggc ccactttgta   3300
gaaaaatctc agtgatttca tggaattcag ttacaaatac taatctgata aaccaagaac   3360
tacactcggt gttgagagca gaattaaagg gacttggcgt ctagcacaaa acgatacttg   3420
acgtcaccac tgtgaacgcg cttccaagct tcggcgatat agctgtactc aatcagctca   3480
acatcacagg tgatgttatt tcaccacag aagtccagca tctcctgagt ctctggcaag    3540
ccaccaatgt ttgagtaagt gatagattta tttccagcca aatgagaggt cagaaccttg   3600
aggggtccaa tttgaccaac aacaacgaga caccaccaa tatcaaggga cttgaggtat    3660
ggctcgaagt cgtgttcaaa gggaatggtg tcgatgatca ggtcaaatgt gccagcgacc   3720
gcctcgagct cattcggatc agaggaagca actacgcggc tagcaccttg tgctttcgct   3780
cctgcggctt tggcgtgact cctgctgaac agtgtgactt cagagcccat ggctgaggca   3840
aatttgatag ccatggaacc aaggcctccg agaccaacta caccgactct ttttccaggt   3900
ccggcgccgt gagccctcag aggagagtag gtagtgatac cagcacagag aagggggcgca   3960 gaagctgcca agtcgaggtt ggaggggatt ttgagcacaa actcctcgcg agcaagaatg   4020
tgttgcgaat accctcccctt cgtgacttcc ccgttctttc cgctggaatt gtaagtttga   4080
gtgcgtgaaa cacaccaatt ttctttgcct aatttacagt tcttgcaagt acgacatgag   4140
t                                                                  4141
```

<210> SEQ ID NO 17
<211> LENGTH: 27
<212> TYPE: DNA
<213> ORGANISM: Artificial
<220> FEATURE:
<223> OTHER INFORMATION: Primer

<400> SEQUENCE: 17
aattgttcga tggatagctt tggagtc                                        27

<210> SEQ ID NO 18

```
<211> LENGTH: 21
<212> TYPE: DNA
<213> ORGANISM: Artificial
<220> FEATURE:
<223> OTHER INFORMATION: Primer

<400> SEQUENCE: 18
ttcggggctc ctgtcgttgt c                                              21

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
gaaatctgat caattctgca aacctg                                         26

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
atgactccta gaaagaaat tgaccag                                         27

<210> SEQ ID NO 21
<211> LENGTH: 22
<212> TYPE: DNA
<213> ORGANISM: Artificial
<220> FEATURE:
<223> OTHER INFORMATION: Primer

<400> SEQUENCE: 21
tgcagacaag ttcctgcagc tg                                             22

<210> SEQ ID NO 22
<211> LENGTH: 23
<212> TYPE: DNA
<213> ORGANISM: Artificial
<220> FEATURE:
<223> OTHER INFORMATION: Primer

<400> SEQUENCE: 22
atgctttatt caggcacgct acg                                            23

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
ggatgagtcg cagtcacgaa c                                              21

<210> SEQ ID NO 24
<211> LENGTH: 26
<212> TYPE: DNA
<213> ORGANISM: Artificial
<220> FEATURE:
<223> OTHER INFORMATION: Primer

<400> SEQUENCE: 24
```

```
tcaatcattg gctcaagact aggaac                                            26

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
attctggtgc tgacctcgcc ac                                                22

<210> SEQ ID NO 26
<211> LENGTH: 25
<212> TYPE: DNA
<213> ORGANISM: Artificial
<220> FEATURE:
<223> OTHER INFORMATION: Primer

<400> SEQUENCE: 26
actcatgtcg tacttgcaag aactg                                             25

<210> SEQ ID NO 27
<211> LENGTH: 27
<212> TYPE: DNA
<213> ORGANISM: Artificial
<220> FEATURE:
<223> OTHER INFORMATION: Primer

<400> SEQUENCE: 27
gtgtcgactc gccaaattcc atcggag                                           27

<210> SEQ ID NO 28
<211> LENGTH: 28
<212> TYPE: DNA
<213> ORGANISM: Artificial
<220> FEATURE:
<223> OTHER INFORMATION: Primer

<400> SEQUENCE: 28
ggttcatagc gagtttcttt gcatgtgc                                          28

<210> SEQ ID NO 29
<211> LENGTH: 28
<212> TYPE: DNA
<213> ORGANISM: Artificial
<220> FEATURE:
<223> OTHER INFORMATION: Primer

<400> SEQUENCE: 29
ctcctttatt aactccgcag catgactg                                          28

<210> SEQ ID NO 30
<211> LENGTH: 27
<212> TYPE: DNA
<213> ORGANISM: Artificial
<220> FEATURE:
<223> OTHER INFORMATION: Primer

<400> SEQUENCE: 30
ctcctcgaag gaccctcaaa acaaagg                                           27

<210> SEQ ID NO 31
<211> LENGTH: 30
<212> TYPE: DNA
```

```
<213> ORGANISM: Artificial
<220> FEATURE:
<223> OTHER INFORMATION: Primer

<400> SEQUENCE: 31
caaatttatc tgggagcaca gttacattgc                                    30

<210> SEQ ID NO 32
<211> LENGTH: 28
<212> TYPE: DNA
<213> ORGANISM: Artificial
<220> FEATURE:
<223> OTHER INFORMATION: Primer

<400> SEQUENCE: 32
cacacattgc tttagtccag caagaacc                                      28

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
attctcctcg cacgtttctc ggggc                                         25

<210> SEQ ID NO 34
<211> LENGTH: 28
<212> TYPE: DNA
<213> ORGANISM: Artificial
<220> FEATURE:
<223> OTHER INFORMATION: Primer

<400> SEQUENCE: 34
ggttgaaata cttgttgccg cactaaag                                      28

<210> SEQ ID NO 35
<211> LENGTH: 31
<212> TYPE: DNA
<213> ORGANISM: Artificial
<220> FEATURE:
<223> OTHER INFORMATION: Primer

<400> SEQUENCE: 35
cgcttcctga attgagttgg tatcgttaat g                                  31

<210> SEQ ID NO 36
<211> LENGTH: 28
<212> TYPE: DNA
<213> ORGANISM: Artificial
<220> FEATURE:
<223> OTHER INFORMATION: Primer

<400> SEQUENCE: 36
gacattgttg gaattggctg cttagtgg                                      28

<210> SEQ ID NO 37
<211> LENGTH: 3107
<212> TYPE: DNA
<213> ORGANISM: Artificial
<220> FEATURE:
<223> OTHER INFORMATION: ExpressionCassette

<400> SEQUENCE: 37
acaaacgacc ccgccccacc cctcacacgg ccttaccagc ccaggaagca atggcccgaa   60
```

```
cctcgtgggc taccgcactc cgtttggaaa cccaatagga actgcagcag cagggaactc    120
agctgctact ccagctggaa accctctagg gaaggtaaga gcagactctt caacgagcct    180
tactactcag ggacagcgaa gggtccgcgt gcatgtccag ggcgacacat ttctcatttt    240
ggtgccaccg gacctgaagt ttgagcatct ttccaatcgt gttgagcgca agctccgact    300
atgtgggaaa atgccgcctt caggccaggc aggctcactc atttttgaat acatggatga    360
agacgaggac cgcgtgcgac tggagagcga cgaggaccta agtgtggcgt ttgaggctgt    420
gcccgaccac catgagctgt ccgtctacgt caaaaactga cgattatgat ctaatgatat    480
ttaaaagata tgtaaaacgg ttatttttg gacctgcgcc ctaaaatggg actttgtcaa     540
aaaaagaacg gcctcctgcg cgatggagag caatcaagaa ttcggagttc cgatgcgaat    600
ccatcaagaa aacggcccct aggcaatcta aaccgtggc cgacatacta taagtcaatt     660
ccgctgtaca ataacaagc gatcaatcca taatctgagg ctcatttcat acggactttt     720
ctaagttcac ataattctat gatgcatact aacaaatacg atgcacaaat gggtacaagg    780
cctaaagagg gccacaatcg cgatttactc gatacggcaa atcagttcca caagtaattc    840
gctatcgtcg gtgttgttat acacctctcg gcttgagtca atatcgagca tgcaaggttg    900
acgcattctg gggaaatgta tccacgtgat cgccgatatc ggagcggata cgctgtgtag    960
tcttcagttg taagatttct tatacagcga cgcaaccatc atgtctgtgc aaacgaaaac   1020
aattgttctt cttcctggag accactgtgg cccagaagtc gttgccgaag cagtgaaagt   1080
actcaaagcc gtggaaactg ctttaccatc ggttaccttc gagtttcagc accatttgat   1140
tggcggtgct gccatagatg ctgctggtgt tcccattacg gaagagactc ttgctgcctc   1200
tagaaaggct gacgctgttt tgcttggtgc tgtaggaggg cccaagtggg gcactggctc   1260
agtgagaccc gaacagggtc tcctcaagat tcgcaaggag cttcaattgt acgcgaatct   1320
gcgtccctgt aacatcattg ctccaaagtt tgccaagctc agtcctctga aggaggagaa   1380
tgttttggga accgacatta tgattgtacg agaactcaca ggtggaatct acttcggaga   1440
tcgcgaagaa gccgatatga gcacggccga ccctcatgcc acagatactg agaagtacag   1500
cgttagtgaa attacgcgca tcgctcgtat ggcaggcttt ttggctctgc aggcccaacc   1560
tccgctacct gttttggagct tggacaaggc caatgtgctt gcttccagcc gtttgtggcg   1620
cgaaaccgtc accaaggtgt tcaaagagga attccctcag ctcaaattgg agcatcagct   1680
cattgattcg gcggccatga tttttggtga agaaccctcga cagctcaatg gtgtcgttat   1740
caccaccaac atgttcggag acatttttcag cgacgaggcg agtgttattc ctggctctct   1800
gggtctgcta ccctcagctt cgctcagtgg actgcctgac acaaactctg cctttggtct   1860
gtacgagcct tgtcacggct ctgctcccga cctcgctgct aacaaggcaa atccagtcgc   1920
taccattctc agcgcagcaa tgatgcttcg tctttcacta ggtcttcctg aagctgctga   1980
tgctgttgag aaagctgttt ccaacgtttt gaactcagtc gcggccacgg cagacattgg   2040
tggaacagcc tccaccacag aggtaggcga tgcaattgcc gcagagacgt tgaagcttct   2100
caaatagtct gctataaatt gacggagttt cgtacagtgc gctcgtacag tgcgctgcca   2160
aatacaattt agtgtagcca gattggatgg ttgaattgct cttcacggtt gcacgctatt   2220
ggcaaaaaag agagagccgc tctgaactgg ttcatccgca gctgaccttc gaaactcttt   2280
aatatttaat aatattgcag caaaatctat agcttatgcc acatctatac ggaagaggta   2340
ttcaacatta gagcttgtgt cgcccattct ctacacgagc ccacgcatca gcagtgaggg   2400
```

| | |
|---|---|
| gcttgtagct cgtgccctct aaccagtaga ttgtttgtcc tgctggggcg ggaatctgct | 2460 |
| ggtttcggaa ttctttcttc tgaactttgt tgttgccggt gatggtgacg gtgtcgacga | 2520 |
| acttaatgaa tatcggcacg gcatagcgtg gcagcctttc caaagatgc ttgccgagtt | 2580 |
| tatccatatc cagctgtttt ctaggattgt tgagcttgat cacagcaaat ccggcacgac | 2640 |
| cctcatgctt gggaacctgc acacctacac agacacacag atcgactcca ccgaagtcca | 2700 |
| caactgcttc ctcgacttcg tttgtgctaa cgttctcgct cttccatcga aacgtatccc | 2760 |
| cgagtcgatc aacaaagtag acgctatgat ctttatcagc cctcagaagg tctccgctgc | 2820 |
| gcacccaggc atctcccttc ttgaaaacat caaacacaag cttctcatcc gtggctgatt | 2880 |
| ggttgccgac atagccctgg aaatcgagtt tgatattctt cgggtcgagt ttgaaaagga | 2940 |
| attcacccgg ctcgtccgag tgtgtctcac ggcacaggcc ggttttggga tcgcgccata | 3000 |
| aatcctgcgt gtcaacatca atcgcggcga tgttccacct ggtacgatgc agcacgcggg | 3060 |
| tggccacagt accataatgg ccacatgcac caacaccata tgcacct | 3107 |

<210> SEQ ID NO 38
<211> LENGTH: 45
<212> TYPE: DNA
<213> ORGANISM: Artificial
<220> FEATURE:
<223> OTHER INFORMATION: Primer
<400> SEQUENCE: 38
atatatatac atatgttaat caaagacatt attctaactc caatg     45

<210> SEQ ID NO 39
<211> LENGTH: 42
<212> TYPE: DNA
<213> ORGANISM: Artificial
<220> FEATURE:
<223> OTHER INFORMATION: Primer
<400> SEQUENCE: 39
atatatggcc ggccaactta agaaaaccgc acaaccacac cg     42

<210> SEQ ID NO 40
<211> LENGTH: 39
<212> TYPE: DNA
<213> ORGANISM: Artificial
<220> FEATURE:
<223> OTHER INFORMATION: Primer
<400> SEQUENCE: 40
atatatatac atatgagccc ttcatcacac aaacccctg     39

<210> SEQ ID NO 41
<211> LENGTH: 39
<212> TYPE: DNA
<213> ORGANISM: Artificial
<220> FEATURE:
<223> OTHER INFORMATION: Primer
<400> SEQUENCE: 41
atatatggcc ggccattcta agaactcacc gctaaggcc     39

<210> SEQ ID NO 42
<211> LENGTH: 38
<212> TYPE: DNA
<213> ORGANISM: Artificial
<220> FEATURE:
<223> OTHER INFORMATION: Primer -continued

<400> SEQUENCE: 42
atatatatac atatggttgt aaactcctcg aaggaccc                                38

<210> SEQ ID NO 43
<211> LENGTH: 42
<212> TYPE: DNA
<213> ORGANISM: Artificial
<220> FEATURE:
<223> OTHER INFORMATION: Primer

<400> SEQUENCE: 43
atatatggcc ggcctaccta gaccttctgg ttagcggtat tg                           42

<210> SEQ ID NO 44
<211> LENGTH: 40
<212> TYPE: DNA
<213> ORGANISM: Artificial
<220> FEATURE:
<223> OTHER INFORMATION: Primer

<400> SEQUENCE: 44
atatatatac atatggtgga tgatatacag gtagagaagc                              40

<210> SEQ ID NO 45
<211> LENGTH: 42
<212> TYPE: DNA
<213> ORGANISM: Artificial
<220> FEATURE:
<223> OTHER INFORMATION: Primer

<400> SEQUENCE: 45
atatatggcc ggccacgtca aatctctccg agaccttgca ag                           42

<210> SEQ ID NO 46
<211> LENGTH: 40
<212> TYPE: DNA
<213> ORGANISM: Artificial
<220> FEATURE:
<223> OTHER INFORMATION: Primer

<400> SEQUENCE: 46
atatatatac atatggccat cgagaaacca gtgatagttg                              40

<210> SEQ ID NO 47
<211> LENGTH: 45
<212> TYPE: DNA
<213> ORGANISM: Artificial
<220> FEATURE:
<223> OTHER INFORMATION: Primer

<400> SEQUENCE: 47
atatatggcc ggccaggtta agaagctaat tcactaattg ccgac                        45

<210> SEQ ID NO 48
<211> LENGTH: 23
<212> TYPE: DNA
<213> ORGANISM: Artificial
<220> FEATURE:
<223> OTHER INFORMATION: Primer

<400> SEQUENCE: 48
ggacctgcgc cctaaaatgg gac                                                23

<210> SEQ ID NO 49

-continued

```
<211> LENGTH: 30
<212> TYPE: DNA
<213> ORGANISM: Artificial
<220> FEATURE:
<223> OTHER INFORMATION: Primer

<400> SEQUENCE: 49
atcctagaaa acagctggat atggataaac                                    30

<210> SEQ ID NO 50
<211> LENGTH: 23
<212> TYPE: DNA
<213> ORGANISM: Artificial
<220> FEATURE:
<223> OTHER INFORMATION: Primer

<400> SEQUENCE: 50
gtgcccgacc accatgagct gtc                                           23

<210> SEQ ID NO 51
<211> LENGTH: 23
<212> TYPE: DNA
<213> ORGANISM: Artificial
<220> FEATURE:
<223> OTHER INFORMATION: Primer

<400> SEQUENCE: 51
cccaagcatg agggtcgtgc cgg                                           23

<210> SEQ ID NO 52
<211> LENGTH: 1572
<212> TYPE: DNA
<213> ORGANISM: Candida bombicola
<220> FEATURE:
<221> NAME/KEY: CDS
<222> LOCATION: (1)..(1572)

<400> SEQUENCE: 52
```

| | | | | | | | | | | | | | | | | |
|---|---|---|---|---|---|---|---|---|---|---|---|---|---|---|---|---|
| atg | att | ctt | tat | gct | gtg | ctg | ggc | gca | ttc | gcc | gcc | ttc | ttg | ctt | tac | 48 |
| Met | Ile | Leu | Tyr | Ala | Val | Leu | Gly | Ala | Phe | Ala | Ala | Phe | Leu | Leu | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| atg | gat | gta | ctt | tac | cct | ttc | gtg | att | tac | cct | ctg | aga | gcg | cga | tgg | 96 |
| Met | Asp | Val | Leu | Tyr | Pro | Phe | Val | Ile | Tyr | Pro | Leu | Arg | Ala | Arg | Trp | |
| | | 20 | | | | | 25 | | | | | 30 | | | | |

| | | | | | | | | | | | | | | | | |
|---|---|---|---|---|---|---|---|---|---|---|---|---|---|---|---|---|
| cac | aaa | tgt | ggt | tac | atc | cct | aga | gat | ttg | agc | tgg | cca | ttg | ggg | att | 144 |
| His | Lys | Cys | Gly | Tyr | Ile | Pro | Arg | Asp | Leu | Ser | Trp | Pro | Leu | Gly | Ile | |
| | | | 35 | | | | | 40 | | | | | 45 | | | |

| | | | | | | | | | | | | | | | | |
|---|---|---|---|---|---|---|---|---|---|---|---|---|---|---|---|---|
| cca | ctc | acc | ctg | gta | gtt | ctc | tcg | aag | ttg | agg | aaa | gat | atg | ctg | ctg | 192 |
| Pro | Leu | Thr | Leu | Val | Val | Leu | Ser | Lys | Leu | Arg | Lys | Asp | Met | Leu | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| caa | ttc | atg | gca | gcg | caa | gac | ctt | agt | cgc | cct | tac | aag | aca | tcc | tta | 240 |
| Gln | Phe | Met | Ala | Ala | Gln | Asp | Leu | Ser | Arg | Pro | Tyr | Lys | Thr | Ser | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cgt | caa | ttt | ctg | ggt | aaa | tgg | gta | atc | gcc | act | aga | gat | cct | gag | aac | 288 |
| Arg | Gln | Phe | Leu | Gly | Lys | Trp | Val | Ile | Ala | Thr | Arg | Asp | Pro | Glu | Asn | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | aag | gct | gtt | cta | tcc | acc | aag | ttc | aat | gac | ttc | tcg | ctg | aaa | gaa | 336 |
| Ile | Lys | Ala | Val | Leu | Ser | Thr | Lys | Phe | Asn | Asp | Phe | Ser | Leu | Lys | Glu | |
| | | | | 100 | | | | | 105 | | | | | 110 | | |

| | | | | | | | | | | | | | | | | |
|---|---|---|---|---|---|---|---|---|---|---|---|---|---|---|---|---|
| aga | ggg | aat | agg | atg | agg | cat | gta | atc | ggt | gat | gga | att | ttt | acc | caa | 384 |
| Arg | Gly | Asn | Arg | Met | Arg | His | Val | Ile | Gly | Asp | Gly | Ile | Phe | Thr | Gln | |
| | | | 115 | | | | | 120 | | | | | 125 | | | |

| | | | | | | | | | | | | | | | | |
|---|---|---|---|---|---|---|---|---|---|---|---|---|---|---|---|---|
| gat | ggc | gca | cca | tgg | aag | cac | tcg | cga | gat | atg | ctc | agg | cct | cag | ttc | 432 |
| Asp | Gly | Ala | Pro | Trp | Lys | His | Ser | Arg | Asp | Met | Leu | Arg | Pro | Gln | Phe | |

```
                    130                 135                 140
acc aag gat caa atc agc cga gtg gaa ttg ttg agc cac cac atc gac       480
Thr Lys Asp Gln Ile Ser Arg Val Glu Leu Leu Ser His His Ile Asp
145                 150                 155                 160 gtt ttg att cgt gaa atc agg aag tcg gga ggt aac gtc gag ttg caa       528
Val Leu Ile Arg Glu Ile Arg Lys Ser Gly Gly Asn Val Glu Leu Gln
                165                 170                 175 cgt tta ttc cac ctc atg act atg gac acc gcc act cac ttt cta ttc       576
Arg Leu Phe His Leu Met Thr Met Asp Thr Ala Thr His Phe Leu Phe
            180                 185                 190 ggc gag tcc gtt ggc tcg ttg gag gtc agt ggc gaa agc aag ggc att       624
Gly Glu Ser Val Gly Ser Leu Glu Val Ser Gly Glu Ser Lys Gly Ile
        195                 200                 205 gag atc acc gac cca aag act gga gag att gtg aac acc gtt gat ttt       672
Glu Ile Thr Asp Pro Lys Thr Gly Glu Ile Val Asn Thr Val Asp Phe
    210                 215                 220 gtt gag tct tat act ttt gca aac aag ttt gct ctc aag aag att atc       720
Val Glu Ser Tyr Thr Phe Ala Asn Lys Phe Ala Leu Lys Lys Ile Ile
225                 230                 235                 240 ctc aac gac ttg gag ttt tta gcc gac ttg acg gag ccc tcg tat aag       768
Leu Asn Asp Leu Glu Phe Leu Ala Asp Leu Thr Glu Pro Ser Tyr Lys
                245                 250                 255 tgg cat ctg cgc cgt gtc cac aca gtc atg gat cac tac gtt cag ctg       816
Trp His Leu Arg Arg Val His Thr Val Met Asp His Tyr Val Gln Leu
            260                 265                 270 gct ttg aag gct act gag aag tat gat cct gat gat gat agc gag aag       864
Ala Leu Lys Ala Thr Glu Lys Tyr Asp Pro Asp Asp Asp Ser Glu Lys
        275                 280                 285 gga gaa tac tac ttt agc cat gag ctg gcg aaa ctc acg aga gac ccc       912
Gly Glu Tyr Tyr Phe Ser His Glu Leu Ala Lys Leu Thr Arg Asp Pro
    290                 295                 300 ttg tcg ttg aga gat cag ctt ttc aat att ctc att gct ggc cgc gac       960
Leu Ser Leu Arg Asp Gln Leu Phe Asn Ile Leu Ile Ala Gly Arg Asp
305                 310                 315                 320 act acc gca gca act ttg tcc tat gcc ttc cac tat cta acg aag aat      1008
Thr Thr Ala Ala Thr Leu Ser Tyr Ala Phe His Tyr Leu Thr Lys Asn
                325                 330                 335 ccc gct atc tac gcc aag gtc cgc gaa gat gtg ctc acg gtc ttc cct      1056
Pro Ala Ile Tyr Ala Lys Val Arg Glu Asp Val Leu Thr Val Phe Pro
            340                 345                 350 aat gga gac gca tca ttg gcg act tac gag gac ttg cga aag gct aag      1104
Asn Gly Asp Ala Ser Leu Ala Thr Tyr Glu Asp Leu Arg Lys Ala Lys
        355                 360                 365 tat ctc caa atg gtg atc aag gag gta ttg cgt ctt gcg cct gcg gtt      1152
Tyr Leu Gln Met Val Ile Lys Glu Val Leu Arg Leu Ala Pro Ala Val
    370                 375                 380 ccc ttg aac acg cgt gcc gcg gtt cgt gac aca tat ctg cca cgg ggc      1200
Pro Leu Asn Thr Arg Ala Ala Val Arg Asp Thr Tyr Leu Pro Arg Gly
385                 390                 395                 400 gga ggc cca gcc gga aac ctg ccc gtt ttt gtt ccc aag ggc act gct      1248
Gly Gly Pro Ala Gly Asn Leu Pro Val Phe Val Pro Lys Gly Thr Ala
                405                 410                 415 gtc aac tac cct aca tat att ttg cac cgc gat cca gat atc tat ggt      1296
Val Asn Tyr Pro Thr Tyr Ile Leu His Arg Asp Pro Asp Ile Tyr Gly
            420                 425                 430 gcc gac gcg tac gag ttc aac ccc gag aga tgg agg cct gag aat aag      1344
Ala Asp Ala Tyr Glu Phe Asn Pro Glu Arg Trp Arg Pro Glu Asn Lys
        435                 440                 445 ctt ccg aat agc cca atg tac tct tgg gga tac att ccc ttc aat ggt      1392
```

```
Leu Pro Asn Ser Pro Met Tyr Ser Trp Gly Tyr Ile Pro Phe Asn Gly
    450                 455                 460 ggc cct cgc atc tgc att gga cag cag ttc gcc ttg act gag atc gct    1440
Gly Pro Arg Ile Cys Ile Gly Gln Gln Phe Ala Leu Thr Glu Ile Ala
465                 470                 475                 480 ttg acg atg atc aag ctg gtt ctg gaa ttt gag agg ctg gag cct gcc    1488
Leu Thr Met Ile Lys Leu Val Leu Glu Phe Glu Arg Leu Glu Pro Ala
                485                 490                 495 gac gac ttt gag ccc aat ctt caa gac aag tcc tct tta act gtc atg    1536
Asp Asp Phe Glu Pro Asn Leu Gln Asp Lys Ser Ser Leu Thr Val Met
                500                 505                 510 gtc gga ggg tcg ggc gtc cga gtg aaa ctg agt taa                    1572
Val Gly Gly Ser Gly Val Arg Val Lys Leu Ser
            515                 520
```

<210> SEQ ID NO 53
<211> LENGTH: 523
<212> TYPE: PRT
<213> ORGANISM: Candida bombicola

<400> SEQUENCE: 53

```
Met Ile Leu Tyr Ala Val Leu Gly Ala Phe Ala Ala Phe Leu Leu Tyr
1               5                   10                  15

Met Asp Val Leu Tyr Pro Phe Val Ile Tyr Pro Leu Arg Ala Arg Trp
                20                  25                  30

His Lys Cys Gly Tyr Ile Pro Arg Asp Leu Ser Trp Pro Leu Gly Ile
            35                  40                  45

Pro Leu Thr Leu Val Val Leu Ser Lys Leu Arg Lys Asp Met Leu Leu
50                  55                  60

Gln Phe Met Ala Ala Gln Asp Leu Ser Arg Pro Tyr Lys Thr Ser Leu
65                  70                  75                  80

Arg Gln Phe Leu Gly Lys Trp Val Ile Ala Thr Arg Asp Pro Glu Asn
                85                  90                  95

Ile Lys Ala Val Leu Ser Thr Lys Phe Asn Asp Phe Ser Leu Lys Glu
            100                 105                 110

Arg Gly Asn Arg Met Arg His Val Ile Gly Asp Gly Ile Phe Thr Gln
        115                 120                 125

Asp Gly Ala Pro Trp Lys His Ser Arg Asp Met Leu Arg Pro Gln Phe
130                 135                 140

Thr Lys Asp Gln Ile Ser Arg Val Glu Leu Leu Ser His His Ile Asp
145                 150                 155                 160

Val Leu Ile Arg Glu Ile Arg Lys Ser Gly Gly Asn Val Glu Leu Gln
                165                 170                 175

Arg Leu Phe His Leu Met Thr Met Asp Thr Ala Thr His Phe Leu Phe
            180                 185                 190

Gly Glu Ser Val Gly Ser Leu Glu Val Ser Gly Glu Ser Lys Gly Ile
        195                 200                 205

Glu Ile Thr Asp Pro Lys Thr Gly Glu Ile Val Asn Thr Val Asp Phe
210                 215                 220

Val Glu Ser Tyr Thr Phe Ala Asn Lys Phe Ala Leu Lys Lys Ile Ile
225                 230                 235                 240

Leu Asn Asp Leu Glu Phe Leu Ala Asp Leu Thr Glu Pro Ser Tyr Lys
                245                 250                 255

Trp His Leu Arg Arg Val His Thr Val Met Asp His Tyr Val Gln Leu
            260                 265                 270

Ala Leu Lys Ala Thr Glu Lys Tyr Asp Pro Asp Asp Asp Ser Glu Lys
```

```
                 275                 280                 285
Gly Glu Tyr Tyr Phe Ser His Glu Leu Ala Lys Leu Thr Arg Asp Pro
    290                 295                 300

Leu Ser Leu Arg Asp Gln Leu Phe Asn Ile Leu Ile Ala Gly Arg Asp
305                 310                 315                 320

Thr Thr Ala Ala Thr Leu Ser Tyr Ala Phe His Tyr Leu Thr Lys Asn
                325                 330                 335

Pro Ala Ile Tyr Ala Lys Val Arg Glu Asp Val Leu Thr Val Phe Pro
            340                 345                 350

Asn Gly Asp Ala Ser Leu Ala Thr Tyr Glu Asp Leu Arg Lys Ala Lys
        355                 360                 365

Tyr Leu Gln Met Val Ile Lys Glu Val Leu Arg Leu Ala Pro Ala Val
    370                 375                 380

Pro Leu Asn Thr Arg Ala Ala Val Arg Asp Thr Tyr Leu Pro Arg Gly
385                 390                 395                 400

Gly Gly Pro Ala Gly Asn Leu Pro Val Phe Val Pro Lys Gly Thr Ala
                405                 410                 415

Val Asn Tyr Pro Thr Tyr Ile Leu His Arg Asp Pro Asp Ile Tyr Gly
            420                 425                 430

Ala Asp Ala Tyr Glu Phe Asn Pro Glu Arg Trp Arg Pro Glu Asn Lys
        435                 440                 445

Leu Pro Asn Ser Pro Met Tyr Ser Trp Gly Tyr Ile Pro Phe Asn Gly
    450                 455                 460

Gly Pro Arg Ile Cys Ile Gly Gln Gln Phe Ala Leu Thr Glu Ile Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Gln Asp Lys Ser Ser Leu Thr Val Met
            500                 505                 510

Val Gly Gly Ser Gly Val Arg Val Lys Leu Ser
        515                 520

<210> SEQ ID NO 54
<211> LENGTH: 1671
<212> TYPE: DNA
<213> ORGANISM: Candida bombicola
<220> FEATURE:
<221> NAME/KEY: CDS
<222> LOCATION: (1)..(1671)

<400> SEQUENCE: 54 atg agg ccc ctg ttg cgg gaa caa gac aca tca cac cca gag cta ttg      48
Met Arg Pro Leu Leu Arg Glu Gln Asp Thr Ser His Pro Glu Leu Leu
1               5                   10                  15 ttg gca agc aat act att ttt aac ccc ctt tcc aag agt gtc caa act      96
Leu Ala Ser Asn Thr Ile Phe Asn Pro Leu Ser Lys Ser Val Gln Thr
            20                  25                  30 gtt caa tac ggc ctc atg aac att aat ttc tct gac gtg ctc gtg cta     144
Val Gln Tyr Gly Leu Met Asn Ile Asn Phe Ser Asp Val Leu Val Leu
        35                  40                  45 gga ggc atc agc gtg agc ttt ttg ctc gcc tac cag gcg att tac ttt     192
Gly Gly Ile Ser Val Ser Phe Leu Leu Ala Tyr Gln Ala Ile Tyr Phe
    50                  55                  60 tat ttc att tac tcg cca cga gcc aaa aag ctc ggt tgc gct ctt cca     240
Tyr Phe Ile Tyr Ser Pro Arg Ala Lys Lys Leu Gly Cys Ala Leu Pro
65                  70                  75                  80 ccg gtc ttc ttc tct ttc cca ctc gga ata ccg gag gtc ata cgt ctt     288
```

|         |         |         |         |         |         |         |         |         |         |         |         |         |         |         |         |      |
|---------|---------|---------|---------|---------|---------|---------|---------|---------|---------|---------|---------|---------|---------|---------|---------|------|
|         | Pro     | Val     | Phe     | Phe     | Ser     | Phe     | Pro     | Leu     | Gly     | Ile     | Pro     | Glu     | Val     | Ile     | Arg     | Leu  |
|         |         |         |         |         | 85      |         |         |         | 90      |         |         |         |         | 95      |         |      |

```
gtg aac gcc tgg ttc aac gat gat ctc ctt gag tat ttc acc ttc aaa        336
Val Asn Ala Trp Phe Asn Asp Asp Leu Leu Glu Tyr Phe Thr Phe Lys
            100                 105                 110 ttc gag gag ttc cag cgc aaa acc gga ttc caa tca gtc gct ggg caa        384
Phe Glu Glu Phe Gln Arg Lys Thr Gly Phe Gln Ser Val Ala Gly Gln
        115                 120                 125 cta tgg att ggg act att gag ccc gag aac atc aag act atg ctc gct        432
Leu Trp Ile Gly Thr Ile Glu Pro Glu Asn Ile Lys Thr Met Leu Ala
130                 135                 140 act tca ttt aaa gac tac tcc cta ggc ttc cgt tac gag gcc atg tac        480
Thr Ser Phe Lys Asp Tyr Ser Leu Gly Phe Arg Tyr Glu Ala Met Tyr
145                 150                 155                 160 ggc ctt ctc gga aat ggc att ttc act ctc agt ggt gag ggc tgg aag        528
Gly Leu Leu Gly Asn Gly Ile Phe Thr Leu Ser Gly Glu Gly Trp Lys
                165                 170                 175 cac agc cgc gct ttg ttg cgt ccg caa ttt agt cgt gag caa gtc tct        576
His Ser Arg Ala Leu Leu Arg Pro Gln Phe Ser Arg Glu Gln Val Ser
            180                 185                 190 cac ctt gaa tca atg cgc aca cac atc aat atg ttg atc aac aac cac        624
His Leu Glu Ser Met Arg Thr His Ile Asn Met Leu Ile Asn Asn His
        195                 200                 205 ttc aag ggt ggc aaa gtc gtc gat gct cag gtt ttg ttc cac aat cta        672
Phe Lys Gly Gly Lys Val Val Asp Ala Gln Val Leu Phe His Asn Leu
    210                 215                 220 acc att gat act gct acc gaa ttc cta ttc gga gag agc acc aac act        720
Thr Ile Asp Thr Ala Thr Glu Phe Leu Phe Gly Glu Ser Thr Asn Thr
225                 230                 235                 240 ctt gac cct gct ctt gct cag cat gga ttc cct gga cct aag ggt ctt        768
Leu Asp Pro Ala Leu Ala Gln His Gly Phe Pro Gly Pro Lys Gly Leu
                245                 250                 255 gta acc ggt gag cag ttt gct gag gct ttt acc tct gct ctc gaa ttg        816
Val Thr Gly Glu Gln Phe Ala Glu Ala Phe Thr Ser Ala Leu Glu Leu
            260                 265                 270 ctt tct gtg cga gtt atg gcc ggc gcc gca tgg ttc ctc gtt tgg acc        864
Leu Ser Val Arg Val Met Ala Gly Ala Ala Trp Phe Leu Val Trp Thr
        275                 280                 285 ccc aaa ttc tgg cgc tca tgc aaa gtc tgc cac aac ttc att gat tac        912
Pro Lys Phe Trp Arg Ser Cys Lys Val Cys His Asn Phe Ile Asp Tyr
    290                 295                 300 ttc gtt ttc aag gct ctg gcc act cct atg gag aag gac cag gaa gct        960
Phe Val Phe Lys Ala Leu Ala Thr Pro Met Glu Lys Asp Gln Glu Ala
305                 310                 315                 320 gat cgc tac gtc ttt att cga gaa ctc aca aag gag acc tct gac cca       1008
Asp Arg Tyr Val Phe Ile Arg Glu Leu Thr Lys Glu Thr Ser Asp Pro
                325                 330                 335 cgg gtc atc cgc gac cag gcc ctc aac atc ctc ttg gct ggt cgt gat       1056
Arg Val Ile Arg Asp Gln Ala Leu Asn Ile Leu Leu Ala Gly Arg Asp
            340                 345                 350 acc act gcg gca ctt ctc agc ttc acc acc tac tac ctt ggt gcc tac       1104
Thr Thr Ala Ala Leu Leu Ser Phe Thr Thr Tyr Tyr Leu Gly Ala Tyr
        355                 360                 365 cct gag gtc tac gat gag ctt cgc gag gct gtt att gcg gac ttc ggc       1152
Pro Glu Val Tyr Asp Glu Leu Arg Glu Ala Val Ile Ala Asp Phe Gly
    370                 375                 380 aag gaa gat gct gag ccc cct acg ttt gag cag ctt aag cag tgc aag       1200
Lys Glu Asp Ala Glu Pro Pro Thr Phe Glu Gln Leu Lys Gln Cys Lys
385                 390                 395                 400
```

```
gtg cta cag aac gtc att cgg gaa gtt ttg cga ttg cac ccg aat gtg      1248
Val Leu Gln Asn Val Ile Arg Glu Val Leu Arg Leu His Pro Asn Val
            405                 410                 415 ccc ctc aac ttc cgc gag gcc att acc gat act aag ttc ccc aca gga      1296
Pro Leu Asn Phe Arg Glu Ala Ile Thr Asp Thr Lys Phe Pro Thr Gly
        420                 425                 430 ggc ggc ccg aat gga gac cag ccc gtt ttc gtt ccc aag gga cag aaa      1344
Gly Gly Pro Asn Gly Asp Gln Pro Val Phe Val Pro Lys Gly Gln Lys
        435                 440                 445 gtg ttt tac gcc acc tac gtc atg cag cga aat gag ggt ctc tgg ggt      1392
Val Phe Tyr Ala Thr Tyr Val Met Gln Arg Asn Glu Gly Leu Trp Gly
        450                 455                 460 cct gac tcc aca aca ttc cgc cct gac cgc tgg aac gag tca aga gag      1440
Pro Asp Ser Thr Thr Phe Arg Pro Asp Arg Trp Asn Glu Ser Arg Glu
465                 470                 475                 480 gcc atc gca tcc gga tgg gac tac att cct ttc aac ggc ggc cct cgt      1488
Ala Ile Ala Ser Gly Trp Asp Tyr Ile Pro Phe Asn Gly Gly Pro Arg
                485                 490                 495 att tgc ctg ggt cag cag ttc gct ctc aca gag gcg agc tac acg ctc      1536
Ile Cys Leu Gly Gln Gln Phe Ala Leu Thr Glu Ala Ser Tyr Thr Leu
        500                 505                 510 gtg cgt atc tgc caa gag ttc tcc agg att gag gtt ctc cac cct gat      1584
Val Arg Ile Cys Gln Glu Phe Ser Arg Ile Glu Val Leu His Pro Asp
        515                 520                 525 gtt att acc tcc agg aac gtg atg aaa cag cgc atg cgt ttg acc aac      1632
Val Ile Thr Ser Arg Asn Val Met Lys Gln Arg Met Arg Leu Thr Asn
        530                 535                 540 tct tcc agc ggc ggc gtc ata gcg aag ttc att cgc tag                  1671
Ser Ser Ser Gly Gly Val Ile Ala Lys Phe Ile Arg
545                 550                 555

<210> SEQ ID NO 55
<211> LENGTH: 556
<212> TYPE: PRT
<213> ORGANISM: Candida bombicola

<400> SEQUENCE: 55

Met Arg Pro Leu Leu Arg Glu Gln Asp Thr Ser His Pro Glu Leu Leu
1               5                   10                  15

Leu Ala Ser Asn Thr Ile Phe Asn Pro Leu Ser Lys Ser Val Gln Thr
            20                  25                  30

Val Gln Tyr Gly Leu Met Asn Ile Asn Phe Ser Asp Val Leu Val Leu
        35                  40                  45

Gly Gly Ile Ser Val Ser Phe Leu Leu Ala Tyr Gln Ala Ile Tyr Phe
    50                  55                  60

Tyr Phe Ile Tyr Ser Pro Arg Ala Lys Lys Leu Gly Cys Ala Leu Pro
65                  70                  75                  80

Pro Val Phe Phe Ser Phe Pro Leu Gly Ile Pro Glu Val Ile Arg Leu
                85                  90                  95

Val Asn Ala Trp Phe Asn Asp Asp Leu Leu Glu Tyr Phe Thr Phe Lys
            100                 105                 110

Phe Glu Glu Phe Gln Arg Lys Thr Gly Phe Gln Ser Val Ala Gly Gln
        115                 120                 125

Leu Trp Ile Gly Thr Ile Glu Pro Glu Asn Ile Lys Thr Met Leu Ala
    130                 135                 140

Thr Ser Phe Lys Asp Tyr Ser Leu Gly Phe Arg Tyr Glu Ala Met Tyr
145                 150                 155                 160

Gly Leu Leu Gly Asn Gly Ile Phe Thr Leu Ser Gly Glu Gly Trp Lys
```

```
                165                 170                 175
His Ser Arg Ala Leu Leu Arg Pro Gln Phe Ser Arg Glu Gln Val Ser
            180                 185                 190
His Leu Glu Ser Met Arg Thr His Ile Asn Met Leu Ile Asn Asn His
        195                 200                 205
Phe Lys Gly Gly Lys Val Val Asp Ala Gln Val Leu Phe His Asn Leu
    210                 215                 220
Thr Ile Asp Thr Ala Thr Glu Phe Leu Phe Gly Glu Ser Thr Asn Thr
225                 230                 235                 240
Leu Asp Pro Ala Leu Ala Gln His Gly Phe Pro Gly Pro Lys Gly Leu
                245                 250                 255
Val Thr Gly Glu Gln Phe Ala Glu Ala Phe Thr Ser Ala Leu Glu Leu
            260                 265                 270
Leu Ser Val Arg Val Met Ala Gly Ala Ala Trp Phe Leu Val Trp Thr
        275                 280                 285
Pro Lys Phe Trp Arg Ser Cys Lys Val Cys His Asn Phe Ile Asp Tyr
    290                 295                 300
Phe Val Phe Lys Ala Leu Ala Thr Pro Met Glu Lys Asp Gln Glu Ala
305                 310                 315                 320
Asp Arg Tyr Val Phe Ile Arg Glu Leu Thr Lys Glu Thr Ser Asp Pro
                325                 330                 335
Arg Val Ile Arg Asp Gln Ala Leu Asn Ile Leu Leu Ala Gly Arg Asp
            340                 345                 350
Thr Thr Ala Ala Leu Leu Ser Phe Thr Thr Tyr Tyr Leu Gly Ala Tyr
        355                 360                 365
Pro Glu Val Tyr Asp Glu Leu Arg Glu Ala Val Ile Ala Asp Phe Gly
    370                 375                 380
Lys Glu Asp Ala Glu Pro Pro Thr Phe Glu Gln Leu Lys Gln Cys Lys
385                 390                 395                 400
Val Leu Gln Asn Val Ile Arg Glu Val Leu Arg Leu His Pro Asn Val
                405                 410                 415
Pro Leu Asn Phe Arg Glu Ala Ile Thr Asp Thr Lys Phe Pro Thr Gly
            420                 425                 430
Gly Gly Pro Asn Gly Asp Gln Pro Val Phe Val Pro Lys Gly Gln Lys
        435                 440                 445
Val Phe Tyr Ala Thr Tyr Val Met Gln Arg Asn Glu Gly Leu Trp Gly
    450                 455                 460
Pro Asp Ser Thr Thr Phe Arg Pro Asp Arg Trp Asn Glu Ser Arg Glu
465                 470                 475                 480
Ala Ile Ala Ser Gly Trp Asp Tyr Ile Pro Phe Asn Gly Gly Pro Arg
                485                 490                 495
Ile Cys Leu Gly Gln Gln Phe Ala Leu Thr Glu Ala Ser Tyr Thr Leu
            500                 505                 510
Val Arg Ile Cys Gln Glu Phe Ser Arg Ile Glu Val Leu His Pro Asp
        515                 520                 525
Val Ile Thr Ser Arg Asn Val Met Lys Gln Arg Met Arg Leu Thr Asn
    530                 535                 540
Ser Ser Ser Gly Gly Val Ile Ala Lys Phe Ile Arg
545                 550                 555

<210> SEQ ID NO 56
<211> LENGTH: 1560
<212> TYPE: DNA
<213> ORGANISM: Candida bombicola
```

```
<220> FEATURE:
<221> NAME/KEY: CDS
<222> LOCATION: (1)..(1560)

<400> SEQUENCE: 56 atg att att gat ctt tca gac gcg ctg ata ata gga ggc atc gcc ctg        48
Met Ile Ile Asp Leu Ser Asp Ala Leu Ile Ile Gly Gly Ile Ala Leu
1               5                   10                  15 tgc ttc ttg ctc tcc tac cag gcg atc tac ttt tac ttt att tac tcg        96
Cys Phe Leu Leu Ser Tyr Gln Ala Ile Tyr Phe Tyr Phe Ile Tyr Ser
            20                  25                  30 cca cgg gcc aag aag ctt gga tgc gct cct cct ctc att gtg cac gct       144
Pro Arg Ala Lys Lys Leu Gly Cys Ala Pro Pro Leu Ile Val His Ala
        35                  40                  45 ttc cca ctg ggt ttg ccg aca att ttc gga ctt ata aga gct tgg cgc       192
Phe Pro Leu Gly Leu Pro Thr Ile Phe Gly Leu Ile Arg Ala Trp Arg
    50                  55                  60 aac gac gat ctt ctc cag tac ttg agc gac aac ttc gct aga atc agg       240
Asn Asp Asp Leu Leu Gln Tyr Leu Ser Asp Asn Phe Ala Arg Ile Arg
65                  70                  75                  80 acc aga acc gga atg caa gta atg gcc ggt cag ctg tgg ctc aac acc       288
Thr Arg Thr Gly Met Gln Val Met Ala Gly Gln Leu Trp Leu Asn Thr
                85                  90                  95 att gag cca gaa aac atc aag gcc atg ctt gcc act tcg ttc aag gat       336
Ile Glu Pro Glu Asn Ile Lys Ala Met Leu Ala Thr Ser Phe Lys Asp
            100                 105                 110 ttc tcg ctt ggg ttc cgc tat gaa gtc atg cat ggc ctc ctc gga gat       384
Phe Ser Leu Gly Phe Arg Tyr Glu Val Met His Gly Leu Leu Gly Asp
        115                 120                 125 ggt atc ttc act ctc agt ggt gag ggc tgg aaa cac agc cgt gcc ttg       432
Gly Ile Phe Thr Leu Ser Gly Glu Gly Trp Lys His Ser Arg Ala Leu
    130                 135                 140 cta cgt cca cag ttc agc cgt gag caa gtc tct cac ttg gac tca atg       480
Leu Arg Pro Gln Phe Ser Arg Glu Gln Val Ser His Leu Asp Ser Met
145                 150                 155                 160 cgc aca cac atc aat ttg atg atc aac aac cac ttc aaa ggt ggc cag       528
Arg Thr His Ile Asn Leu Met Ile Asn Asn His Phe Lys Gly Gly Gln
                165                 170                 175 gtc gtc gac gct cag gtt cta tac cat aac ctg aca atc gac act gcc       576
Val Val Asp Ala Gln Val Leu Tyr His Asn Leu Thr Ile Asp Thr Ala
            180                 185                 190 act gaa ttc ctg ttc ggt gag agc acc aac act ctt gac cct gtt ctt       624
Thr Glu Phe Leu Phe Gly Glu Ser Thr Asn Thr Leu Asp Pro Val Leu
        195                 200                 205 gca cag cag gga cta ccg ggt cct agg ggc gtt gtt act ggt gag cag       672
Ala Gln Gln Gly Leu Pro Gly Pro Arg Gly Val Val Thr Gly Glu Gln
    210                 215                 220 ttc gct aac gct ttc acc tac gct caa gag ttg ctc agt att cga gtc       720
Phe Ala Asn Ala Phe Thr Tyr Ala Gln Glu Leu Leu Ser Ile Arg Val
225                 230                 235                 240 atg gcc ggc tca gca tgg ttc ctc gtc tgg act cct aag ttc agg cgc       768
Met Ala Gly Ser Ala Trp Phe Leu Val Trp Thr Pro Lys Phe Arg Arg
                245                 250                 255 tcg tgc aag gtg tgc cac aac ttt att gac tac ttc gtc ttt aag gct       816
Ser Cys Lys Val Cys His Asn Phe Ile Asp Tyr Phe Val Phe Lys Ala
            260                 265                 270 ctg gcc act cct atg gag aaa gac cag gag gct gat cgc tat gta ttc       864
Leu Ala Thr Pro Met Glu Lys Asp Gln Glu Ala Asp Arg Tyr Val Phe
        275                 280                 285 atc cga gaa ctc act aag gag act tct gac cca aag gtt ata cgt gac       912
```

```
Ile Arg Glu Leu Thr Lys Glu Thr Ser Asp Pro Lys Val Ile Arg Asp
        290                 295                 300 cag gct ctc aac atc ctt tta gct ggc cgc gat acc act gca gca ctc      960
Gln Ala Leu Asn Ile Leu Leu Ala Gly Arg Asp Thr Thr Ala Ala Leu
305                 310                 315                 320 ctc agc ttc acc act tac tac ctt ggc gca tat cct gag gtc tac gac     1008
Leu Ser Phe Thr Thr Tyr Tyr Leu Gly Ala Tyr Pro Glu Val Tyr Asp
                325                 330                 335 gag ctt cgc gag gca gtt ctt gca gac ttc ggc cct gcc gat tct gag     1056
Glu Leu Arg Glu Ala Val Leu Ala Asp Phe Gly Pro Ala Asp Ser Glu
            340                 345                 350 ccc cct acc ttt gag agg ctc aag cag tgc aag gtg ttg cag aat gtc     1104
Pro Pro Thr Phe Glu Arg Leu Lys Gln Cys Lys Val Leu Gln Asn Val
        355                 360                 365 atc cgc gag gtt ctg cga ttg cac ccg aat gtg ccc ctc aac ttc cgc     1152
Ile Arg Glu Val Leu Arg Leu His Pro Asn Val Pro Leu Asn Phe Arg
370                 375                 380 cag gcc atc gtt gat act aag ttc cct act ggt ggt ggc ccg aat aga     1200
Gln Ala Ile Val Asp Thr Lys Phe Pro Thr Gly Gly Gly Pro Asn Arg
385                 390                 395                 400 gac cag ccc atc ttt gtt cca aaa gga cag aag gtg ttc tac tcc acg     1248
Asp Gln Pro Ile Phe Val Pro Lys Gly Gln Lys Val Phe Tyr Ser Thr
                405                 410                 415 tac gtc atg cag cga agc aag gac atc tgg ggc gct gac tcc aca tcg     1296
Tyr Val Met Gln Arg Ser Lys Asp Ile Trp Gly Ala Asp Ser Thr Ser
            420                 425                 430 ttc cga cca gaa cgc tgg aac gag ccc aga gaa gct ctt gca tca ggt     1344
Phe Arg Pro Glu Arg Trp Asn Glu Pro Arg Glu Ala Leu Ala Ser Gly
        435                 440                 445 tgg gat tac att cct ttc aat ggt ggc cct cgc att tgt atc ggt cag     1392
Trp Asp Tyr Ile Pro Phe Asn Gly Gly Pro Arg Ile Cys Ile Gly Gln
450                 455                 460 cag ttc gct ctc act gag gct agc tac acg ctt gtc cgt att tgc cag     1440
Gln Phe Ala Leu Thr Glu Ala Ser Tyr Thr Leu Val Arg Ile Cys Gln
465                 470                 475                 480 gag ttt acc aga att gag gtt ctt cat ccc gat gtc att act tct agg     1488
Glu Phe Thr Arg Ile Glu Val Leu His Pro Asp Val Ile Thr Ser Arg
                485                 490                 495 aaa gag atg aag cag cgc atg cgc ttg acc aac tcg gct agc ggt ggc     1536
Lys Glu Met Lys Gln Arg Met Arg Leu Thr Asn Ser Ala Ser Gly Gly
            500                 505                 510 gtg atg gcg aga ttc att cgt tag                                     1560
Val Met Ala Arg Phe Ile Arg
        515
```

<210> SEQ ID NO 57
<211> LENGTH: 519
<212> TYPE: PRT
<213> ORGANISM: Candida bombicola

<400> SEQUENCE: 57

```
Met Ile Ile Asp Leu Ser Asp Ala Leu Ile Gly Gly Ile Ala Leu
1               5                   10                  15

Cys Phe Leu Leu Ser Tyr Gln Ala Ile Tyr Phe Tyr Phe Ile Tyr Ser
                20                  25                  30

Pro Arg Ala Lys Lys Leu Gly Cys Ala Pro Pro Leu Ile Val His Ala
            35                  40                  45

Phe Pro Leu Gly Leu Pro Thr Ile Phe Gly Leu Ile Arg Ala Trp Arg
        50                  55                  60
```

```
Asn Asp Asp Leu Leu Gln Tyr Leu Ser Asp Asn Phe Ala Arg Ile Arg
 65                  70                  75                  80

Thr Arg Thr Gly Met Gln Val Met Ala Gly Gln Leu Trp Leu Asn Thr
                 85                  90                  95

Ile Glu Pro Glu Asn Ile Lys Ala Met Leu Ala Thr Ser Phe Lys Asp
            100                 105                 110

Phe Ser Leu Gly Phe Arg Tyr Glu Val Met His Gly Leu Leu Gly Asp
            115                 120                 125

Gly Ile Phe Thr Leu Ser Gly Glu Gly Trp Lys His Ser Arg Ala Leu
            130                 135                 140

Leu Arg Pro Gln Phe Ser Arg Glu Gln Val Ser His Leu Asp Ser Met
145                 150                 155                 160

Arg Thr His Ile Asn Leu Met Ile Asn Asn His Phe Lys Gly Gly Gln
                165                 170                 175

Val Val Asp Ala Gln Val Leu Tyr His Asn Leu Thr Ile Asp Thr Ala
                180                 185                 190

Thr Glu Phe Leu Phe Gly Glu Ser Thr Asn Thr Leu Asp Pro Val Leu
            195                 200                 205

Ala Gln Gln Gly Leu Pro Gly Pro Arg Gly Val Val Thr Gly Glu Gln
210                 215                 220

Phe Ala Asn Ala Phe Thr Tyr Ala Gln Glu Leu Leu Ser Ile Arg Val
225                 230                 235                 240

Met Ala Gly Ser Ala Trp Phe Leu Val Trp Thr Pro Lys Phe Arg Arg
                245                 250                 255

Ser Cys Lys Val Cys His Asn Phe Ile Asp Tyr Phe Val Phe Lys Ala
            260                 265                 270

Leu Ala Thr Pro Met Glu Lys Asp Gln Glu Ala Asp Arg Tyr Val Phe
            275                 280                 285

Ile Arg Glu Leu Thr Lys Glu Thr Ser Asp Pro Lys Val Ile Arg Asp
            290                 295                 300

Gln Ala Leu Asn Ile Leu Leu Ala Gly Arg Asp Thr Thr Ala Ala Leu
305                 310                 315                 320

Leu Ser Phe Thr Thr Tyr Tyr Leu Gly Ala Tyr Pro Glu Val Tyr Asp
            325                 330                 335

Glu Leu Arg Glu Ala Val Leu Ala Asp Phe Gly Pro Ala Asp Ser Glu
            340                 345                 350

Pro Pro Thr Phe Glu Arg Leu Lys Gln Cys Lys Val Leu Gln Asn Val
            355                 360                 365

Ile Arg Glu Val Leu Arg Leu His Pro Asn Val Pro Leu Asn Phe Arg
            370                 375                 380

Gln Ala Ile Val Asp Thr Lys Phe Pro Thr Gly Gly Gly Pro Asn Arg
385                 390                 395                 400

Asp Gln Pro Ile Phe Val Pro Lys Gly Gln Lys Val Phe Tyr Ser Thr
            405                 410                 415

Tyr Val Met Gln Arg Ser Lys Asp Ile Trp Gly Ala Asp Ser Thr Ser
                420                 425                 430

Phe Arg Pro Glu Arg Trp Asn Glu Pro Arg Glu Ala Leu Ala Ser Gly
            435                 440                 445

Trp Asp Tyr Ile Pro Phe Asn Gly Gly Pro Arg Ile Cys Ile Gly Gln
            450                 455                 460

Gln Phe Ala Leu Thr Glu Ala Ser Tyr Thr Leu Val Arg Ile Cys Gln
465                 470                 475                 480

Glu Phe Thr Arg Ile Glu Val Leu His Pro Asp Val Ile Thr Ser Arg
```

```
                        485                 490                 495
Lys Glu Met Lys Gln Arg Met Arg Leu Thr Asn Ser Ala Ser Gly Gly
                        500                 505                 510

Val Met Ala Arg Phe Ile Arg
        515

<210> SEQ ID NO 58
<211> LENGTH: 1572
<212> TYPE: DNA
<213> ORGANISM: Candida bombicola
<220> FEATURE:
<221> NAME/KEY: CDS
<222> LOCATION: (1)..(1572)

<400> SEQUENCE: 58 atg att ttt tat gct gtg ctt ggc gct gtg gtc acc ttc tta ctt tac      48
Met Ile Phe Tyr Ala Val Leu Gly Ala Val Val Thr Phe Leu Leu Tyr
1               5                   10                  15 gta gat gtg atc tac cct ttc gtg ata tat cct tta aaa gca cga tgg      96
Val Asp Val Ile Tyr Pro Phe Val Ile Tyr Pro Leu Lys Ala Arg Trp
            20                  25                  30 cac aaa tgt ggc tcc gta cct cga gag ctt agc tgg cca ttg ggg att     144
His Lys Cys Gly Ser Val Pro Arg Glu Leu Ser Trp Pro Leu Gly Ile
        35                  40                  45 cca acc acc ata gga gtt ttt tcg aac ata aag aag gat cta cat ctt     192
Pro Thr Thr Ile Gly Val Phe Ser Asn Ile Lys Lys Asp Leu His Leu
    50                  55                  60 caa gtc ctg gca gcg tac gac ctc agc cgg tct tat aag aca agc ttg     240
Gln Val Leu Ala Ala Tyr Asp Leu Ser Arg Ser Tyr Lys Thr Ser Leu
65                  70                  75                  80 cgt caa agt ctc ggc aca tgg gta gtt gct acg cgg gat cct gag aac     288
Arg Gln Ser Leu Gly Thr Trp Val Val Ala Thr Arg Asp Pro Glu Asn
                85                  90                  95 atc aag gcc gtt ttg tct acc aag ttc aat gac ttt tca ctg aaa gag     336
Ile Lys Ala Val Leu Ser Thr Lys Phe Asn Asp Phe Ser Leu Lys Glu
            100                 105                 110 aga gga att cgg tta agg cat gta att ggt gat ggt atc ttt acc caa     384
Arg Gly Ile Arg Leu Arg His Val Ile Gly Asp Gly Ile Phe Thr Gln
        115                 120                 125 gat ggt gca ccg tgg aag cac tcg cga gat atg ctc aga cct caa ttc     432
Asp Gly Ala Pro Trp Lys His Ser Arg Asp Met Leu Arg Pro Gln Phe
    130                 135                 140 agt agg gaa caa atc agc cgc gtg gag gtg ttg agt cac cac atc gat     480
Ser Arg Glu Gln Ile Ser Arg Val Glu Val Leu Ser His His Ile Asp
145                 150                 155                 160 gtt ttg att cgt gag atc aaa aag tcg gga ggt aat gtt gag ttg caa     528
Val Leu Ile Arg Glu Ile Lys Lys Ser Gly Gly Asn Val Glu Leu Gln
                165                 170                 175 cga cta ttc cac ctc atg act atg gac acc gcc aca cag ttt ctt ttc     576
Arg Leu Phe His Leu Met Thr Met Asp Thr Ala Thr Gln Phe Leu Phe
            180                 185                 190 ggc gaa tca att ggc tcg cta gaa gtc agt ggc gac agc aag ggc att     624
Gly Glu Ser Ile Gly Ser Leu Glu Val Ser Gly Asp Ser Lys Gly Ile
        195                 200                 205 gag att act gac cca aat act gga gat att gtg agt acc gtt gac ttc     672
Glu Ile Thr Asp Pro Asn Thr Gly Asp Ile Val Ser Thr Val Asp Phe
    210                 215                 220 gtt gag tct tat act ttc aca aac aga ttt gct atg aag aag gta ttc     720
Val Glu Ser Tyr Thr Phe Thr Asn Arg Phe Ala Met Lys Lys Val Phe
225                 230                 235                 240
```

```
ctg aac aaa tgg gaa ttc ttg gca aac ttg tcg aac ccc tca tat gag      768
Leu Asn Lys Trp Glu Phe Leu Ala Asn Leu Ser Asn Pro Ser Tyr Glu
            245                 250                 255 agg cat atg cgg cgt gtc cac aca gtc ctg gat cac tac gtt cag ctg      816
Arg His Met Arg Arg Val His Thr Val Leu Asp His Tyr Val Gln Leu
        260                 265                 270 gct ttg aag gct act gag aag tat gat cct gaa gat gac agc gag aaa      864
Ala Leu Lys Ala Thr Glu Lys Tyr Asp Pro Glu Asp Asp Ser Glu Lys
    275                 280                 285 gga gaa tac tac ttt agc cat gag ctg gct aaa ctc acg aga gac ccc      912
Gly Glu Tyr Tyr Phe Ser His Glu Leu Ala Lys Leu Thr Arg Asp Pro
290                 295                 300 ttg tcg ttg cgc aat cag ctt ttt aat atc ctg att gct ggc cgc gac      960
Leu Ser Leu Arg Asn Gln Leu Phe Asn Ile Leu Ile Ala Gly Arg Asp
305                 310                 315                 320 act acc gca gca aca ttg tcc tat gcc ttc cat tac tta acg aag aac     1008
Thr Thr Ala Ala Thr Leu Ser Tyr Ala Phe His Tyr Leu Thr Lys Asn
                325                 330                 335 cca gcc atc tac gcc aag gtt cgc gaa gat gtg ctc acc gtc ttc ccc     1056
Pro Ala Ile Tyr Ala Lys Val Arg Glu Asp Val Leu Thr Val Phe Pro
            340                 345                 350 gat gga gac gcc tca ttg gcg acc ttt gag gac ttg cga aag gcc aag     1104
Asp Gly Asp Ala Ser Leu Ala Thr Phe Glu Asp Leu Arg Lys Ala Lys
        355                 360                 365 tat ctc caa atg gta atc aag gag gta ttg cgc ctt gcg cct gcg gtt     1152
Tyr Leu Gln Met Val Ile Lys Glu Val Leu Arg Leu Ala Pro Ala Val
    370                 375                 380 ccc aca aat tcg cgt act gcg gtt cgt gac acc tat ctg cca cgg ggt     1200
Pro Thr Asn Ser Arg Thr Ala Val Arg Asp Thr Tyr Leu Pro Arg Gly
385                 390                 395                 400 gga ggc cca gct gga aac cta ccc gtt ttc gtt ccc aag ggc act att     1248
Gly Gly Pro Ala Gly Asn Leu Pro Val Phe Val Pro Lys Gly Thr Ile
                405                 410                 415 atc agg tat cct gca tat atc ttg cac cgc gat cct gat ata tat ggt     1296
Ile Arg Tyr Pro Ala Tyr Ile Leu His Arg Asp Pro Asp Ile Tyr Gly
            420                 425                 430 gcc gac tcg tat gac ttc aac cct gag agg tgg aga ccc gag aat aag     1344
Ala Asp Ser Tyr Asp Phe Asn Pro Glu Arg Trp Arg Pro Glu Asn Lys
        435                 440                 445 ctc cca ggt agc cca atg tac tca tgg ggc tat att ccc ttt aat ggc     1392
Leu Pro Gly Ser Pro Met Tyr Ser Trp Gly Tyr Ile Pro Phe Asn Gly
    450                 455                 460 ggc cct cgc att tgc gtt gga cag cag ttt gcc ttg act gaa atc gct     1440
Gly Pro Arg Ile Cys Val Gly Gln Gln Phe Ala Leu Thr Glu Ile Ala
465                 470                 475                 480 ttg aca atg atc aag ctg gtt ttg gaa ttt gag agg ctg gag cct gct     1488
Leu Thr Met Ile Lys Leu Val Leu Glu Phe Glu Arg Leu Glu Pro Ala
                485                 490                 495 gat gac ttt gag ccc aat ctt cga gat agg acc tca tta act tcc atg     1536
Asp Asp Phe Glu Pro Asn Leu Arg Asp Arg Thr Ser Leu Thr Ser Met
            500                 505                 510 gtc gga ggg tcg ggc gtc cga gta aaa ctg agt taa                     1572
Val Gly Gly Ser Gly Val Arg Val Lys Leu Ser
        515                 520
```

<210> SEQ ID NO 59
<211> LENGTH: 523
<212> TYPE: PRT
<213> ORGANISM: Candida bombicola

<400> SEQUENCE: 59

-continued

```
Met Ile Phe Tyr Ala Val Leu Gly Ala Val Thr Phe Leu Leu Tyr
1               5                   10                  15

Val Asp Val Ile Tyr Pro Phe Val Ile Tyr Pro Leu Lys Ala Arg Trp
            20                  25                  30

His Lys Cys Gly Ser Val Pro Arg Glu Leu Ser Trp Pro Leu Gly Ile
            35                  40                  45

Pro Thr Thr Ile Gly Val Phe Ser Asn Ile Lys Lys Asp Leu His Leu
        50                  55                  60

Gln Val Leu Ala Ala Tyr Asp Leu Ser Arg Ser Tyr Lys Thr Ser Leu
65                  70                  75                  80

Arg Gln Ser Leu Gly Thr Trp Val Val Ala Thr Arg Asp Pro Glu Asn
                85                  90                  95

Ile Lys Ala Val Leu Ser Thr Lys Phe Asn Asp Phe Ser Leu Lys Glu
            100                 105                 110

Arg Gly Ile Arg Leu Arg His Val Ile Gly Asp Gly Ile Phe Thr Gln
            115                 120                 125

Asp Gly Ala Pro Trp Lys His Ser Arg Asp Met Leu Arg Pro Gln Phe
        130                 135                 140

Ser Arg Glu Gln Ile Ser Arg Val Glu Val Leu Ser His His Ile Asp
145                 150                 155                 160

Val Leu Ile Arg Glu Ile Lys Lys Ser Gly Gly Asn Val Glu Leu Gln
                165                 170                 175

Arg Leu Phe His Leu Met Thr Met Asp Thr Ala Thr Gln Phe Leu Phe
            180                 185                 190

Gly Glu Ser Ile Gly Ser Leu Glu Val Ser Gly Asp Ser Lys Gly Ile
            195                 200                 205

Glu Ile Thr Asp Pro Asn Thr Gly Asp Ile Val Ser Thr Val Asp Phe
        210                 215                 220

Val Glu Ser Tyr Thr Phe Thr Asn Arg Phe Ala Met Lys Lys Val Phe
225                 230                 235                 240

Leu Asn Lys Trp Glu Phe Leu Ala Asn Leu Ser Asn Pro Ser Tyr Glu
                245                 250                 255

Arg His Met Arg Arg Val His Thr Val Leu Asp His Tyr Val Gln Leu
            260                 265                 270

Ala Leu Lys Ala Thr Glu Lys Tyr Asp Pro Glu Asp Ser Glu Lys
            275                 280                 285

Gly Glu Tyr Tyr Phe Ser His Glu Leu Ala Lys Leu Thr Arg Asp Pro
        290                 295                 300

Leu Ser Leu Arg Asn Gln Leu Phe Asn Ile Leu Ile Ala Gly Arg Asp
305                 310                 315                 320

Thr Thr Ala Ala Thr Leu Ser Tyr Ala Phe His Tyr Leu Thr Lys Asn
                325                 330                 335

Pro Ala Ile Tyr Ala Lys Val Arg Glu Asp Val Leu Thr Val Phe Pro
            340                 345                 350

Asp Gly Asp Ala Ser Leu Ala Thr Phe Glu Asp Leu Arg Lys Ala Lys
        355                 360                 365

Tyr Leu Gln Met Val Ile Lys Glu Val Leu Arg Leu Ala Pro Ala Val
        370                 375                 380

Pro Thr Asn Ser Arg Thr Ala Val Arg Asp Thr Tyr Leu Pro Arg Gly
385                 390                 395                 400

Gly Gly Pro Ala Gly Asn Leu Pro Val Phe Val Pro Lys Gly Thr Ile
                405                 410                 415
```

```
Ile Arg Tyr Pro Ala Tyr Ile Leu His Arg Asp Pro Asp Ile Tyr Gly
            420                 425                 430

Ala Asp Ser Tyr Asp Phe Asn Pro Glu Arg Trp Arg Pro Glu Asn Lys
        435                 440                 445

Leu Pro Gly Ser Pro Met Tyr Ser Trp Gly Tyr Ile Pro Phe Asn Gly
    450                 455                 460

Gly Pro Arg Ile Cys Val Gly Gln Gln Phe Ala Leu Thr Glu Ile Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Arg Asp Arg Thr Ser Leu Thr Ser Met
            500                 505                 510

Val Gly Gly Ser Gly Val Arg Val Lys Leu Ser
        515                 520

<210> SEQ ID NO 60
<211> LENGTH: 1572
<212> TYPE: DNA
<213> ORGANISM: Candida bombicola
<220> FEATURE:
<221> NAME/KEY: CDS
<222> LOCATION: (1)..(1572)

<400> SEQUENCE: 60 atg att ttt tat gct gtg ctt ggc act gtg gtc gcc ttc tta ctt tac      48
Met Ile Phe Tyr Ala Val Leu Gly Thr Val Val Ala Phe Leu Leu Tyr
1               5                   10                  15 gta gat gtg atc tac cct ttc gtg ata tat cct tta aag gca cga tgg     96
Val Asp Val Ile Tyr Pro Phe Val Ile Tyr Pro Leu Lys Ala Arg Trp
            20                  25                  30 cac aaa tgt ggc ttc gtc cct cga gag ctg agc tgg cca ttg ggg att    144
His Lys Cys Gly Phe Val Pro Arg Glu Leu Ser Trp Pro Leu Gly Ile
        35                  40                  45 cca gac acc ata gca gtt ttt tcg agg ata aag aag gat cta cat ctt    192
Pro Asp Thr Ile Ala Val Phe Ser Arg Ile Lys Lys Asp Leu His Leu
    50                  55                  60 caa ttc ctg gca gcg cac gac ctc agc cgg tct tat aag aca agc ttg    240
Gln Phe Leu Ala Ala His Asp Leu Ser Arg Ser Tyr Lys Thr Ser Leu
65                  70                  75                  80 cgt caa act ctc ggc aca tgg gta gtt gat acg cga gat cct gag aat    288
Arg Gln Thr Leu Gly Thr Trp Val Val Asp Thr Arg Asp Pro Glu Asn
                85                  90                  95 atc aag gcc gtt ttg tct acc aag ttc aat gac ttt tca ctg aaa gat    336
Ile Lys Ala Val Leu Ser Thr Lys Phe Asn Asp Phe Ser Leu Lys Asp
            100                 105                 110 aga gga att cgg tta agg caa gta att ggt gat ggt att ttt acc caa    384
Arg Gly Ile Arg Leu Arg Gln Val Ile Gly Asp Gly Ile Phe Thr Gln
        115                 120                 125 gat ggt gca ccg tgg aag cac tcg cga gat atg ctc aga cct caa ttc    432
Asp Gly Ala Pro Trp Lys His Ser Arg Asp Met Leu Arg Pro Gln Phe
    130                 135                 140 agt agg gaa caa att agc cgc gtg gag gtg ttg agt cac cac atc gat    480
Ser Arg Glu Gln Ile Ser Arg Val Glu Val Leu Ser His His Ile Asp
145                 150                 155                 160 gtt ttg att cgt gag atc aaa aag tcg gga ggt aat gtt gag ttg caa    528
Val Leu Ile Arg Glu Ile Lys Lys Ser Gly Gly Asn Val Glu Leu Gln
                165                 170                 175 cga cta ttc cac ctc atg act atg gac act gct aca cag ttt ctt ttc    576
Arg Leu Phe His Leu Met Thr Met Asp Thr Ala Thr Gln Phe Leu Phe
            180                 185                 190
```

```
ggc gaa tca att ggc tcg cta gaa gtc agt ggc gac agc aag ggc att      624
Gly Glu Ser Ile Gly Ser Leu Glu Val Ser Gly Asp Ser Lys Gly Ile
        195                 200                 205 gag att act gac cca aat act gga gat att gtg aat acc gtt gac ttc      672
Glu Ile Thr Asp Pro Asn Thr Gly Asp Ile Val Asn Thr Val Asp Phe
    210                 215                 220 gtt gag tct tat act ttt gca aac aga ttt gct atg aaa aag ata tta      720
Val Glu Ser Tyr Thr Phe Ala Asn Arg Phe Ala Met Lys Lys Ile Leu
225                 230                 235                 240 ctg aac aaa tgg gaa ttc gtg gta aac ttg tcg aac ccc tca tat gag      768
Leu Asn Lys Trp Glu Phe Val Val Asn Leu Ser Asn Pro Ser Tyr Glu
                245                 250                 255 agg cat atg cga cgt gtc cac aca gtc ctg gat cac tac gtt cag ctg      816
Arg His Met Arg Arg Val His Thr Val Leu Asp His Tyr Val Gln Leu
            260                 265                 270 gct ttg aag gct act gag aag tat gat cct gaa gat gac tgc gag aaa      864
Ala Leu Lys Ala Thr Glu Lys Tyr Asp Pro Glu Asp Asp Cys Glu Lys
        275                 280                 285 gga gaa tac tac ttt agc cat gag ctg gct aaa ctc acg aga gac ccc      912
Gly Glu Tyr Tyr Phe Ser His Glu Leu Ala Lys Leu Thr Arg Asp Pro
    290                 295                 300 ttg tgc ttg cgc aat cag ctt ttt aat atc ctg att gct ggc cgc gac      960
Leu Cys Leu Arg Asn Gln Leu Phe Asn Ile Leu Ile Ala Gly Arg Asp
305                 310                 315                 320 act acc gca gca aca ttg gcc tat gcc ttc cat tac ttg acg aag aac     1008
Thr Thr Ala Ala Thr Leu Ala Tyr Ala Phe His Tyr Leu Thr Lys Asn
                325                 330                 335 cca gcc atc tac gcc aag gtg cgc gaa gat gtg ctc acc gtc ttc ccc     1056
Pro Ala Ile Tyr Ala Lys Val Arg Glu Asp Val Leu Thr Val Phe Pro
            340                 345                 350 aat gga gat gcc tca ttg gcg acc ttt gag gac ttg cga aag gcc aag     1104
Asn Gly Asp Ala Ser Leu Ala Thr Phe Glu Asp Leu Arg Lys Ala Lys
        355                 360                 365 tat ctc caa atg gta atc aag gag gta ttg cgc ctt gcg cct gtg gtt     1152
Tyr Leu Gln Met Val Ile Lys Glu Val Leu Arg Leu Ala Pro Val Val
    370                 375                 380 ccc aca aat tcg cgt act gcg gtt cgt gac acc tat ctg cca cgg ggt     1200
Pro Thr Asn Ser Arg Thr Ala Val Arg Asp Thr Tyr Leu Pro Arg Gly
385                 390                 395                 400 gga ggc cca gct gga aac cta ccc gtt ttc gtt ccc aag ggc aca aat     1248
Gly Gly Pro Ala Gly Asn Leu Pro Val Phe Val Pro Lys Gly Thr Asn
                405                 410                 415 gtc agg tat tct gca tat gtc ttg cac cgc gat cct gat ata tat ggt     1296
Val Arg Tyr Ser Ala Tyr Val Leu His Arg Asp Pro Asp Ile Tyr Gly
            420                 425                 430 gcc gac tcg tat gac ttc aac cct gag agg tgg aga ccc gag aat aag     1344
Ala Asp Ser Tyr Asp Phe Asn Pro Glu Arg Trp Arg Pro Glu Asn Lys
        435                 440                 445 ctc cca ggt agc cca atg tac tca tgg ggc tat att ccc ttt aat ggc     1392
Leu Pro Gly Ser Pro Met Tyr Ser Trp Gly Tyr Ile Pro Phe Asn Gly
    450                 455                 460 ggc cct cgc att tgc gtt gga cag cag ttt gcc ttg act gaa ttc gct     1440
Gly Pro Arg Ile Cys Val Gly Gln Gln Phe Ala Leu Thr Glu Phe Ala
465                 470                 475                 480 ttg aca atg atc aag ctg gtt tta gaa ttt gag agg ctg gag cct gct     1488
Leu Thr Met Ile Lys Leu Val Leu Glu Phe Glu Arg Leu Glu Pro Ala
                485                 490                 495 gat gac ttt gag ccc aat ctt cta gat agg acc tca tta act gcc atg     1536
Asp Asp Phe Glu Pro Asn Leu Leu Asp Arg Thr Ser Leu Thr Ala Met
```

```
                500                 505                 510
gtc gga ggg tcg ggc gtc cga gta aaa ctg agt taa                          1572
Val Gly Gly Ser Gly Val Arg Val Lys Leu Ser
        515                 520
```

<210> SEQ ID NO 61
<211> LENGTH: 523
<212> TYPE: PRT
<213> ORGANISM: Candida bombicola

<400> SEQUENCE: 61

```
Met Ile Phe Tyr Ala Val Leu Gly Thr Val Ala Phe Leu Leu Tyr
1               5                   10                  15

Val Asp Val Ile Tyr Pro Phe Val Ile Tyr Pro Leu Lys Ala Arg Trp
                20                  25                  30

His Lys Cys Gly Phe Val Pro Arg Glu Leu Ser Trp Pro Leu Gly Ile
            35                  40                  45

Pro Asp Thr Ile Ala Val Phe Ser Arg Ile Lys Lys Asp Leu His Leu
        50                  55                  60

Gln Phe Leu Ala Ala His Asp Leu Ser Arg Ser Tyr Lys Thr Ser Leu
65                  70                  75                  80

Arg Gln Thr Leu Gly Thr Trp Val Val Asp Thr Arg Asp Pro Glu Asn
                85                  90                  95

Ile Lys Ala Val Leu Ser Thr Lys Phe Asn Asp Phe Ser Leu Lys Asp
            100                 105                 110

Arg Gly Ile Arg Leu Arg Gln Val Ile Gly Asp Gly Ile Phe Thr Gln
        115                 120                 125

Asp Gly Ala Pro Trp Lys His Ser Arg Asp Met Leu Arg Pro Gln Phe
    130                 135                 140

Ser Arg Glu Gln Ile Ser Arg Val Glu Val Leu Ser His His Ile Asp
145                 150                 155                 160

Val Leu Ile Arg Glu Ile Lys Lys Ser Gly Gly Asn Val Glu Leu Gln
                165                 170                 175

Arg Leu Phe His Leu Met Thr Met Asp Thr Ala Thr Gln Phe Leu Phe
            180                 185                 190

Gly Glu Ser Ile Gly Ser Leu Glu Val Ser Gly Asp Ser Lys Gly Ile
        195                 200                 205

Glu Ile Thr Asp Pro Asn Thr Gly Asp Ile Val Asn Thr Val Asp Phe
    210                 215                 220

Val Glu Ser Tyr Thr Phe Ala Asn Arg Phe Ala Met Lys Lys Ile Leu
225                 230                 235                 240

Leu Asn Lys Trp Glu Phe Val Val Asn Leu Ser Asn Pro Ser Tyr Glu
                245                 250                 255

Arg His Met Arg Arg Val His Thr Leu Asp His Tyr Val Gln Leu
            260                 265                 270

Ala Leu Lys Ala Thr Glu Lys Tyr Asp Pro Glu Asp Cys Glu Lys
        275                 280                 285

Gly Glu Tyr Tyr Phe Ser His Glu Leu Ala Lys Leu Thr Arg Asp Pro
    290                 295                 300

Leu Cys Leu Arg Asn Gln Leu Phe Asn Ile Leu Ile Ala Gly Arg Asp
305                 310                 315                 320

Thr Thr Ala Ala Thr Leu Ala Tyr Ala Phe His Tyr Leu Thr Lys Asn
                325                 330                 335

Pro Ala Ile Tyr Ala Lys Val Arg Glu Asp Val Leu Thr Val Phe Pro
            340                 345                 350
```

```
Asn Gly Asp Ala Ser Leu Ala Thr Phe Glu Asp Leu Arg Lys Ala Lys
        355                 360                 365

Tyr Leu Gln Met Val Ile Lys Glu Val Leu Arg Leu Ala Pro Val Val
    370                 375                 380

Pro Thr Asn Ser Arg Thr Ala Val Arg Asp Thr Tyr Leu Pro Arg Gly
385                 390                 395                 400

Gly Gly Pro Ala Gly Asn Leu Pro Val Phe Val Pro Lys Gly Thr Asn
                405                 410                 415

Val Arg Tyr Ser Ala Tyr Val Leu His Arg Asp Pro Asp Ile Tyr Gly
            420                 425                 430

Ala Asp Ser Tyr Asp Phe Asn Pro Glu Arg Trp Arg Pro Glu Asn Lys
        435                 440                 445

Leu Pro Gly Ser Pro Met Tyr Ser Trp Gly Tyr Ile Pro Phe Asn Gly
    450                 455                 460

Gly Pro Arg Ile Cys Val Gly Gln Gln Phe Ala Leu Thr Glu Phe Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Leu Asp Arg Thr Ser Leu Thr Ala Met
            500                 505                 510

Val Gly Gly Ser Gly Val Arg Val Lys Leu Ser
        515                 520

<210> SEQ ID NO 62
<211> LENGTH: 1206
<212> TYPE: DNA
<213> ORGANISM: Candida bombicola
<220> FEATURE:
<221> NAME/KEY: CDS
<222> LOCATION: (1)..(1206)

<400> SEQUENCE: 62 atg ttt gcg aaa gct tta tgg gag gat gat gtt ttg gag tac gcc tgc      48
Met Phe Ala Lys Ala Leu Trp Glu Asp Asp Val Leu Glu Tyr Ala Cys
1               5                   10                  15 cgc agg ttt gca ggc atg aag gtc aga act ggg ctt caa act gtc gct      96
Arg Arg Phe Ala Gly Met Lys Val Arg Thr Gly Leu Gln Thr Val Ala
                20                  25                  30 ggc cag cta tgg ata gca act atc gag ccg gag aac atc aag acc gta     144
Gly Gln Leu Trp Ile Ala Thr Ile Glu Pro Glu Asn Ile Lys Thr Val
            35                  40                  45 ctt gcc acc tcg ttc aat gac tac tcc ctt ggc ttc cgt tat aat gcc     192
Leu Ala Thr Ser Phe Asn Asp Tyr Ser Leu Gly Phe Arg Tyr Asn Ala
        50                  55                  60 cta tac ggc ctt ctc gga aat ggt att ttc acc ctt agt ggt gat ggc     240
Leu Tyr Gly Leu Leu Gly Asn Gly Ile Phe Thr Leu Ser Gly Asp Gly
65                  70                  75                  80 tgg aag cac agt cgt gct ttg ttg cgt ccg cag ttc agt cgt gag caa     288
Trp Lys His Ser Arg Ala Leu Leu Arg Pro Gln Phe Ser Arg Glu Gln
                85                  90                  95 gtt tct cac ttg gac tcc atg cgt aca cac atc aac ttg atg atc aac     336
Val Ser His Leu Asp Ser Met Arg Thr His Ile Asn Leu Met Ile Asn
                100                 105                 110 aac cat ttc aaa ggc ggc cac gtc gtt gac gca cag gct cga tac cac     384
Asn His Phe Lys Gly Gly His Val Val Asp Ala Gln Ala Arg Tyr His
            115                 120                 125 aat ttg acc atc gat act gcg act gaa ttc ctt ttc ggt gag agc act     432
Asn Leu Thr Ile Asp Thr Ala Thr Glu Phe Leu Phe Gly Glu Ser Thr
```

```
aac aca ctc gac cct gtt ctt gca cag caa gga ctc cct ggt cct aag    480
Asn Thr Leu Asp Pro Val Leu Ala Gln Gln Gly Leu Pro Gly Pro Lys
145                 150                 155                 160 ggc acc gtt acc gga gag cag ttt gct gaa gct ttc acc tcc gct ctt    528
Gly Thr Val Thr Gly Glu Gln Phe Ala Glu Ala Phe Thr Ser Ala Leu
                165                 170                 175 caa gtg ctg agt gtc cga gtt atg gcc ggc tcc gca tgg ttc ctc att    576
Gln Val Leu Ser Val Arg Val Met Ala Gly Ser Ala Trp Phe Leu Ile
            180                 185                 190 tgg act cct aaa ttc tgg cgc tcg tgc aag gtg tgc cac aac ttc att    624
Trp Thr Pro Lys Phe Trp Arg Ser Cys Lys Val Cys His Asn Phe Ile
        195                 200                 205 gac tac ttc gta tac aag gcc ttg gcc act ccg atg gag aag ggc caa    672
Asp Tyr Phe Val Tyr Lys Ala Leu Ala Thr Pro Met Glu Lys Gly Gln
    210                 215                 220 gag gct gat cgc tat gtt ttt att cga gag ctc aca aag gag act tct    720
Glu Ala Asp Arg Tyr Val Phe Ile Arg Glu Leu Thr Lys Glu Thr Ser
225                 230                 235                 240 gac cca aga gtc atc cgt gac cag gct cta aat atc ctg ctg gct ggt    768
Asp Pro Arg Val Ile Arg Asp Gln Ala Leu Asn Ile Leu Leu Ala Gly
                245                 250                 255 cgt gat acc act gcg gca ctc ctc atc att gcg gac ttt ggc tct gag    816
Arg Asp Thr Thr Ala Ala Leu Leu Ile Ile Ala Asp Phe Gly Ser Glu
            260                 265                 270 gac gct gag ccc cct acc ttt gag cag ctc aag cag tgc aag gta ctg    864
Asp Ala Glu Pro Pro Thr Phe Glu Gln Leu Lys Gln Cys Lys Val Leu
        275                 280                 285 cag aat gtc att cgc gag gtt tta cgt ttg cac cct aat gtg ccg ctc    912
Gln Asn Val Ile Arg Glu Val Leu Arg Leu His Pro Asn Val Pro Leu
    290                 295                 300 aac ttc cgc cag gct ata act gat act aag ctc ccc act ggt ggt ggc    960
Asn Phe Arg Gln Ala Ile Thr Asp Thr Lys Leu Pro Thr Gly Gly Gly
305                 310                 315                 320 ccg aac aga gac cag cct gtc ttt gtt cca aag gga cag aaa gtg ttc   1008
Pro Asn Arg Asp Gln Pro Val Phe Val Pro Lys Gly Gln Lys Val Phe
                325                 330                 335 tac gcc acc tac gtc atg cag cga gat ccg gaa ata tgg ggc ccc gac   1056
Tyr Ala Thr Tyr Val Met Gln Arg Asp Pro Glu Ile Trp Gly Pro Asp
            340                 345                 350 tct aca agc ttc cgc cct gat cga tgg aat gag ccg aga gag gct ctt   1104
Ser Thr Ser Phe Arg Pro Asp Arg Trp Asn Glu Pro Arg Glu Ala Leu
        355                 360                 365 gca tca ggt tgg gat tat att cct ttc aat ggc ggc cct cgc att tgt   1152
Ala Ser Gly Trp Asp Tyr Ile Pro Phe Asn Gly Gly Pro Arg Ile Cys
    370                 375                 380 atc ggt cag cag ttc gct ctc act gag gct agc tac aca ctt gtc cgt   1200
Ile Gly Gln Gln Phe Ala Leu Thr Glu Ala Ser Tyr Thr Leu Val Arg
385                 390                 395                 400 atc tag                                                            1206
Ile

<210> SEQ ID NO 63
<211> LENGTH: 401
<212> TYPE: PRT
<213> ORGANISM: Candida bombicola

<400> SEQUENCE: 63

Met Phe Ala Lys Ala Leu Trp Glu Asp Asp Val Leu Glu Tyr Ala Cys
1               5                   10                  15
```

Arg Arg Phe Ala Gly Met Lys Val Arg Thr Gly Leu Gln Thr Val Ala
            20                  25                  30

Gly Gln Leu Trp Ile Ala Thr Ile Glu Pro Glu Asn Ile Lys Thr Val
        35                  40                  45

Leu Ala Thr Ser Phe Asn Asp Tyr Ser Leu Gly Phe Arg Tyr Asn Ala
 50                  55                  60

Leu Tyr Gly Leu Leu Gly Asn Gly Ile Phe Thr Leu Ser Gly Asp Gly
 65                  70                  75                  80

Trp Lys His Ser Arg Ala Leu Leu Arg Pro Gln Phe Ser Arg Glu Gln
                85                  90                  95

Val Ser His Leu Asp Ser Met Arg Thr His Ile Asn Leu Met Ile Asn
            100                 105                 110

Asn His Phe Lys Gly Gly His Val Val Asp Ala Gln Ala Arg Tyr His
        115                 120                 125

Asn Leu Thr Ile Asp Thr Ala Thr Glu Phe Leu Phe Gly Glu Ser Thr
130                 135                 140

Asn Thr Leu Asp Pro Val Leu Ala Gln Gln Gly Leu Pro Gly Pro Lys
145                 150                 155                 160

Gly Thr Val Thr Gly Glu Gln Phe Ala Glu Ala Phe Thr Ser Ala Leu
                165                 170                 175

Gln Val Leu Ser Val Arg Val Met Ala Gly Ser Ala Trp Phe Leu Ile
            180                 185                 190

Trp Thr Pro Lys Phe Trp Arg Ser Cys Lys Val Cys His Asn Phe Ile
        195                 200                 205

Asp Tyr Phe Val Tyr Lys Ala Leu Ala Thr Pro Met Glu Lys Gly Gln
210                 215                 220

Glu Ala Asp Arg Tyr Val Phe Ile Arg Glu Leu Thr Lys Glu Thr Ser
225                 230                 235                 240

Asp Pro Arg Val Ile Arg Asp Gln Ala Leu Asn Ile Leu Leu Ala Gly
                245                 250                 255

Arg Asp Thr Thr Ala Ala Leu Leu Ile Ile Ala Asp Phe Gly Ser Glu
            260                 265                 270

Asp Ala Glu Pro Pro Thr Phe Glu Gln Leu Lys Gln Cys Lys Val Leu
        275                 280                 285

Gln Asn Val Ile Arg Glu Val Leu Arg Leu His Pro Asn Val Pro Leu
290                 295                 300

Asn Phe Arg Gln Ala Ile Thr Asp Thr Lys Leu Pro Thr Gly Gly Gly
305                 310                 315                 320

Pro Asn Arg Asp Gln Pro Val Phe Val Pro Lys Gly Gln Lys Val Phe
                325                 330                 335

Tyr Ala Thr Tyr Val Met Gln Arg Asp Pro Glu Ile Trp Gly Pro Asp
            340                 345                 350

Ser Thr Ser Phe Arg Pro Asp Arg Trp Asn Glu Pro Arg Glu Ala Leu
        355                 360                 365

Ala Ser Gly Trp Asp Tyr Ile Pro Phe Asn Gly Gly Pro Arg Ile Cys
370                 375                 380

Ile Gly Gln Gln Phe Ala Leu Thr Glu Ala Ser Tyr Thr Leu Val Arg
385                 390                 395                 400

Ile

<210> SEQ ID NO 64
<211> LENGTH: 6084
<212> TYPE: DNA

<213> ORGANISM: Artificial
<220> FEATURE:
<223> OTHER INFORMATION: Vector

<400> SEQUENCE: 64

```
ctaaattgta agcgttaata ttttgttaaa attcgcgtta aattttttgtt aaatcagctc      60
attttttaac caataggccg aaatcggcaa atcccttat aaatcaaaag aatagaccga      120
gataggttg agtggccgct acagggcgct cccattcgcc attcaggctg cgcaactgtt      180
gggaagggcg tttcggtgcg ggcctcttcg ctattacgcc agctggcgaa agggggatgt      240
gctgcaaggc gattaagttg gtaacgcca gggttttccc agtcacgacg ttgtaaaacg      300
acggccagtg agcgcgacgt aatacgactc actatagggc gaattggcgg aaggccgtca      360
aggcctaggc gcgcctgcag gatcctagaa aacagctgga tatggataaa ctcggcaagc      420
atcttttgga aaggctgcca cgctatgccg tgccgatatt cattaagttc gtcgacaccg      480
tcaccatcac cggcaacaac aaagttcaga agaaagaatt ccgaaaccag cagattcccg      540
ccccagcagg acaaacaatc tactggttag agggcacgag ctacaagccc ctcactgctg      600
atgcgtgggc tcgtgtagag aatgggcgac acaagctcta atgttgaata cctcttccgt      660
atagatgtgg cataagctat agattttgct gcaatattat taaatattaa agagtttcga      720
aggtcagctg cggatgaacc agttcagagc ggctctctct ttttttgccaa tagcgtgcaa      780
ccgtgaagag caattcaacc atccaatctg gctacactaa attgtatttg gcagcgcact      840
gtacgagcgc actgtacgaa actccgtcaa tttatagcag aacgcgtgcg atcgcgggcc      900
ccagcgatat gacgagaatc aggcaataat agcttaagct gaagtgtttt tagatttagt      960
tcggagtgcg cttctcaaaa gtgctgggat caacaagttt ttaacatggg ttttgattta     1020
tattgtttta tatgagcgcc tcagatatgc gctgacagcc tattaggaga aatggccggc     1080
ctacaagtcc atatgtgtag agttgttttt gttgttaagt cttctcttaa gagcttgacc     1140
gactataacc gttcaacggc gcattatata cttgggtat cggccagtgc tgacaactca     1200
cacgttgcga ccccttaccc agaagcatac ccagcgcgat gtcgatcgtg ttatatcgta     1260
gacgcacacc ctgcaatgac gggtaggctc taaatcggga tgcgaaaaag aggttgcctt     1320
gcttttgcc ctggtagatg gcatgctgag cgtgcgcttg ccgcctaatt tttgtgtgtc     1380
gcctgctatt tattgctgaa gctagcccgc gcatctttc cccaaggctt cgattgctcg     1440
tattggggca gggattggta ctcaaccttg cagatgagac tccagcaaca acgtcgtact     1500
gcttagcgat cgcacatgtt tcatcatcgt cactatacac atcgtcatca actccatggc     1560
gtgaggactt ccgagactgc tgggcccttc gtttctttaa tgcctcaaga gatgacttcg     1620
tacccgaaga gacgcctgtt gtaccccgtt gacgcttggc ggaggggggct tcgtcctcgt     1680
cagcaacccg cgtcatctgc ttccttcgct gagcaagata ccttctctcc tcgtaccgct     1740
gcatctcctg agctcggtca tacaagatct cttctcgctc aatctctggc agcgcgtcca     1800
acttcgcccct gtcttcagca tcgagatatt tgccttctag aggatagggga ttgacgacct     1860
cattgcttgg cggcgacggc agcgagattt cctcttcgga gtcggagcca acgtcggcca     1920
atgccagcag atcatcatca ctgtcactca tagtaggaag gttgaagtgt gctgacgaat     1980
cagaatcgcg aaggatgcca ttgaaggcat atatatttta atctgtacct tttatggtaa     2040
tttaatcaga ttttataggt attcatgtgc aagttgcatt gaaggaactg tttgagaaaa     2100
tcatcttgac tgaactttc tcagatatgc attccagccc gccttttggt aacgctgagc     2160
ttcgtgcaca ggatctcgtc ccttgctata gagcccgcgt ccgacgataa taacgtctgt     2220
```

```
gccggtctct atgacgtcgt ccacagtacg atactgctgc cccaatccat cacctttgtc    2280
gtccaggccc accccaggag tcataatgac ccagtcttcc tctggctttc cgacttttg     2340 ctgagcgatg aaaccaaaca caaatgcgcg gttactgcga gcgatgtcta ctgtcgcttg    2400
cgagtattcg ccgtgagcca gtgtgccctt cgaactcagt tctgcaagca tgacaaggcc    2460
gcgaggttca tccgtagttt ccttcgcagc ctcttctagt ccgctcacaa ttcccggccc    2520
aggaacaccg tgagcatttg ttatatcagc ccattgagcg atcttaaaca ctccacctgc    2580
atattgggcc ttaacagtgg aaccgatgtc tgcgaacttt cggtcttcaa aaatgagaaa    2640
attgtgcttc gttgaaagct gtttcaaacc gctgacagtt gtgtcgtatt cgaagtcgtc    2700
aattatgtca atgtgggtct taaccataca aatgtaaggt ccaatgcggt ccaggatact    2760
cagtaactca gaggtagttc gcacatccaa gcttgcgcaa agatttgttt gcttgctcac    2820
aatgatgtcg aatagccggg ctgctacagc cggcagcctc tctcggcgct cctcatagct    2880
cagcttcata ttatttctct acagtagtgc ccgtgccctc gatcagctag gacttttcaa    2940
attaatcggg ctgtttgatg taagtaagat gaagtcacgc gcgtgcagga gactgcgtcc    3000
cgcgatattc tgcaggcttg aaaaatttac cctaacggta ggcatcaagt gagtgagtct    3060
cagcgtcgat atgggtcaaa aaggggaaa  actagccgag atcgttgcga gctgtttcga    3120
aaattatgcc ctatggcaat tatcacgtgg agtatccgaa tttctccagg ctgtcaagcg    3180
gcaattataa ccgagactga gatcgagaag tatataaccg cagcagtagt ggataaataa    3240
ttgcgaagtc ttcccagcag agcgggctgt tttttggagt tggttactgt aaaatgctaa    3300
aatgactgac aacaatggag cgtctacagc attggcaaca gtgggaacag tatgctggtg    3360
catccagttg ataccccagg ttctgcgaaa ctggtatgtt cgggattgcg agggcgttcc    3420
tcctctgatg ttcttttttgt tcgccgtttc ggggattccc ttcgcagtgt acttcattga    3480
tcagaattcg aacactgcca tcatggttca acctcacttg tttactttct ttagccttat    3540
aggcttttgg caaagcctgt actatccgcc cgtcagacca gcacgggccg tcacatgtat    3600
ggttgcgtcg ctgtataaga aatcttacaa ctgaagacta cacagcgtat ccgctccgat    3660
atcggcgatc acgtggatac atttccccag aatgcgtcaa ccttgcatgc tcgatattga    3720
ctcaagccga gaggtgtata acaacaccga cgatagcgaa ttacttgtgg aactgatttg    3780
ccgtatcgag taaatcgcga ttgtggccct ctttaggcct tgtacccatt tgtgcatcgt    3840
atttgttagt atgcatcata gaattatgtg aacttagaaa agtccgtatg aaatgagcct    3900
cagattatgg attgatcgct tgttatttgt acagcggaat tgacttatag tatgtcggcc    3960
acggttttag attgcctagg ggccgttttc ttgatggatt cgcatcggaa ctccgaattc    4020
ttgattgctc tccatcgcgc aggaggccgt tcttttttg acaaagtccc attttagggc     4080
gcaggtccaa aaaataagcg gccgcttaat taactggcct catgggcctt ccgctcactg    4140
cccgctttcc agtcgggaaa cctgtcgtgc cagctgcatt aacatggtca tagctgtttc    4200
cttgcgtatt gggcgctctc cgcttcctcg ctcactgact cgctgcgctc ggtcgttcgg    4260
gtaaagcctg gggtgcctaa tgagcaaaag gccagcaaaa ggccaggaac cgtaaaaagg    4320
ccgcgttgct ggcgtttttc cataggctcc gcccccctga cgagcatcac aaaaatcgac    4380
gctcaagtca gaggtggcga aacccgacag gactataaag ataccaggcg tttccccctg    4440
gaagctccct cgtgcgctct cctgttccga ccctgccgct taccggatac ctgtccgcct    4500
ttctcccttc gggaagcgtg cgctttctc  atagctcacg ctgtaggtat ctcagttcgg    4560
```

| | |
|---|---:|
| tgtaggtcgt tcgctccaag ctgggctgtg tgcacgaacc ccccgttcag cccgaccgct | 4620 |
| gcgccttatc cggtaactat cgtcttgagt ccaacccggt aagacacgac ttatcgccac | 4680 |
| tggcagcagc cactggtaac aggattagca gagcgaggta tgtaggcggt gctacagagt | 4740 |
| tcttgaagtg gtggcctaac tacggctaca ctagaagaac agtatttggt atctgcgctc | 4800 |
| tgctgaagcc agttaccttc ggaaaaagag ttggtagctc ttgatccggc aaacaaacca | 4860 |
| ccgctggtag cggtggtttt tttgtttgca agcagcagat tacgcgcaga aaaaaggat | 4920 |
| ctcaagaaga tcctttgatc ttttctacgg ggtctgacgc tcagtggaac gaaaactcac | 4980 |
| gttaagggat tttggtcatg agattatcaa aaaggatctt cacctagatc cttttaaatt | 5040 |
| aaaaatgaag ttttaaatca atctaaagta tatatgagta aacttggtct gacagttacc | 5100 |
| aatgcttaat cagtgaggca cctatctcag cgatctgtct atttcgttca tccatagttg | 5160 |
| cctgactccc cgtcgtgtag ataactacga tacgggaggg cttaccatct ggccccagtg | 5220 |
| ctgcaatgat accgcgagaa ccacgctcac cggctccaga tttatcagca ataaaccagc | 5280 |
| cagccggaag ggccgagcgc agaagtggtc ctgcaacttt atccgcctcc atccagtcta | 5340 |
| ttaattgttg ccgggaagct agagtaagta gttcgccagt taatagtttg cgcaacgttg | 5400 |
| ttgccattgc tacaggcatc gtggtgtcac gctcgtcgtt tggtatggct tcattcagct | 5460 |
| ccggttccca acgatcaagg cgagttacat gatcccccat gttgtgcaaa aaagcggtta | 5520 |
| gctccttcgg tcctccgatc gttgtcagaa gtaagttggc cgcagtgtta tcactcatgg | 5580 |
| ttatggcagc actgcataat tctcttactg tcatgccatc cgtaagatgc ttttctgtga | 5640 |
| ctggtgagta ctcaaccaag tcattctgag aatagtgtat gcggcgaccg agttgctctt | 5700 |
| gcccggcgtc aatacgggat aataccgcgc cacatagcag aactttaaaa gtgctcatca | 5760 |
| ttggaaaacg ttcttcgggg cgaaaactct caaggatctt accgctgttg agatccagtt | 5820 |
| cgatgtaacc cactcgtgca cccaactgat cttcagcatc ttttactttc accagcgttt | 5880 |
| ctgggtgagc aaaaacagga aggcaaaatg ccgcaaaaaa gggaataagg gcgacacgga | 5940 |
| aatgttgaat actcatactc ttcctttttc aatattattg aagcatttat cagggttatt | 6000 |
| gtctcatgag cggatacata tttgaatgta tttagaaaaa taaacaaata ggggttccgc | 6060 |
| gcacatttcc ccgaaaagtg ccac | 6084 |

<210> SEQ ID NO 65
<211> LENGTH: 7693
<212> TYPE: DNA
<213> ORGANISM: Artificial
<220> FEATURE:
<223> OTHER INFORMATION: Vector

<400> SEQUENCE: 65

| | |
|---|---:|
| ctaaattgta agcgttaata ttttgttaaa attcgcgtta aattttttgtt aaatcagctc | 60 |
| attttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa agggggatgt | 240 |
| gctgcaaggc gattaagttg ggtaacgcca gggttttccc agtcacgacg ttgtaaaacg | 300 |
| acggccagtg agcgcgacgt aatacgactc actataggc gaattggcgg aaggccgtca | 360 |
| aggcctaggc gcgcctgcag gatcctagaa aacagctgga tatggataaa ctcggcaagc | 420 |
| atcttttgga aaggctgcca cgctatgccg tgccgatatt cattaagttc gtcgacaccg | 480 |
| tcaccatcac cggcaacaac aaagttcaga agaaagaatt ccgaaaccag cagattcccg | 540 |

-continued

```
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agattttgct gcaatattat taaatattaa agagtttcga    720
aggtcagctg cggatgaacc agttcagagc ggctctctct ttttttgccaa tagcgtgcaa    780 ccgtgaagag caattcaacc atccaatctg ctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga aatggccggc   1080
caacttaaga aaaccgcaca accacaccgg gaggagcgtg ttgagctgta agcgttgttg   1140
agaaacgagg ggactctggg aagtcgggac ccatctcaat cttggaatac tcctgtaaga   1200
gtctcaccag agttagcgaa agctctgtca gggcgaattg ttggccgaga caaattcggg   1260
gaccgccatt gaagggcaag aatgcccaca cattatctag cttcaagttc tcccatcgat   1320
tgggattgaa ttcgtgggcg tcaggacccc aatacttgat gtccctgtgg accatgtaaa   1380
ttgaatagta aactgcggtg cccttaggaa cgaagatcgg atccttctgc tcgggaccac   1440
cacctatggg tagagttgta tctctcacag cagtacggaa gttcaatggc aataccggcg   1500
caagacgcaa gacttcattt ataacttgct tcaaataagg tgcttgcttc agaagttcga   1560
atgataaagg cctttgctcc tccttggttc caaaatgatc gaggacctcc tcacgtagtt   1620
tgttgaatac gtcaggattt ctggcaagga aatgaatagc gaagctcaac gtagcagctg   1680
ttgtatctct accagcaatg agaatgttga aaatttgatc acgtatcgtc actgggtctc   1740
gggtaacttt agccatctca agcgagaaca catagatgcc actagactct gcagcagcat   1800
ccttctctgc aatagagttc tcagcagcga aagatgtggc gtaaagagcc ttatcaacgt   1860
agtagtcaat ataggactga gcacgtttct tgtgatctcg gaattcctta gagttgaaca   1920
accagtagac tttgcttgat agggtccgtt tgaaagcgta attcagtaga aagttgtagg   1980
actccacgaa ttgttcggca gtaatctccg aaccatcacg ggctacaata catgactgat   2040
tctcagggtt caagctctcg caggactccc caaataggaa ttcagtcgct gtatccagcg   2100
taagtttgtg gaaataatgt tgaacatcaa taaattggtc cactttcatt gcacggttca   2160
tctcctttat taactccgca gcatgactgg aaatctgatc aattctgcaa acctgatctt   2220
tagtgaactg aggtctcaac atcgatcgag actgtttcca tccatttccg ctgagtgtaa   2280
atatcccttg gccaaacact tttcccactg tgtggaaacg tgctccaaga ccaaaatcat   2340
tgaatttggt tgccaggatt gtcttaatgt tttctggctc gattgtgaag atttggtatt   2400
gaaggggagc ttgtcgaaga tacgtccgtg ctttgaactt attgaagact ctgtcgtatt   2460
gaacttccag taaggtgtat gacttggccg tcttgatcat gtccatggtt ctttgtattc   2520
ccagtgggaa cgatttctca atgaagcgag gcatactaca cttgtgccta cgtgctgcat   2580
agcggtacca taggagccag ataggctcgt gtagaactaa gaaagctacg aagagcagtg   2640
gcaacaagcc agcaacagcg gataaactca ttggagttag aataatgtct ttgattaaca   2700
tatgtgtaga gttgtttttg ttgttaagtc tttctttaag agcttgaccg actataaccg   2760
ttcaacggcg cattatatac tttgggtatc ggccagtgct gacaactcac acgttgcgac   2820
cccttaccca gaagcatacc cagcgcgatg tcgatcgtgt tatatcgtag acgcacaccc   2880
```

```
tgcaatgacg ggtaggctct aaatcgggat gcgaaaaaga ggttgccttg cttttttgccc    2940 tggtagatgg catgctgagc gtgcgcttgc cgcctaattt ttgtgtgtcg cctgctattt    3000
attgctgaag ctagcccgcc gcatctttcc ccaaggcttc gattgctcgt attggggcag    3060
ggattggtac tcaaccttgc agatgagact ccagcaacaa cgtcgtactg cttagcgatc    3120
gcacatgttt catcatcgtc actatacaca tcgtcatcaa ctccatggcg tgaggacttc    3180
cgagactgct gggcccttcg tttctttaat gcctcaagag atgacttcgt acccgaagag    3240
acgcctgttg taccccgttg acgcttggcg gaggggcctt cgtcctcgtc agcaacccgc    3300
gtcatctgct tccttcgctg agcaagatac cttctctcct cgtaccgctg catctcctga    3360
gctcggtcat acaagatctc ttctcgctca atctctggca gcgcgtccaa cttcgccctg    3420
tcttcagcat cgagatattt gccttctaga ggatagggat tgacgacctc attgcttggc    3480
ggcgacggca gcgagatttc ctcttcggag tcggagccaa cgtcggccaa tgccagcaga    3540
tcatcatcac tgtcactcat agtaggaagg ttgaagtgtg ctgacgaatc agaatcgcga    3600
aggatgccat tgaaggcata tatattttaa tctgtacctt ttatggtaat ttaatcagat    3660
tttataggta ttcatgtgca agttgcattg aaggaactgt ttgagaaaat catcttgact    3720
gaacttttct cagatatgca ttccagcccg ccttttggta acgctgagct tcgtgcacag    3780
gatctcgtcc cttgctatag agcccgcgtc cgacgataat aacgtctgtg ccggtctcta    3840
tgacgtcgtc cacagtacga tactgctgcc ccaatccatc acctttgtcg tccaggccca    3900
ccccaggagt cataatgacc cagtcttcct ctggctttcc gactttttgc tgagcgatga    3960
aaccaaacac aaatgcgcgg ttactgcgag cgatgtctac tgtcgcttgc gagtattcgc    4020
cgtgagccag tgtgcccttc gaactcagtt ctgcaagcat gacaaggccg cgaggttcat    4080
ccgtagtttc cttcgcagcc tcttctagtc cgctcacaat tcccggccca ggaacaccgt    4140
gagcatttgt tatatcagcc cattgagcga tcttaaacac tccacctgca tattgggcct    4200
taacagtgga accgatgtct gcgaactttc ggtcttcaaa aatgagaaaa ttgtgcttcg    4260
ttgaaagctg tttcaaaccg ctgacagttg tgtcgtattc gaagtcgtca attatgtcaa    4320
tgtgggtctt aaccatacaa atgtaaggtc caatgcggtc caggatactc agtaactcag    4380
aggtagttcg cacatccaag cttgcgcaaa gatttgtttg cttgctcaca atgatgtcga    4440
atagccgggc tgctacagcc ggcagcctct ctcggcgctc ctcatagctc agcttcatat    4500
tatttctcta cagtagtgcc cgtgccctcg atcagctagg acttttcaaa ttaatcgggc    4560
tgtttgatgt aagtaagatg aagtcacgcg cgtgcaggag actgcgtccc gcgatattct    4620
gcaggcttga aaaatttacc ctaacggtag gcatcaagtg agtgagtctc agcgtcgata    4680
tgggtcaaaa aagggaaaa ctagccgaga tcgttgcgag ctgtttcgaa aattatgccc    4740
tatggcaatt atcacgtgga gtatccgaat ttctccaggc tgtcaagcgg caattataac    4800
cgagactgag atcgagaagt atataaccgc agcagtagtg gataaataat tgcgaagtct    4860
tcccagcaga gcgggctgtt ttttggagtt ggttactgta aaatgctaaa atgactgaca    4920
acaatggagc gtctacagca ttggcaacag tgggaacagt atgctggtgc atccagttga    4980 tacccccaggt tctgcgaaac tggtatgttc gggattgcga gggcgttcct cctctgatgt    5040 tcttttttgtt cgccgtttcg gggattccct tcgcagtgta cttcattgat cagaattcga    5100
acactgccat catggttcaa cctcacttgt ttactttctt tagccttata ggcttttggc    5160
aaagcctgta ctatccgccc gtcagaccag cacgggccgt cacatgtatg gttgcgtcgc    5220
tgtataagaa atcttacaac tgaagactac acagcgtatc cgctccgata tcggcgatca    5280
```

```
cgtggataca tttccccaga atgcgtcaac cttgcatgct cgatattgac tcaagccgag   5340
aggtgtataa caacaccgac gatagcgaat tacttgtgga actgatttgc cgtatcgagt   5400
aaatcgcgat tgtggccctc tttaggcctt gtacccattt gtgcatcgta tttgttagta   5460
tgcatcatag aattatgtga acttagaaaa gtccgtatga aatgagcctc agattatgga   5520
ttgatcgctt gttatttgta cagcggaatt gacttatagt atgtcggcca cggttttaga   5580
ttgcctaggg gccgttttct tgatggattc gcatcggaac tccgaattct tgattgctct   5640
ccatcgcgca ggaggccgtt cttttttga caaagtccca ttttagggcg caggtccaaa   5700
aaataagcgg ccgcttaatt aactggcctc atgggccttc cgctcactgc ccgctttcca   5760
gtcgggaaac ctgtcgtgcc agctgcatta acatggtcat agctgtttcc ttgcgtattg   5820
ggcgctctcc gcttcctcgc tcactgactc gctgcgctcg gtcgttcggg taaagcctgg   5880
ggtgcctaat gagcaaaagg ccagcaaaag gccaggaacc gtaaaaaggc cgcgttgctg   5940 gcgttttttcc ataggctccg ccccctgac gagcatcaca aaaatcgacg ctcaagtcag   6000
aggtggcgaa acccgacagg actataaaga taccaggcgt ttccccctgg aagctccctc   6060
gtgcgctctc ctgttccgac cctgccgctt accggatacc tgtccgcctt ctcccttcg   6120 ggaagcgtgg cgctttctca tagctcacgc tgtaggtatc tcagttcggt gtaggtcgtt   6180
cgctccaagc tgggctgtgt gcacgaaccc cccgttcagc ccgaccgctg cgccttatcc   6240
ggtaactatc gtcttgagtc aacccggta agacacgact tatcgccact ggcagcagcc   6300
actggtaaca ggattagcag agcgaggtat gtaggcggtg ctacagagtt cttgaagtgg   6360
tggcctaact acggctacac tagaagaaca gtatttggta tctgcgctct gctgaagcca   6420
gttaccttcg gaaaaagagt tggtagctct tgatccggca acaaaccac cgctggtagc   6480 ggtggttttt ttgtttgcaa gcagcagatt acgcgcagaa aaaaggatc tcaagaagat   6540 cctttgatct tttctacggg gtctgacgct cagtggaacg aaaactcacg ttaagggatt   6600
ttggtcatga gattatcaaa aaggatcttc acctagatcc ttttaaatta aaatgaagt   6660 tttaaatcaa tctaaagtat atatgagtaa acttggtctg acagttacca atgcttaatc   6720
agtgaggcac ctatctcagc gatctgtcta tttcgttcat ccatagttgc ctgactcccc   6780
gtcgtgtaga taactacgat acgggagggc ttaccatctg gccccagtgc tgcaatgata   6840
ccgcgagaac cacgctcacc ggctccagat ttatcagcaa taaaccagcc agccggaagg   6900
gccgagcgca gaagtggtcc tgcaacttta tccgcctcca tccagtctat taattgttgc   6960
cgggaagcta gagtaagtag ttcgccagtt aatagtttgc gcaacgttgt tgccattgct   7020
acaggcatcg tggtgtcacg ctcgtcgttt ggtatggctt cattcagctc cggttcccaa   7080
cgatcaaggc gagttacatg atcccccatg ttgtgcaaaa aagcggttag ctccttcggt   7140
cctccgatcg ttgtcagaag taagttggcc gcagtgttat cactcatggt tatggcagca   7200
ctgcataatt ctcttactgt catgccatcc gtaagatgct tttctgtgac tggtgagtac   7260
tcaaccaagt cattctgaga atagtgtatg cggcgaccga gttgctcttg cccggcgtca   7320
atacgggata taccgcgcc acatagcaga actttaaaag tgctcatcat tggaaaacgt   7380
tcttcggggc gaaaactctc aaggatctta ccgctgttga gatccagttc gatgtaaccc   7440
actcgtgcac ccaactgatc ttcagcatct tttactttca ccagcgtttc tgggtgagca   7500
aaaacaggaa ggcaaaatgc cgcaaaaaag ggaataaggg cgacacggaa atgttgaata   7560
ctcatactct tcctttttca atattattga agcatttatc agggttattg tctcatgagc   7620
```

```
ggatacatat tgaatgtat ttagaaaaat aaacaaatag gggttccgcg cacatttccc    7680
cgaaaagtgc cac                                                      7693

<210> SEQ ID NO 66
<211> LENGTH: 7465
<212> TYPE: DNA
<213> ORGANISM: Artificial
<220> FEATURE:
<223> OTHER INFORMATION: Vector

<400> SEQUENCE: 66
ctaaattgta agcgttaata ttttgttaaa attcgcgtta aattttgtt aaatcagctc      60 attttttaac caataggccg aaatcggcaa atcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctgcgaa aggggatgt     240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgcctgcag gatcctagaa acagctgga tatggataaa ctcggcaagc    420
atcttttgga aaggctgcca cgctatgccg tgccgatatt cattaagttc gtcgacaccg    480
tcaccatcac cggcaacaac aaagttcaga agaaagaatt ccgaaaccag cagattcccg    540
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agattttgct gcaatattat taaatattaa agagtttcga    720
aggtcagctg cggatgaacc agttcagagc ggctctctct tttttgccaa tagcgtgcaa    780
ccgtgaagag caattcaacc atccaatctg gctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga atggccggc    1080 cctaagaact caccgctaag gccggacctt tgacaggtat atcttcagtt tcctcgtcac   1140
tcttggtcaa aagaccaaag tcatggctgg cgatttcctc gatgctttcc tcaagaattt   1200
tcaaggagtt gtggctttcc aactccattt gaaccttctt cgaggcttcg tggaatttcg   1260
gatttccaat tatcgaatca acagcttctt tgatttgctc cactgtaggc aagccagttt   1320
tcaaatcaat tgccacgcca gcggcctcag ctctcgatgc caccattggc ttgtcttcag   1380
agtcaccagc aataacaact ggaacagagt ggcttaagct gtgctgaagt ccgccatatc   1440
caccattgta gacaagagca tcaacgtgag gaagtagagc atcgtagttg aagtagtcga   1500
tcacgcgagc attctcagga accacaacat catccggtag cttggcaccg cggcggccca   1560
atatggctac tgttaaagtg tcaggctcgt ccttcaaggc ctcaagagta ggcacaataa   1620
gatgcttgta actgacagca aaagttcctt gagtgaccat gatgactcgc ttggcactca   1680
gaacatcccc ccaccaggaa ggaggggtga attgagttcg gtgcttgggc gttgagccgg   1740
cgaatttgaa gttgctaggc agatggtctc tgctgaactc aagagaaggc gggcacagct   1800
gcaggaactt gtctgcagca atgtaactgt gctcccagat aaatttggga tcttcagtgc   1860
aacctaactc tcggcagatt tccttgtgct tagcagtggc tttaacgaaa atttggtgct   1920
caagagcgtg gttcatagcg agtttctttg catgtgcttc ggggctcctg tcgttgtcaa   1980
```

```
gtcctaaggt atgatcactg cggatcaaaa gaggcaaaac ccctaaacaa atccagccag   2040
cgggtttgaa accaggagca ccgaggctga tagggtgtgc accgaaaaac agcacttcac   2100
tgacaagaac gacagggcga ccgcttgcgc tgagcttttt gaaagccctc tgaatagcgg   2160
caaactgctc aggaagagta gctaccatca tgtgctccac atcttgaact gtacgatcga   2220
agcttggggc catgtcttta cggcccggga ccagatcgtc taaggtgtgg tcatcaaaat   2280
ctgcgttccc ttctaaagga acaaagtctg cacccacatc tcgaactttt tgttcaaacg   2340
ctctgcctgt cacaacagta gcttcgtatc cgtcgtccgt aaggccgtgt accagactca   2400
aaacgggcat tatatggcct gaaagaggca agccgcaagc gagaatcagg gtttgtgtg    2460 atgaagggct catatgtgta gagttgtttt tgttgttaag tctttcttta agagcttgac   2520
cgactataac cgttcaacgg cgcattatat actttgggta tcggccagtg ctgacaactc   2580
acacgttgcg accccttacc cagaagcata cccagcgcga tgtcgatcgt gttatatcgt   2640
agacgcacac cctgcaatga cgggtaggct ctaaatcggg atgcgaaaaa gaggttgcct   2700 tgcttttgc cctggtagat ggcatgctga gcgtgcgctt gccgcctaat ttttgtgtgt    2760
cgcctgctat ttattgctga agctagcccg ccgcatcttt ccccaaggct tcgattgctc   2820 gtattgggc agggattggt actcaacctt gcagatgaga ctccagcaac aacgtcgtac    2880
tgcttagcga tcgcacatgt ttcatcatcg tcactataca catcgtcatc aactccatgg   2940
cgtgaggact tccgagactg ctgggccctt cgtttcttta atgcctcaag agatgacttc   3000
gtacccgaag agacgcctgt tgtacccgt gacgcttgg cggagggggc ttcgtcctcg     3060
tcagcaaccc gcgtcatctg cttccttcgc tgagcaagat accttctctc ctcgtaccgc   3120
tgcatctcct gagctcggtc atacaagatc tcttctcgct caatctctgg cagcgcgtcc   3180
aacttcgccc tgtcttcagc atcgagatat ttgccttcta gaggatagg attgacgacc    3240 tcattgcttg gcggcgacgg cagcgagatt cctcttcgg agtcggagcc aacgtcggcc    3300
aatgccagca gatcatcatc actgtcactc atagtaggaa ggttgaagtg tgctgacgaa   3360
tcagaatcgc gaaggatgcc attgaaggca tatatatttt aatctgtacc ttttatggta   3420
atttaatcag atttatagg tattcatgtg caagttgcat tgaaggaact gtttgagaaa    3480
atcatcttga ctgaactttt ctcagatatg cattccagcc cgccttttgg taacgctgag   3540
cttcgtgcac aggatctcgt cccttgctat agagcccgcg tccgacgata taacgtctg    3600 tgccggtctc tatgacgtcg tccacagtac gatactgctg ccccaatcca tcacctttgt   3660
cgtccaggcc caccccagga gtcataatga cccagtcttc ctctggcttt ccgacttttt   3720
gctgagcgat gaaaccaaac acaaatgcgc ggttactgcg agcgatgtct actgtcgctt   3780
gcgagtattc gccgtgagcc agtgtgccct tcgaactcag ttctgcaagc atgacaaggc   3840
cgcgaggttc atccgtagtt tccttcgcag cctcttctag tccgctcaca attcccggcc   3900
caggaacacc gtgagcattt gttatatcag cccattgagc gatcttaaac actccacctg   3960
catattgggc cttaacagtg gaaccgatgt ctgcgaactt tcggtcttca aaaatgagaa   4020
aattgtgctt cgttgaaagc tgtttcaaac cgctgacagt tgtgtcgtat tcgaagtcgt   4080
caattatgtc aatgtgggtc ttaaccatac aaatgtaagg tccaatgcgg tccaggatac   4140
tcagtaactc agaggtagtt cgcacatcca agcttgcgca agatttgtt tgcttgctca    4200 caatgatgtc gaatagccgg gctgctacag ccggcagcct ctctcggcgc tcctcatagc   4260
tcagcttcat attatttctc tacagtagtg cccgtgccct cgatcagcta ggacttttca   4320
```

```
aattaatcgg gctgtttgat gtaagtaaga tgaagtcacg cgcgtgcagg agactgcgtc    4380
ccgcgatatt ctgcaggctt gaaaaattta ccctaacggt aggcatcaag tgagtgagtc    4440
tcagcgtcga tatgggtcaa aaaggggaa aactagccga gatcgttgcg agctgtttcg     4500
aaaattatgc cctatggcaa ttatcacgtg gagtatccga atttctccag gctgtcaagc    4560
ggcaattata accgagactg agatcgagaa gtatataacc gcagcagtag tggataaata    4620
attgcgaagt cttcccagca gagcgggctg ttttttggag ttggttactg taaaatgcta    4680
aaatgactga caacaatgga gcgtctacag cattggcaac agtgggaaca gtatgctggt    4740
gcatccagtt gataccccag gttctgcgaa actggtatgt tcgggattgc gagggcgttc    4800
ctcctctgat gttcttttg ttcgccgttt cggggattcc cttcgcagtg tacttcattg     4860
atcagaattc gaacactgcc atcatggttc aacctcactt gtttactttc tttagcctta    4920
taggcttttg gcaaagcctg tactatccgc ccgtcagacc agcacgggcc gtcacatgta    4980
tggttgcgtc gctgtataag aaatcttaca actgaagact acacagcgta tccgctccga    5040
tatcggcgat cacgtggata catttcccca gaatgcgtca accttgcatg ctcgatattg    5100
actcaagccg agaggtgtat aacaacaccg acgatagcga attacttgtg gaactgattt    5160
gccgtatcga gtaaatcgcg attgtggccc tcttaggcc ttgtacccat tgtgcatcg     5220 tatttgttag tatgcatcat agaattatgt gaacttagaa aagtccgtat gaaatgagcc    5280
tcagattatg gattgatcgc ttgttatttg tacagcggaa ttgacttata gtatgtcggc    5340
cacggtttta gattgcctag gggccgtttt cttgatggat tcgcatcgga actccgaatt    5400
cttgattgct ctccatcgcg caggaggccg ttctttttt gacaaagtcc cattttaggg    5460
cgcaggtcca aaaataagc ggccgcttaa ttaactggcc tcatgggcct tccgctcact     5520
gcccgctttc cagtcgggaa acctgtcgtg ccagctgcat taacatggtc atagctgttt    5580
ccttgcgtat tgggcgctct ccgcttcctc gctcactgac tcgctgcgct cggtcgttcg    5640
ggtaaagcct ggggtgccta atgagcaaaa ggccagcaaa aggccaggaa ccgtaaaaag    5700
gccgcgttgc tggcgttttt ccataggctc cgcccccctg acgagcatca aaaaatcga    5760 cgctcaagtc agaggtggcg aaacccgaca ggactataaa gataccaggc gtttccccct    5820
ggaagctccc tcgtgcgctc tcctgttccg accctgccgc ttaccggata cctgtccgcc    5880
tttctccctt cgggaagcgt ggcgctttct catagctcac gctgtaggta tctcagttcg    5940
gtgtaggtcg ttcgctccaa gctgggctgt gtgcacgaac ccccgttca gcccgaccgc     6000 tgcgccttat ccggtaacta tcgtcttgag tccaacccgg taagacacga cttatcgcca    6060
ctggcagcag ccactggtaa caggattagc agagcgaggt atgtaggcgg tgctacagag    6120
ttcttgaagt ggtggcctaa ctacggctac actagaagaa cagtatttgg tatctgcgct    6180
ctgctgaagc cagttacctt cggaaaaaga gttggtagct cttgatccgg caaacaaacc    6240
accgctggta gcggtggttt ttttgtttgc aagcagcaga ttacgcgcag aaaaaaagga    6300
tctcaagaag atcctttgat cttttctacg ggtctgacg ctcagtggaa cgaaaactca     6360
cgttaaggga ttttggtcat gagattatca aaaaggatct tcacctagat ccttttaaat    6420
taaaaatgaa gttttaaatc aatctaaagt atatatgagt aaacttggtc tgacagttac    6480
caatgcttaa tcagtgaggc acctatctca gcgatctgtc tatttcgttc atccatagtt    6540
gcctgactcc ccgtcgtgta gataactacg atacgggagg gcttaccatc tggccccagt    6600
gctgcaatga taccgcgaga accacgctca ccggctccag atttatcagc aataaaccag    6660
ccagccggaa gggccgagcg cagaagtggt cctgcaactt tatccgcctc catccagtct    6720
```

```
attaattgtt gccgggaagc tagagtaagt agttcgccag ttaatagttt gcgcaacgtt    6780
gttgccattg ctacaggcat cgtggtgtca cgctcgtcgt ttggtatggc ttcattcagc    6840
tccggttccc aacgatcaag gcgagttaca tgatccccca tgttgtgcaa aaaagcggtt    6900
agctccttcg gtcctccgat cgttgtcaga gtaagttgg ccgcagtgtt atcactcatg    6960
gttatggcag cactgcataa ttctcttact gtcatgccat ccgtaagatg cttttctgtg    7020
actggtgagt actcaaccaa gtcattctga gaatagtgta gcggcgacc gagttgctct    7080 tgcccggcgt caatacggga taataccgcg ccacatagca gaactttaaa agtgctcatc    7140
attggaaaac gttcttcggg gcgaaaactc tcaaggatct taccgctgtt gagatccagt    7200
tcgatgtaac ccactcgtgc acccaactga tcttcagcat cttttacttt caccagcgtt    7260
tctgggtgag caaaaacagg aaggcaaaat gccgcaaaaa agggaataag ggcgacacgg    7320
aaatgttgaa tactcatact cttccttttt caatattatt gaagcattta tcagggttat    7380
tgtctcatga gcggatacat atttgaatgt atttagaaaa ataaacaaat aggggttccg    7440
cgcacatttc cccgaaaagt gccac                                          7465

<210> SEQ ID NO 67
<211> LENGTH: 6856
<212> TYPE: DNA
<213> ORGANISM: Artificial
<220> FEATURE:
<223> OTHER INFORMATION: Vector

<400> SEQUENCE: 67
ctaaattgta agcgttaata ttttgttaaa attcgcgtta aattttttgtt aaatcagctc      60 attttttaac caataggccg aaatcggcaa atcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgcctgcag gatcctagaa aacagctgga tatggataaa ctcggcaagc    420
atcttttgga aaggctgcca cgctatgccg tgccgatatt cattaagttc gtcgacaccg    480
tcaccatcac cggcaacaac aaagttcaga gaaagaatt ccgaaaccag cagattcccg    540
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agatttttgct gcaatattat taaatattaa agagtttcga    720
aggtcagctg cggatgaacc agttcagagc ggctctctct ttttgccaa tagcgtgcaa    780 ccgtgaagag caattcaacc atccaatctg ctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga atggccggc    1080 ctacctagac cttctggtta gcggtattga cgttcatttc aactggaaga aggaattcca   1140
gttcctctcc ttcagcctcg tcgggatcct cctctggaat atgcttgagg attcgcgcag   1200
ggactcctcc caccacagta cgaggaggaa catcttctcg aacgacagca ccagccgcaa   1260
```

```
ttgttgagcc atctccaatc gtaacacccg gcaggacagt cacattcgca ccaatccata    1320
cattattccc caccttgata ggaagagcat acacaattct cctcgcacgt ttctcggggc    1380
taataggatg agtcgcagtc acgaacgttg tattgggccc tacaatcacc tcatcaccaa    1440
agattattgg agccgagtcc aagaagcaaa cgttgaagtt ggcgtaaaag tgctcgccta    1500
cgctgatgtt gaatccaaaa tcaactgaga atggagcggt cagccagaca atatcctttg    1560
tttgaccaaa agtgtctttg agaatctcga ccttcttgat ataagcagcg tgatttgact    1620
caaaagtacg actttcactt gcaatggtat tgaactccct aactttctca ctagtagcca    1680
gggctctaaa cataagatct ggatcgtatg gattgtaagg aactcctgag accatcttct    1740
catagttttc attgccaggg gtgttttga ggtttttttt ggcccaagag accatttcct     1800
ggtcaatttc ttttctagga gtcattcctt tgttttgagg gtccttcgag gagtttacaa    1860
ccatatgtgt agagttgttt ttgttgttaa gtctttcttt aagagcttga ccgactataa    1920
ccgttcaacg gcgcattata tactttgggt atcggccagt gctgacaact cacacgttgc    1980
gacccttac ccagaagcat acccagcgcg atgtcgatcg tgttatatcg tagacgcaca     2040
ccctgcaatg acgggtaggc tctaaatcgg gatgcgaaaa agaggttgcc ttgcttttg     2100
ccctggtaga tggcatgctg agcgtgcgct tgccgcctaa tttttgtgtg tcgcctgcta    2160
tttattgctg aagctagccc gccgcatctt tccccaaggc ttcgattgct cgtattgggg    2220
cagggattgg tactcaacct tgcagatgag actccagcaa caacgtcgta ctgcttagcg    2280
atcgcacatg tttcatcatc gtcactatac acatcgtcat caactccatg gcgtgaggac    2340
ttccgagact gctgggccct tcgtttcttt aatgcctcaa gagatgactt cgtacccgaa    2400
gagacgcctg ttgtaccccg ttgacgcttg gcggaggggg cttcgtcctc gtcagcaacc    2460
cgcgtcatct gcttccttcg ctgagcaaga taccttctct cctcgtaccg ctgcatctcc    2520
tgagctcggt catacaagat ctcttctcgc tcaatctctg gcagcgcgtc caacttcgcc    2580
ctgtcttcag catcgagata tttgccttct agaggatagg gattgacgac ctcattgctt    2640
ggcggcgacg gcagcgagat ttcctcttcg gagtcggagc caacgtcggc caatgccagc    2700
agatcatcat cactgtcact catagtagga aggttgaagt gtgctgacga atcagaatcg    2760
cgaaggatgc cattgaaggc atatatattt taatctgtac cttttatggt aatttaatca    2820
gattttatag gtattcatgt gcaagttgca ttgaaggaac tgtttgagaa atcatcttg     2880
actgaacttt tctcagatat gcattccagc ccgccttttg gtaacgctga gcttcgtgca    2940
caggatctcg tcccttgcta tagagcccgc gtccgacgat aataacgtct gtgccggtct    3000
ctatgacgtc gtccacagta cgatactgct gccccaatcc atcacctttg tcgtccaggc    3060
ccaccccagg agtcataatg acccagtctt cctctggctt tccgactttt tgctgagcga    3120
tgaaaccaaa cacaaatgcg cggttactgc gagcgatgtc tactgtcgct tgcgagtatt    3180
cgccgtgagc cagtgtgccc ttcgaactca gttctgcaag catgacaagg ccgcgaggtt    3240
catccgtagt ttccttcgca gcctcttcta gtccgctcac aattcccggc caggaacac    3300
cgtgagcatt tgttatatca gcccattgag cgatcttaaa cactccacct gcatattggg    3360
ccttaacagt ggaaccgatg tctgcgaact ttcggtcttc aaaaatgaga aaattgtgct    3420
tcgttgaaag ctgtttcaaa ccgctgacag ttgtgtcgta ttcgaagtcg tcaattatgt    3480
caatgtgggt cttaaccata caaatgtaag gtccaatgcg gtccaggata ctcagtaact    3540
cagaggtagt tcgcacatcc aagcttgcgc aaagatttgt ttgcttgctc acaatgatgt    3600
cgaatagccg ggctgctaca gccggcagcc tctctcggcg ctcctcatag ctcagcttca    3660
```

```
tattatttct ctacagtagt gcccgtgccc tcgatcagct aggacttttc aaattaatcg    3720
ggctgtttga tgtaagtaag atgaagtcac gcgcgtgcag gagactgcgt cccgcgatat    3780
tctgcaggct tgaaaaattt accctaacgg taggcatcaa gtgagtgagt ctcagcgtcg    3840
atatgggtca aaaaagggga aaactagccg agatcgttgc gagctgtttc gaaaattatg    3900
ccctatggca attatcacgt ggagtatccg aatttctcca ggctgtcaag cggcaattat    3960
aaccgagact gagatcgaga agtatataac cgcagcagta gtggataaat aattgcgaag    4020
tcttcccagc agagcgggct gttttttgga gttggttact gtaaaatgct aaaatgactg    4080
acaacaatgg agcgtctaca gcattggcaa cagtgggaac agtatgctgg tgcatccagt    4140
tgatacccca ggttctgcga aactggtatg ttcgggattg cgagggcgtt cctcctctga    4200
tgttcttttt gttcgccgtt tcggggattc ccttcgcagt gtacttcatt gatcagaatt    4260
cgaacactgc catcatggtt caacctcact tgtttacttt ctttagcctt ataggctttt    4320
ggcaaagcct gtactatccg cccgtcgacc agcacgggc cgtcacatgt atggttgcgt    4380
cgctgtataa gaaatcttac aactgaagac tacacagcgt atccgctccg atatcggcga    4440
tcacgtggat acatttcccc agaatgcgtc aaccttgcat gctcgatatt gactcaagcc    4500
gagaggtgta taacaacacc gacgatagcg aattacttgt ggaactgatt tgccgtatcg    4560
agtaaatcgc gattgtggcc ctctttaggc cttgtaccca tttgtgcatc gtatttgtta    4620
gtatgcatca tagaattatg tgaacttaga aaagtccgta tgaaatgagc ctcagattat    4680
ggattgatcg cttgttattt gtacagcgga attgacttat agtatgtcgg ccacggtttt    4740
agattgccta ggggccgttt tcttgatgga ttcgcatcgg aactccgaat tcttgattgc    4800
tctccatcgc gcaggaggcc gttctttttt tgacaaagtc ccattttagg gcgcaggtcc    4860
aaaaaataag cggccgctta attaactggc ctcatgggcc ttccgctcac tgcccgcttt    4920
ccagtcggga aacctgtcgt gccagctgca ttaacatggt catagctgtt tccttgcgta    4980
ttgggcgctc tccgcttcct cgctcactga ctcgctgcgc tcggtcgttc gggtaaagcc    5040
tggggtgcct aatgagcaaa aggccagcaa aaggccagga accgtaaaaa ggccgcgttg    5100
ctggcgtttt tccataggct ccgcccccct gacgagcatc acaaaaatcg acgctcaagt    5160
cagaggtggc gaaacccgac aggactataa agataccagg cgtttccccc tggaagctcc    5220
ctcgtgcgct ctcctgttcc gaccctgccg cttaccggat acctgtccgc ctttctccct    5280
tcgggaagcg tggcgctttc tcatagctca cgctgtaggt atctcagttc ggtgtaggtc    5340
gttcgctcca agctgggctg tgtgcacgaa ccccccgttc agcccgaccg ctgcgcctta    5400
tccggtaact atcgtcttga gtccaacccg gtaagacacg acttatcgcc actggcagca    5460
gccactggta acaggattag cagagcgagg tatgtaggcg gtgctacaga gttcttgaag    5520
tggtggccta actacggcta cactagaaga acagtatttg gtatctgcgc tctgctgaag    5580
ccagttacct tcggaaaaag agttggtagc tcttgatccg gcaaacaaac caccgctggt    5640
agcggtggtt tttttgtttg caagcagcag attacgcgca gaaaaaaagg atctcaagaa    5700
gatcctttga tcttttctac ggggtctgac gctcagtgga acgaaaactc acgttaaggg    5760
attttggtca tgagattatc aaaaaggatc ttcacctaga tccttttaaa ttaaaaatga    5820
agttttaaat caatctaaag tatatatgag taaacttggt ctgacagtta ccaatgctta    5880
atcagtgagg cacctatctc agcgatctgt ctatttcgtt catccatagt tgcctgactc    5940
cccgtcgtgt agataactac gatacgggag ggcttaccat ctggccccag tgctgcaatg    6000
```

```
ataccgcgag aaccacgctc accggctcca gatttatcag caataaacca gccagccgga    6060
agggccgagc gcagaagtgg tcctgcaact ttatccgcct ccatccagtc tattaattgt    6120
tgccgggaag ctagagtaag tagttcgcca gttaatagtt tgcgcaacgt tgttgccatt    6180
gctacaggca tcgtggtgtc acgctcgtcg tttggtatgg cttcattcag ctccggttcc    6240
caacgatcaa ggcgagttac atgatccccc atgttgtgca aaaaagcggt tagctccttc    6300
ggtcctccga tcgttgtcag aagtaagttg gccgcagtgt tatcactcat ggttatggca    6360
gcactgcata attctcttac tgtcatgcca tccgtaagat gcttttctgt gactggtgag    6420
tactcaacca agtcattctg agaatagtgt atgcggcgac cgagttgctc ttgcccggcg    6480
tcaatacggg ataataccgc gccacatagc agaactttaa aagtgctcat cattggaaaa    6540
cgttcttcgg ggcgaaaact ctcaaggatc ttaccgctgt tgagatccag ttcgatgtaa    6600
cccactcgtg cacccaactg atcttcagca tcttttactt tcaccagcgt ttctgggtga    6660
gcaaaaacag gaaggcaaaa tgccgcaaaa aagggaataa gggcgacacg gaaatgttga    6720
atactcatac tcttcctttt tcaatattat tgaagcattt atcagggtta ttgtctcatg    6780
agcggataca tatttgaatg tatttagaaa aataaacaaa tagggggttcc gcgcacattt    6840 ccccgaaaag tgccac                                                   6856

<210> SEQ ID NO 68
<211> LENGTH: 9973
<212> TYPE: DNA
<213> ORGANISM: Artificial
<220> FEATURE:
<223> OTHER INFORMATION: Vector

<400> SEQUENCE: 68
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa aggggggatgt    240 gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgcctgcag gatcctagaa aacagctgga tatggataaa ctcggcaagc    420
atcttttgga aaggctgcca cgctatgccg tgccgatatt cattaagttc gtcgacaccg    480
tcaccatcac cggcaacaac aaagttcaga gaaagaatt ccgaaaccag cagattcccg    540
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agattttgct gcaatattat taaatattaa agagtttcga    720
aggtcagctg cggatgaacc agttcagagc ggctctctct ttttttgccaa tagcgtgcaa    780 ccgtgaagag caattcaacc atccaatctg gctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga aatggccggc   1080
ctcaaatctc tccgagacct tgcaagttca ccaattcagc gtaccatcca ttgagttcaa   1140
ggaggctctg atggtcgccc tgctccacga tgcgccctcc tgagaacaca tatatgacat   1200
```

```
ctgctttctg aattgttgat aatctatgcg caacggcgat tgtagtacgg cccttcgctg    1260
ctgcgtcgag tgctgcttga actactttct cagattcgga atccagagct gaggtggcct    1320
catcgaggag gagtaccttt ggatttctga tcagggccct tgcaattgca attcgctgct    1380
tttgccccc  agatagcaac gatccctag  atccgctgag cgtttcgtag ccatcaggca    1440
acgacatgat gaattcgtga atgttcgctt tgcgagcggc atcctcaatc atctcctgcg    1500
ttacttcaga ctcagggcca gaccatccca ttagaatatt ctcacgtagc gtgcctgaat    1560
aaagcattgg ttcttgctgg actaaagcaa tgtgtgatct caatgcattc aggttatatt    1620
cgcgtaaatc tttcccatcg aaaagtactt gacctgctaa tggatcataa aatctttcca    1680
ccagtccaat agtagtagac ttaccgcatc cactggctcc aactagagcg atgtattggc    1740
ccttttttgac tgttaagttg agatcttgta aaactggtac ttgaggtcga gtaggatatc    1800
ggaaattcac atgacggaac tcaatatctc ctctcaccga ctcctcggga gcaacgtaac    1860
cttcctcact ccatacatct atagaaggag tggcagtcaa gattctgtaa atgttacgcg    1920
ctgcatcttt ggctgagttc atgtttggag catagctgaa aatttggcca gcggcttgag    1980
aacctgtaat aatagccatg aagacagtca tatatcctgc gaccgaagct tcacctcgtc    2040
tcattacagt gcttccccac caaaaaacga gggctaccac ccagggtgtc attccttccg    2100
agagtgcgta gtacaatgct gagcgggcaa tggcaattct ggagctgaaa atctgagagt    2160
ctactgtctt tgtgtatttt acgaccacgt ctaactcacg agttaaggac tggactgtgc    2220
ggacagcact tgtatactca gatgccatgg agccacttcg ttcgtaaact tctctcgcac    2280
gatccgataa ttgggtaaga acccagactc tgacgaagcc acacaccaac atgacaggaa    2340
caacagacgt agccacgagt ccaattctcc aattgaaagg tataccagta actatgccgc    2400
caatcaaggt caccagactc tgttgaattt gaccgagggt ggccccactc aaaccctcga    2460
tcattttagc ttccttcgcc aaaattgagg ttagcgcacc cggcgtgttg ttttgtggt     2520
cgaagaatgc aatatccatt cgcatcaatt ggcggaacaa agctaatctg atattttga    2580
ccaacttatc agatgcaagt gataaagcag ctatagtgat aaaagccgtc atgaatgaaa    2640
tgcagcctac gaaaaaatac caccatccca tgatattcac cacatgccgc attttttccgt    2700
attcactggg aggtagaacc atgcttccag tggtttggcc agttattatt gccattgcag    2760
gatagcaata gcccaaaata atggaggcta aactaccaat gagaatgtaa ccccattctt    2820
tcctattcag cccccaaacc agtttggtat tggtcatcaa cgtgctatgt gggggggttgc    2880
gcacaccagg gatgtcattt tcttgatatt caggaggttg agtggtctga gtacctgcac    2940
tgtgaacact caatgtgctc acatccttgg gattgaactt ttcgttcagt gagtccagag    3000
gcgaaatgtc tagagcttca atatcgagga cctcaacgtt agtgctcttt gctttagtta    3060
ctctttgagc atcaaccaaa gctttataag gcccttctcg ctgtatgagc tcattgtgag    3120
taccctgctc tatgacgtta cctttagaca tgacaactat cttgttggca tccttgatcg    3180
tagagagtct gtgtgcaacg actatagtgg tacgaccttc ggccgctttg tcgagcgcat    3240
cttgaacgat accttcagat ttggtatcca gagcagaagt cgcttcatcg agcagcagaa    3300
ttttagggtc tgagacgatt gctcttgcta ttgcaatgcg ttgtttctga ccaccgctga    3360
gaagaaatcc tcgatctcca acattggttt ggatgccttc tgagagagtc tgaatgaaat    3420
cccaggcatt ggcatctttta caagcttgaa tgattttagc ttccttaaca tgctcgtcag    3480
cgaactcaat gtcagtgcca atcaaaccat agctgatatt ctcatatatt gactctgaaa    3540
```

```
agagtactgg ttcctgctga acataaccaa tttgttgacg gagccatctt gtgttcaggt    3600
cgctaatctc ctggccatcc agagtaacgc ttccttcgag aggtaaatag aacctctcaa    3660
gaatacctac aattgtagac ttccctgatc ccgaggcacc taccagtgcc acagtagatc    3720
cagcaggaac ttcaaggcta aaatcggaga ggaccaaaac gtctgggcga ctaggatatc    3780
ggaacttgac attttttgagc tcaattctgc caacggcctt agtttggggg acaattcctt    3840
tatctatgga ctggccatcg atgactggga cacgatcaat ggcctcattg agaatgctcg    3900
cggcagtgag acccttgaca agaaacctca cgtttggcgc gatattccca agctggaagc    3960
ttccaagtaa catagctgtg attacaacta ttatctttcc aacgtcagca ctcccactaa    4020
cgatttctct ggaaccctgc cacagagcta aggcatacac ccaaaaagta ctagcccaaa    4080
tgcacgctaa catgaccccc aatgagtaac tgctccgctt cgattccttc acaacacgat    4140
caagtacctt ttcatacttg acggcgagat gaggttgagc gccaaatgct actgtagtcc    4200
tgacagcact gagagcctcc tccgcaacgg tagctccaga ctgcgaatat atcgcgtcag    4260
atctgagctg atatttggcc atgaaggtgg cgccagttcc cattgtgatt accatgaacc    4320
ctacagcact caggaggatg caagccagtt tccattgcga agcaaaactt ataacggtgg    4380
ccgcaatgaa ggaagctatt ccctgtacga cgtttccaag cttgtcgctg atcgcttcct    4440
gaattgagtt ggtatcgtta atgattctgg tgctgacctc gccaccacct agtttgtcgt    4500
aaaacgcgat attctggcga ataacagcac tcagataatg ctttcggtaa cgtcctgcca    4560
acacttcgcc tctgtccaca agcaggaagc tctcgagaaa cgcactgccg agcataccaa    4620
tgccaatata gacaaaatag agagacaggt gattcacctt atgctggaac tcattgccct    4680
tgaggtcata gctagtgaag tctctgaatg tgttgaagat ggcgcccact actaacgtga    4740
acattggaag cgcggctcca tgcaccgctg caaaaaaaag cgcaagtatc tccaagaaaa    4800
cgtcaagggg agtgcaaaat ctgaacaacc tgaaaaagct tgtggcgact ctctttgttt    4860
caagctgact tcgcaataca ttggcctcat gtggatctaa cgcagagagc ttctcctcga    4920
gaagcttgtc cttagtctcg atgagttttct cacgcttctc tacctgtata tcatccacca    4980
tatgtgtaga gttgtttttg ttgttaagtc tttctttaag agcttgaccg actataaccg    5040
ttcaacggcg cattatatac tttgggtatc ggccagtgct gacaactcac acgttgcgac    5100
cccttaccca gaagcatacc cagcgcgatg tcgatcgtgt tatatcgtag acgcacaccc    5160
tgcaatgacg ggtaggctct aaatcgggat gcgaaaaaga ggttgccttg cttttttgccc    5220 tggtagatgg catgctgagc gtgcgcttgc cgcctaattt ttgtgtgtcg cctgctattt    5280
attgctgaag ctagcccgcc gcatctttcc ccaaggcttc gattgctcgt attggggcag    5340
ggattggtac tcaaccttgc agatgagact ccagcaacaa cgtcgtactg cttagcgatc    5400
gcacatgttt catcatcgtc actatacaca tcgtcatcaa ctccatggcg tgaggacttc    5460
cgagactgct gggcccttcg tttctttaat gcctcaagag atgacttcgt acccgaagag    5520
acgcctgttg taccccgttg acgcttggcg gagggggctt cgtcctcgtc agcaacccgc    5580
gtcatctgct tccttcgctg agcaagatac cttctctcct cgtaccgctg catctcctga    5640
gctcggtcat acaagatctc ttctcgctca atctctggca gcgcgtccaa cttcgccctg    5700
tcttcagcat cgagatattt gccttctaga ggatagggat tgacgacctc attgcttggc    5760
ggcgacggca gcgagatttc ctcttcggag tcggagccaa cgtcggccaa tgccagcaga    5820
tcatcatcac tgtcactcat agtaggaagg ttgaagtgtg ctgacgaatc agaatcgcga    5880
aggatgccat tgaaggcata tatatttttaa tctgtacctt ttatggtaat ttaatcagat    5940
```

```
tttataggta ttcatgtgca agttgcattg aaggaactgt ttgagaaaat catcttgact    6000
gaacttttct cagatatgca ttccagcccg ccttttggta acgctgagct tcgtgcacag    6060
gatctcgtcc cttgctatag agcccgcgtc cgacgataat aacgtctgtg ccggtctcta    6120
tgacgtcgtc cacagtacga tactgctgcc ccaatccatc acctttgtcg tccaggccca    6180
ccccaggagt cataatgacc cagtcttcct ctggctttcc gacttttgc tgagcgatga     6240 aaccaaacac aaatgcgcgg ttactgcgag cgatgtctac tgtcgcttgc gagtattcgc    6300
cgtgagccag tgtgcccttc gaactcagtt ctgcaagcat gacaaggccg cgaggttcat    6360
ccgtagtttc cttcgcagcc tcttctagtc cgctcacaat tcccggccca ggaacaccgt    6420
gagcatttgt tatatcagcc cattgagcga tcttaaacac tccacctgca tattgggcct    6480
taacagtgga accgatgtct gcgaactttc ggtcttcaaa aatgagaaaa ttgtgcttcg    6540
ttgaaagctg tttcaaaccg ctgacagttg tgtcgtattc gaagtcgtca attatgtcaa    6600
tgtgggtctt aaccatacaa atgtaaggtc aatgcggtc caggatactc agtaactcag     6660
aggtagttcg cacatccaag cttgcgcaaa gatttgtttg cttgctcaca atgatgtcga    6720
atagccgggc tgctacagcc ggcagcctct ctcggcgctc ctcatagctc agcttcatat    6780
tatttctcta cagtagtgcc cgtgccctcg atcagctagg acttttcaaa ttaatcgggc    6840
tgtttgatgt aagtaagatg aagtcacgcg cgtgcaggag actgcgtccc gcgatattct    6900
gcaggcttga aaaatttacc ctaacggtag gcatcaagtg agtgagtctc agcgtcgata    6960
tgggtcaaaa aagggaaaa ctagccgaga tcgttgcgag ctgtttcgaa aattatgccc      7020
tatggcaatt atcacgtgga gtatccgaat ttctccaggc tgtcaagcgg caattataac    7080
cgagactgag atcgagaagt atataaccgc agcagtagtg gataaataat tgcgaagtct    7140
tcccagcaga gcgggctgtt ttttggagtt ggttactgta aaatgctaaa atgactgaca    7200
acaatggagc gtctacagca ttggcaacag tgggaacagt atgctggtgc atccagttga    7260
taccccaggt tctgcgaaac tggtatgttc gggattgcga gggcgttcct cctctgatgt    7320 tcttttttgtt cgccgtttcg gggattccct tcgcagtgta cttcattgat cagaattcga    7380
acactgccat catggttcaa cctcacttgt ttactttctt tagccttata ggcttttggc    7440
aaagcctgta ctatccgccc gtcagaccag cacgggccgt cacatgtatg gttgcgtcgc    7500
tgtataagaa atcttacaac tgaagactac acagcgtatc cgctccgata tcggcgatca    7560
cgtggataca tttccccaga atgcgtcaac cttgcatgct cgatattgac tcaagccgag    7620
aggtgtataa caacaccgac gatagcgaat tacttgtgga actgatttgc cgtatcgagt    7680
aaatcgcgat tgtggccctc tttaggcctt gtacccattt gtgcatcgta tttgttagta    7740
tgcatcatag aattatgtga acttagaaaa gtccgtatga aatgagcctc agattatgga    7800
ttgatcgctt gttatttgta cagcggaatt gacttatagt atgtcggcca cggttttaga    7860
ttgcctaggg gccgttttct tgatggattc gcatcggaac tccgaattct tgattgctct    7920
ccatcgcgca ggaggccgtt ctttttttga caaagtccca tttagggcg caggtccaaa     7980 aaataagcgg ccgcttaatt aactggcctc atgggccttc cgctcactgc ccgctttcca    8040
gtcgggaaac ctgtcgtgcc agctgcatta acatggtcat agctgtttcc ttgcgtattg    8100
ggcgctctcc gcttcctcgc tcactgactc gctgcgctcg tcgttcggg taaagcctgg     8160 ggtgcctaat gagcaaaagg ccagcaaaag gccaggaacc gtaaaaaggc cgcgttgctg    8220 gcgttttttcc ataggctccg ccccctgac gagcatcaca aaaatcgacg ctcaagtcag    8280
```

-continued

```
aggtggcgaa acccgacagg actataaaga taccaggcgt ttccccctgg aagctccctc    8340
gtgcgctctc ctgttccgac cctgccgctt accggatacc tgtccgcctt tctcccttcg    8400
ggaagcgtgg cgcttctca tagctcacgc tgtaggtatc tcagttcggt gtaggtcgtt    8460
cgctccaagc tgggctgtgt gcacgaaccc cccgttcagc ccgaccgctg cgccttatcc    8520
ggtaactatc gtcttgagtc caacccggta agacacgact tatcgccact ggcagcagcc    8580
actggtaaca ggattagcag agcgaggtat gtaggcggtg ctacagagtt cttgaagtgg    8640
tggcctaact acggctacac tagaagaaca gtatttggta tctgcgctct gctgaagcca    8700
gttaccttcg gaaaaagagt tggtagctct tgatccggca acaaaccac cgctggtagc    8760
ggtggttttt ttgtttgcaa gcagcagatt acgcgcagaa aaaaggatc tcaagaagat    8820
cctttgatct tttctacggg gtctgacgct cagtggaacg aaaactcacg ttaagggatt    8880
ttggtcatga gattatcaaa aaggatcttc acctagatcc ttttaaatta aaaatgaagt    8940
tttaaatcaa tctaaagtat atatgagtaa acttggtctg acagttacca atgcttaatc    9000
agtgaggcac ctatctcagc gatctgtcta tttcgttcat ccatagttgc ctgactcccc    9060
gtcgtgtaga taactacgat acgggagggc ttaccatctg gccccagtgc tgcaatgata    9120
ccgcgagaac cacgctcacc ggctccagat ttatcagcaa taaaccagcc agccggaagg    9180
gccgagcgca gaagtggtcc tgcaacttta tccgcctcca tccagtctat taattgttgc    9240
cgggaagcta gagtaagtag ttcgccagtt aatagtttgc gcaacgttgt tgccattgct    9300
acaggcatcg tggtgtcacg ctcgtcgttt ggtatggctt cattcagctc cggttcccaa    9360
cgatcaaggc gagttacatg atcccccatg ttgtgcaaaa aagcggttag ctccttcggt    9420
cctccgatcg ttgtcagaag taagttggcc gcagtgttat cactcatggt tatggcagca    9480
ctgcataatt ctcttactgt catgccatcc gtaagatgct tttctgtgac tggtgagtac    9540
tcaaccaagt cattctgaga atagtgtatg cggcgaccga gttgctcttg cccggcgtca    9600
atacgggata taccgcgcc acatagcaga actttaaaag tgctcatcat ggaaaacgt    9660
tcttcggggc gaaaactctc aaggatctta ccgctgttga gatccagttc gatgtaaccc    9720
actcgtgcac ccaactgatc ttcagcatct tttactttca ccagcgtttc tgggtgagca    9780
aaaacaggaa ggcaaaatgc cgcaaaaaag ggaataaggg cgacacggaa atgttgaata    9840
ctcatactct tcctttttca atattattga agcatttatc agggttattg tctcatgagc    9900
ggatacatat ttgaatgtat ttagaaaaat aaacaaatag gggttccgcg cacatttccc    9960
cgaaaagtgc cac    9973

<210> SEQ ID NO 69
<211> LENGTH: 7375
<212> TYPE: DNA
<213> ORGANISM: Artificial
<220> FEATURE:
<223> OTHER INFORMATION: Vector

<400> SEQUENCE: 69
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtggccgct acaggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
```

```
aggcctaggc gcgcctgcag gatcctagaa aacagctgga tatggataaa ctcggcaagc    420
atctttgga  aaggctgcca cgctatgccg tgccgatatt cattaagttc gtcgacaccg    480
tcaccatcac cggcaacaac aaagttcaga agaaagaatt ccgaaaccag cagattcccg    540
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agattttgct gcaatattat taaatattaa agagtttcga   720
aggtcagctg cggatgaacc agttcagagc ggctctctct tttttgccaa tagcgtgcaa    780
ccgtgaagag caattcaacc atccaatctg gctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga aatggccggc   1080
caggttaaga agctaattca ctaattgccg actctagaat atcaagagac ttgtattttt   1140
caagctcttt cttgactgcc atggctttct cgtgatacga gggagtagcc aacacctcct   1200
taacggccgt ggagactagc tcagaagttg cctgcaaggt ttgaagatca taaccaacac   1260
cagcccatac agctcgtgaa gcaacagctg gcttgtctac caacattcct cctccgatga   1320
tgacgggaac gccatggctc aaactgtgct gcagacctcc gtatccaccg ttgtatatga   1380
aaacagaggc atgcggtagt agctcatcgt aaggaaaata atcaacaatt cgagcgtttg   1440
caggaacttt aacgctatca ggaagtgacg cccctttgac gcccaatata ccaactacga   1500
gagtgtcttc ttcgtcagca aaggcctgca atgctggaat gagcagatct tcatagttga   1560
tggctgctgt tccttgtgta acaacaatca gacgcttcgc actcagcaca tcaggccacc   1620
aagacggcag gtgaggtgga gttgctaatc cagcagactt tacatgcggt gcactaccag   1680
cgaacgagaa gccaggagga ggcgaagtca agtgaaattc aagagatgga gggcacagtt   1740
gcaaaaatct gtcagggctg ctgtatatat tctccaggag aaattcgggc tccttcgtgg   1800
ccccgagcgt cttcatgatc tccttctcag agtcagttcc tggttgaaat acttgttgcc   1860
gcactaaagt atcaatcatt ggctcaagac taggaactcc aggcgccttc tctgctttca   1920
gcatgcacgg aatagttcct aacgtgatta cgccttgggg cttgagacct ggggcaccca   1980
gtgatatcgg atgcacccct agaaacatgg tctcgccaat caccacagct gatttatttt   2040
cagcctcaac ctgttttaga gcagtttgaa gtgcatcgta ctgctcagga atcgccttca   2100
caaaaatctc attcattgag taaccggtct gctcaaggcc tggaggaatc gtgagcaatc   2160
ctggagcgat ttcagggaga ttgtattcat ggtagtcagc tcgtccttgg agagggacga   2220
aagtgcatcc tgcctcaata actttctcct tgaatgcgtt ccctgttacg aaagtcacct   2280
catatcctct attgagtaga ccgcggacca ggctgagcac tgggcccacg tgccccgcta   2340
gtgggcaggc acaagcaact atcactggtt tctcgatggc catatgtgta gagttgtttt   2400
tgttgttaag tctttctta  agagcttgac cgactataac cgttcaacgg cgcattatat   2460
actttgggta tcggccagtg ctgacaactc acacgttgcg accccttacc cagaagcata   2520
cccagcgcga tgtcgatcgt gttatatcgt agacgcacac cctgcaatga cgggtaggct   2580
ctaaatcggg atgcgaaaaa gaggttgcct tgcttttgc  cctggtagat ggcatgctga   2640
gcgtgcgctt gccgcctaat ttttgtgtgt cgcctgctat ttattgctga agctagcccg   2700
```

```
ccgcatcttt ccccaaggct tcgattgctc gtattggggc agggattggt actcaacctt    2760
gcagatgaga ctccagcaac aacgtcgtac tgcttagcga tcgcacatgt ttcatcatcg    2820
tcactataca catcgtcatc aactccatgg cgtgaggact tccgagactg ctgggccctt    2880
cgtttcttta atgcctcaag agatgacttc gtacccgaag agacgcctgt tgtaccccgt    2940
tgacgcttgg cggaggggggc ttcgtcctcg tcagcaaccc gcgtcatctg cttccttcgc    3000
tgagcaagat accttctctc ctcgtaccgc tgcatctcct gagctcggtc atacaagatc    3060
tcttctcgct caatctctgg cagcgcgtcc aacttcgccc tgtcttcagc atcgagatat    3120
ttgccttcta gaggatagggg attgacgacc tcattgcttg gcggcgacgg cagcgagatt    3180
tcctcttcgg agtcggagcc aacgtcggcc aatgccagca gatcatcatc actgtcactc    3240
atagtaggaa ggttgaagtg tgctgacgaa tcagaatcgc gaaggatgcc attgaaggca    3300
tatatatttt aatctgtacc ttttatggta atttaatcag attttatagg tattcatgtg    3360
caagttgcat tgaaggaact gtttgagaaa atcatcttga ctgaactttt ctcagatatg    3420
cattccagcc cgccttttgg taacgctgag cttcgtgcac aggatctcgt cccttgctat    3480
agagcccgcg tccgacgata ataacgtctg tgccggtctc tatgacgtcg tccacagtac    3540
gatactgctg ccccaatcca tcacctttgt cgtccaggcc cacccagga gtcataatga    3600
cccagtcttc ctctggcttt ccgacttttt gctgagcgat gaaaccaaac acaaatgcgc    3660
ggttactgcg agcgatgtct actgtcgctt gcgagtattc gccgtgagcc agtgtgccct    3720
tcgaactcag ttctgcaagc atgacaaggc cgcgaggttc atccgtagtt tccttcgcag    3780
cctcttctag tccgctcaca attcccggcc caggaacacc gtgagcattt gttatatcag    3840
cccattgagc gatcttaaac actccacctg catattgggc cttaacagtg gaaccgatgt    3900
ctgcgaactt tcggtcttca aaatgagaa aattgtgctt cgttgaaagc tgtttcaaac    3960
cgctgacagt tgtgtcgtat tcgaagtcgt caattatgtc aatgtgggtc ttaaccatac    4020
aaatgtaagg tccaatgcgg tccaggatac tcagtaactc agaggtagtt cgcacatcca    4080
agcttgcgca aagatttgtt tgcttgctca caatgatgtc gaatagccgg gctgctacag    4140
ccggcagcct ctctcggcgc tcctcatagc tcagcttcat attatttctc tacagtagtg    4200
cccgtgccct cgatcagcta ggacttttca aattaatcgg gctgtttgat gtaagtaaga    4260
tgaagtcacg cgcgtgcagg agactgcgtc ccgcgatatt ctgcaggctt gaaaaattta    4320
ccctaacggt aggcatcaag tgagtgagtc tcagcgtcga tatgggtcaa aaaggggaa    4380
aactagccga gatcgttgcg agctgtttcg aaaattatgc cctatggcaa ttatcacgtg    4440
gagtatccga atttctccag gctgtcaagc ggcaattata accgagactg agatcgagaa    4500
gtatataacc gcagcagtag tggataaata attgcgaagt cttcccagca gagcgggctg    4560
ttttttggag ttggttactg taaaatgcta aaatgactga caacaatgga gcgtctacag    4620
cattggcaac agtgggaaca gtatgctggt gcatccagtt gataccccag gttctgcgaa    4680
actggtatgt tcgggattgc gagggcgttc ctcctctgat gttcttttttg ttcgccgttt    4740
cggggattcc cttcgcagtg tacttcattg atcagaattc gaacactgcc atcatggttc    4800
aacctcactt gtttactttc tttagcctta taggcttttg gcaaagcctg tactatccgc    4860
ccgtcagacc agcacgggcc gtcacatgta tggttgcgtc gctgtataag aaatcttaca    4920
actgaagact acacagcgta tccgctccga tatcggcgat cacgtggata catttcccca    4980
gaatgcgtca accttgcatg ctcgatattg actcaagccg agaggtgtat aacaacaccg    5040
acgatagcga attacttgtg gaactgattt gccgtatcga gtaaatcgcg attgtggccc    5100
```

-continued

```
tctttaggcc ttgtacccat ttgtgcatcg tatttgttag tatgcatcat agaattatgt    5160
gaacttagaa aagtccgtat gaaatgagcc tcagattatg gattgatcgc ttgttatttg    5220
tacagcggaa ttgacttata gtatgtcggc cacggtttta gattgcctag gggccgtttt    5280
cttgatggat tcgcatcgga actccgaatt cttgattgct ctccatcgcg caggaggccg    5340
ttcttttttt gacaaagtcc cattttaggg cgcaggtcca aaaataagc ggccgcttaa      5400 ttaactggcc tcatgggcct tccgctcact gcccgctttc cagtcgggaa acctgtcgtg    5460
ccagctgcat taacatggtc atagctgttt ccttgcgtat gggcgctct ccgcttcctc      5520 gctcactgac tcgctgcgct cggtcgttcg ggtaaagcct ggggtgccta atgagcaaaa    5580
ggccagcaaa aggccaggaa ccgtaaaaag gccgcgttgc tggcgttttt ccataggctc    5640
cgcccccctg acgagcatca aaaaatcga cgctcaagtc agaggtggcg aaacccgaca      5700
ggactataaa gataccaggc gtttccccct ggaagctccc tcgtgcgctc tcctgttccg    5760
accctgccgc ttaccggata cctgtccgcc tttctccctt cgggaagcgt ggcgctttct    5820
catagctcac gctgtaggta tctcagttcg gtgtaggtcg ttcgctccaa gctgggctgt    5880
gtgcacgaac cccccgttca gcccgaccgc tgcgccttat ccggtaacta tcgtcttgag    5940
tccaacccgg taagacacga cttatcgcca ctggcagcag ccactggtaa caggattagc    6000
agagcgaggt atgtaggcgg tgctacagag ttcttgaagt ggtggcctaa ctacggctac    6060
actagaagaa cagtatttgg tatctgcgct ctgctgaagc cagttacctt cggaaaaaga    6120
gttggtagct cttgatccgg caaacaaacc accgctggta gcggtggttt ttttgtttgc    6180
aagcagcaga ttacgcgcag aaaaaaagga tctcaagaag atcctttgat cttttctacg    6240
gggtctgacg ctcagtggaa cgaaaactca cgttaaggga ttttggtcat gagattatca    6300
aaaaggatct tcacctagat ccttttaaat taaaaatgaa gttttaaatc aatctaaagt    6360
atatatgagt aaacttggtc tgacagttac caatgcttaa tcagtgaggc acctatctca    6420
gcgatctgtc tatttcgttc atccatagtt gcctgactcc ccgtcgtgta gataactacg    6480
atacgggagg gcttaccatc tggccccagt gctgcaatga taccgcgaga accacgctca    6540
ccggctccag atttatcagc aataaaccag ccagccggaa gggccgagcg cagaagtggt    6600
cctgcaactt tatccgcctc catccagtct attaattgtt gccgggaagc tagagtaagt    6660
agttcgccag ttaatagttt gcgcaacgtt gttgccattg ctacaggcat cgtggtgtca    6720
cgctcgtcgt ttggtatggc ttcattcagc tccggttccc aacgatcaag gcgagttaca    6780
tgatccccca tgttgtgcaa aaaagcggtt agctccttcg gtcctccgat cgttgtcaga    6840
agtaagttgg ccgcagtgtt atcactcatg gttatggcag cactgcataa ttctcttact    6900
gtcatgccat ccgtaagatg cttttctgtg actggtgagt actcaaccaa gtcattctga    6960
gaatagtgta tgcggcgacc gagttgctct tgcccggcgt caatacggga taataccgcg    7020
ccacatagca gaactttaaa agtgctcatc attggaaaac gttcttcggg gcgaaaactc    7080
tcaaggatct taccgctgtt gagatccagt tcgatgtaac ccactcgtgc acccaactga    7140
tcttcagcat cttttacttt caccagcgtt tctgggtgag caaaaacagg aaggcaaaat    7200
gccgcaaaaa agggaataag ggcgacacgg aaatgttgaa tactcatact cttcctttt     7260 caatattatt gaagcatttta tcagggttat tgtctcatga gcggatacat atttgaatgt    7320
atttagaaaa ataaacaaat agggggttccg cgcacatttc cccgaaaagt gccac         7375
```

<210> SEQ ID NO 70

<211> LENGTH: 5316
<212> TYPE: DNA
<213> ORGANISM: Artificial
<220> FEATURE:
<223> OTHER INFORMATION: koCasssette

<400> SEQUENCE: 70

```
ggacctgcgc cctaaaatgg gactttgtca aaaaaagaac ggcctcctgc gcgatggaga      60
gcaatcaaga attcggagtt ccgatgcgaa tccatcaaga aaacggcccc taggcaatct     120
aaaaccgtgg ccgacatact ataagtcaat tccgctgtac aaataacaag cgatcaatcc     180
ataatctgag gctcatttca tacggacttt tctaagttca cataattcta tgatgcatac     240
taacaaatac gatgcacaaa tgggtacaag gcctaaagag ggccacaatc gcgatttact     300
cgatacggca atcagttccc acaagtaatt cgctatcgtc ggtgttgtta tacacctctc     360
ggcttgagtc aatatcgagc atgcaaggtt gacgcattct ggggaaatgt atccacgtga     420
tcgccgatat cggagcggat acgctgtgta gtcttcagtt gtaagatttc ttatacagcg     480
acgcaaccat acatgtgacg gcccgtgctg gtctgacggg cggatagtac aggctttgcc     540
aaaagcctat aaggctaaag aaagtaaaca agtgaggttg aaccatgatg gcagtgttcg     600
aattctgatc aatgaagtac actgcgaagg gaatccccga aacggcgaac aaaaagaaca     660
tcagaggagg aacgccctcg caatcccgaa cataccagtt tcgcagaacc tggggtatca     720
actggatgca ccagcatact gttcccactg ttgccaatgc tgtagacgct ccattgttgt     780
cagtcatttt agcattttac agtaaccaac tccaaaaaac agcccgctct gctgggaaga     840
cttcgcaatt atttatccac tactgctgcg gttatatact tctcgatctc agtctcggtt     900
ataattgccg cttgacagcc tggagaaatt cggatactcc acgtgataat tgccataggg     960
cataattttc gaaacagctc gcaacgatct cggctagttt tccccttttt tgacccatat    1020
cgacgctgag actcactcac ttgatgccta ccgttagggt aaattttcca gcctgcaga     1080
atatcgcggg acgcagtctc ctgcacgcgc gtgacttcat cttacttaca tcaaacagcc    1140
cgattaattt gaaaagtcct agctgatcga gggcacgggc actactgtag agaaataata    1200
tgaagctgag ctatgaggag cgccgagaga ggctgccggc tgtagcagcc ggctattcg     1260
acatcattgt gagcaagcaa acaaatcttt gcgcaagctt ggatgtgcga actacctctg    1320
agttactgag tatcctggac cgcattggac cttacatttg tatggttaag acccacattg    1380
acataattga cgacttcgaa tacgacacaa ctgtcagcgg tttgaaacag ctttcaacga    1440
agcacaattt tctcattttt gaagaccgaa agttcgcaga catcggttcc actgttaagg    1500
cccaatatgc aggtggagtg tttaagatcg ctcaatgggc tgatataaca aatgctcacg    1560
gtgttcctgg gccgggaatt gtgagcggac tagaagaggc tgcgaaggaa actacgatg     1620
aacctcgcgg ccttgtcatg cttgcagaac tgagttcgaa gggcacactg gctcacggcg    1680
aatactcgca agcgacagta gacatcgctc gcagtaaccg cgcatttgtg tttggtttca    1740
tcgctcagca aaaagtcgga aagccagagg aagactgggt cattatgact cctggggtgg    1800
gcctggacga caaggtgat ggattggggc agcagtatcg tactgtggac gacgtcatag     1860
agaccggcac agacgttatt atcgtcggac gcgggctcta tagcaaggga cgagatcctg    1920
tgcacgaagc tcagcgttac caaaaggcgg gctggaatgc atatctgaga aaagttcagt    1980
caagatgatt ttctcaaaca gttccttcaa tgcaacttgc acatgaatac ctataaaatc    2040
tgattaaatt accataaaag gtacagatta aaatatatat gccttcaatg gcatccttcg    2100
cgattctgat tcgtcagcac acttcaacct tcctactatg agtgacagtg atgatgatct    2160
```

```
gctggcattg gccgacgttg gctccgactc cgaagaggaa atctcgctgc cgtcgccgcc    2220
aagcaatgag gtcgtcaatc cctatcctct agaaggcaaa tatctcgatg ctgaagacag    2280
ggcgaagttg gacgcgctgc cagagattga gcgagaagag atcttgtatg accgagctca    2340
ggagatgcag cggtacgagg agagaaggta tcttgctcag cgaaggaagc agatgacgcg    2400
ggttgctgac gaggacgaag ccccctccgc caagcgtcaa cggggtacaa caggcgtctc    2460
ttcgggtacg aagtcatctc ttgaggcatt aaagaaacga agggcccagc agtctcggaa    2520
gtcctcacgc catggagttg atgacgatgt gtatagtgac gatgatgaaa catgtgcgat    2580
cgctaagcag tacgacgttg ttgctggagt ctcatctgca aggttgagta ccaatccctg    2640
ccccaatacg agcaatcgaa gccttgggga agatgcggc gggctagctt cagcaataaa    2700
tagcaggcga cacacaaaaa ttaggcggca agcgcacgct cagcatgcca tctaccaggg    2760
caaaaagcaa ggcaacctct ttttcgcatc ccgatttaga gcctacccgt cattgcaggg    2820
tgtgcgtcta cgatataaca cgatcgacat cgcgctgggt atgcttctgg gtaaggggtc    2880
gcaacgtgtg agttgtcagc actggccgat acccaaagta tataatgcgc cgttgaacgg    2940
ttatagtcgg tcaagctctt aaagaaagac ttaacaacaa aaacaactct acacatatgt    3000
taatcaaaga cattattcta actccaatga gtttatccgc tgttgctggc ttgttgccac    3060
tgctcttcgt agcttttctta gttctacacg agcctatctg gctccatatgg taccgctatg    3120 cagcacgtag gcacaagtgt agtatgcctc gcttcattga gaaatcgttc ccactgggaa    3180
tacaaagaac catggacatg atcaagacgg ccaagtcata caccttactg gaagttcaat    3240
acgacagagt cttcaataag ttcaaagcac ggacgtatct tcgacaagct ccccttcaat    3300
accaaatctt cacaatcgag ccagaaaaca ttaagacaat cctggcaacc aaattcaatg    3360
attttggtct tggagcacgt ttccacacag tgggaaaagt gtttggccaa gggatattta    3420
cactcagcgg aaatggatgg aaacagtctc gatcgatgtt gagacctcag ttcactaaag    3480
atcaggtttg cagaattgat cagatttcca gtcatgctgc ggagttaata aaggagatga    3540
accgtgcaat gaaagtggac caatttattg atgttcaaca ttatttccac aaacttacgc    3600
tggatacagc gactgaattc ctatttgggg agtcctgcga gagcttgaac cctgagaatc    3660
agtcatgtat tgtagcccgt gatggttcgg agattactgc cgaacaattc gtggagtcct    3720
acaactttct actgaattac gctttcaaac ggacccatc aagcaaagtc tactggttgt    3780
tcaactctaa ggaattccga gatcacaaga acgtgctca gtcctatatt gactactacg    3840
ttgataaggc tctttacgcc acatctttcg ctgctgagaa ctctattgca gagaaggatg    3900
ctgctgcaga gtctagtggc atctatgtgt tctcgcttga gatggctaaa gttacccgag    3960
acccagtgac gatacgtgat caaatttttca acattctcat tgctggtaga gatacaacag    4020
ctgctacgtt gagcttcgct attcattttcc ttgccagaaa tcctgacgta ttcaacaaac    4080
tacgtgagga ggtcctcgat catttttggaa ccaaggagga gcaaaggcct ttatcattcg    4140
aacttctgaa gcaagcacct tatttgaagc aagttataaa tgaagtcttg cgtcttgcgc    4200
cggtattgcc attgaacttc cgtactgctg tgagagatac aactctaccc ataggtggtg    4260
gtcccgagca gaaggatccg atcttcgttc ctaagggcac cgcagtttac tattcaattt    4320
acatggtcca cagggacatc aagtattggg gtcctgacgc ccacgaattc aatcccaatc    4380
gatgggagaa cttgaagcta gataatgtgt gggcattctt gcccttcaat ggcggtcccc    4440
gaatttgtct cggccaacaa ttcgccctga cagagctttc gctaactctg gtgagactct    4500
```

```
tacaggagta ttccaagatt gagatgggtc ccgacttccc agagtcccct cgtttctcaa      4560
caacgcttac agctcaacac gctcctcccg gtgtggttgt gcggttttct taagttggcc      4620
ggccatttct cctaataggc tgtcagcgca tatctgaggc gctcatataa aacaatataa      4680
atcaaaaccc atgttaaaaa cttgttgatc ccagcacttt tgagaagcgc actccgaact      4740
aaatctaaaa acacttcagc ttaagctatt attgcctgat tctcgtcata tcgctggggc      4800
ccgcgatcgc acgcgttctg ctataaattg acggagtttc gtacagtgcg ctcgtacagt      4860
gcgctgccaa atacaattta gtgtagccag attggatggt tgaattgctc ttcacggttg      4920
cacgctattg gcaaaaaaga gagagccgct ctgaactggt tcatccgcag ctgaccttcg      4980 aaactctttta atatttaata atattgcagc aaaatctata gcttatgcca catctatacg      5040
gaagaggtat tcaacattag agcttgtgtc gcccattctc tacacgagcc cacgcatcag      5100
cagtgagggg cttgtagctc gtgccctcta accagtagat tgtttgtcct gctgggggcgg      5160 gaatctgctg gtttcggaat tctttcttct gaactttgtt gttgccggtg atggtgacgg      5220
tgtcgacgaa cttaatgaat atcggcacgg catagcgtgg cagcctttcc aaaagatgct      5280
tgccgagttt atccatatcc agctgttttc taggat                               5316
```

<210> SEQ ID NO 71
<211> LENGTH: 5088
<212> TYPE: DNA
<213> ORGANISM: Artificial
<220> FEATURE:
<223> OTHER INFORMATION: koCassette

<400> SEQUENCE: 71

```
ggacctgcgc cctaaaatgg gactttgtca aaaaagaaac ggcctcctgc gcgatggaga        60
gcaatcaaga attcggagtt ccgatgcgaa tccatcaaga aaacggcccc taggcaatct       120
aaaaccgtgg ccgacatact ataagtcaat tccgctgtac aaataacaag cgatcaatcc       180
ataatctgag gctcatttca tacgggcttt tctaagttca cataattcta tgatgcatac       240
taacaaatac gatgcacaaa tgggtacaag gcctaaagag ggccacaatc gcgatttact       300
cgatacggca aatcagttcc acaagtaatt cgctatcgtc ggtgttgtta tacacctctc       360
ggcttgagtc aatatcgagc atgcaaggtt gacgcattct ggggaaatgt atccacgtga       420
tcgccgatat cggagcggat acgctgtgta gtcttcagtt gtaagatttc ttatacagcg       480
acgcaaccat acatgtgacg gcccgtgctg gtctgacggg cggatagtac aggctttgcc       540
aaaagcctat aaggctaaag aaagtaaaca agtgaggttg aaccatgatg gcagtgttcg       600
aattctgatc aatgaagtac actgcgaagg gaatcccga aacggcgaac aaaaagaaca        660
tcagaggagg aacgccctcg caatcccgaa cataccagtt tcgcagaacc tggggtatca      720
actggatgca ccagcatact gttcccactg ttgccaatgc tgtagacgct ccattgttgt       780
cagtcatttt agcatttac agtaaccaac tccaaaaaac agcccgctct ctgggaaga        840 cttcgcaatt atttatccac tactgctgcg gttatatact tctcgatctc agtctcggtt       900
ataattgccg cttgacagcc tggagaaatt cggatactcc acgtgataat tgccataggg       960
cataattttc gaaacagctc gcaacgatct cggctagttt tccccttttt tgacccatat      1020
cgacgctgag actcactcac ttgatgccta ccgttagggt aaattttttca agcctgcaga      1080 atatcgcggg acgcagtctc ctgcacgcgc gtgacttcat cttacttaca tcaaacagcc      1140
cgattaattt gaaaagtcct agctgatcga gggcacgggc actactgtag agaaataata      1200
tgaagctgag ctatgaggag cgccgagaga ggctgccggc tgtagcagcc cggctattcg      1260
```

```
acatcattgt gagcaagcaa acaaatcttt gcgcaagctt ggatgtgcga actacctctg    1320
agttactgag tatcctggac cgcattggac cttacatttg tatggttaag acccacattg    1380
acataattga cgacttcgaa tacgacacaa ctgtcagcgg tttgaaacag ctttcaacga    1440
agcacaattt tctcattttt gaagaccgaa agttcgcaga catcggttcc actgttaagg    1500
cccaatatgc aggtggagtg tttaagatcg ctcaatgggc tgatataaca aatgctcacg    1560
gtgttcctgg gccgggaatt gtgagcggac tagaagaggc tgcgaaggaa actacggatg    1620
aacctcgcgg ccttgtcatg cttgcagaac tgagttcgaa gggcacactg gctcacggcg    1680
aatactcgca agcgacagta gacatcgctc gcagtaaccg cgcatttgtg tttggtttca    1740
tcgctcagca aaaagtcgga aagccagagg aagactgggt cattatgact cctggggtgg    1800
gcctggacga caaggtgat  ggattggggc agcagtatcg tactgtggac gacgtcatag    1860
agaccggcac agacgttatt atcgtcggac gcgggctcta tagcaaggga cgagatcctg    1920
tgcacgaagc tcagcgttac caaaaggcgg gctggaatgc atatctgaga aaagttcagt    1980
caagatgatt ttctcaaaca gttccttcaa tgcaacttgc acatgaatac ctataaaatc    2040
tgattaaatt accataaaag gtacagatta aaatatatat gccttcaatg gcatccttcg    2100
cgattctgat tcgtcagcac acttcaacct tcctactatg agtgacagtg atgatgatct    2160
gctggcattg gccgacgttg gctccgactc cgaagaggaa atctcgctgc cgtcgccgcc    2220
aagcaatgag gtcgtcaatc cctatcctct agaaggcaaa tatctcgatg ctgaagacag    2280
ggcgaagttg gacgcgctgc cagagattga gcgagaagag atcttgtatg accgagctca    2340
ggagatgcag cggtacgagg agagaaggta tcttgctcag cgaaggaagc agatgacgcg    2400
ggttgctgac gaggacgaag cccccctccgc caagcgtcaa cggggtacaa caggcgtctc    2460
ttcgggtacg aagtcatctc ttgaggcatt aaagaaacga agggcccagc agtctcggaa    2520
gtcctcacgc catggagttg atgacgatgt gtatagtgac gatgatgaaa catgtgcgat    2580
cgctaagcag tacgacgttg ttgctggagt ctcatctgca aggttgagta ccaatccctg    2640
ccccaatacg agcaatcgaa gccttgggga agatgcggc  gggctagctt cagcaataaa    2700
tagcaggcga cacacaaaaa ttaggcggca agcgcacgct cagcatgcca tctaccaggg    2760
caaaaagcaa ggcaacctct ttttcgcatc ccgatttaga gcctacccgt cattgcaggg    2820
tgtgcgtcta cgatataaca cgatcgacat cgcgctgggc atgcttctgg gtaagggggtc   2880 gcaacgtgtg agttgtcagc actggccgat acccaaagta tataatgcgc cgttgaacgg    2940
ttatagtcgg tcaagctctt aaagaaagac ttaacaacaa aaacaactct acacatatga    3000
gcccttcatc acacaaaccc ctgattctcg cttgcggctt gcctctttca ggccatataa    3060
tgcccgtttt gagtctggta cacggcctta cggacgacgg atacgaagct actgttgtga    3120
caggcagagc gtttgaacaa aaagttcgag atgtgggtgc agactttgtt cctttagaag    3180
ggaacgcaga ttttgatgac cacaccttag acgatctggt cccgggccgt aaagacatgg    3240
ccccaagctt cgatcgtaca gttcaagatg tggagcacat gatggtagct actcttcctg    3300
agcagtttgc cgctattcag agggctttca aaaagctcag cgcaagcggt cgccctgtcg    3360
ttcttgtcag tgaagtgctg tttttcggtg cacaccctat cagcctcggt gctcctggtt    3420
tcaaacccgc tggctggatt tgtttagggg ttttgcctct tttgatccgc agtgatcata    3480
ccttaggact tgcaacgac  aggagccccg aagcacatgc aaagaaactc gctatgaacc    3540
acgctcttga gcaccaaatt ttcgttaaag ccactgctaa gcacaaggaa atctgccgag    3600
```

```
agttaggttg cactgaagat cccaaattta tctgggagca cagttacatt gctgcagaca   3660
agttcctgca gctgtgcccg ccttctcttg agttcagcag agaccatctg cctagcaact   3720
tcaaattcgc cggctcaacg cccaagcacc gaactcaatt caccctcct tcctggtggg    3780 gggatgttct gagtgccaag cgagtcatca tggtcactca aggaactttt gctgtcagtt   3840
acaagcatct tattgtgcct actcttgagg ccttgaagga cgagcctgac actttaacag   3900
tagccatatt gggccgccgc ggtgccaagc taccggatga tgttgtggtt cctgagaatg   3960
ctcgcgtgat cgactacttc aactacgatg ctctacttcc tcacgttgat gctcttgtct   4020
acaatggtgg atatgcggga cttcagcaca gcttaagcca ctctgttcca gttgttattg   4080
ctggtgactc tgaagacaag ccaatggtgg catcgagagc tgaggccgct ggcgtggcaa   4140
ttgatttgaa aactggcttg cctacagtgg agcaaatcaa agaagctgtt gattcgataa   4200
ttggaaatcc gaaattccac gaagcctcga agaaggttca aatggagttg gaaagccaca   4260
actccttgaa aattcttgag gaaagcatcg aggaaatcgc cagccatgac tttggtctt    4320 tgaccaagag tgacgaggaa actgaagata tacctgtcaa aggtccggcc ttagcggtga   4380
gttcttaggg ccggccattt ctcctaatag gctgtcagcg catatctgag gcgctcatat   4440
aaaacaatat aaatcaaaac ccatgttaaa aacttgttga tcccagcact tttgagaagc   4500
gcactccgaa ctaaatctaa aaacacttca gcttaagcta ttattgcctg attctcgtca   4560
tatcgctggg gcccgcgatc gcacgcgttc tgctataaat tgacggagtt tcgtacagtg   4620
cgctcgtaca gtgcgctgcc aaatacaatt tagtgtagcc agattggatg gttgaattgc   4680
tcttcacggt tgcacgctat tggcaaaaaa gagagagccg ctctgaactg gttcatccgc   4740
agctgacctt cgaaactctt taatattta taatattgca gcaaaatcta tagcttatgc    4800
cacatctata cggaagaggt attcaacatt agagcttgtg tcgcccattc tctacacgag   4860
cccacgcatc agcagtgagg ggcttgtagc tcgtgccctc taaccagtag attgttttgtc  4920 ctgctggggc gggaatctgc tggtttcgga attctttctt ctgaactttg ttgttgccgg   4980
tgatggtgac ggtgtcgacg aacttaatga atatcggcac ggcatagcgt ggcagccttt   5040
ccaaaagatg cttgccgagt ttatccatat ccagctgttt tctaggat                 5088
```

<210> SEQ ID NO 72
<211> LENGTH: 4479
<212> TYPE: DNA
<213> ORGANISM: Artificial
<220> FEATURE:
<223> OTHER INFORMATION: koCassette

<400> SEQUENCE: 72

```
ggacctgcgc cctaaaatgg gactttgtca aaaaagaac ggcctcctgc gcgatggaga    60
gcaatcaaga attcggagtt ccgatgcgaa tccatcaaga aaacggcccc taggcaatct  120
aaaaccgtgg ccgacatact ataagtcaat tccgctgtac aaataacaag cgatcaatcc  180
ataatctgag gctcatttca tacggacttt tctaagttca cataattcta tgatgcatac  240
taacaaatac gatgcacaaa tgggtacaag gcctaaagag ggccacaatc gcgatttact  300
cgatacggca atcagttcc acaagtaatt cgctatcgtc ggtgttgtta tacacctctc    360
ggcttgagtc aatatcgagc atgcaaggtt gacgcattct ggggaaatgt atccacgtga  420
tcgccgatat cggagcggat acgctgtgta gtcttcagtt gtaagatttc ttatacagcg  480
acgcaaccat acatgtgacg gcccgtgctg gtctgacggg cggatagtac aggctttgcc  540
aaaagcctat aaggctaaag aaagtaaaca agtgaggttg aaccatgatg gcagtgttcg  600
```

```
aattctgatc aatgaagtac actgcgaagg gaatccccga aacggcgaac aaaaagaaca    660
tcagaggagg aacgccctcg caatcccgaa cataccagtt tcgcagaacc tggggtatca    720
actggatgca ccagcatact gttcccactg ttgccaatgc tgtagacgct ccattgttgt    780
cagtcatttt agcattttac agtaaccaac tccaaaaaac agcccgctct gctgggaaga    840
cttcgcaatt atttatccac tactgctgcg gttatatact tctcgatctc agtctcggtt    900
ataattgccg cttgacagcc tggagaaatt cggatactcc acgtgataat tgccataggg    960
cataattttc gaaacagctc gcaacgatct cggctagttt tcccctttttt tgacccatat   1020 cgacgctgag actcactcac ttgatgccta ccgttagggt aaattttttca agcctgcaga   1080 atatcgcggg acgcagtctc ctgcacgcgc gtgacttcat cttacttaca tcaaacagcc   1140
cgattaattt gaaaagtcct agctgatcga gggcacgggc actactgtag agaaataata   1200
tgaagctgag ctatgaggag cgccgagaga ggctgccggc tgtagcagcc cggctattcg   1260
acatcattgt gagcaagcaa acaaatcttt cgcaagcttt ggatgtgcga actacctctg   1320
agttactgag tatcctggac cgcattggac cttacatttg tatggttaag acccacattg   1380
acataattga cgacttcgaa tacgacacaa ctgtcagcgg tttgaaacag cttcaacga    1440 agcacaattt tctcattttt gaagaccgaa agttcgcaga catcggttcc actgttaagg   1500
cccaatatgc aggtggagtg tttaagatcg ctcaatgggc tgatataaca aatgctcacg   1560
gtgttcctgg gccgggaatt gtgagcggac tagaagaggc tgcgaaggaa actacggatg   1620
aacctcgcgg ccttgtcatg cttgcagaac tgagttcgaa gggcacactg gctcacggcg   1680
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aaatatatat gccttcaatg gcatccttcg   2100
cgattctgat tcgtcagcac acttcaacct tcctactatg agtgacagtg atgatgatct   2160
gctggcattg gccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagat atcttgtatg accgagctca   2340
ggagatgcag cggtacgagg agagaaggta tcttgctcag cgaaggaagc agatgacgcg   2400
ggttgctgac gaggacgaag cccctccgc caagcgtcaa cggggtacaa caggcgtctc    2460
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga aagatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaagggtc    2880 gcaacgtgtg agttgtcagc actggccgat acccaaagta tataatgcgc cgttgaacgg   2940
```

```
ttatagtcgg tcaagctctt aaagaaagac ttaacaacaa aaacaactct acacatatgg    3000
ttgtaaactc ctcgaaggac cctcaaaaca aaggaatgac tcctagaaaa gaaattgacc    3060
aggaaatggt ctcttgggcc aaaaaaaacc tcaaaacac ccctggcaat gaaaactatg     3120
agaagatggt ctcaggagtt ccttacaatc catacgatcc agatcttatg tttagagccc    3180
tggctactag tgagaaagtt agggagttca ataccattgc aagtgaaagt cgtacttttg    3240
agtcaaatca cgctgcttat atcaagaagg tcgagattct caaagacact tttggtcaaa    3300
caaaggatat tgtctggctg accgctccat tctcagttga ttttggattc aacatcagcg    3360
taggcgagca cttttacgcc aacttcaacg tttgcttctt ggactcggct ccaataatct    3420
ttggtgatga ggtgattgta gggcccaata caacgttcgt gactgcgact catcctatta    3480
gccccgagaa acgtgcgagg agaattgtgt atgctcttcc tatcaaggtg gggaataatg    3540
tatggattgg tgcgaatgtg actgtcctgc cgggtgttac gattggagat ggctcaacaa    3600
ttgcggctgg tgctgtcgtt cgagaagatg ttcctcctcg tactgtggtg ggaggagtcc    3660
ctgcgcgaat cctcaagcat attccagagg aggatcccga cgaggctgaa ggagaggaac    3720
tggaattcct tcttccagtt gaaatgaacg tcaataccgc taaccagaag gtctaggtag    3780
gccggccatt tctcctaata ggctgtcagc gcatatctga ggcgctcata taaacaata    3840 taaatcaaaa cccatgttaa aaacttgttg atcccagcac ttttgagaag cgcactccga    3900
actaaatcta aaaacacttc agcttaagct attattgcct gattctcgtc atatcgctgg    3960
ggcccgcgat cgcacgcgtt ctgctataaa ttgacggagt ttcgtacagt gcgctcgtac    4020
agtgcgctgc caaatacaat ttagtgtagc cagattggat ggttgaattg ctcttcacgg    4080
ttgcacgcta ttggcaaaaa agagagagcc gctctgaact ggttcatccg cagctgacct    4140
tcgaaactct ttaatattta ataatattgc agcaaaatct atagcttatg ccacatctat    4200
acggaagagg tattcaacat tagagcttgt gtcgcccatt ctctacacga gcccacgcat    4260
cagcagtgag gggcttgtag ctcgtgccct ctaaccagta gattgtttgt cctgctgggg    4320
cgggaatctg ctggtttcgg aattctttct tctgaacttt gttgttgccg gtgatggtga    4380
cggtgtcgac gaacttaatg aatatcggca cggcatagcg tggcagcctt tccaaaagat    4440
gcttgccgag tttatccata tccagctgtt ttctaggat                         4479
```

```
<210> SEQ ID NO 73
<211> LENGTH: 7596
<212> TYPE: DNA
<213> ORGANISM: Artificial
<220> FEATURE:
<223> OTHER INFORMATION: koCassette

<400> SEQUENCE: 73
ggacctgcgc cctaaaatgg actttgtca aaaaagaac ggcctcctgc gcgatggaga         60
gcaatcaaga attcggagtt ccgatgcgaa tccatcaaga aaacggcccc taggcaatct      120
aaaaccgtgg ccgacatact ataagtcaat tccgctgtac aaataacaag cgatcaatcc      180
ataatctgag gctcatttca tacggacttt tctaagttca cataattcta tgatgcatac      240
taacaaatac gatgcacaaa tgggtacaag gcctaaagag ggccacaatc gcgatttact      300
cgatacggca atcagttcc acaagtaatt cgctatcgtc ggtgttgtta tacacctctc       360
ggcttgagtc aatatcgagc atgcaaggtt gacgcattct ggggaaatgt atccacgtga      420
tcgccgatat cggagcggat acgctgtgta gtcttcagtt gtaagatttc ttatacagcg      480
acgcaaccat acatgtgacg gcccgtgctg gtctgacggg cggatagtac aggctttgcc      540
```

```
aaaagcctat aaggctaaag aaagtaaaca agtgaggttg aaccatgatg gcagtgttcg    600
aattctgatc aatgaagtac actgcgaagg gaatccccga aacggcgaac aaaaagaaca    660
tcagaggagg aacgccctcg caatcccgaa cataccagtt tcgcagaacc tggggtatca    720
actggatgca ccagcatact gttcccactg ttgccaatgc tgtagacgct ccattgttgt    780
cagtcatttt agcattttac agtaaccaac tccaaaaaac agcccgctct gctgggaaga    840
cttcgcaatt atttatccac tactgctgcg gttatatact tctcgatctc agtctcggtt    900
ataattgccg cttgacagcc tggagaaatt cggatactcc acgtgataat tgccataggg    960
cataattttc gaaacagctc gcaacgatct cggctagttt tccccttttt tgacccatat   1020
cgacgctgag actcactcac ttgatgccta ccgttagggt aaatttttca agcctgcaga   1080
atatcgcggg acgcagtctc ctgcacgcgc gtgacttcat cttacttaca tcaaacagcc   1140
cgattaattt gaaagtcct agctgatcga gggcacgggc actactgtag agaaataata   1200
tgaagctgag ctatgaggag cgccgagaga ggctgccggc tgtagcagcc cggctattcg   1260
acatcattgt gagcaagcaa acaaatcttt gcgcaagctt ggatgtgcga actacctctg   1320
agttactgag tatcctggac cgcattggac cttacatttg tatggttaag acccacattg   1380
acataattga cgacttcgaa tacgacacaa ctgtcagcgg tttgaaacag cttttcaacga   1440
agcacaattt tctcattttt gaagaccgaa agttcgcaga catcggttcc actgttaagg   1500
cccaatatgc aggtggagtg tttaagatcg ctcaatgggc tgatataaca aatgctcacg   1560
gtgttcctgg gccgggaatt gtgagcggac tagaagaggc tgcgaaggaa actacgatg   1620
aacctcgcgg ccttgtcatg cttgcagaac tgagttcgaa gggcacactg gctcacggcg   1680
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aatatatat gccttcaatg gcatccttcg   2100
cgattctgat tcgtcagcac acttcaacct tcctactatg agtgacagtg atgatgatct   2160
gctggcattg ccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagag atcttgtatg accgagctca   2340
ggagatgcag cggtacgagg agagaaggta tcttgctcag cgaaggaagc agatgacgcg   2400
ggttgctgac gaggacgaag cccctccgc caagcgtcaa cggggtacaa caggcgtctc   2460
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga agatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaaggggtc   2880
```

```
gcaacgtgtg agttgtcagc actggccgat acccaaagta tataatgcgc cgttgaacgg    2940
ttatagtcgg tcaagctctt aaagaaagac ttaacaacaa aaacaactct acacatatgg    3000
tggatgatat acaggtagag aagcgtgaga aactcatcga gactaaggac aagcttctcg    3060
aggagaagct ctctgcgtta gatccacatg aggccaatgt attgcgaagt cagcttgaaa    3120
caaagagagt cgccacaagc tttttcaggt tgttcagatt ttgcactccc cttgacgttt    3180
tcttggagat acttgcgctt ttttttgcag cggtgcatgg agccgcgctt ccaatgttca    3240
cgttagtagt gggcgccatc ttcaacacat tcagagactt cactagctat gacctcaagg    3300
gcaatgagtt ccagcataag gtgaatcacc tgtctctcta ttttgtctat attggcattg    3360
gtatgctcgg cagtgcgttt ctcgagagct tcctgcttgt ggacagaggc gaagtgttgg    3420
caggacgtta ccgaaagcat tatctgagtg ctgttattcg ccagaatatc gcgttttacg    3480
acaaactagg tggtggcgag gtcagcacca gaatcattaa cgataccaac tcaattcagg    3540
aagcgatcag cgacaagctt ggaaacgtcg tacagggaat agcttccttc attgcggcca    3600
ccgttataag ttttgcttcg caatggaaac tggcttgcat cctcctgagt gctgtagggt    3660
tcatggtaat cacaatggga actggcgcca ccttcatggc caaatatcag ctcagatctg    3720
acgcgatata ttcgcagtct ggagctaccg ttgcggagga ggctctcagt gctgtcagga    3780
ctacagtagc atttgcgct caacctcatc tcgccgtcaa gtatgaaaag gtacttgatc    3840
gtgttgtgaa ggaatcgaag cggagcagtt actcattggg ggtcatgtta gcgtgcattt    3900
gggctagtac tttttgggtg tatgccttag ctctgtggca gggttccaga gaaatcgtta    3960
gtgggagtgc tgacgttgga aagataatag ttgtaatcac agctatgtta cttggaagct    4020
tccagcttgg gaatatcgcg ccaaacgtga ggtttcttgt caagggtctc actgccgcga    4080
gcattctcaa tgaggccatt gatcgtgtcc cagtcatcga tggccagtcc atagataaag    4140
gaattgtccc ccaaactaag gccgttggca gaattgagct caaaaatgtc aagttccgat    4200
atcctagtcg cccagacgtt ttggtcctct ccgattttag ccttgaagtt cctgctggat    4260
ctactgtggc actggtaggt gcctcgggat cagggaagtc tacaattgta ggtattcttg    4320
agaggttcta tttacctctc gaaggaagcg ttactctgga tggccaggag attagcgacc    4380
tgaacacaag atggctccgt caacaaattg gttatgttca gcaggaacca gtactctttt    4440
cagagtcaat atatgagaat atcagctatg gtttgattgg cactgacatt gagttcgctg    4500
acgagcatgt taaggaagct aaaatcattc aagcttgtaa agatgccaat gcctgggatt    4560
tcattcgagc tctctcagaa ggcatccaaa ccaatgttgg agatcgagga tttcttctca    4620
gcggtggtca gaaacaacgc attgcaatag caagagcaat cgtctcagac cctaaaattc    4680
tgctgctcga tgaagcgact tctgctctgg ataccaaatc tgaaggtatc gttcaagatg    4740
cgctcgacaa agcggccgaa ggtcgtacca ctatagtcgt tgcacacaga ctctctacga    4800
tcaaggatgc caacaagata gttgtcatgt ctaaaggtaa cgtcatagag cagggtactc    4860
acaatgagct catacagcga gaagggcctt ataaagcttt ggttgatgct caaagagtaa    4920
ctaaagcaaa gagcactaac gttgaggtcc tcgatattga agctctagac atttcgcctc    4980
tggactcact gaacgaaaag ttcaatccca aggatgtgag cacattgagt gttcacagtg    5040
caggtactca gaccactcaa cctcctgaat atcaagaaaa tgacatccct ggtgtgcgca    5100 acccccaca tagcacgttg atgaccaata ccaaactggt ttgggggctg aataggaaag    5160 aatgggtta cattctcatt ggtagtttag cctccattat tttgggctat tgctatcctg    5220
caatggcaat aataactggc caaccactg gaagcatggt tctacctccc agtgaatacg    5280
```

```
gaaaaatgcg gcatgtggtg aatatcatgg gatggtggta ttttttcgta ggctgcattt    5340
cattcatgac ggctttatc actatagctg ctttatcact tgcatctgat aagttggtca    5400
aaaatatcag attagctttg ttccgccaat tgatgcgaat ggatattgca ttcttcgacc    5460
acaaaaacaa cacgccgggt gcgctaacct caattttggc gaaggaagct aaaatgatcg    5520
agggtttgag tggggccacc ctcggtcaaa ttcaacagag tctggtgacc ttgattggcg    5580
gcatagttac tggtataccct ttcaattgga gaattggact cgtggctacg tctgttgttc    5640
ctgtcatgtt ggtgtgtggc ttcgtcagag tctgggttct tacccaatta tcggatcgtg    5700
cgagagaagt ttacgaacga agtggctcca tggcatctga gtatacaagt gctgtccgca    5760
cagtccagtc cttaactcgt gagttagacg tggtcgtaaa atacacaaag acagtagact    5820
ctcagatttt cagctccaga attgccattg cccgctcagc attgtactac gcactctcgg    5880
aaggaatgac accctgggtg gtagccctcg ttttttggtg gggaagcact gtaatgagac    5940
gaggtgaagc ttcggtcgca ggatatatga ctgtcttcat ggctattatt acaggttctc    6000
aagccgctgg ccaaattttc agctatgctc caaacatgaa ctcagccaaa gatgcagcgc    6060
gtaacattta cagaatcttg actgccactc cttctataga tgtatggagt gaggaaggtt    6120
acgttgctcc cgaggagtcg gtgagaggag atattgagtt ccgtcatgtg aatttccgat    6180
atcctactcg acctcaagta ccagttttac aagatctcaa cttaacagtc aaaaagggcc    6240
aatacatcgc tctagttgga gccagtggat gcggtaagtc tactactatt ggactggtgg    6300
aaagatttta tgatccatta gcaggtcaag tacttttcga tgggaaagat ttacgcgaat    6360
ataacctgaa tgcattgaga tcacacattg ctttagtcca gcaagaacca atgctttatt    6420
caggcacgct acgtgagaat attctaatgg gatggtctgg ccctgagtct gaagtaacgc    6480
aggagatgat tgaggatgcc gctcgcaaag cgaacattca cgaattcatc atgtcgttgc    6540
ctgatggcta cgaaacgctc agcggatcta ggggatcgtt gctatctggg gggcaaaagc    6600
agcgaattgc aattgcaagg gccctgatca gaaatccaaa ggtactcctc ctcgatgagg    6660
ccacctcagc tctggattcc gaatctgaga aagtagttca agcagcactc gacgcagcag    6720
cgaagggccg tactacaatc gccgttgcgc atagattatc aacaattcag aaagcagatg    6780
tcatatatgt gttctcagga gggcgcatcg tggagcaggg cgaccatcag agcctccttg    6840
aactcaatga tggtacgct gaattggtga acttgcaagg tctcggagag atttgaggcc    6900
ggccatttct cctaataggc tgtcagcgca tatctgaggc gctcatataa aacaatataa    6960
atcaaaaccc atgttaaaaa cttgttgatc ccagcacttt tgagaagcgc actccgaact    7020
aaatctaaaa acacttcagc ttaagctatt attgcctgat tctcgtcata tcgctggggc    7080
ccgcgatcgc acgcgttctg ctataaattg acggagtttc gtacagtgcg ctcgtacagt    7140
gcgctgccaa atacaattta gtgtagccag attggatggt tgaattgctc ttcacggttg    7200
cacgctattg gcaaaaaaga gagagccgct ctgaactggt tcatccgcag ctgaccttcg    7260
aaactcttta atatttaata atattgcagc aaaatctata gcttatgcca catctatacg    7320
gaagaggtat tcaacattag agcttgtgtc gcccattctc tacacgagcc cacgcatcag    7380
cagtgagggg cttgtagctc gtgccctcta accagtagat tgtttgtcct gctggggcgg    7440
gaatctgctg gtttcggaat tctttcttct gaactttgtt gttgccggtg atggtgacgg    7500
tgtcgacgaa cttaatgaat atcggcacgg catagcgtgg cagcctttcc aaaagatgct    7560
tgccgagttt atccatatcc agctgttttc taggat                              7596
```

<210> SEQ ID NO 74
<211> LENGTH: 4998
<212> TYPE: DNA
<213> ORGANISM: Artificial
<220> FEATURE:
<223> OTHER INFORMATION: koCassette

<400> SEQUENCE: 74

```
ggacctgcgc cctaaaatgg gactttgtca aaaaaagaac ggcctcctgc gcgatggaga      60
gcaatcaaga attcggagtt ccgatgcgaa tccatcaaga aaacggcccc taggcaatct     120
aaaaccgtgg ccgacatact ataagtcaat tccgctgtac aaataacaag cgatcaatcc     180
ataatctgag gctcatttca tacggacttt tctaagttca cataattcta tgatgcatac     240
taacaaatac gatgcacaaa tgggtacaag gcctaaagag ggccacaatc gcgatttact     300
cgatacggca aatcagttcc acaagtaatt cgctatcgtc ggtgttgtta tacacctctc     360
ggcttgagtc aatatcgagc atgcaaggtt gacgcattct ggggaaatgt atccacgtga     420
tcgccgatat cggagcggat acgctgtgta gtcttcagtt gtaagatttc ttatacagcg     480
acgcaaccat acatgtgacg gcccgtgctg gtctgacggg cggatagtac aggctttgcc     540
aaaagcctat aaggctaaag aaagtaaaca agtgaggttg aaccatgatg gcagtgttcg     600
aattctgatc aatgaagtac actgcgaagg gaatccccga aacggcgaac aaaaagaaca     660
tcagaggagg aacgccctcg caatcccgaa ataccagttt cgcagaacc tggggtatca      720
actggatgca ccagcatact gttcccactg ttgccaatgc tgtagacgct ccattgttgt     780
cagtcatttt agcattttac agtaaccaac tccaaaaaac agcccgctct gctgggaaga     840
cttcgcaatt atttatccac tactgctgcg gttatatact tctcgatctc agtctcggtt     900
ataattgccg cttgacagcc tggagaaatt cggatactcc acgtgataat tgccataggg     960
cataattttc gaaacagctc gcaacgatct cggctagttt tccccttttt tgacccatat    1020
cgacgctgag actcactcac ttgatgccta ccgttagggt aaatttttca agcctgcaga    1080
atatcgcggg acgcagtctc ctgcacgcgc gtgacttcat cttacttaca tcaaacagcc    1140
cgattaattt gaaagtcct agctgatcga gggcacgggc actactgtag agaaataata     1200
tgaagctgag ctatgaggag cgccgagaga ggctgccggc tgtagcagcc cggctattcg    1260
acatcattgt gagcaagcaa acaaatcttt gcgcaagctt ggatgtgcga actacctctg    1320
agttactgag tatcctggac cgcattggac cttacatttg tatggttaag acccacattg    1380
acataattga cgacttcgaa tacgacacaa ctgtcagcgg tttgaaacag ctttcaacga    1440
agcacaattt tctcattttt gaagaccgaa agttcgcaga catcggttcc actgttaagg    1500
cccaatatgc aggtggagtg tttaagatcg ctcaatgggc tgatataaca aatgctcacg    1560
gtgttcctgg gccgggaatt gtgagcggac tagaagaggc tgcgaaggaa actacggatg    1620
aacctcgcgg ccttgtcatg cttgcagaac tgagttcgaa gggcacactg gctcacggcg    1680
aatactcgca agcgacagta gacatcgctc gcagtaaccg cgcattgtg tttggtttca     1740
tcgctcagca aaaagtcgga aagccagagg aagactgggt cattatgact cctggggtgg    1800
gcctggacga caaaggtgat ggattggggc agcagtatcg tactgtggac gacgtcatag    1860
agaccggcac agacgttatt atcgtcggac gcgggctcta tagcaaggga cgagatcctg    1920
tgcacgaagc tcagcgttac caaaaggcgg gctggaatgc atatctgaga aaagttcagt    1980
caagatgatt ttctcaaaca gttccttcaa tgcaacttgc acatgaatac ctataaaatc    2040
tgattaaatt accataaaag gtacagatta aaatatatat gccttcaatg gcatccttcg    2100
```

-continued

```
cgattctgat tcgtcagcac acttcaacct tcctactatg agtgacagtg atgatgatct    2160
gctggcattg gccgacgttg gctccgactc cgaagaggaa atctcgctgc cgtcgccgcc    2220
aagcaatgag gtcgtcaatc cctatcctct agaaggcaaa tatctcgatg ctgaagacag    2280
ggcgaagttg gacgcgctgc cagagattga gcgagaagag atcttgtatg accgagctca    2340
ggagatgcag cggtacgagg agagaaggta tcttgctcag cgaaggaagc agatgacgcg    2400
ggttgctgac gaggacgaag cccctccgc caagcgtcaa cggggtacaa caggcgtctc     2460
ttcgggtacg aagtcatctc ttgaggcatt aaagaaacga agggcccagc agtctcggaa    2520
gtcctcacgc catggagttg atgacgatgt gtatagtgac gatgatgaaa catgtgcgat    2580
cgctaagcag tacgacgttg ttgctggagt ctcatctgca aggttgagta ccaatccctg    2640
ccccaatacg agcaatcgaa gccttgggga aagatgcggc gggctagctt cagcaataaa    2700
tagcaggcga cacacaaaaa ttaggcggca agcgcacgct cagcatgcca tctaccaggg    2760
caaaaagcaa ggcaacctct ttttcgcatc ccgatttaga gcctacccgt cattgcaggg    2820
tgtgcgtcta cgatataaca cgatcgacat cgcgctgggt atgcttctgg gtaaggggtc    2880
gcaacgtgtg agttgtcagc actggccgat acccaaagta tataatgcgc cgttgaacgg    2940
ttatagtcgg tcaagctctt aaagaaagac ttaacaacaa aaacaactct acacatatgg    3000
ccatcgagaa accagtgata gttgcttgtg cctgcccact agcggggcac gtgggcccag    3060
tgctcagcct ggtccgcggt ctactcaata gaggatatga ggtgactttc gtaacaggga    3120
acgcattcaa ggagaaagtt attgaggcag gatgcacttt cgtccctctc caaggacgag    3180
ctgactacca tgaatacaat ctccctgaaa tcgctccagg attgctcacg attcctccag    3240
gccttgagca gaccggttac tcaatgaatg agatttttgt gaaggcgatt cctgagcagt    3300
acgatgcact tcaaactgct ctaaaacagg ttgaggctga aaataaatca gctgtggtga    3360
ttggcgagac catgttttcta ggggtgcatc cgatatcact gggtgcccca ggtctcaagc    3420
cccaaggcgt aatcacgtta ggaactattc cgtgcatgct gaaagcagag aaggcgcctg    3480
gagttcctag tcttgagcca atgattgata ctttagtgcg gcaacaagta tttcaaccag    3540
gaactgactc tgagaaggag atcatgaaga cgctcggggc cacgaaggag cccgaatttc    3600
tcctggagaa tatatacagc agccctgaca gattttttgca actgtgccct ccatctcttg    3660
aatttcactt gacttcgcct cctcctggct tctcgttcgc tggtagtgca ccgcatgtaa    3720
agtctgctgg attagcaact ccacctcacc tgccgtcttg gtggcctgat gtgctgagtg    3780
cgaagcgtct gattgttgtt acacaaggaa cagcagccat caactatgaa gatctgctca    3840
ttccagcatt gcaggccttt gctgacgaag aagacactct cgtagttggt atattgggcg    3900 tcaaggggc gtcacttcct gatagcgtta agttcctgc aaacgctcga attgttgatt      3960
attttcctta cgatgagcta ctaccgcatg cctctgtttt catatacaac ggtggatacg    4020
gaggtctgca gcacagtttg agccatggcg ttcccgtcat catcggagga ggaatgttgg    4080
tagacaagcc agctgttgct tcacgagctg tatgggctgg tgttggttat gatcttcaaa    4140
ccttgcaggc aacttctgag ctagtctcca cggccgttaa ggaggtgttg gctactccct    4200
cgtatcacga gaaagccatg gcagtcaaga aagagcttga aaaatacaag tctcttgata    4260
ttctagagtc ggcaattagt gaattagctt cttaacctgg ccggccattt ctcctaatag    4320
gctgtcagcg catatctgag gcgctcatat aaaacaatat aaatcaaaac ccatgttaaa    4380
aacttgttga tcccagcact tttgagaagc gcactccgaa ctaaatctaa aaacacttca    4440
```

```
gcttaagcta ttattgcctg attctcgtca tatcgctggg gcccgcgatc gcacgcgttc      4500
tgctataaat tgacggagtt tcgtacagtg cgctcgtaca gtgcgctgcc aaatacaatt      4560
tagtgtagcc agattggatg gttgaattgc tcttcacggt tgcacgctat ggcaaaaaa       4620 gagagagccg ctctgaactg gttcatccgc agctgacctt cgaaactctt aatatttaa       4680 taatattgca gcaaaatcta tagcttatgc cacatctata cggaagaggt attcaacatt      4740
agagcttgtg tcgcccattc tctacacgag cccacgcatc agcagtgagg gcttgtagc      4800 tcgtgccctc taaccagtag attgtttgtc ctgctgggc gggaatctgc tggtttcgga      4860
attctttctt ctgaactttg ttgttgccgg tgatggtgac ggtgtcgacg aacttaatga      4920
atatcggcac ggcatagcgt ggcagccttt ccaaaagatg cttgccgagt ttatccatat      4980
ccagctgttt tctaggat                                                   4998

<210> SEQ ID NO 75
<211> LENGTH: 3732
<212> TYPE: DNA
<213> ORGANISM: Artificial
<220> FEATURE:
<223> OTHER INFORMATION: IntegrationCassette

<400> SEQUENCE: 75
gcggccgctt attttttgga cctgcgccct aaaatgggac tttgtcaaaa aaagaacggc        60
ctcctgcgcg atggagagca atcaagaatt cggagttccg atgcgaatcc atcaagaaaa       120
cggcccctag gcaatctaaa accgtggccg acatactata agtcaattcc gctgtacaaa       180
taacaagcga tcaatccata atctgaggct catttcatac ggactttttct aagttcacat      240 aattctatga tgcatactaa caaatacgat gcacaaatgg gtacaaggcc taaagagggc       300
cacaatcgcg atttactcga tacggcaaat cagttccaca agtaattcgc tatcgtcggt       360
gttgttatac acctctcggc ttgagtcaat atcgagcatg caaggttgac gcattctggg       420
gaaatgtatc cacgtgatcg ccgatatcgg agcggatacg ctgtgtagtc ttcagttgta       480
agatttctta tacagcgacg caaccataca tgtgacggcc cgtgctggtc tgacgggcgg       540
atagtacagg ctttgccaaa agcctataag gctaaagaaa gtaaacaagt gaggttgaac       600
catgatggca gtgttcgaat tctgatcaat gaagtacact gcgaagggaa tccccgaaac       660
ggcgaacaaa aagaacatca gaggaggaac gccctcgcaa tcccgaacat accagtttcg       720
cagaacctgg ggtatcaact ggatgcacca gcatactgtt cccactgttg ccaatgctgt       780
agacgctcca ttgttgtcag tcattttagc attttacagt aaccaactcc aaaaaacagc       840
ccgctctgct gggaagactt cgcaattatt tatccactac tgctgcggtt atatacttct       900
cgatctcagt ctcggttata attgccgctt gacagcctgg agaaattcgg atactccacg       960
tgataattgc cataaggcat aaattttcgaa acagctcgca acgatctcgg ctagttttcc     1020
ccttttttga cccatatcga cgctgagact cactcacttg atgcctaccg ttagggtaaa     1080 ttttttcaagc ctgcagaata tcgcgggacg cagtctcctg cacgcgcgtg acttcatctt     1140
acttacatca aacagcccga ttaatttgaa aagtcctagc tgatcgaggg cacgggcact     1200
actgtagaga ataatatga agctgagcta tgaggagcgc cgagagaggc tgccggctgt     1260
agcagcccgg ctattcgaca tcattgtgag caagcaaaca aatctttgcg caagcttgga     1320
tgtgcgaact acctctgagt tactgagtat cctggaccgc attggacctt acatttgtat     1380
ggttaagacc cacattgaca taattgacga cttcgaatac gacacaactg tcagcggttt     1440
gaaacagctt tcaacgaagc acaatttcct cattttgaa gaccgaaagt tcgcagacat     1500
```

-continued

```
cggttccact gttaaggccc aatatgcagg tggagtgttt aagatcgctc aatgggctga      1560
tataacaaat gctcacggtg ttcctgggcc gggaattgtg agcggactag aagaggctgc      1620
gaaggaaact acggatgaac ctcgcggcct tgtcatgctt gcagaactga gttcgaaggg      1680
cacactggct cacggcgaat actcgcaagc gacagtagac atcgctcgca gtaaccgcgc      1740
atttgtgttt ggtttcatcg ctcagcaaaa agtcggaaag ccagaggaag actgggtcat      1800
tatgactcct ggggtgggcc tggacgacaa aggtgatgga ttggggcagc agtatcgtac      1860
tgtggacgac gtcatagaga ccggcacaga cgttattatc gtcggacgcg ggctctatag      1920
caagggacga gatcctgtgc acgaagctca gcgttaccaa aaggcgggct ggaatgcata      1980
tctgagaaaa gttcagtcaa gatgattttc tcaaacagtt ccttcaatgc aacttgcaca      2040
tgaataccta taaatctga ttaaattacc ataaaggta cagattaaaa tatatatgcc       2100
ttcaatggca tccttcgcga ttctgattcg tcagcacact caaccttcc tactatgagt      2160 gacagtgatg atgatctgct ggcattggcc gacgttggct ccgactccga agaggaaatc      2220
tcgctgccgt cgccgccaag caatgaggtc gtcaatccct atcctctaga aggcaaatat      2280
ctcgatgctg aagacagggc gaagttggac gcgctgccag agattgagcg agaagagatc      2340
ttgtatgacc gagctcagga gatgcagcgg tacgaggaga aaggtatct tgctcagcga       2400 aggaagcaga tgacgcgggt tgctgacgag gacgaagccc cctccgccaa gcgtcaacgg      2460
ggtacaacag gcgtctcttc gggtacgaag tcatctcttg aggcattaaa gaaacgaagg      2520
gcccagcagt ctcggaagtc ctcacgccat ggagttgatg acgatgtgta tagtgacgat      2580
gatgaaacat gtgcgatcgc taagcagtac gacgttgttg ctggagtctc atctgcaagg      2640
ttgagtacca atccctgccc caatacgagc aatcgaagcc ttggggaaag atgcggcggg      2700
ctagcttcag caataaatag caggcgacac acaaaaatta ggcggcaagc gcacgctcag      2760
catgccatct accagggcaa aaagcaaggc aacctctttt tcgcatcccg atttagagcc      2820
tacccgtcat tgcagggtgt gcgtctacga tataacacga tcgacatcgc gctgggtatg      2880
cttctgggta aggggtcgca acgtgtgagt tgtcagcact ggccgatacc caaagtatat      2940
aatgcgccgt tgaacggtta tagtcggtca agctcttaaa gaaagactta acaacaaaaa      3000
caactctaca catatggact tgtaggccgg ccatttctcc taataggctg tcagcgcata      3060
tctgaggcgc tcatataaaa caatataaat caaacccat gttaaaaact tgttgatccc       3120 agcactttg agaagcgcac tccgaactaa atctaaaaac acttcagctt aagctattat       3180
tgcctgattc tcgtcatatc gctggggccc gcgatcgcac gcgttctgct ataaattgac      3240
ggagtttcgt acagtgcgct cgtacagtgc gctgccaaat acaatttagt gtagccagat      3300
tggatggttg aattgctctt cacggttgca cgctattggc aaaaaagaga gagccgctct      3360
gaactggttc atccgcagct gaccttcgaa actctttaat atttaataat attgcagcaa      3420
aatctatagc ttatgccaca tctatacgga agaggtattc aacattagag cttgtgtcgc      3480
ccattctcta cacgagccca cgcatcagca gtgagggct tgtagctcgt gccctctaac       3540
cagtagattg tttgtcctgc tggggcggga atctgctggt ttcggaattc tttcttctga      3600
actttgttgt tgccggtgat ggtgacgtg tcgacgaact taatgaatat cggcacggca       3660
tagcgtggca gcctttccaa aagatgcttg ccgagtttat ccatatccag ctgtttttcta     3720 ggatcctgca gg                                                          3732
```

<210> SEQ ID NO 76

<211> LENGTH: 50
<212> TYPE: DNA
<213> ORGANISM: Artificial
<220> FEATURE:
<223> OTHER INFORMATION: Primer

<400> SEQUENCE: 76
aaacgtctca gatgcaccac caccaccacc acatggttgt aaactcctcg            50

<210> SEQ ID NO 77
<211> LENGTH: 30
<212> TYPE: DNA
<213> ORGANISM: Artificial
<220> FEATURE:
<223> OTHER INFORMATION: Primer

<400> SEQUENCE: 77
aaaggcgcgc cctagacctt ctggttagcg                                  30

<210> SEQ ID NO 78
<211> LENGTH: 6700
<212> TYPE: DNA
<213> ORGANISM: Artificial
<220> FEATURE:
<223> OTHER INFORMATION: Vector

<400> SEQUENCE: 78
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggatttt gccgatttc ggcctattgg ttaaaaaatg agctgattta    420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg aattaattct tagaaaaact catcgagcat caaatgaaac tgcaatttat   600
tcatatcagg attatcaata ccatatttt gaaaagccg tttctgtaat gaaggagaaa    660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa atcccttaa   1440

```
cgtgagtttt cgttccactg agcgtcagac cccgtagaaa agatcaaagg atcttcttga   1500 gatcctttt  ttctgcgcgt aatctgctgc ttgcaaacaa aaaaaccacc gctaccagcg   1560
gtggtttgtt tgccggatca agagctacca actcttttc  cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggg  cggagcctat ggaaaaacgc cagcaacgcg   2100 gccttttac  ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac accgctgac  gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga agcggtcct  cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc cggtgcctaa   3480 tgagtgagc  taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
```

```
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccgacgc agacgcgccg     4020 agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgcttttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacg atgcaccacc accaccacca catgagccct    5100
tcatcacaca aaccccctgat tctcgcttgc ggcttgcctc tttcaggcca tataatgccc    5160
gttttgagtc tggtacacgg ccttacggac gacggatacg aagctactgt tgtgacaggc    5220
agagcgtttg aacaaaaagt tcgagatgtg ggtgcagact ttgttccttt agaagggaac    5280
gcagattttg atgaccacac cttagacgat ctggtcccgg gccgtaaaga catggcccca    5340
agcttcgatc gtacagttca agatgtggag cacatgatgg tagctactct tcctgagcag    5400
tttgccgcta ttcagagggc tttcaaaaag ctcagcgcaa gcggtcgccc tgtcgttctt    5460
gtcagtgaag tgctgttttt cggtgcacac cctatcagcc tcggtgctcc tggtttcaaa    5520
cccgctggct ggatttgttt aggggttttg cctcttttga tccgcagtga tcataccttta   5580 ggacttgaca acgacaggag ccccgaagca catgcaaaga aactcgctat gaaccacgct    5640
cttgagcacc aaattttcgt taaagccact gctaagcaca aggaaatctg ccgagagtta    5700
ggttgcactg aagatcccaa atttatctgg gagcacagtt acattgctgc agacaagttc    5760
ctgcagctgt gcccgccttc tcttgagttc agcagagacc atctgcctag caacttcaaa    5820
ttcgccggct caacgcccaa gcaccgaact caattcaccc ctccttcctg gtgggggat    5880 gttctgagtg ccaagcgagt catcatggtc actcaaggaa cttttgctgt cagttacaag    5940
catcttattg tgcctactct tgaggccttg aaggacgagc ctgacacttt aacagtagcc    6000
atattgggcc gccgcggtgc caagctaccg gatgatgttg tggttcctga gaatgctcgc    6060
gtgatcgact acttcaacta cgatgctcta cttcctcacg ttgatgctct tgtctacaat    6120
ggtggatatg gcggacttca gcacagctta agccactctg ttccagttgt tattgctggt    6180
```

```
gactctgaag acaagccaat ggtggcatcg agagctgagg ccgctggcgt ggcaattgat     6240
ttgaaaactg gcttgcctac agtggagcaa atcaaagaag ctgttgattc gataattgga     6300
aatccgaaat tccacgaagc ctcgaagaag gttcaaatgg agttggaaag ccacaactcc     6360
ttgaaaattc ttgaggaaag catcgaggaa atcgccagcc atgactttgg tcttttgacc     6420
aagagtgacg aggaaactga agatatacct gtcaaaggtc cggccttagc ggtgagttct     6480
tagggcgcgc cctcgaggga tccgaattcg agctccgtcg acaagcttgc ggccgcactc     6540
gagcaccacc accaccacca ctgagatccg gctgctaaca aagcccgaaa ggaagctgag     6600
ttggctgctg ccaccgctga gcaataacta gcataacccc ttggggcctc taaacgggtc     6660
ttgaggggtt ttttgctgaa aggaggaact atatccggat                          6700
```

<210> SEQ ID NO 79
<211> LENGTH: 51
<212> TYPE: DNA
<213> ORGANISM: Artificial
<220> FEATURE:
<223> OTHER INFORMATION: Primer

<400> SEQUENCE: 79

```
aaacgtctca gatgcaccac caccaccacc acatggccat cgagaaacca g               51
```

<210> SEQ ID NO 80
<211> LENGTH: 36
<212> TYPE: DNA
<213> ORGANISM: Artificial
<220> FEATURE:
<223> OTHER INFORMATION: Primer

<400> SEQUENCE: 80

```
aaaggcgcgc cttaagaagc taattcacta attgcc                                36
```

<210> SEQ ID NO 81
<211> LENGTH: 6607
<212> TYPE: DNA
<213> ORGANISM: Artificial
<220> FEATURE:
<223> OTHER INFORMATION: Vector

<400> SEQUENCE: 81

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tcccttaagg     180 gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
```

```
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
cttttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gtttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actcttttc gaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc gaagggaga    1920
aaggcggaca ggtatccggt aagcggcagg gtcggaacag gagagcgcac gagggagctt   1980
ccaggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gccttttac ggttcctggc cttttgctgg ccttttgctc acatgttctt tcctgcgtta    2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
```

-continued

```
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc gttccgcta   3960 tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac gcacctgtg   4920 gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacg atgcaccacc accaccacca catggccatc   5100
gagaaaccag tgatagttgc ttgtgcctgc ccactagcgg ggcacgtggg cccagtgctc   5160
agcctggtcc gcggtctact caatagagga tatgaggtga ctttcgtaac agggaacgca   5220
ttcaaggaga aagttattga ggcaggatgc acttcgtcc ctctccaagg acgagctgac   5280
taccatgaat acaatctccc tgaaatcgct ccaggattgc tcacgattcc tccaggcctt   5340
gagcagaccg gttactcaat gaatgagatt tttgtgaagg cgattcctga gcagtacgat   5400
gcacttcaaa ctgctctaaa acaggttgag gctgaaaata aatcagctgt ggtgattggc   5460
gagaccatgt ttctaggggt gcatccgata tcactgggtg ccccaggtct caagccccaa   5520
```

-continued

```
ggcgtaatca cgttaggaac tattccgtgc atgctgaaag cagagaaggc gcctggagtt      5580
cctagtcttg agccaatgat tgatacttta gtgcggcaac aagtatttca accaggaact      5640
gactctgaga aggagatcat gaagacgctc ggggccacga aggagcccga atttctcctg      5700
gagaatatat acagcagccc tgacagattt ttgcaactgt gccctccatc tcttgaattt      5760
cacttgactt cgcctcctcc tggcttctcg ttcgctggta gtgcaccgca tgtaaagtct      5820
gctggattag caactccacc tcacctgccg tcttggtggc ctgatgtgct gagtgcgaag      5880
cgtctgattg ttgttacaca aggaacagca gccatcaact atgaagatct gctcattcca      5940
gcattgcagg cctttgctga cgaagaagac actctcgtag ttggtatatt gggcgtcaaa      6000
ggggcgtcac ttcctgatag cgttaaagtt cctgcaaacg ctcgaattgt tgattatttt      6060
ccttacgatg agctactacc gcatgcctct gttttcatat acaacggtgg atacggaggt      6120
ctgcagcaca gtttgagcca tggcgttccc gtcatcatcg gaggaggaat gttggtagac      6180
aagccagctg ttgcttcacg agctgtatgg gctggtgttg ttatgatctc tcaaaccttg      6240
caggcaactt ctgagctagt ctccacggcc gttaaggagg tgttggctac tccctcgtat      6300
cacgagaaag ccatggcagt caagaaagag cttgaaaaat acaagtctct tgatattcta      6360
gagtcggcaa ttagtgaatt agcttcttaa ggcgcgccct cgaggatcc gaattcgagc      6420 tccgtcgaca gcttgcggc cgcactcgag caccaccacc accaccactg agatccggct      6480
gctaacaaag cccgaaagga agctgagttg gctgctgcca ccgctgagca ataactagca      6540
taaccccttg gggcctctaa acgggtcttg aggggttttt tgctgaaagg aggaactata      6600
tccggat                                                               6607
```

<210> SEQ ID NO 82
<211> LENGTH: 50
<212> TYPE: DNA
<213> ORGANISM: Artificial
<220> FEATURE:
<223> OTHER INFORMATION: Primer

<400> SEQUENCE: 82

```
aaacgtctca gatgcaccac caccaccacc acatggttgt aaactcctcg                  50
```

<210> SEQ ID NO 83
<211> LENGTH: 30
<212> TYPE: DNA
<213> ORGANISM: Artificial
<220> FEATURE:
<223> OTHER INFORMATION: Primer

<400> SEQUENCE: 83

```
aaaggcgcgc cctagacctt ctggttagcg                                        30
```

<210> SEQ ID NO 84
<211> LENGTH: 6088
<212> TYPE: DNA
<213> ORGANISM: Artificial
<220> FEATURE:
<223> OTHER INFORMATION: Vector

<400> SEQUENCE: 84

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcggggc tccctttagg      180 gttccgattt agtgctttac ggcacctcga ccccaaaaaa cttgattagg gtgatggttc     240
```

```
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat aaggagaaa    660 actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500 gatcctttt ttctgcgcgt aatctgctgc ttgcaaacaa aaaaaccacc gctaccagcg    1560
gtggtttgtt tgccggatca agagctacca actcttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc gaagggaga    1920 aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
```

```
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccgaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg tgtccggga    4680 tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttcccatc ggtgatgtcg gcgatatagg cgccagcaac cgcacctgtg    4920
gcgccggtga tgccggccac gatgcgtccg gcgtagagga tcgagatctc gatcccgcga    4980
```

```
aattaatacg actcactata ggggaattgt gagcggataa caattcccct ctagaaataa      5040
ttttgtttaa ctttaagaag gagatatacg atgcaccacc accaccacca catggttgta      5100
aactcctcga aggaccctca aaacaaagga atgactccta gaaagaaat tgaccaggaa       5160 atggtctctt gggccaaaaa aaacctcaaa acaccccctg gcaatgaaaa ctatgagaag      5220
atggtctcag gagttcctta caatccatac gatccagatc ttatgtttag agccctggct     5280
actagtgaga aagttaggga gttcaatacc attgcaagtg aaagtcgtac ttttgagtca      5340
aatcacgctg cttatatcaa gaaggtcgag attctcaaag acactttgg tcaaacaaag      5400 gatattgtct ggctgaccgc tccattctca gttgattttg gattcaacat cagcgtaggc     5460
gagcactttt acgccaactt caacgtttgc ttcttggact cggctccaat aatctttggt     5520
gatgaggtga ttgtagggcc aatacaacg ttcgtgactg cgactcatcc tattagcccc      5580
gagaaacgtg cgaggagaat tgtgtatgct cttcctatca aggtggggaa taatgtatgg     5640
attggtgcga atgtgactgt cctgccgggt gttacgattg gagatggctc aacaattgcg     5700
gctggtgctg tcgttcgaga agatgttcct cctcgtactg tggtgggagg agtccctgcg    5760
cgaatcctca agcatattcc agaggaggat cccgacgagg ctgaaggaga ggaactggaa     5820
ttccttcttc cagttgaaat gaacgtcaat accgctaacc agaaggtcta gggcgcgccc     5880
tcgagggatc cgaattcgag ctccgtcgac aagcttgcgg ccgcactcga gcaccaccac    5940
caccaccact gagatccggc tgctaacaaa gcccgaaagg aagctgagtt ggctgctgcc     6000
accgctgagc aataactagc ataacccctt ggggcctcta acgggtctt gagggggtttt    6060 ttgctgaaag gaggaactat atccggat                                         6088

<210> SEQ ID NO 85
<211> LENGTH: 10065
<212> TYPE: DNA
<213> ORGANISM: Artificial
<220> FEATURE:
<223> OTHER INFORMATION: Vector
<220> FEATURE:
<221> NAME/KEY: misc_feature
<222> LOCATION: (3998)..(3998)
<223> OTHER INFORMATION: n is a, c, g, or t

<400> SEQUENCE: 85
gaattctcat gtttgacagc ttatcatcga taagctttaa tgcggtagtt tatcacagtt       60
aaattgctaa cgcagtcagg caccgtgtat gaaatctaac aatgcgctca tcgtcatcct      120
cggcaccgtc accctggatg ctgtaggcat aggcttggtt atgccggtac tgccgggcct     180
cttgcgggat atcgtccatt ccgacagcat cgccagtcac tatggcgtgc tgctagcgct      240
atatgcgttg atgcaatttc tatgcgcacc cgttctcgga gcactgtccg accgctttgg    300
ccgccgccca gtcctgctcg cttcgctact tggagccact atcgactacg cgatcatggc     360
gaccacaccc gtcctgtgga tccaggccgt gagcaccgc cgccgcaagg aatggtgcat     420
gctgaggtgt ctcacaagtg ccgtgcagtc ccgcccccac ttgcttctct tgtgtgtag    480 tgtacgtaca ttatcgagac cgttgttccc gcccacctcg atccggcatg ctgaggtgtc      540
tcacaagtgc cgtgcagtcc cgcccccact tgcttctctt tgtgtgtagt gtacgtacat      600
tatcgagacc gttgttcccg cccacctcga tccggcatgc tgaggtgtct cacaagtgcc     660
gtgcagtccc gcccccactt gcttctcttt gtgtgtagtg tacgtacatt atcgagaccg     720
ttgttcccgc ccacctcgat ccggcatgct gaggtgtctc acaagtgccg tgcagtcccg    780
```

```
cccccacttg cttctctttg tgtgtagtgt acgtacatta tcgagaccgt tgttcccgcc    840
cacctcgatc cggcatgcac tgatcacggg caaaagtgcg tatatataca agagcgtttg    900
ccagccacag attttcactc cacacaccac atcacacata caaccacaca catccacaat    960
gaaaaagcct gaactcaccg cgacgagcgt cgagaagttt ctgatcgaaa agttcgacag   1020
cgtctccgac ctgatgcagc tctcggaggg cgaagaatct cgtgctttca gcttcgatgt   1080
aggagggcgt ggatatgtcc tgcgggtaaa tagctgcgcc gatggtttct acaaagatcg   1140
ttatgtttat cggcactttg catcggccgc gctcccgatt ccggaagtgc ttgacattgg   1200
ggagttcagc gagagcctga cctattgcat ctcccgccgt gcacagggtg tcacgttgca   1260
agacctgcct gaaaccgaac tgcccgctgt tctgcagccg gtcgcggagg ccatggatgc   1320
gatcgctgcg gccgatctta gccagacgag cgggttcggc ccattcggac cgcaaggaat   1380
cggtcaatac actacatggc gtgatttcat atgcgcgatt gctgatcccc atgtgtatca   1440
ctggcaaact gtgatggacg acaccgtcag tgccgtccgt cgcgcaggctc tcgatgagct   1500
gatgctttgg gccgaggact gccccgaagt ccggcacctc gtgcacgcgg atttcggctc   1560
caacaatgtc ctgacggaca atggccgcat aacagcggtc attgactgga gcgaggcgat   1620
gttcggggat tcccaatacg aggtcgccaa catcttcttc tggaggccgt ggttggcttg   1680
tatggagcag cagacgcgct acttcgagcg gaggcatccg gagcttgcag gatcgccgcg   1740
gctccgggcg tatatgctcc gcattggtct tgaccaactc tatcagagct ggttgacgg    1800
caatttcgat gatgcagctt gggcgcaggg tcgatgcgac gcaatcgtcc gatccggagc   1860
cgggactgtc gggcgtacac aaatcgcccg cagaagcgcg gccgtctgga ccgatggctg   1920
tgtagaagta ctcgccgata gtggaaaccg acgcccagc actcgtccga gggcaaagga    1980
atagtcgacg ctctccctta tgcgactcct gcattaggaa gcagcccagt agtaggttga   2040
ggccgttgag caccgccgcc gcaaggaatg gtgcatgctg aggtgtctca caagtgccgt   2100
gcagtcccgc ccccacttgc ttctctttgt gtgtagtgta cgtacattat cgagaccgtt   2160
gttcccgccc acctcgatcc ggcatgctga ggtgtctcac aagtgccgtg cagtcccgcc   2220
cccacttgct tctctttgtg tgtagtgtac gtacattatc gagaccgttg ttcccgccca   2280
cctcgatccg gcatgctgag gtgtctcaca agtgccgtgc agtcccgccc ccacttgctt   2340
ctctttgtgt gtagtgtacg tacattatcg agaccgttgt tcccgcccac ctcgatccgg   2400
catgctgagg tgtctcacaa gtgccgtgca gtcccgcccc cacttgcttc tctttgtgtg   2460
tagtgtacgt acattatcga gaccgttgtt cccgcccacc tcgatccggc atgcactgat   2520
cacgggcaaa agtgcgtata tacaagagcg tttgccagcc acagattttt cactccaca    2580
caccacatca cacatacaac cacacacatc cacgggctgc aggaattcga tatcaagctt   2640
atcgataccg tcgaggggca gagccgatcc tgtacacttt acttaaaacc attatctgag   2700
tgttaaatgt ccaatttact gaccgtacac caaaatttgc ctgcattacc ggtcgatgca   2760
acgagtgatg aggttcgcaa gaacctgatg gacatgttca gggatcgcca ggcgttttct   2820
gagcatacct ggaaaatgct tctgtccgtt tgccggtcgt gggcggcatg gtgcaagttg   2880
aataaccgga atggtttcc cgcagaacct gaagatgttc gcgattatct tctatatctt    2940
caggcgcgcg gtctggcagt aaaaactatc cagcaacatt tgggccagct aaacatgctt   3000
catcgtcggt ccgggctgcc acgaccaagt gacagcaatg ctgtttcact ggttatgcgg   3060
cggatccgaa aagaaaacgt tgatgccggt gaacgtgcaa aacaggctct agcgttcgaa   3120
cgcactgatt tcgaccaggt tcgttcactc atggaaaata gcgatcgctg ccaggatata   3180
```

```
cgtaatctgg catttctggg gattgcttat aacaccctgt tacgtatagc cgaaattgcc    3240
aggatcaggg ttaaagatat ctcacgtact gacggtggga gaatgttaat ccatattggc    3300
agaacgaaaa cgctggttag caccgcaggt gtagagaagg cacttagcct gggggtaact    3360
aaactggtcg agcgatggat ttccgtctct ggtgtagctg atgatccgaa taactacctg    3420
ttttgccggg tcagaaaaaa tggtgttgcc gcgccatctg ccaccagcca gctatcaact    3480
cgcgccctga agggatttt tgaagcaact catcgattga tttacggcgc taaggatgac    3540
tctggtcaga gatacctggc ctggtctgga cacagtgccc gtgtcggagc cgcgcgagat    3600
atggcccgcg ctggagtttc aataccggag atcatgcaag ctggtggctg gaccaatgta    3660
aatattgtca tgaactatat ccgtaccctg gatagtgaaa caggggcaat ggtgcgcctg    3720
ctggaagatg gcgattagcc attaacgcgt aaatgattgc tataattatt tgatatttat    3780
ggtgacatat gagaaaggat ttcaacatcg acggaaaata tgtagtgctg tctgtaagca    3840
ctaatattca gtcgccagcc gtcattgtca ctgtaaagct gagcgataga atgcctgata    3900
ttgactcaat atccgttgcg tttcctgtca aaagtatgcg tagtgctgaa catttcgtga    3960
tgaatgccac cgaggaagaa gcacggcgcg gttttgcnta aagtgatgtc tgagtttggc    4020
gaactcttgg gtaaggttgg aattgtcgac cgatgcccct gagagccttc aacccagtca    4080
gctccttccg gtgggcgcgg ggcatgacta tcgtcgccgc acttatgact gtcttcttta    4140
tcatgcaact cgtaggacag gtgccggcag cgctctgggt cattttcggc gaggaccgct    4200
ttcgctggag cgcgacgatg atcggcctgt cgcttgcggt attcggaatc ttgcacgccc    4260
tcgctcaagc cttcgtcact ggtcccgcca ccaaacgttt cggcgagaag caggccatta    4320
tcgccggcat ggcggccgac gcgctgggct acgtcttgct ggcgttcgcg acgcgaggct    4380
ggatggcctt ccccattatg attcttctcg cttccggcgg catcgggatg cccgcgttgc    4440
aggccatgct gtccaggcag gtagatgacg accatcaggg acagcttcaa ggatcgctcg    4500
cggctcttac cagcctaact tcgatcactg gaccgctgat cgtcacggcg atttatgccg    4560
cctcggcgag cacatggaac gggttggcat ggattgtagg cgccgcccta taccttgtct    4620
gcctccccgc gttgcgtcgc ggtgcatgga gccgggccac ctcgacctga atggaagccg    4680
gcggcacctc gctaacggat tcaccactcc aagaattgga gccaatcaat tcttgcggag    4740
aactgtgaat gcgcaaacca acccttggca gaacatatcc atcgcgtccg ccatctccag    4800
cagccgcacg cggcgcatct cgggcagcgt tgggtcctgg ccacgggtgc gcatgatcgt    4860
gctcctgtcg ttgaggaccc ggctaggctg gcggggttgc cttactggtt agcagaatga    4920
atcaccgata cgcgagcgaa cgtgaagcga ctgctgctgc aaaacgtctg cgacctgagc    4980
aacaacatga atggtcttcg gtttccgtgt ttcgtaaagt ctggaaacgc ggaagtcagc    5040
gccctgcacc attatgttcc ggatctgcat cgcaggatgc tgctggctac cctgtggaac    5100
acctacatct gtattaacga agcgctggca ttgaccctga gtgatttttc tctggtcccg    5160
ccgcatccat accgccagtt gtttaccctc acaacgttcc agtaaccggg catgttcatc    5220
atcagtaacc cgtatcgtga gcatcctctc tcgtttcatc ggtatcatta cccccatgaa    5280
cagaaattcc cccttacacg gaggcatcaa gtgaccaaac aggaaaaaac cgcccttaac    5340
atggcccgct ttatcagaag ccagacatta acgcttctgg agaaactcaa cgagctggac    5400
gcggatgaac aggcagacat ctgtgaatcg cttcacgacc acgctgatga gctttaccgc    5460
agcagatctg tatatatata tatatatgca agccattttt tttctctcac catctatttt    5520
```

```
aatatataaa attagatcat ctatctaaac ttttcatta aataaattag atggcgaaaa      5580
taatggagac gtattccatt ataatatata aaaacctaaa actatgtttc attataacaa      5640
tttacttcct aatttggaaa attcgaagtt ggttattata tgtgcatata tactgaatgt      5700
tcataacttc tagtcaacag atataattta ttcctcgtag taacttgccc gcaaacattt      5760
tatatctaaa ttaatttcaa gggaagttct tgtaaatata tatttatctc aagtaaacag      5820
ttagaaatat cagccatgat gacattttcc aggatggcaa tgactcatga tcacactgag      5880
atttttaata gatatttcgt tagagatgat ggtatctcaa aacaaaacga ctgtagctct      5940
tttaccacct catttacaat ttcatctttc atcaaattta gggatgccat caactttcag      6000
ttcataatta atatcttacc aaattaggta atctgcaaaa gttcagactg tgaaatgtaa      6060
cattttatat atcaagctct atttaatgcc tcacagtagt taacataaag agatacagaa      6120
ttgtcgtgtc agtgtatact atccatgtgt atactctgga tatccatttg tattccatta      6180
tctacgaaaa gcacttagat aaatactaaa ttgttatttg gtatgtatcg tataagttga      6240
aagttttgag cccatcttgt tgttttcttt tattaaataa aataaaataa ctaacgttat      6300
gatactttga tgtgtttttt aatttaatta taccagtact tgtttgaaat tttttctgc      6360
agaatttgg ccggctcatt tctatttgtt gtaagtacga gtatttgaac ttttagtcag      6420
atactggtag ttatatattt attttgtttt tgtttatttt gttgggtttt ttgtttgttg      6480
ttttttttcg gggggttgtg ttccaacttc gtttttggaa ttttaattta gtttctcgat      6540
cttcgctttt ggaatttatt taatttatcc ctccccttga ggtgtgaata acttaaaaat      6600
gctagaagga gctacacagg tgtttgtaca gtaaaaacta tcagcaggat accatcgcaa      6660
gatgttcata tcgctttgtt gagtcactgc aggggaccgc tgaggtattc gctggttcgg      6720
tgagggcggc cgtccctgtg attcgtacga ataaattctt tgtacaagta ccagtgctac      6780
aattgtaggt ggtgctcata caggtacacc ccgtgtgtaa gtaaactcca attatgttat      6840
gtctgataaa aggatgtaac ataggcaagc tgctcgtgag tgttgagtac gaaccttaga      6900
tccaaatcac ccgcacccta cggatatact tgcttgaata tacttgtaat aaggctgtct      6960
gctgacatcg gtgcgcgtat gttctgggcg cgactctct ccgaaccatc gaacagttcc      7020
tgaacacgac gagctagcta caacatgact cgcaagagct ctgtgcgtgt acacaacgag      7080
ccgtgcccgt gtaacagtct tcggttccga cccccaaaaa acccaccata caccgaaata      7140
gcacatcctt acgaccagta gcagcagagt gcgctacagt aagtattcgt caatacaagt      7200
aaatcacgag tacgacagtt gccgacacgg acagaaagga actacagatt taaatatacc      7260
aaacaataat tcattactaa tgtcaatcct tacagctgga taaaaaaact gggggatttt      7320
gttaacgagc tcattcgcaa atgaaacggg aaaagttctt cgatttagtg ttaaatctcc      7380
gttaaaaacc gcttatttgg atcgagctcg gaccttgcgg cgctttcgct tgagtcgtct      7440
gactctcttc tttctccact tagctctcat tctgggttag ttccatgttc tccgctggcg      7500
ggggcgacca ccgctaatcg agccgacttg tattgaaagg caggcaagaa ggtatcgaag      7560
gggaagaacc gttttgtggt tgctgcacca cggcttccaa tgctctccca atgaagaacc      7620
aaggtcggta attaatactc acttgaaaga tcaagacaag aacctgatga atgtgaggaa      7680
aaaagacaa gaagggaaa gtttgaccat ttttaagctg tgcgagccac aggccgggta      7740
acagataaat taggttctga aaattcggat ctgctgcctc gcgcgtttcg gtgatgacgg      7800
tgaaaacctc tgcacatgc agctcccgga gacggtcaca gcttgtctgt aagcggatgc      7860
cgggagcaga caagcccgtc agggcgcgtc agcgggtgtt ggcgggtgtc ggggcgcagc      7920
```

```
catgacccag tcacgtagcg atagcggagt gtatactggc ttaactatgc ggcatcagag    7980
cagattgtac tgagagtgca ccatatgcgg tgtgaaatac cgcacagatg cgtaaggaga    8040
aaataccgca tcaggcgctc ttccgcttcc tcgctcactg actcgctgcg ctcggtcgtt    8100
cggctgcggc gagcggtatc agctcactca aaggcggtaa tacggttatc cacagaatca    8160
ggggataacg caggaaagaa catgtgagca aaaggccagc aaaaggccag gaaccgtaaa    8220
aaggccgcgt tgctggcgtt tttccatagg ctccgccccc ctgacgagca tcacaaaaat    8280
cgacgctcaa gtcagaggtg gcgaaacccg acaggactat aaagatacca ggcgtttccc    8340
cctggaagct ccctcgtgcg ctctcctgtt ccgaccctgc cgcttaccgg atacctgtcc    8400
gcctttctcc cttcgggaag cgtggcgctt tctcatagct cacgctgtag gtatctcagt    8460
tcggtgtagg tcgttcgctc caagctgggc tgtgtgcacg aaccccccgt tcagcccgac    8520
cgctgcgcct tatccggtaa ctatcgtctt gagtccaacc cggtaagaca cgacttatcg    8580
ccactggcag cagccactgg taacaggatt agcagagcga gtatgtaggc ggtgctaca    8640
gagttcttga agtggtggcc taactacggc tacactagaa ggacagtatt tggtatctgc    8700
gctctgctga agccagttac cttcggaaaa agagttggta gctcttgatc cggcaaacaa    8760
accaccgctg gtagcggtgg tttttttgtt tgcaagcagc agattacgcg cagaaaaaaa    8820
ggatctcaag aagatccttt gatcttttct acggggtctg acgctcagtg gaacgaaaac    8880
tcacgttaag ggattttggt catgagatta tcaaaaagga tcttcaccta gatccttta    8940
aattaaaaat gaagttttaa atcaatctaa agtatatatg agtaaacttg gtctgacagt    9000
taccaatgct taatcagtga ggcacctatc tcagcgatct gtctatttcg ttcatccata    9060
gttgcctgac tccccgtcgt gtagataact acgatacggg agggcttacc atctggcccc    9120
agtgctgcaa tgataccgcg agacccacgc tcaccggctc cagatttatc agcaataaac    9180
cagccagccg aagggccga gcgcagaagt ggtcctgcaa ctttatccgc ctccatccag    9240
tctattaatt gttgccggga agctagagta agtagttcgc cagttaatag tttgcgcaac    9300
gttgttgcca ttgctgcagg catcgtggtg tcacgctcgt cgtttggtat ggcttcattc    9360
agctccggtt cccaacgatc aaggcgagtt acatgatccc ccatgttgtg caaaaaagcg    9420
gttagctcct tcggtcctcc gatcgttgtc agaagtaagt tggccgcagt gttatcactc    9480
atggttatgg cagcactgca taattctctt actgtcatgc catccgtaag atgcttttct    9540
gtgactggtg agtactcaac caagtcattc tgagaatagt gtatgcggcg accgagttgc    9600
tcttgcccgg cgtcaacacg ggataatacc gcgccacata gcagaacttt aaaagtgctc    9660
atcattggaa aacgttcttc ggggcgaaaa ctctcaagga tcttaccgct gttgagatcc    9720
agttcgatgt aacccactcg tgcacccaac tgatcttcag catcttttac tttcaccagc    9780
gtttctgggt gagcaaaaac aggaaggcaa aatgccgcaa aaaagggaat aagggcgaca    9840
cggaaatgtt gaatactcat actcttcctt tttcaatatt attgaagcat ttatcagggt    9900
tattgtctca tgagcggata catatttgaa tgtatttaga aaaataaaca ataggggtt    9960
ccgcgcacat ttccccgaaa agtgccacct gacgtctaag aaaccattat tatcatgaca   10020
ttaacctata aaaataggcg tatcacgagg ccctttcgtc ttcaa                   10065
```

<210> SEQ ID NO 86
<211> LENGTH: 28
<212> TYPE: DNA
<213> ORGANISM: Artificial
<220> FEATURE:

```
<223> OTHER INFORMATION: Primer

<400> SEQUENCE: 86
aaagatatct ctatgcgcac ccgttctc                                              28

<210> SEQ ID NO 87
<211> LENGTH: 39
<212> TYPE: DNA
<213> ORGANISM: Artificial
<220> FEATURE:
<223> OTHER INFORMATION: Primer

<400> SEQUENCE: 87
tttagatcta agcttgagac acctcagcat gcaccattc                                  39

<210> SEQ ID NO 88
<211> LENGTH: 8114
<212> TYPE: DNA
<213> ORGANISM: Artificial
<220> FEATURE:
<223> OTHER INFORMATION: Vector

<400> SEQUENCE: 88
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagctca    240
gaattaaccc tcactaaagg gactagtcct gcaggtttaa acgaattcgc cctttcatct    300
cgagatgctt tattcaggca cgctacgtga gaatattcta atgggatggt ctggccctga    360
gtctgaagta acgcaggaga tgattgagga tgccgctcgc aaagcgaaca ttcacgaatt    420
catcatgtcg ttgcctgatg gctacgaaac gctcagcgga tctaggggat cgttgctatc    480 tgggggcaa aagcagcgaa ttgcaattgc aaggcctg atcagaaatc caaaggtact    540
cctcctcgat gaggccacct cagctctgga ttccgaatct gagaaagtag ttcaagcagc    600
actcgacgca gcagcgaagg gccgtactac aatcgccgtt gcgcatagat tatcaacaat    660
tcagaaagca gatgtcatat atgtgttctc aggagggcgc atcgtggagc agggcgacca    720
tcagagcctc cttgaactca atggatggta cgctgaattg gtgaacttgc aaggtctcgg    780
agagatttga cgttcattta ttttttggcca ctgcttgcat acattatttg attaaaggca    840
ctcattaatt gaaatagcat atcgaatttc tctagttatg gcccctgagt caccatacat    900
tgtctgatta aagggactcg ttaattgaaa tagcacattg gattcctctg attatgaccc    960
ctgagtcacc tatcctgcat aattcactcg tgacgataat ctgtagatat agggaactgt   1020
cgtagtactt gaagagacag caacaatcta tctctgggat ttcgtgctga ttttgggctt   1080
ttgctttgac gggctatgac tgaggtaatg tagaccaata ataaccctca cgcgaattag   1140
atatgccctg agggttagct tgcatcacct tacccatatg cacactgact tgcattaccc   1200
ggagcatatt ccggtagtcg gagataagca ctttgagata tcttaaggta caactcaata   1260
cgttcctcct tccttgcctc attccactca cattctaga attcaataac ttcgtatagc   1320
atacattata cgaagttatt aattaacatc atcgtcacta tacacatcgt catcaactcc   1380
atggcgtgag gacttccgag actgctgggc ccttcgtttc tttaatgcct caagagatga   1440
cttcgtaccc gaagagacgc ctgttgtacc ccgttgacgc ttggcggagg gggcttcgtc   1500
ctcgtcagca acccgcgtca tctgcttcct tcgctgagca agatacctttc tctcctcgta   1560
```

```
ccgctgcatc tcctgagctc ggtcatacaa gatctcttct cgctcaatct ctggcagcgc    1620
gtccaacttc gccctgtctt cagcatcgag atatttgcct tctagaggat agggattgac    1680
gacctcattg cttggcggcg acggcagcga gatttcctct tcggagtcgg agccaacgtc    1740
ggccaatgcc agcagatcat catcactgtc actcatagta ggaaggttga agtgtgctga    1800
cgaatcagaa tcgcgaagga tgccattgaa ggcatatata ttttaatctg tacctttat    1860 ggtaatttaa tcagatttta taggtattca tgtgcaagtt gcattgaagg aactgtttga    1920
gaaaatcatc ttgactgaac ttttctcaga tatgcattcc agcccgcctt ttggtaacgc    1980
tgagcttcgt gcacaggatc tcgtcccttg ctatagagcc cgcgtccgac gataataacg    2040
tctgtgccgg tctctatgac gtcgtccaca gtacgatact gctgcccaa tccatcacct     2100 ttgtcgtcca ggcccacccc aggagtcata atgacccagt cttcctctgg ctttccgact    2160
ttttgctgag cgatgaaacc aaacacaaat gcgcggttac tgcgagcgat gtctactgtc    2220
gcttgcgagt attcgccgtg agccagtgtg cccttcgaac tcagttctgc aagcatgaca    2280
aggccgcgag gttcatccgt agtttccttc gcagcctctt ctagtccgct cacaattccc    2340
ggcccaggaa caccgtgagc atttgttata tcagcccatt gagcgatctt aaacactcca    2400
cctgcatatt gggccttaac agtggaaccg atgtctgcga actttcggtc ttcaaaaatg    2460
agaaaattgt gcttcgttga aagctgtttc aaaccgctga cagttgtgtc gtattcgaag    2520
tcgtcaatta tgtcaatgtg ggtcttaacc atacaaatgt aaggtccaat gcggtccagg    2580
atactcagta actcagaggt agttcgcaca tccaagcttg cgcaaagatt tgtttgcttg    2640
ctcacaatga tgtcgaatag ccgggctgct acagccggca gcctctctcg gcgctcctca    2700
tagctcagct tcatattatt tctctacagt agtgcccgtg ccctcgatca gctaggactt    2760
ttcaaattaa tcgggctgtt tgatgtaagt aagatgaagt cacgcgcgtg caggagactg    2820
cgtcccgcga tattctgcag gcttgaaaaa tttaccctaa cggtaggcat caagtgagtg    2880
agtctcagcg tcgatatggg tcaaaaagg ggaaaactag ccgagatcgt tgcgagctgt    2940
ttcgaaaatt atgccctatg gcaattatca cgtggagtat ccgaatttct ccaggctgtc    3000
aagcggcaat tataaccgag actgagatcg agaagtatat aaccgcagca gtagtggata    3060 ataattgcg aagtcttccc agcagagcgg gctgttttt ggagttggtt actgtaaaat     3120
gctaaaatga ctgacaacaa tggagcgtct acagcattgg caacagtggg aacagtatgc    3180
tggtgcatcc agttgatacc ccaggttctg cgaaactggt atgttcggga ttgcgagggc    3240
gttcctcctc tgatgttctt tttgttcgcc gtttcgggga ttcccttcgc agtgtacttc    3300
attgatcaga attcgaacac tgccatcatg gttcaacctc acttgtttac tttctttagc    3360
cttataggct tttggcaaag cctgtactat ccgcccgtca gttaattaat aacttcgtat    3420
agcatacatt atacgaagtt attaggtaaa ctaaattcat gacagccttt tcttctttct    3480
ttccacaaaa caattaaaaa aaataacaga attagaagaa ggtaaatata ttggcaaact    3540
cctctcttcc ttttacttat ttttttgaaa gttgcagtgt gtgtgtgtgt tgttgtttgt    3600
tcaaattaat ttgatggttg ttgtattgta aatttcaatc aataaaaaca aagacataaa    3660
taaaaaaaac cctacctctc ttccctgatc tgatttgatc gtacgattct aagaactcac    3720
cgctaaggcc ggccctttga caggtatatc ttcagtttcc tcgtcactct tggtcaaaag    3780
accaaagtca tggctggcga tttcctcgat gctttcctca agaattttca aggagttgtg    3840
gctttccaac tccatttgaa ccttcttcga ggcttcgtgg aatttcggat ttccaattat    3900
```

-continued

```
cgaatcaaca gcttctttga tttgctccac tgtaggcaag ccagttttca aatcaattgc    3960
cacgccagcg gcctcagctc tcgatgccac cattggcttg tcttcagagt caccagcaat    4020
aacaactgga acagagtggc ttaagctgtg ctgaagtccg ccatatccac cattgtagac    4080
aagagcatca acgtgaggaa gtagagcatc gtagttgaag tagtcgatca cgcgagcatt    4140
ctcaggaacc acaacatcat ccggtagctt ggcaccgcgg cggcccaata tggctactgt    4200
taaagtgtca ggctcgtcct tcaaggcctc aagagtaggc acaataagat gcttgtaact    4260
gacagcaaaa gttccttgag tgaccatgat gactcgcttg cactcagaa catcccccca     4320 ccaggaagga ggggtgaatt gagttcggtg cttgggcgtt gagccggcga atttgaagtt    4380
gctaggcaga tggtctctgc tgaactcaag agaaggcggg cacagctgca ggaacttgtc    4440
tgcaggtacc tcaagggcga attcgcggcc gctaaattca attcgcccta tagtgagtcg    4500
tattacaatt cactggccgt cgttttacaa cgtcgtgact gggaaaaccc tggcgttacc    4560
caacttaatc gccttgcagc acatccccct ttcgccagct ggcgtaatag cgaagaggcc    4620
cgcaccgatc gcccttccca acagttgcgc agcctatacg tacggcagtt aaggtttac    4680 acctataaaa gagagagccg ttatcgtctg tttgtggatg tacagagtga tattattgac    4740
acgccggggc gacggatggt gatcccctg gccagtgcac gtctgctgtc agataaagtc     4800
tcccgtgaac tttacccggt ggtgcatatc ggggatgaaa gctggcgcat gatgaccacc    4860
gatatggcca gtgtgccggt ctccgttatc ggggaagaag tggctgatct cagccaccgc    4920
gaaaatgaca tcaaaaacgc cattaacctg atgttctggg aatataaat gtcaggcatg     4980 agattatcaa aaaggatctt cacctagatc cttttcacgt agaaagccag tccgcagaaa    5040
cggtgctgac cccggatgaa tgtcagctac tgggctatct ggacaaggga aaacgcaagc    5100
gcaaagagaa agcaggtagc ttgcagtggg cttacatggc gatagctaga ctgggcggtt    5160
ttatggacag caagcgaacc ggaattgcca gctggggcgc cctctggtaa ggttgggaag    5220
ccctgcaaag taaactggat ggctttcttg ccgccaagga tctgatggcg caggggatca    5280
agctctgatc aagagacagg atgaggatcg tttcgcatga ttgaacaaga tggattgcac    5340
gcaggttctc cggccgcttg ggtggagagg ctattcggct atgactgggc acaacagaca    5400
atcggctgct ctgatgccgc cgtgttccgg ctgtcagcgc aggggcgccc ggttcttttt    5460
gtcaagaccg acctgtccgg tgccctgaat gaactgcaag acgaggcagc gcggctatcg    5520
tggctggcca cgacgggcgt tccttgcgca gctgtgctcg acgttgtcac tgaagcggga    5580
agggactggc tgctattggg cgaagtgccg gggcaggatc tcctgtcatc tcaccttgct    5640
cctgccgaga aagtatccat catggctgat gcaatgcggc ggctgcatac gcttgatccg    5700
gctacctgcc cattcgacca ccaagcgaaa catcgcatcg agcgagcacg tactcggatg    5760
gaagccggtc ttgtcgatca ggatgatctg gacgaagagc atcagggct cgcgccagcc    5820 gaactgttcg ccaggctcaa ggcgagcatg cccgacggcg aggatctcgt cgtgacccat    5880
ggcgatgcct gcttgccgaa tatcatggtg gaaaatggcc gcttttctgg attcatcgac    5940
tgtggccggc tgggtgtggc ggaccgctat caggacatag cgttggctac ccgtgatatt    6000
gctgaagagc ttggcggcga atgggctgac cgcttcctcg tgctttacgg tatcgccgct    6060
cccgattcgc agcgcatcgc cttctatcgc cttcttgacg agttcttctg aattattaac    6120
gcttacaatt tcctgatgcg gtattttctc cttacgcatc tgtgcggtat tcacaccgc    6180 atcaggtggc acttttcggg gaaatgtgcg cggaacccct atttgtttat ttttctaaat    6240
acattcaaat atgtatccgc tcatgagatt atcaaaaagg atcttcacct agatcctttt    6300
```

```
aaattaaaaa tgaagtttta aatcaatcta aagtatatat gagtaaactt ggtctgacag    6360
ttaccaatgc ttaatcagtg aggcacctat ctcagcgatc tgtctatttc gttcatccat    6420
agttgcctga ctccccgtcg tgtagataac tacgatacgg gagggcttac catctggccc    6480
cagtgctgca atgataccgc gagacccacg ctcaccggct ccagatttat cagcaataaa    6540
ccagccagcc ggaagggccg agcgcagaag tggtcctgca actttatccg cctccatcca    6600
gtctattaat tgttgccggg aagctagagt aagtagttcg ccagttaata gtttgcgcaa    6660
cgttgttgcc attgctacag gcatcgtggt gtcacgctcg tcgtttggta tggcttcatt    6720
cagctccggt tcccaacgat caaggcgagt tacatgatcc cccatgttgt gcaaaaaagc    6780
ggttagctcc ttcggtcctc cgatcgttgt cagaagtaag ttggccgcag tgttatcact    6840
catggttatg gcagcactgc ataattctct tactgtcatg ccatccgtaa gatgcttttc    6900
tgtgactggt gagtactcaa ccaagtcatt ctgagaatag tgtatgcggc gaccgagttg    6960
ctcttgcccg gcgtcaatac gggataatac cgcgccacat agcagaactt taaaagtgct    7020
catcattgga aaacgttctt cggggcgaaa actctcaagg atcttaccgc tgttgagatc    7080
cagttcgatg taacccactc gtgcacccaa ctgatcttca gcatctttta ctttcaccag    7140
cgtttctggg tgagcaaaaa caggaaggca aaatgccgca aaaagggaa taagggcgac    7200 acggaaatgt tgaatactca tactcttcct ttttcaatat tattgaagca tttatcaggg    7260
ttattgtctc atgaccaaaa tcccttaacg tgagttttcg ttccactgag cgtcagaccc    7320
cgtagaaaag atcaaaggat cttcttgaga tcctttttt ctgcgcgtaa tctgctgctt    7380
gcaaacaaaa aaaccaccgc taccagcggt ggtttgtttg ccggatcaag agctaccaac    7440 tcttttccg aaggtaactg gcttcagcag agcgcagata ccaaatactg ttcttctagt    7500
gtagccgtag ttaggccacc acttcaagaa ctctgtagca ccgcctacat acctcgctct    7560
gctaatcctg ttaccagtgg ctgctgccag tggcgataag tcgtgtctta ccgggttgga    7620
ctcaagacga tagttaccgg ataaggcgca gcggtcgggc tgaacggggg gttcgtgcac    7680
acagcccagc ttggagcgaa cgacctacac cgaactgaga tacctacagc gtgagctatg    7740
agaaagcgcc acgcttcccg aagggagaaa ggcggacagg tatccggtaa gcggcagggt    7800
cggaacagga gagcgcacga gggagcttcc agggggaaac gcctggtatc tttatagtcc    7860
tgtcgggttt cgccacctct gacttgagcg tcgatttttg tgatgctcgt caggggggcg    7920
gagcctatgg aaaaacgcca gcaacgcggc cttttacgg ttcctggcct tttgctggcc    7980
ttttgctcac atgttctttc ctgcgttatc ccctgattct gtggataacc gtattaccgc    8040
ctttgagtga gctgataccg ctcgccgcag ccgaacgacc gagcgcagcg agtcagtgag    8100
cgaggaagcg gaag                                                     8114

<210> SEQ ID NO 89
<211> LENGTH: 8578
<212> TYPE: DNA
<213> ORGANISM: Artificial
<220> FEATURE:
<223> OTHER INFORMATION: Vector

<400> SEQUENCE: 89
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
```

```
ttgtgagcgg ataacaattt cacacaggaa acagctatga ccatgattac gccaagctca    240
gaattaaccc tcactaaagg gactagtcct gcaggtttaa acgaattcgc cctttcatct    300
cgagatgctt tattcaggca cgctacgtga gaatattcta atgggatggt ctggccctga    360
gtctgaagta acgcaggaga tgattgagga tgccgctcgc aaagcgaaca ttcacgaatt    420
catcatgtcg ttgcctgatg gctacgaaac gctcagcgga tctaggggat cgttgctatc    480
tgggggcaa aagcagcgaa ttgcaattgc aagggccctg atcagaaatc caaaggtact    540
cctcctcgat gaggccacct cagctctgga ttccgaatct gagaaagtag ttcaagcagc    600
actcgacgca gcagcgaagg gccgtactac aatcgccgtt gcgcatagat tatcaacaat    660
tcagaaagca gatgtcatat atgtgttctc aggagggcgc atcgtggagc agggcgacca    720
tcagagcctc cttgaactca atggatggta cgctgaattg gtgaacttgc aaggtctcgg    780
agagatttga cgttcattta ttttggcca ctgcttgcat acattatttg attaaaggca    840
ctcattaatt gaaatagcat atcgaatttc tctagttatg gcccctgagt caccatacat    900
tgtctgatta aagggactcg ttaattgaaa tagcacattg gattcctctg attatgaccc    960
ctgagtcacc tatcctgcat aattcactcg tgacgataat ctgtagatat agggaactgt   1020
cgtagtactt gaagagacag caacaatcta tctctgggat ttcgtgctga ttttgggctt   1080
ttgctttgac gggctatgac tgaggtaatg tagaccaata ataaccctca cgcgaattag   1140
atatgccctg agggttagct tgcatcacct tacccatatg cacactgact tgcattaccc   1200
ggagcatatt ccggtagtcg gagataagca ctttgagata tcttaaggta caactcaata   1260
cgttcctcct tccttgcctc attccactc acattctaga attcaataac ttcgtatagc   1320
atacattata cgaagttatt aattaacatc atcgtcacta tacacatcgt catcaactcc   1380
atggcgtgag gacttccgag actgctgggc ccttcgtttc tttaatgcct caagagatga   1440
cttcgtaccc gaagagacgc ctgttgtacc ccgttgacgc ttggcggagg gggcttcgtc   1500
ctcgtcagca acccgcgtca tctgcttcct tcgctgagca agatacctc tctcctcgta   1560
ccgctgcatc tcctgagctc ggtcatacaa gatctaagct tgagacacct cagcatgcac   1620
cattccttgc ggcggcggtg ctcaacggcc tcaacctact actgggctgc ttcctaatgc   1680
aggagtcgca taagggagag cgtcgactat tcctttgccc tcggacgagt gctggggcgt   1740
cggtttccac tatcggcgag tacttctaca cagccatcgg tccagacggc cgcgcttctg   1800
cgggcgattt gtgtacgccc gacagtccg gctccggatc ggacgattgc gtcgcatcga   1860
ccctgcgccc aagctgcatc atcgaaattg ccgtcaacca agctctgata gagttggtca   1920
agaccaatgc ggagcatata cgcccggagc cgcggcgatc ctgcaagctc cggatgcctc   1980
cgctcgaagt agcgcgtctg ctgctccata caagccaacc acggcctcca gaagaagatg   2040
ttggcgacct cgtattggga atccccgaac atcgcctcgc tccagtcaat gaccgctgtt   2100
atgcggccat tgtccgtcag gacattgttg gagccgaaat ccgcgtgcac gaggtgccgg   2160
acttcggggc agtcctcggc ccaaagcatc agctcatcga gagcctgcgc gacggacgca   2220
ctgacggtgt cgtccatcac agtttgccag tgatacacat ggggatcagc aatcgcgcat   2280
atgaaatcac gccatgtagt gtattgaccg attccttgcg gtccgaatgg gccgaacccg   2340
ctcgtctggc taagatcggc cgcagcgatc gcatccatgg cctccgcgac cggctgcaga   2400
acagcgggca gttcggtttc aggcaggtct tgcaacgtga caccctgtgc acggcgggag   2460
atgcaatagg tcaggctctc gctaaattcc ccaatgtcaa gcacttccgg aatcgggagc   2520
gcggccgatg caaagtgccg ataaacataa cgatctttgt agaaaccatc ggcgcagcta   2580
```

```
tttacccgca ggacatatcc acgccctcct acatcgaagc tgaaagcacg agattcttcg   2640
ccctccgaga gctgcatcag gtcggagacg ctgtcgaact tttcgatcag aaacttctcg   2700
acagacgtgg cggtgagttc aggcttttc attgtggatg tgtgtggttg tatgtgtgat    2760
gtggtgtgtg gagtgaaaat ctgtggctgg caaacgctct tgtatatata cgcacttttg   2820
cccgtgatca gtgcatgccg gatcgaggtg ggcgggaaca acggtctcga taatgtacgt   2880
acactacaca caaagagaag caagtggggg cgggactgca cggcacttgt gagacacctc   2940
agcatgccgg atcgaggtgg gcgggaacaa cggtctcgat aatgtacgta cactacacac   3000
aaagagaagc aagtggggc gggactgcac ggcacttgtg agacacctca gcatgccgga    3060
tcgaggtggg cggaacaac ggtctcgata tgtacgtac actacacaca aagagaagca     3120 agtggggcg gactgcacg gcacttgtga gacacctcag catgccggat cgaggtgggc     3180
gggaacaacg gtctcgataa tgtacgtaca ctacacacaa agagaagcaa gtggggcgg    3240 gactgcacgg cacttgtgag acacctcagc atgccaccatt ccttgcggcg cggtgctca   3300 acggcctgga tccacaggac gggtgtggtc gccatgatcg cgtagtcgat agtggctcca   3360
agtagcgaag cgagcaggac tgggcggcgg ccaaagcggt cggacagtgc tccgagaacg   3420
ggtgcgcata gagatgtgga gtatccgaat ttctccaggc tgtcaagcgg caattataac   3480
cgagactgag atcgagaagt atataaccgc agcagtagtg gataaataat tgcgaagtct   3540
tcccagcaga gcgggctgtt ttttggagtt ggttactgta aaatgctaaa atgactgaca   3600
acaatggagc gtctacagca ttggcaacag tgggaacagt atgctggtgc atccagttga   3660
taccccaggt tctgcgaaac tggtatgttc gggattgcga gggcgttcct cctctgatgt   3720 tcttttgtt cgccgtttcg gggattccct tcgcagtgta cttcattgat cagaattcga    3780
acactgccat catggttcaa cctcacttgt ttactttctt tagccttata ggcttttggc    3840
aaagcctgta ctatccgccc gtcagttaat taataacttc gtatagcata cattatacga   3900
agttattagg taaactaaat tcatgacagc ttttcttct ttctttccac aaaacaatta    3960
aaaaaaataa cagaattaga agaaggtaaa tatattggca aactcctctc ttccttttac   4020
ttattttttt gaaagttgca gtgtgtgtgt gtgttgttgt ttgttcaaat taatttgatg   4080
gttgttgtat tgtaaatttc aatcaataaa aacaaagaca taaataaaaa aaaccctacc   4140
tctcttccct gatctgattt gatcgtacga ttctaagaac tcaccgctaa ggccggccct   4200
ttgacaggta tatcttcagt ttcctcgtca ctcttggtca aaagaccaaa gtcatggctg   4260
gcgatttcct cgatgctttc ctcaagaatt ttcaaggagt tgtggctttc caactccatt   4320
tgaaccttct tcgaggcttc gtggaatttc ggatttccaa ttatcgaatc aacagcttct   4380
ttgatttgct ccactgtagg caagccagtt ttcaaatcaa ttgccacgcc agcggcctca   4440
gctctcgatg ccaccattgg cttgtcttca gagtcaccag caataacaac tggaacagag   4500
tggcttaagc tgtgctgaag tccgccatat ccaccattgt agacaagagc atcaacgtga   4560
ggaagtagag catcgtagtt gaagtagtcg atcacgcgag cattctcagg aaccacaaca   4620
tcatccggta gcttggcacc gcggcggccc aatatggcta ctgttaaagt gtcaggctcg   4680
tccttcaagg cctcaagagt aggcacaata agatgcttgt aactgacagc aaaagttcct   4740
tgagtgacca tgatgactcg cttggcactc agaacatccc cccaccagga aggagggtg    4800 aattgagttc ggtgcttggg cgttgagccg gcgaatttga agttgctagg cagatggtct   4860
ctgctgaact caagagaagg cgggcacagc tgcaggaact tgtctgcagg tacctcaagg   4920
```

```
gcgaattcgc ggccgctaaa ttcaattcgc cctatagtga gtcgtattac aattcactgg      4980
ccgtcgtttt acaacgtcgt gactgggaaa accctggcgt tacccaactt aatcgccttg      5040
cagcacatcc cccttccgcc agctggcgta atagcgaaga ggcccgcacc gatcgccctt      5100
cccaacagtt gcgcagccta tacgtacggc agtttaaggt ttacacctat aaaagagaga      5160
gccgttatcg tctgtttgtg gatgtacaga gtgatattat tgacacgccg gggcgacgga      5220
tggtgatccc cctggccagt gcacgtctgc tgtcagataa agtctcccgt gaactttacc      5280
cggtggtgca tatcggggat gaaagctggc gcatgatgac caccgatatg gccagtgtgc      5340
cggtctccgt tatcggggaa gaagtggctg atctcagcca ccgcgaaaat gacatcaaaa      5400
acgccattaa cctgatgttc tggggaatat aaatgtcagg catgagatta tcaaaaagga      5460
tcttcaccta gatccttttc acgtagaaag ccagtccgca gaaacggtgc tgaccccgga      5520
tgaatgtcag ctactgggct atctggacaa gggaaaacgc aagcgcaaag agaaagcagg      5580
tagcttgcag tgggcttaca tggcgatagc tagactgggc ggttttatgg acagcaagcg      5640
aaccggaatt gccagctggg gcgccctctg gtaaggttgg gaagccctgc aaagtaaact      5700
ggatggcttt cttgccgcca aggatctgat ggcgcagggg atcaagctct gatcaagaga      5760
caggatgagg atcgtttcgc atgattgaac aagatggatt gcacgcaggt tctccggccg      5820
cttgggtgga gaggctattc ggctatgact gggcacaaca gacaatcggc tgctctgatg      5880
ccgccgtgtt ccggctgtca gcgcaggggc gcccggttct ttttgtcaag accgacctgt      5940
ccggtgccct gaatgaactg caagacgagg cagcgcggct atcgtggctg gccacgacgg      6000
gcgttccttg cgcagctgtg ctcgacgttg tcactgaagc gggaagggac tggctgctat      6060
tgggcgaagt gccggggcag gatctcctgt catctcacct tgctcctgcc gagaaagtat      6120
ccatcatggc tgatgcaatg cggcggctgc atacgcttga tccggctacc tgcccattcg      6180
accaccaagc gaaacatcgc atcgagcgag cacgtactcg gatggaagcc ggtcttgtcg      6240
atcaggatga tctggacgaa gagcatcagg ggctcgcgcc agccgaactg ttcgccaggc      6300
tcaaggcgag catgcccgac ggcgaggatc tcgtcgtgac ccatggcgat gcctgcttgc      6360
cgaatatcat ggtggaaaat ggccgctttt ctggattcat cgactgtggc cggctgggtg      6420
tggcggaccg ctatcaggac atagcgttgg ctacccgtga tattgctgaa gagcttggcg      6480
gcgaatgggc tgaccgcttc ctcgtgcttt acggtatcgc cgctcccgat tcgcagcgca      6540
tcgccttcta tcgccttctt gacgagttct tctgaattat taacgcttac aatttcctga      6600
tgcggtattt tctccttacg catctgtgcg gtatttcaca ccgcatcagg tggcactttt      6660
cggggaaatg tgcgcggaac ccctatttgt ttatttttct aaatacattc aaatatgtat      6720
ccgctcatga gattatcaaa aaggatcttc acctagatcc ttttaaatta aaaatgaagt      6780
tttaaatcaa tctaaagtat atatgagtaa acttggtctg acagttacca atgcttaatc      6840
agtgaggcac ctatctcagc gatctgtcta tttcgttcat ccatagttgc ctgactcccc      6900
gtcgtgtaga taactacgat acgggagggc ttaccatctg gccccagtgc tgcaatgata      6960
ccgcgagacc cacgctcacc ggctccagat ttatcagcaa taaaccagcc agccggaagg      7020
gccgagcgca gaagtggtcc tgcaacttta tccgcctcca tccagtctat taattgttgc      7080
cgggaagcta gagtaagtag ttcgccagtt aatagtttgc gcaacgttgt tgccattgct      7140
acaggcatcg tggtgtcacg ctcgtcgttt ggtatggctt cattcagctc cggttcccaa      7200
cgatcaaggc gagttacatg atcccccatg ttgtgcaaaa aagcggttag ctccttcggt      7260
cctccgatcg ttgtcagaag taagttggcc gcagtgttat cactcatggt tatggcagca      7320
```

```
ctgcataatt ctcttactgt catgccatcc gtaagatgct tttctgtgac tggtgagtac    7380
tcaaccaagt cattctgaga atagtgtatg cggcgaccga gttgctcttg cccggcgtca    7440
atacgggata ataccgcgcc acatagcaga actttaaaag tgctcatcat tggaaaacgt    7500
tcttcggggc gaaaactctc aaggatctta ccgctgttga tccagttc gatgtaaccc      7560 actcgtgcac ccaactgatc ttcagcatct tttactttca ccagcgtttc tgggtgagca    7620
aaaacaggaa ggcaaaatgc cgcaaaaaag gaataaggg cgacacggaa atgttgaata    7680
ctcatactct cctttttca atattattga agcatttatc agggttattg tctcatgacc    7740
aaaatccctt aacgtgagtt ttcgttccac tgagcgtcag accccgtaga aaagatcaaa    7800
ggatcttctt gagatccttt ttttctgcgc gtaatctgct gcttgcaaac aaaaaaacca    7860
ccgctaccag cggtggtttg tttgccggat caagagctac caactctttt tccgaaggta    7920
actggcttca gcagagcgca gataccaaat actgttcttc tagtgtagcc gtagttaggc    7980
caccacttca agaactctgt agcaccgcct acatacctcg ctctgctaat cctgttacca    8040
gtggctgctg ccagtggcga taagtcgtgt cttaccgggt tggactcaag acgatagtta    8100
ccggataagg cgcagcggtc gggctgaacg gggggttcgt gcacacagcc cagcttggag    8160
cgaacgacct acaccgaact gagataccta cagcgtgagc tatgagaaag cgccacgctt    8220
cccgaaggga gaaaggcgga caggtatccg gtaagcggca gggtcggaac aggagagcgc    8280
acgagggagc ttccaggggg aaacgcctgg tatctttata gtcctgtcgg gtttcgccac    8340
ctctgacttg agcgtcgatt tttgtgatgc tcgtcagggg ggcggagcct atggaaaaac    8400
gccagcaacg cggccttttt acggttcctg gccttttgct ggccttttgc tcacatgttc    8460
tttcctgcgt tatccctga ttctgtggat aaccgtatta ccgcctttga gtgagctgat    8520
accgctcgcc gcagccgaac gaccgagcgc agcgagtcag tgagcgagga agcggaag     8578
```

<210> SEQ ID NO 90
<211> LENGTH: 4657
<212> TYPE: DNA
<213> ORGANISM: Artificial
<220> FEATURE:
<223> OTHER INFORMATION: Vector

<400> SEQUENCE: 90

```
ggtttaaacg aattcgccct ttcatctcga gatgctttat tcaggcacgc tacgtgagaa      60
tattctaatg ggatggtctg gccctgagtc tgaagtaacg caggagatga ttgaggatgc     120
cgctcgcaaa gcgaacattc acgaattcat catgtcgttg cctgatggct acgaaacgct    180
cagcggatct aggggatcgt tgctatctgg ggggcaaaag cagcgaattg caattgcaag    240
ggccctgatc agaaatccaa aggtactcct cctcgatgag gccacctcag ctctggattc    300
cgaatctgag aaagtagttc aagcagcact cgacgcagca gcgaagggcc gtactacaat    360
cgccgttgcg catagattat caacaattca gaaagcagat gtcatatatg tgttctcagg    420
agggcgcatc gtggagcagg gcgaccatca gagcctcctt gaactcaatg gatggtacgc    480
tgaattggtg aacttgcaag gtctcggaga gatttgacgt tcatttattt ttggccactg    540
cttgcataca ttatttgatt aaaggcactc attaattgaa atagcatatc gaatttctct    600
agttatggcc cctgagtcac catacattgt ctgattaaag ggactcgtta attgaaatag    660
cacattggat tcctctgatt atgacccctg agtcacctat cctgcataat tcactcgtga    720
cgataatctg tagatatagg gaactgtcgt agtacttgaa gagacagcaa caatctatct    780
```

```
ctgggatttc gtgctgattt tgggcttttg ctttgacggg ctatgactga ggtaatgtag    840
accaataata accctcacgc gaattagata tgccctgagg gttagcttgc atcaccttac    900
ccatatgcac actgacttgc attacccgga gcatattccg gtagtcggag ataagcactt    960
tgagatatct taaggtacaa ctcaatacgt tcctccttcc ttgcctcatt ccacctcaca   1020
ttctagaatt caataacttc gtatagcata cattatacga agttattaat taacatcatc   1080
gtcactatac acatcgtcat caactccatg gcgtgaggac ttccgagact gctgggccct   1140
tcgtttcttt aatgcctcaa gagatgactt cgtacccgaa gagacgcctg ttgtaccccg   1200
ttgacgcttg gcggaggggg cttcgtcctc gtcagcaacc cgcgtcatct gcttccttcg   1260
ctgagcaaga taccttctct cctcgtaccg ctgcatctcc tgagctcggt catacaagat   1320
ctaagcttga gacacctcag catgcaccat tccttgcggc ggcggtgctc aacggcctca   1380
acctactact gggctgcttc ctaatgcagg agtcgcataa gggagagcgt cgactattcc   1440
tttgccctcg gacgagtgct gggggcgtcg ttttccactat cggcgagtac ttctacacag   1500
ccatcggtcc agacggccgc gcttctgcgg gcgatttgtg tacgcccgac agtcccggct   1560
ccggatcgga cgattgcgtc gcatcgaccc tgcgcccaag ctgcatcatc gaaattgccg   1620
tcaaccaagc tctgatagag ttggtcaaga ccaatgcgga gcatatacgc ccggagccgc   1680
ggcgatcctg caagctccgg atgcctccgc tcgaagtagc gcgtctgctg ctccatacaa   1740
gccaaccacg gcctccagaa gaagatgttg gcgacctcgt attgggaatc cccgaacatc   1800
gcctcgctcc agtcaatgac cgctgttatg cggccattgt ccgtcaggac attgttggag   1860
ccgaaatccg cgtgcacgag gtgccggact tcggggcagt cctcggccca agcatcagc    1920 tcatcgagag cctgcgcgac ggacgcactg acggtgtcgt ccatcacagt ttgccagtga   1980
tacacatggg gatcagcaat cgcgcatatg aaatcacgcc atgtagtgta ttgaccgatt   2040
ccttgcggtc cgaatgggcc gaacccgctc gtctggctaa gatcggccgc agcgatcgca   2100
tccatggcct ccgcgaccgg ctgcagaaca gcgggcagtt cggtttcagg caggtcttgc   2160
aacgtgacac cctgtgcacg gcgggagatg caataggtca ggctctcgct aaattcccca   2220
atgtcaagca cttccggaat cgggagcgcg gccgatgcaa agtgccgata acataacga    2280 tctttgtaga aaccatcggc gcagctattt acccgcagga catatccacg ccctcctaca   2340
tcgaagctga aagcacgaga ttcttcgccc tccgagagct gcatcaggtc ggagacgctg   2400
tcgaactttt cgatcagaaa cttctcgaca gacgtggcgg tgagttcagg cttttttcatt   2460 gtggatgtgt gtggttgtat gtgtgatgtg gtgtgtggag tgaaaatctg tggctggcaa   2520
acgctcttgt atatatacgc acttttgccc gtgatcagtg catgccggat cgaggtgggc   2580
gggaacaacg gtctcgataa tgtacgtaca ctacacacaa agagaagcaa gtggggcgg    2640 gactgcacgg cacttgtgag acacctcagc atgccggatc gaggtgggcg ggaacaacgg   2700
tctcgataat gtacgtacac tacacacaaa gagaagcaag tggggcggg actgcacggc    2760 acttgtgaga cacctcagca tgccggatcg aggtgggcgg gaacaacggt ctcgataatg   2820
tacgtacact acacacaaag agaagcaagt ggggcgggga ctgcacggca cttgtgagac   2880
acctcagcat gccggatcga ggtgggcggg aacaacggtc tcgataatgt acgtacacta   2940
cacacaaaga gaagcaagtg ggggcgggac tgcacggcac ttgtgagaca cctcagcatg   3000
caccattcct tgcggcggcg gtgctcaacg gcctggatcc acaggacggg tgtggtcgcc   3060
atgatcgcgt agtcgatagt ggctccaagt agcgaagcga gcaggactgg gcggcggcca   3120
aagcggtcgg acagtgctcc gagaacgggt gcgcatagag atgtggagta tccgaatttc   3180
```

```
tccaggctgt caagcggcaa ttataaccga gactgagatc gagaagtata taaccgcagc    3240
agtagtggat aaataattgc gaagtcttcc cagcagagcg ggctgttttt tggagttggt    3300
tactgtaaaa tgctaaaatg actgacaaca atggagcgtc tacagcattg gcaacagtgg    3360
gaacagtatg ctggtgcatc cagttgatac cccaggttct gcgaaactgg tatgttcggg    3420
attgcgaggg cgttcctcct ctgatgttct ttttgttcgc cgtttcgggg attcccttcg    3480
cagtgtactt cattgatcag aattcgaaca ctgccatcat ggttcaacct cacttgttta    3540
ctttctttag ccttataggc ttttggcaaa gcctgtacta tccgcccgtc agttaattaa    3600
taacttcgta tagcatacat tatacgaagt tattaggtaa actaaattca tgacagcctt    3660
ttcttctttc tttccacaaa acaattaaaa aaaataacag aattagaaga aggtaaatat    3720 attgcaaac  tcctctcttc cttttactta ttttttgaa  agttgcagtg tgtgtgtgtg    3780
ttgttgtttg ttcaaattaa tttgatggtt gttgtattgt aaatttcaat caataaaaac    3840
aaagacataa ataaaaaaaa ccctacctct cttccctgat ctgatttgat cgtacgattc    3900
taagaactca ccgctaaggc cggcccttg  acaggtatat cttcagtttc ctcgtcactc    3960
ttggtcaaaa gaccaaagtc atggctggcg atttcctcga tgctttcctc aagaattttc    4020
aaggagttgt ggctttccaa ctccatttga accttcttcg aggcttcgtg gaatttcgga    4080
tttccaatta tcgaatcaac agcttctttg atttgctcca ctgtaggcaa gccagttttc    4140
aaatcaattg ccacgccagc ggcctcagct ctcgatgcca ccattggctt gtcttcagag    4200
tcaccagcaa taacaactgg aacagagtgg cttaagctgt gctgaagtcc gccatatcca    4260
ccattgtaga caagagcatc aacgtgagga agtagagcat cgtagttgaa gtagtcgatc    4320
acgcgagcat tctcaggaac cacaacatca tccggtagct tggcaccgcg gcggcccaat    4380
atggctactg ttaaagtgtc aggctcgtcc ttcaaggcct caagagtagg cacaataaga    4440
tgcttgtaac tgacagcaaa agttccttga gtgaccatga tgactcgctt ggcactcaga    4500 acatccccc  accaggaagg aggggtgaat tgagttcggt gcttgggcgt tgagccggcg    4560
aatttgaagt tgctaggcag atggtctctg ctgaactcaa gagaaggcgg gcacagctgc    4620
aggaacttgt ctgcaggtac ctcaagggcg aattcgc                            4657
```